(12) United States Patent
Nishimura et al.

(10) Patent No.: US 8,710,493 B2
(45) Date of Patent: Apr. 29, 2014

(54) ORGANIC ELECTROLUMINESCENT ELEMENT

(75) Inventors: Kazuki Nishimura, Sodegaura (JP); Toshinari Ogiwara, Sodegaura (JP); Hitoshi Kuma, Sodegaura (JP); Kenichi Fukuoka, Sodegaura (JP); Chishio Hosokawa, Sodegaura (JP); Yukitoshi Jinde, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 66 days.

(21) Appl. No.: 13/386,826

(22) PCT Filed: May 23, 2011

(86) PCT No.: PCT/JP2011/061786
§ 371 (c)(1),
(2), (4) Date: Jan. 24, 2012

(87) PCT Pub. No.: WO2011/148909
PCT Pub. Date: Dec. 1, 2011

(65) Prior Publication Data
US 2012/0119197 A1 May 17, 2012

(30) Foreign Application Priority Data

May 24, 2010 (JP) .................................. 2010-118160
Oct. 19, 2010 (JP) .................................. 2010-234926
Apr. 22, 2011 (JP) .................................. 2011-096087

(51) Int. Cl.
*H01L 51/54* (2006.01)

(52) U.S. Cl.
USPC ....... 257/40; 257/E51.026; 313/498; 313/504

(58) Field of Classification Search
USPC ..................... 257/13; 313/498–504
See application file for complete search history.

(56) References Cited

U.S. PATENT DOCUMENTS

2003/0205696 A1* 11/2003 Thoms et al. ............. 252/301.16
2006/0257684 A1* 11/2006 Arakane et al. ............... 428/690
(Continued)

FOREIGN PATENT DOCUMENTS

JP    2001 319779    11/2001
JP    2003 317966    11/2003
(Continued)

OTHER PUBLICATIONS

"Reduced efficiency roll-off in high-efficiency hybrid white organic lightemitting Diodes," Applied Physics Letters, vol. 92, p. 053311, (2008).
International Search Report Issued Jul. 5, 2011 in PCT/JP11/61786 Filed May 23, 2011.
U.S. Appl. No. 13/388,576, filed Feb. 2, 2012, Ogiwara, et al.

Primary Examiner — David Vu
Assistant Examiner — Jonathan Han
(74) Attorney, Agent, or Firm — Oblon, Spivak, McClelland, Maier & Neustadt, L.L.P.

(57) ABSTRACT

An organic electroluminescence device includes an anode, a cathode and layers between the anode and the cathode, the layers at least including a hole transporting layer, a first emitting layer, a second emitting layer and an electron transporting layer, in which the first emitting layer includes a first host material and a first luminescent material and the second emitting layer is continuously formed on the first emitting layer near the cathode and includes a second host material and a second luminescent material. The second host material is a monoazine derivative, a diazine derivative, or a triazine derivative. The first and second luminescent materials are different metal complexes.

20 Claims, 3 Drawing Sheets

(56) References Cited

U.S. PATENT DOCUMENTS

| | | |
|---|---|---|
| 2007/0215889 A1 | 9/2007 | Kawakami et al. |
| 2007/0257600 A1* | 11/2007 | Matsuura et al. ............. 313/498 |
| 2009/0096360 A1* | 4/2009 | Tanaka et al. ................ 313/504 |
| 2009/0218561 A1* | 9/2009 | Kitamura et al. ............... 257/13 |
| 2009/0302742 A1* | 12/2009 | Komori et al. ................ 313/504 |
| 2010/0187977 A1* | 7/2010 | Kai et al. ..................... 313/504 |
| 2010/0295027 A1 | 11/2010 | Kawamura et al. |
| 2010/0295444 A1 | 11/2010 | Kuma et al. |
| 2010/0301318 A1 | 12/2010 | Kuma et al. |
| 2010/0314644 A1 | 12/2010 | Nishimura et al. |
| 2011/0049483 A1 | 3/2011 | Nishimura et al. |

FOREIGN PATENT DOCUMENTS

| | | |
|---|---|---|
| JP | 2006 269232 | 10/2006 |
| JP | 2009 141336 | 6/2009 |
| JP | 2009 211892 | 9/2009 |
| WO | 2004 034751 | 4/2004 |
| WO | 2005 076669 | 8/2005 |
| WO | 2007 063754 | 6/2007 |
| WO | 2008 056746 | 5/2008 |
| WO | 2009 136596 | 11/2009 |
| WO | 2010 044342 | 4/2010 |

* cited by examiner

ORGANIC ELECTROLUMINESCENT ELEMENT

TECHNICAL FIELD

The present invention relates to an organic electroluminescence device (hereinafter, occasionally abbreviated as an organic EL device).

BACKGROUND ART

An organic EL device is a self-emitting device that is based on a principle according to which, with an electric field applied, a luminescent material emits light by recombination energy caused by holes injected from an anode and electrons injected from a cathode.

Organic EL devices formed from organic materials have been vigorously studied since a report on a low voltage-driven organic EL device formed by laminating layers was made by C. W. Tang et al. of Eastman Kodak Company.

Moreover, a phosphorescent organic EL device in which a phosphorescent material is used as a luminescent material has been proposed. The phosphorescent organic EL device can achieve a high luminous efficiency by using a singlet state and a triplet state of excited states of a phosphorescent material. The reason is presumed as follows. When holes and electrons are recombined in the emitting layer, it is presumed that singlet excitons and triplet excitons are produced at a rate of 1:3 due to difference in spin multiplicity. Accordingly, luminous efficiency of the device using a phosphorescent material can reach three to four times as much as that of the device using only a fluorescent material.

Thus, an organic EL device provided with two or more emitting layers for enhancing luminous efficiency has been proposed (see, for instance, Patent Literature 1 and non-Patent Literature 1).

Patent Literature 1 and non-Patent Literature 1 disclose an organic EL device provided with a first emitting layer and a second emitting layer that are continuous with each other.

In the organic EL device of Patent Literature 1, a host material of the second emitting layer is a monoazine derivative having a higher electron transporting performance than a host material of the first emitting layer. Luminescent materials of the first and second emitting layers are the same ortho-metalated complex.

In contrast, in the organic EL device of non-Patent Literature 1, luminescent materials of the first and second emitting layers are different ortho-metalated complexes (see device A in FIG. 1).

CITATION LIST

Patent Literature

Patent Document 1: JP-A-2001-319779

Non-Patent Literature

Non-Patent Literature 1 "Reduced efficiency roll-off in high-efficiency hybrid white organic light-emitting diodes" by Gregor Schwartz et al. APPLIED PHYSICS LETTERS (2008), vol. 92, p. 053311-1 to 053311-3

SUMMARY OF THE INVENTION

Problems to be Solved by the Invention

In the organic EL device of Patent Literature 1, since the luminescent materials of the first and second emitting layers are the same ortho-metalated complex, luminous efficiency, current efficiency and durability are low in practical use.

On the other hand, in the organic EL device of non-Patent Literature 1, although luminescent materials of the first and second emitting layers are different ortho-metalated complexes, only a luminescence peak of about 600 nm is strongly exhibited as shown in FIG. 3 of non-Patent Literature 1. In other words, the organic EL device of non-Patent Literature 1 substantially emits only red light to cause unbalanced emission.

An object of the invention is to provide an organic EL device that is suitable as a surface light source for an illumination unit, a backlight and the like and exhibits a high luminous efficiency, a high current efficiency and an excellent durability while being driven at a low voltage. An object of the invention is also to provide an organic EL device of which color shift generated when luminance intensity is increased is extremely small. Further, an object of the invention is to provide an organic EL device including a plurality of emitting layers emittable in good balance.

Means for Solving the Problems (1) According to an aspect of the invention, an organic electroluminescence device includes an anode, a cathode and layers between the anode and the cathode, the layers at least including a hole transporting layer, a first emitting layer, a second emitting layer and an electron transporting layer, in which the first emitting layer includes a first host material and a first luminescent material, the second emitting layer is continuously formed on the first emitting layer near the cathode and includes a second host material and a second luminescent material, the second host material is a monoazine derivative, a diazine derivative or a triazine derivative, and the first and second luminescent materials are different metal complexes.

(2) According to the above aspect of the invention, the first and second host materials are different from each other.

(3) According to the above aspect of the invention, the first host material is an amine derivative.

(4) According to the above aspect of the invention, the amine derivative is compounds represented by the following formulae (1) to (7).

[Chemical Formula 1]

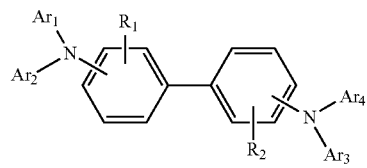

(1)

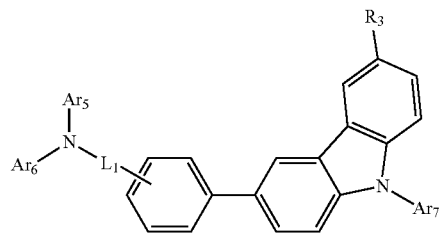

(2)

-continued

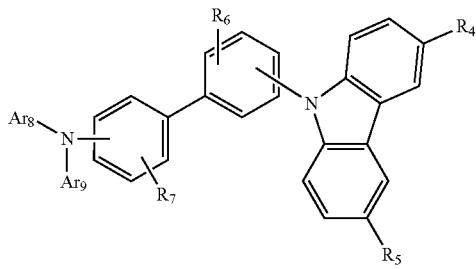

(3)

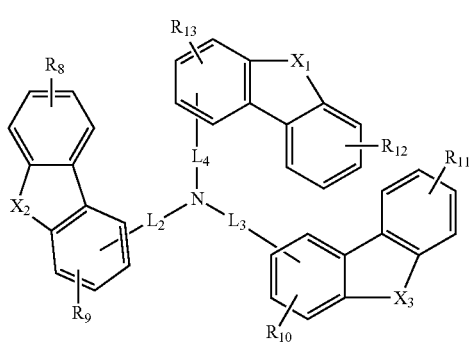

(4)

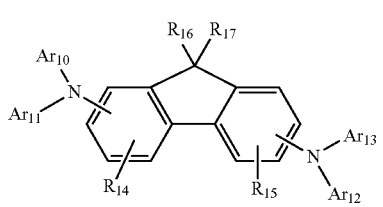

(5)

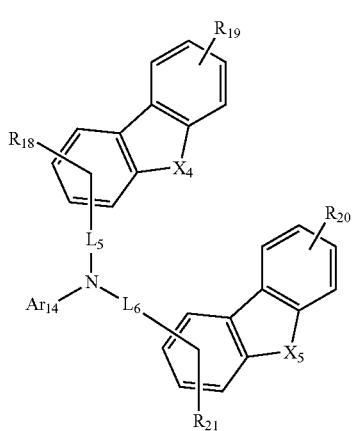

(6)

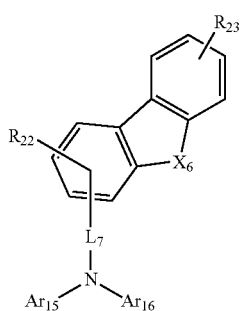

(7)

In the formula (1), $Ar_1$ to $Ar_4$ each represent a substituted or unsubstituted aryl group having 6 to 30 carbon atoms, or a substituted or unsubstituted aromatic heterocyclic group having 5 to 40 carbon atoms.

In the formulae (2) to (7), $Ar_5$ to $Ar_{16}$ are a substituted or unsubstituted aryl group having 6 to 40 carbon atoms, a substituted or unsubstituted aromatic heterocyclic group having 5 to 40 carbon atoms, a substituted or unsubstituted aryl group having 8 to 40 carbon atoms bonded with an aromatic amino group, or a substituted or unsubstituted aryl group having 8 to 40 carbon atoms bonded with an aromatic heterocyclic group.

In the formulae (1) to (7), $Ar_1$ to $Ar_{16}$ may be a ladder-type furan.

In the formulae (1) to (7), $Ar_1$, $Ar_3$, $Ar_5$, $Ar_8$, $Ar_{10}$, $Ar_{12}$ and $Ar_{15}$ may be respectively bonded to $Ar_2$, $Ar_4$, $Ar_6$, $Ar_9$, $Ar_{11}$, $Ar_{13}$ and $Ar_{16}$ to form a ring.

In the formulae (2), (4), (6) and (7), $L_1$ to $L_7$ represent a direct bond or a bonding group having 1 to 30 carbon atoms.

In the formulae (1) to (7), $R_1$ to $R_{23}$ each represent a hydrogen atom, a halogen atom, a substituted or unsubstituted alkyl group having 1 to 40 carbon atoms, a substituted or unsubstituted heterocyclic group having 3 to 20 carbon atoms, a substituted or unsubstituted non-fused aryl group having 6 to 40 carbon atoms, a substituted or unsubstituted fused aryl group having 6 to 12 carbon atoms, a substituted or unsubstituted fused/non-fused-mixed aryl group having 12 to 40 carbon atoms, a substituted or unsubstituted aralkyl group having 7 to 20 carbon atoms, a substituted or unsubstituted alkenyl group having 2 to 40 carbon atoms, a substituted or unsubstituted alkyl amino group having 1 to 40 carbon atoms, a substituted or unsubstituted aralkyl amino group having 7 to 60 carbon atoms, a substituted or unsubstituted alkylsilyl group having 3 to 20 carbon atoms, a substituted or unsubstituted arylsilyl group having 8 to 40 carbon atoms, a substituted or unsubstituted aralkylsilyl group having 8 to 40 carbon atoms, or a substituted or unsubstituted halogenated alkyl group having 1 to 40 carbon atoms.

In the formula (4), (6) and (7), $X_1$ to $X_6$ each represent a sulfur atom, an oxygen atom, or a nitrogen atom substituted by a monoaryl group.

(5) According to the above aspect of the invention, the second host material has a carbazole skeleton.

(6) According to the above aspect of the invention, the second host material is compounds represented by the following formulae (8) to (12A).

[Chemical Formula 2]

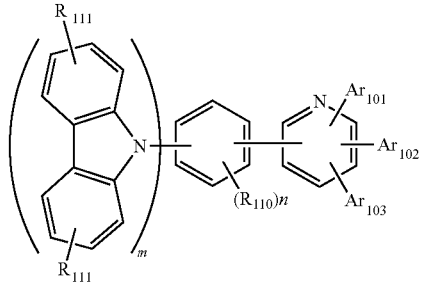

(8)

-continued

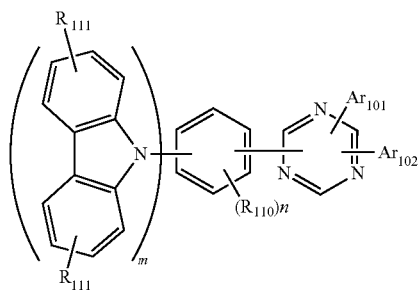

(9)

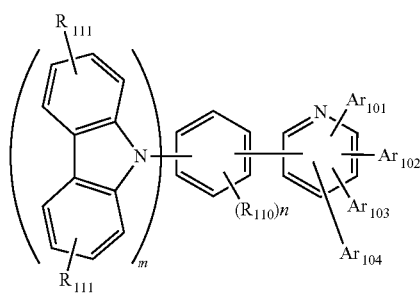

(10)

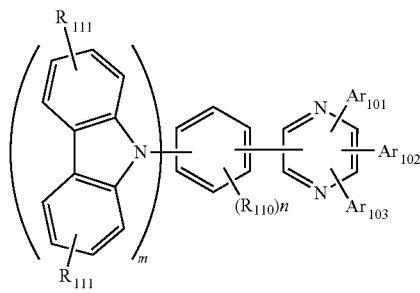

(11)

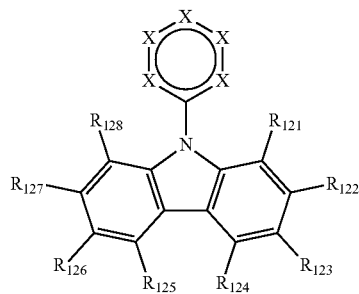

(12)

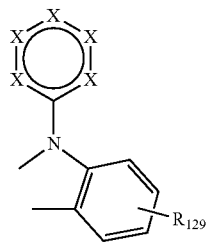

(12A)

In the formulae (8) to (11), $Ar_{101}$ to $Ar_{104}$ each represent a substituted or unsubstituted aryl group having 6 to 60 carbon atoms, or a substituted or unsubstituted heterocyclic group having 3 to 60 carbon atoms.

In the formulae (8) to (11), $R_{110}$ and $R_{111}$ represent the same as $R_1$.

In the formulae (8) to (11), n is an integer of 1 to 4, m is an integer of 1 to 4, and the sum (n+m) of n and m satisfies a relationship of $2 \leq (n+m) \leq 5$.

In the formulae (12) and (12A), X is N or CH, in which the number of N is from 1 to 4.

In the formula (12), $R_{121}$ to $R_{128}$ each are a hydrogen atom, an aryl group or an alkyl group, or $R_{121}$ to $R_{128}$ is bonded with a skeleton represented by the formula (12A) is bonded.

$R_{121}$ to $R_{128}$ are bonded with the skeleton represented by the formula (12A) such that at least one of combinations of $R_{121}$ and $R_{122}$, $R_{122}$ and $R_{123}$, $R_{123}$ and $R_{124}$, $R_{125}$ and $R_{126}$, $R_{126}$ and $R_{127}$, and $R_{127}$ and $R_{128}$ is bonded with the skeleton represented by the formula (12A).

In the formula (12A), $R_{129}$ is a hydrogen atom, an aryl group or an alkyl group.

(7) According to the above aspect of the invention, the second host material is compounds represented by the following formulae (8A) to (11A).

[Chemical Formula 3]

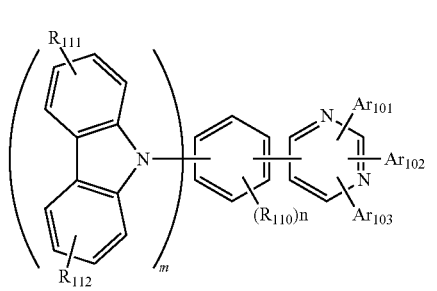

(8A)

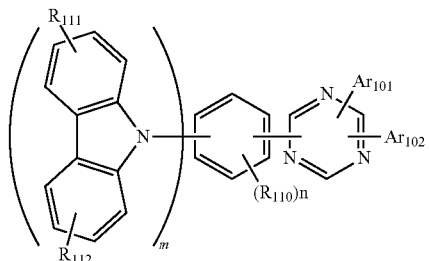

(9A)

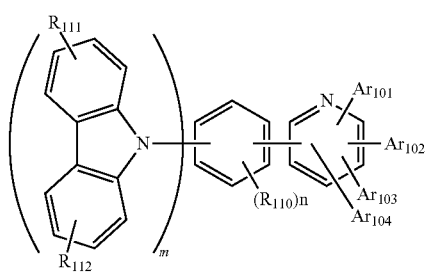

(10A)

-continued

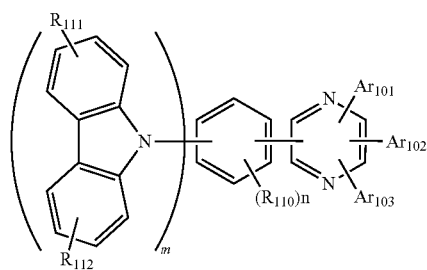

(11A)

In the formulae (8A) to (11A), $Ar_{101}$ to $Ar_{104}$ each represent a hydrogen atom, a substituted or unsubstituted aryl group having 6 to 60 carbon atoms, or a substituted or unsubstituted heterocyclic group having 3 to 60 carbon atoms. All of $Ar_{101}$ to $Ar_{103}$ are not a hydrogen atom at the same time in the formulae (8A), (9A) and (11A), and all of $Ar_{101}$ to $Ar_{104}$ are not a hydrogen atom at the same time in the formula (10A).

In the formulae (8A) to (11A), $R_{110}$ to $R_{112}$ each represent a hydrogen atom, a halogen atom, a substituted or unsubstituted alkyl group having 1 to 40 carbon atoms, a substituted or unsubstituted heterocyclic group having 3 to 20 carbon atoms, a substituted or unsubstituted non-fused aryl group having 6 to 40 carbon atoms, a substituted or unsubstituted fused aryl group having 6 to 12 carbon atoms, a substituted or unsubstituted fused/non-fused-mixed aryl group having 12 to 40 carbon atoms, a substituted or unsubstituted aralkyl group having 7 to 20 carbon atoms, a substituted or unsubstituted alkenyl group having 2 to 40 carbon atoms, a substituted or unsubstituted alkyl amino group having 1 to 40 carbon atoms, a substituted or unsubstituted aralkyl amino group having 7 to 60 carbon atoms, a substituted or unsubstituted alkylsilyl group having 3 to 20 carbon atoms, a substituted or unsubstituted arylsilyl group having 8 to 40 carbon atoms, a substituted or unsubstituted aralkylsilyl group having 8 to 40 carbon atoms, or a substituted or unsubstituted halogenated alkyl group having 1 to 40 carbon atoms.

In the formulae (8A) to (11A), n is an integer of 1 to 4, m is an integer of 1 to 4, and the sum (n+m) of n and m satisfies a relationship of 2≤(n+m)≤5.

(8) According to the above aspect of the invention, the second host material is a compound represented by the following formula (13).

[Chemical Formula 4]

(13)

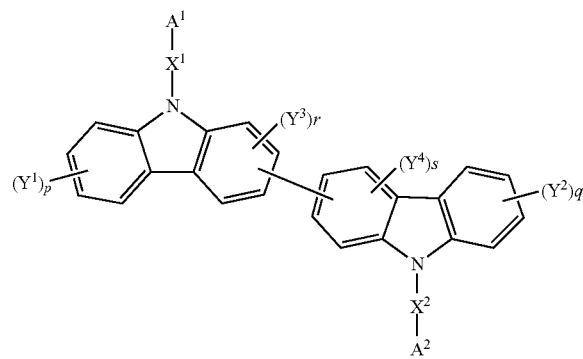

In the formula (13), $A^1$ represents a substituted or unsubstituted nitrogen-containing heterocyclic group having 1 to 30 carbon atoms forming an aromatic ring (hereinafter referred to as ring carbon atoms) (except for a substituted or unsubstituted carbazolyl group and a substituted or unsubstituted indolyl group). $A^2$ represents a substituted or unsubstituted aromatic hydrocarbon group having 6 to 30 ring carbon atoms, or a substituted or unsubstituted nitrogen-containing heterocyclic group having 1 to 30 ring carbon atoms.

$X^1$ and $X^2$ each independently represent a single bond, a substituted or unsubstituted aromatic hydrocarbon group having 6 to 30 ring carbon atoms, a substituted or unsubstituted fused aromatic hydrocarbon group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms.

$Y^1$ to $Y^4$ each independently represent a hydrogen atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, a substituted or unsubstituted fused aromatic hydrocarbon group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms. Adjacent ones of $Y^1$ to $Y^4$ may be bonded to each other to form a cyclic structure.

p and q each are an integer of 1 to 4, and r and s each are an integer of 1 to 3.

When p and q each are an integer of 2 to 4 and r and s each are an integer of 2 to 3, a plurality of $Y^1$ to $Y^4$ may be the same or different.

At least one of $A^1$, $A^2$, $X^1$, $X^2$ and $Y^1$ to $Y^4$ is a group derived from a monoazine derivative, a diazine derivative or a triazine derivative.

(9) According to the above aspect of the invention, the second host material is a compound represented by the following formula (14) or (15).

[Chemical Formula 5]

(14)

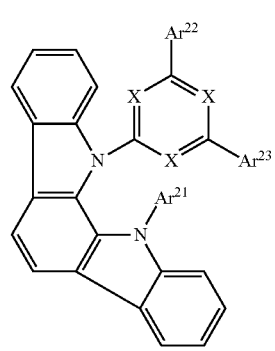

(15)

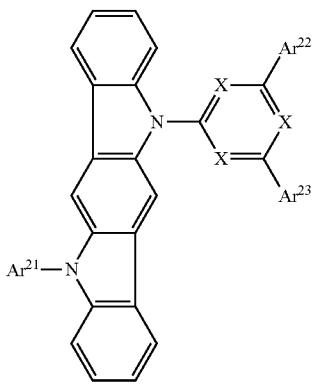

In the formulae (14) and (15), X is CH or N, in which at least one of X is N. $Ar^{21}$ to $Ar^{23}$ each independently are a substituted or unsubstituted non-fused aromatic hydrocarbon group or aromatic heterocyclic ring. $Ar^{22}$ or $Ar^{23}$ may form a fused ring with a ring including X.

(10) According to the above aspect of the invention, the second host material is a compound represented by the following formula (16) or (17).

[Chemical Formula 6]

(16)

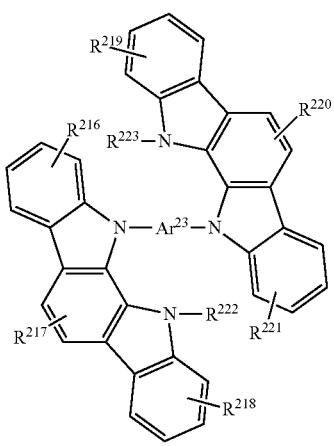

In the formula (16), $Ar^{23}$ is a divalent bonding group including a substituted or unsubstituted non-fused aromatic hydrocarbon group or an aromatic heterocyclic group; $R^{217}$ and $R^{220}$ are a hydrogen atom, a substituted or unsubstituted non-fused aromatic hydrocarbon group or an aromatic heterocyclic group; $R^{222}$ and $R^{223}$ are a substituted or unsubstituted non-fused aromatic hydrocarbon group or aromatic heterocyclic group; $R^{216}$, $R^{218}$, $R^{219}$ and $R^{221}$ are a hydrogen atom, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amido group, substituted or unsubstituted aromatic hydrocarbon group, or substituted or unsubstituted aromatic heterocyclic group. In the formula (16), one of $Ar^{23}$ and $R^{216}$ to $R^{223}$ is a group derived from a monoazine derivative, a diazine derivative or a triazine derivative,

[Chemical Formula 7]

(17)

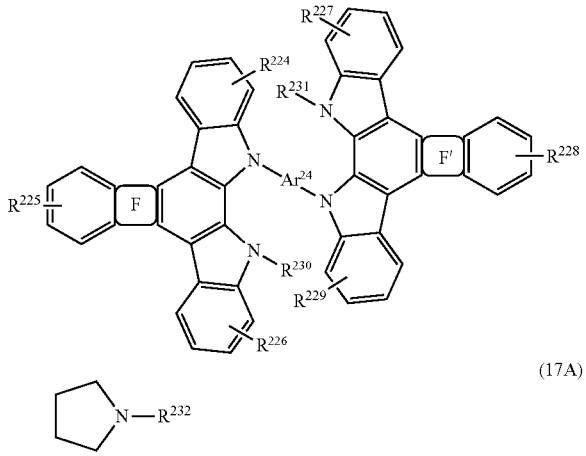

(17A)

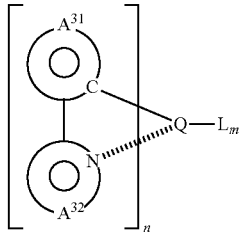

In the formulae (17) and (17A), rings F and F' are a heterocyclic ring fused to adjacent rings and represented by the formula (17A). $Ar^{24}$ represents the same as $Ar^{23}$. $R^{230}$ to $R^{232}$ each independently represent the same as $R^{222}$. $R^{224}$ to $R^{229}$ each independently represent the same as $R^{216}$. In the formula (17), one of $Ar^{24}$ and $R^{224}$ to $R^{231}$ in the formula (17) and $R^{232}$ in the formula (17A) is a group derived from a monoazine derivative, a diazine derivative or a triazine derivative.

(11) According to the above aspect of the invention, the second host material exhibits a higher affinity level than the first host material.

(12) According to the above aspect of the invention, the second host material exhibits a higher ionization potential than the first host material.

(13) According to the above aspect of the invention, the first and second luminescent materials are a metal complex. The metal complex preferably includes at least one of illidium (Ir), palladium (Pd) and platinum (Pt).

(14) According to the above aspect of the invention, the metal complex is preferably an ortho-metalated complex represented by the following formula (20).

[Chemical Formula 8]

(20)

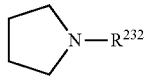

In the formula (20), $A^{31}$ is a ring bonded to $A^{32}$ and Q, and is a substituted or unsubstituted aromatic hydrocarbon ring group or a substituted or unsubstituted aromatic heterocyclic ring, $A^{32}$ is an aromatic heterocyclic group bonded to $A^{31}$. Specifically, $A^{32}$ is a substituted or unsubstituted aromatic heterocyclic group containing nitrogen as an atom for forming an aromatic hetero ring. A ring including $A^{31}$ and a ring including $A^{32}$ may be bonded to each other at portions other than $A^{31}$ and $A^{32}$ to form a fused ring or an unsaturated ring.

Q is one of palladium (Pd), illidium (Ir) and platinum (Pt).
L is a bidentate ligand.
m and n represent an integer,
when Q is a divalent metal, n=2 and m=0, and
when Q is a trivalent metal, n=3 and m=0, or n=2 and m=1.

(15) According to the above aspect of the invention, it is preferable that the first luminescent material exhibits a luminescence peak of 570 nm or more and the second luminescent material exhibits a luminescence peak of 565 nm or less.

Effects of the Invention

The organic EL device according to the above aspect of the invention is excellent in all of luminous efficiency, current efficiency and durability since a specific azine derivative is used as the second host material and different ortho-metalated complexes are used as the first and second luminescent material.

Accordingly, the organic EL device according to the above aspect of the invention is suitable as a surface light source for an illumination unit, a backlight and the like. Moreover, in the organic EL device according to the above aspect of the invention, color shift generated when luminance intensity is increased is extremely small.

Further, in the organic EL device according to the above aspect of the invention, the first and second emitting layers each are emittable in good balance.

DESCRIPTION OF EXEMPLARY EMBODIMENTS

First Exemplary Embodiment
Arrangement of Organic EL Device
Arrangement(s) of an organic EL device of the invention will be described below.

The organic EL device of the invention includes an anode, a cathode, and an emitting unit provided between the anode and the cathode.

The emitting unit includes at least one emitting layer and is formed in a single layer or in a laminate. An anode side of the emitting unit has a function to inject and transport holes from the anode to the cathode. A cathode side of the emitting unit near the cathode has a function to inject and transport electrons from the cathode to the anode. Emission occurs when the holes and the electrons are recombined in at least one emitting layer described above.

Typical arrangements of the emitting unit are as follows:
(1) emitting layer;
(2) hole injecting layer/emitting layer;
(3) electron injecting·transporting layer/emitting layer;
(4) hole injecting layer/emitting layer/electron injecting·transporting layer;
(5) organic semiconductor layer/emitting layer;
(6) organic semiconductor layer/electron blocking layer/emitting layer;
(7) organic semiconductor layer/emitting layer/adhesion improving layer;
(8) hole injecting·transporting layer/emitting layer/electron injecting·transporting layer;
(9) insulating layer/emitting layer/insulating layer;
(10) inorganic semiconductor layer/insulating layer/emitting layer/insulating layer;
(11) organic semiconductor layer/insulating layer/emitting layer/insulating layer;
(12) insulating layer/hole injecting·transporting layer/emitting layer/insulating layer; and
(13) insulating layer/hole injecting·transporting layer/emitting layer/electron injecting·transporting layer.

It should be noted that the "hole injecting·transporting layer" means "at least one of hole injecting layer and hole transporting layer" while the "electron injecting·transporting layer" means "at least one of electron injecting layer and electron transporting layer."

While the arrangement (8) is preferably used among the above, the arrangement of the invention is not limited to the above arrangements.

The "emitting layer" in this exemplary embodiment of the invention includes a first emitting layer and a second emitting layer continuous with a side of the first emitting layer near the cathode.

Figure 1:
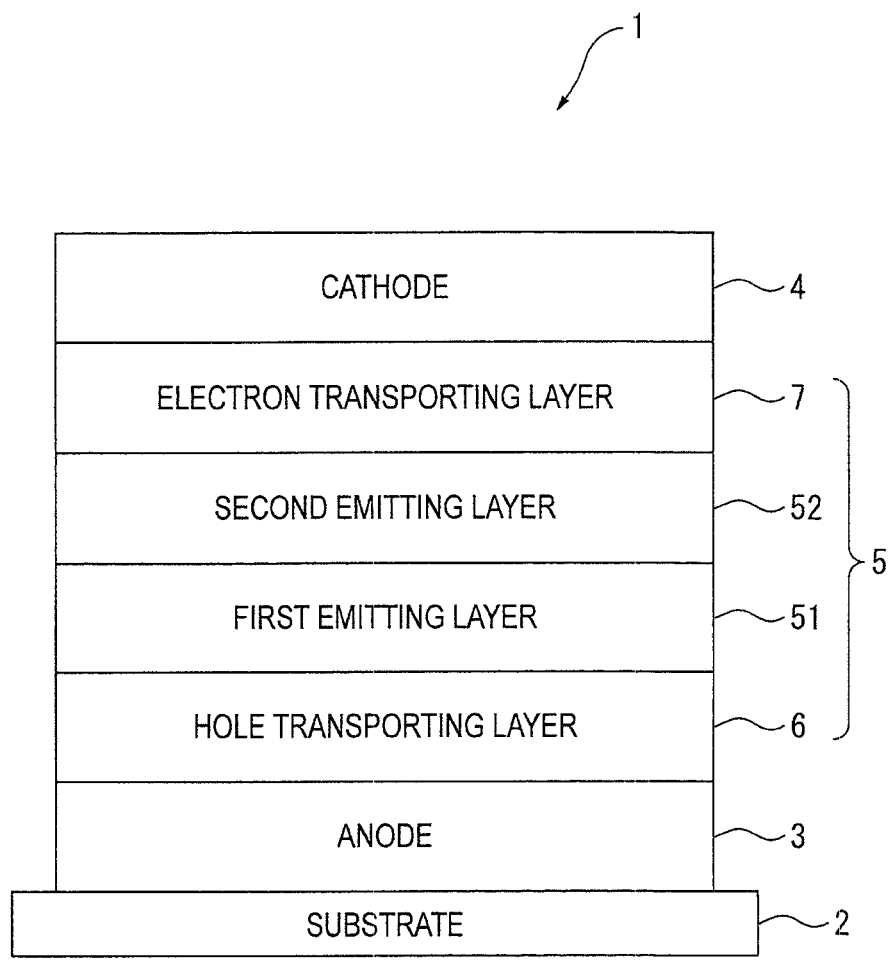
FIG. 1 schematically shows an exemplary arrangement of an organic EL device according to a first exemplary embodiment of the invention.

As shown in FIG. 1, an organic EL device 1 includes a transparent substrate 2, an anode 3, a cathode 4 and an emitting unit 5 formed between the anode 3 and the cathode 4. The emitting unit 5 includes, in sequence from the anode 3, a hole transporting layer 6, a first emitting layer 51, a second emitting layer 52 and an electron transporting layer 7.

Anode and Cathode

The anode 3 of the organic EL device 1 serves for injecting holes into the hole transporting layer 6. Accordingly, it is favorable in terms of efficiency that the anode 3 has a work function of 4.5 eV or higher.

Specific examples of a material of the anode 3 are alloys of indium-tin oxide (ITO), tin oxide (NESA), indium zinc oxide, gold, silver, platinum and copper.

The anode 3 may be made by forming a thin film from these electrode materials through a method such as vapor deposition or sputtering.

When light from the emitting unit 5 is to be extracted through the anode 3 as in this exemplary embodiment, the anode 3 preferably transmits more than 10% of the light in the visible region. Sheet resistance of the anode 3 is preferably several hundreds Ω/sq. or lower. Although depending on the material of the anode 3, a thickness of the anode 3 is typically in a range of 10 nm to 1 μm, and preferably in a range of 10 nm to 200 nm.

The cathode 4 serves for injecting electrons into the electron transporting layer 7 and is preferably formed of a material having a smaller work function.

Although the material of the cathode 4 is subject to no specific limitation, examples of the material are indium, aluminum, magnesium, alloy of magnesium and indium, alloy of magnesium and aluminum, alloy of aluminum and lithium, alloy of aluminum, scandium and lithium, and alloy of magnesium and silver.

Like the anode 3, the cathode 4 may be made by forming a thin film from the above materials through a method such as vapor deposition or sputtering. In addition, the light may be emitted through the cathode 4.

Emitting Layer

The first emitting layer 51 includes a first host material and a first luminescent material. The second emitting layer 52 includes a second host material and a second luminescent material.

Host Material

The first host material is preferably an amine derivative such as a monoamine compound, diamine compound, triamine compound, tetramine compound and amine compound substituted by a carbazole group. The first host material and the following second host material may be the same material.

The amine derivative is preferably compounds represented by the following formulae (1) to (7).

[Chemical Formula 9]

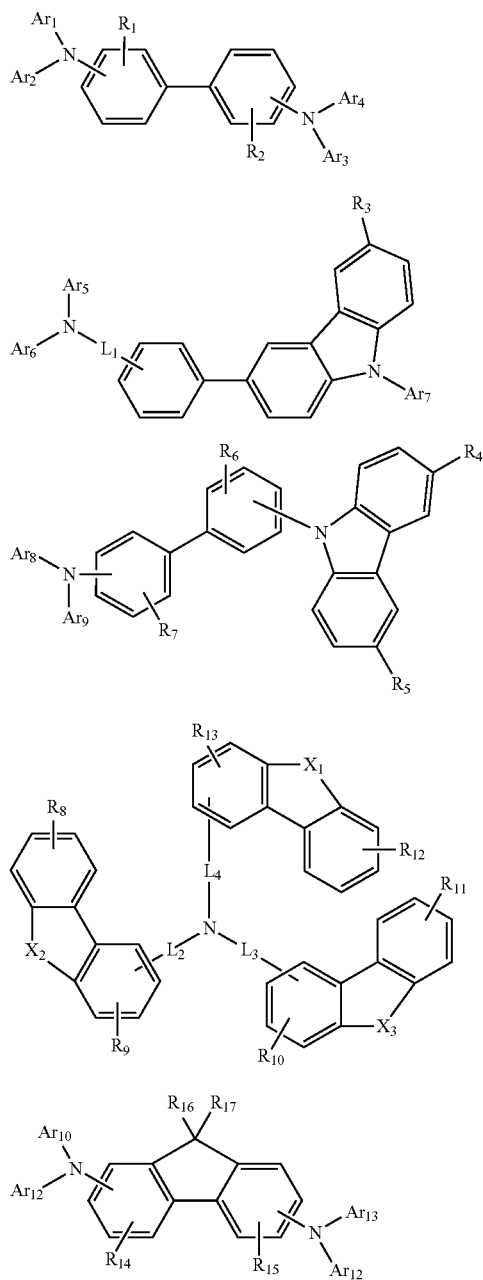

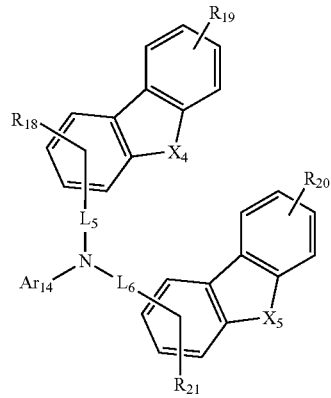

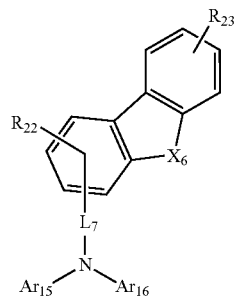

In the formula (1), $Ar_1$ to $Ar_4$ each represent a substituted or unsubstituted aryl group having 6 to 30 carbon atoms, or a substituted or unsubstituted aromatic heterocyclic group having 5 to 40 carbon atoms.

Examples of the aryl group are a phenyl group, biphenyl group, terphenyl group, naphthyl group, 9,9'-dimethylfluorene group and phenanthrene group.

Examples of the aromatic heterocyclic group are a monovalent residue of thiophene, a monovalent residue of benzothiophene, a monovalent residue of dibenzothiophene, a monovalent residue of furan, a monovalent residue of benzofuran and a monovalent residue of dibenzofuran.

In the formulae (2) to (7), $Ar_5$ to $Ar_{16}$ are a substituted or unsubstituted aryl group having 6 to 40 carbon atoms, a substituted or unsubstituted aromatic heterocyclic group having 5 to 40 carbon atoms, a substituted or unsubstituted aryl group having 8 to 40 carbon atoms bonded with an aromatic amino group, or a substituted or unsubstituted aryl group having 8 to 40 carbon atoms bonded with an aromatic heterocyclic group.

In the formulae (1) to (7), $Ar_1$ to $Ar_{16}$ may be a ladder-type furan group.

In the formulae (1) to (7), $Ar_1$, $Ar_3$, $Ar_5$, $Ar_8$, $Ar_{10}$, $Ar_{12}$ and $Ar_{15}$ may be respectively bonded to $Ar_2$, $Ar_4$, $Ar_6$, $Ar_9$, $Ar_{11}$, $Ar_{13}$ and $Ar_{16}$ to form a ring.

In the formulae (2), (4), (6) and (7), $L_1$ to $L_7$ represent a direct bond or a bonding group having 1 to 30 carbon atoms.

For instance, when $L_1$ is a direct bond, N and a phenylene ring are directly bonded to each other In the formulae (1) to (7), $R_1$ to $R_{23}$ each represent a hydrogen atom, a halogen atom, a substituted or unsubstituted alkyl group having 1 to 40 carbon atoms, a substituted or unsubstituted heterocyclic group having 3 to 20 carbon atoms, a substituted or unsubstituted non-fused aryl group having 6 to 40 carbon atoms, a substituted or unsubstituted fused aryl group having 6 to 12 carbon atoms, a substituted or unsubstituted fused/non-fused-mixed aryl group having 12 to 40 carbon atoms, a substituted or unsubstituted aralkyl group having 7 to 20 carbon atoms, a substituted or unsubstituted alkenyl group having 2 to 40 carbon atoms, a substituted or unsubstituted alkyl amino group having 1 to 40 carbon atoms, a substituted or unsubstituted aralkyl amino group having 7 to 60 carbon atoms, a substituted or unsubstituted alkylsilyl group having 3 to 20 carbon atoms, a substituted or unsubstituted arylsilyl group having 8 to 40 carbon atoms, a substituted or unsubstituted aralkylsilyl group having 8 to 40 carbon atoms, or a substituted or unsubstituted halogenated alkyl group having 1 to 40 carbon atoms.

In the formula (4), (6) and (7), $X_1$ to $X_6$ each represent a sulfur atom, an oxygen atom, or a nitrogen atom substituted by a monoaryl group.

In the formula (1), a phenylene group, which is directly bonded to an N atom directly bonded to $Ar_1$ and $Ar_2$, may be directly bonded to $Ar_1$ or $Ar_2$. In the formula (1), a phenylene group, which is directly bonded to an N atom directly bonded to $Ar_3$ and $Ar_4$, may be directly bonded to $Ar_3$ or $Ar_4$. In the formula (1), $Ar_2$ and $Ar_3$ are preferably a fused aromatic hydrocarbon having 6 to 30 carbon atoms. $Ar_2$ and $Ar_3$ are more preferably a naphthyl group.

In the formula (2), a phenylene group, which is bonded via $L_1$ to an N atom directly bonded to $Ar_5$ and $Ar_6$, may be directly bonded to $Ar_5$ and $Ar_6$.

The amine derivative represented by the formula (1) is exemplified by the following compounds.

[Chemical Formula 10]

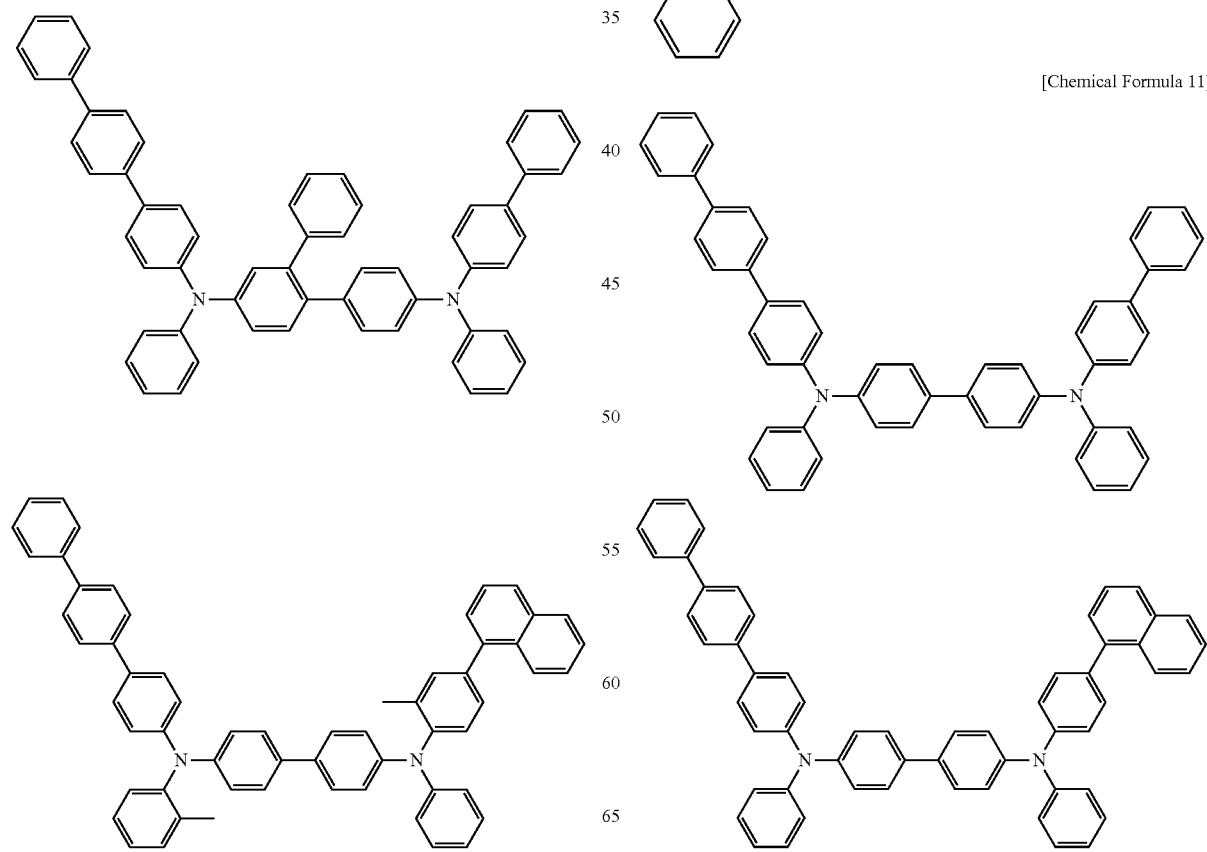

[Chemical Formula 11]

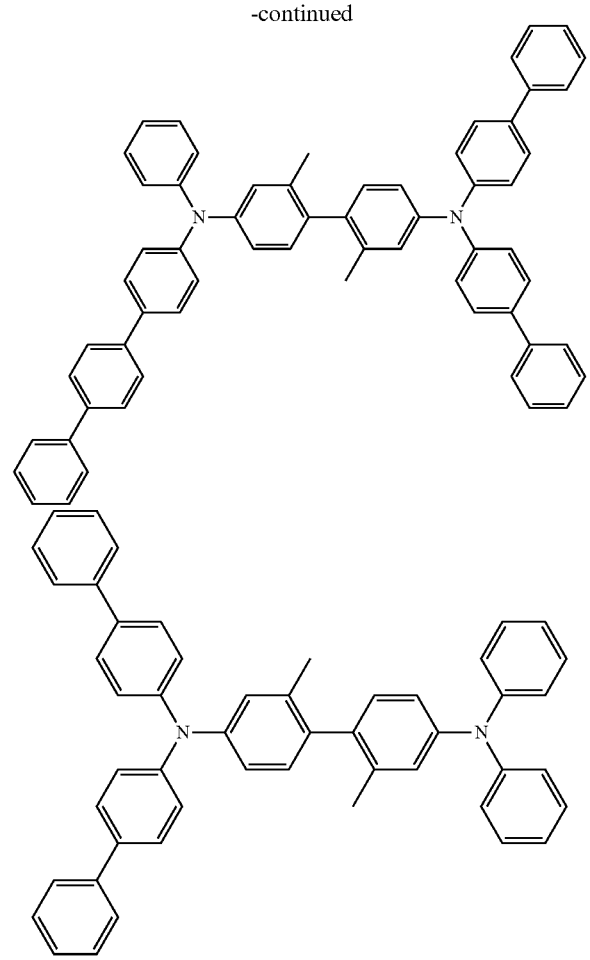

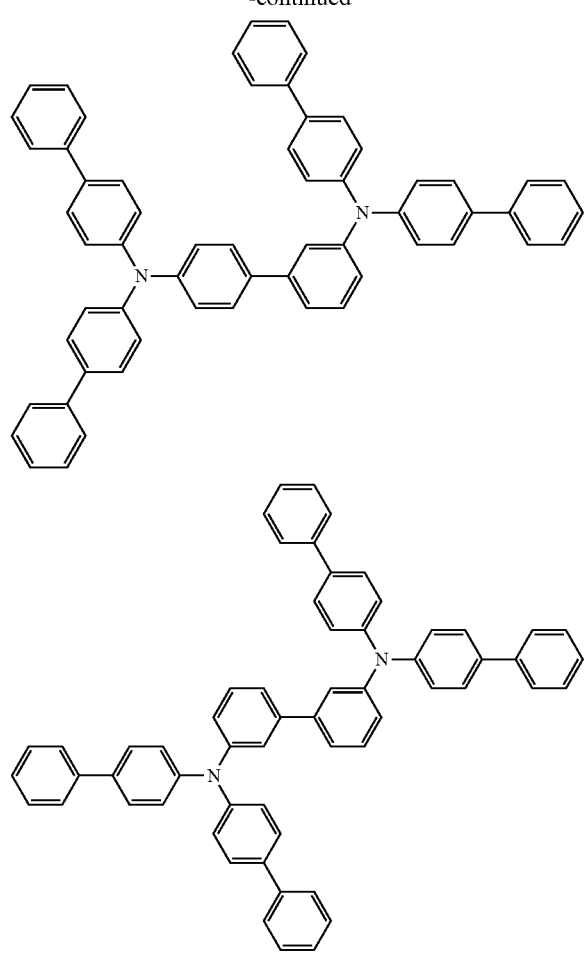
[Chemical Formula 12]
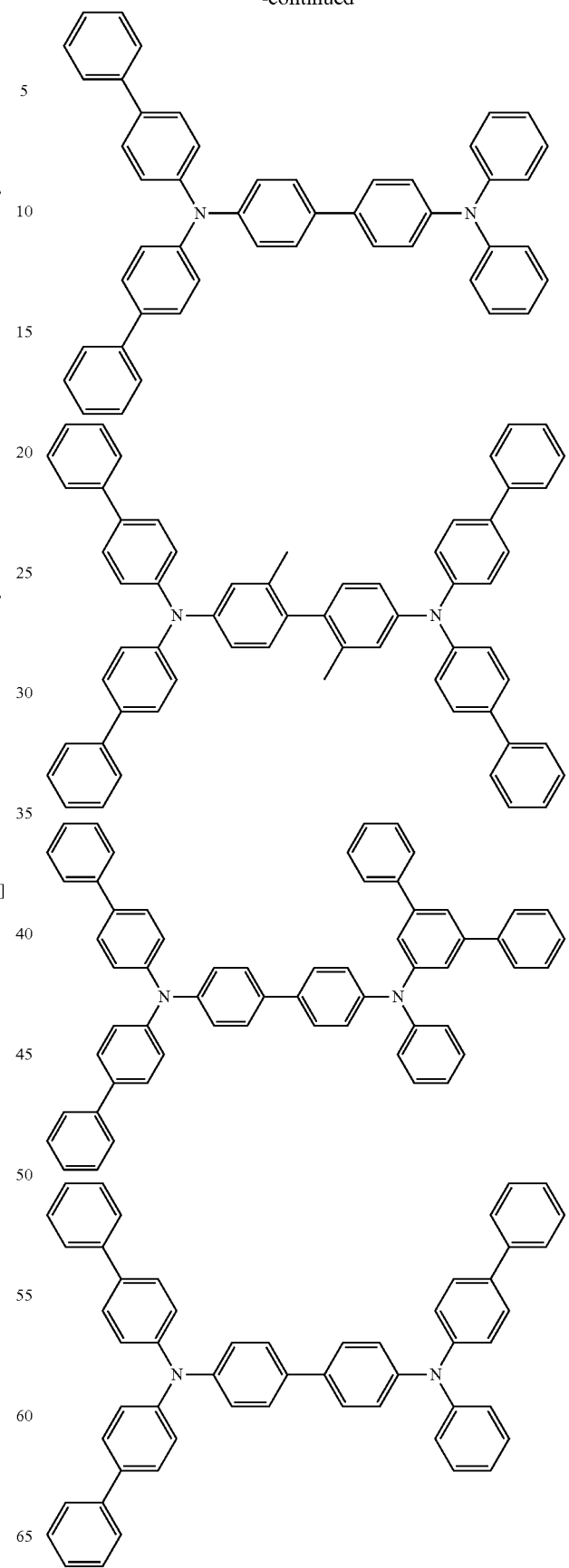

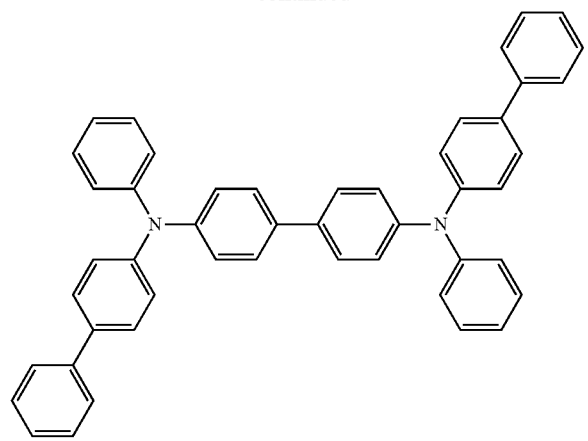
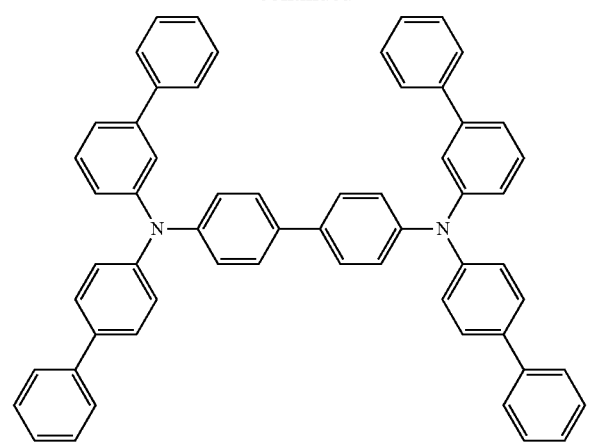
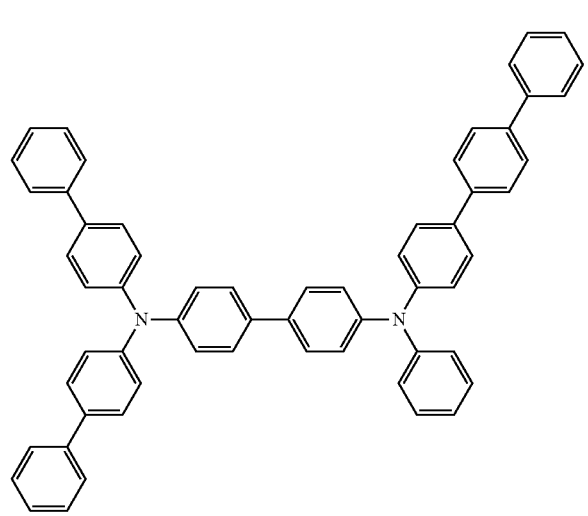
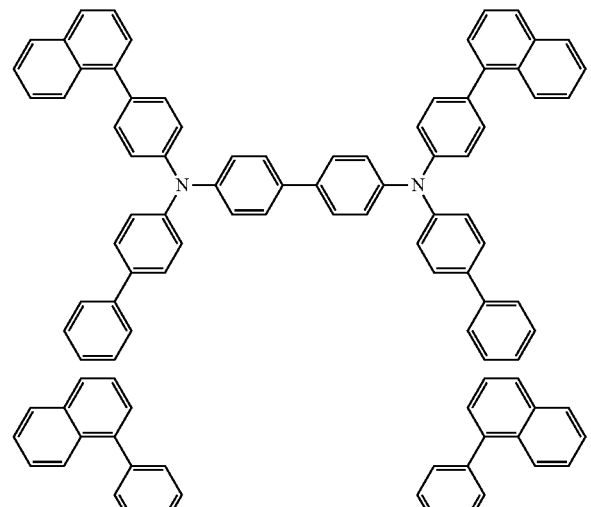
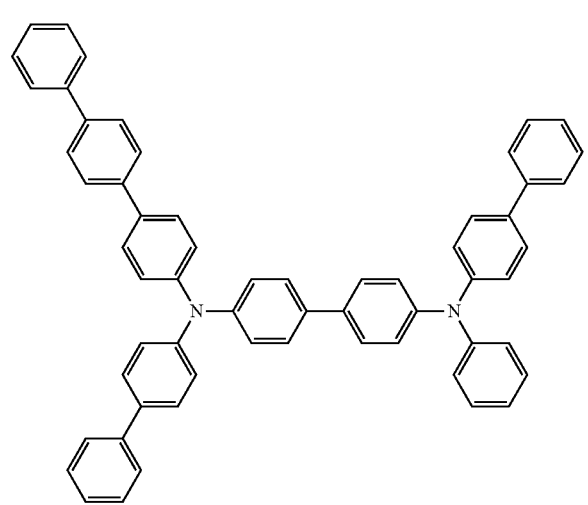
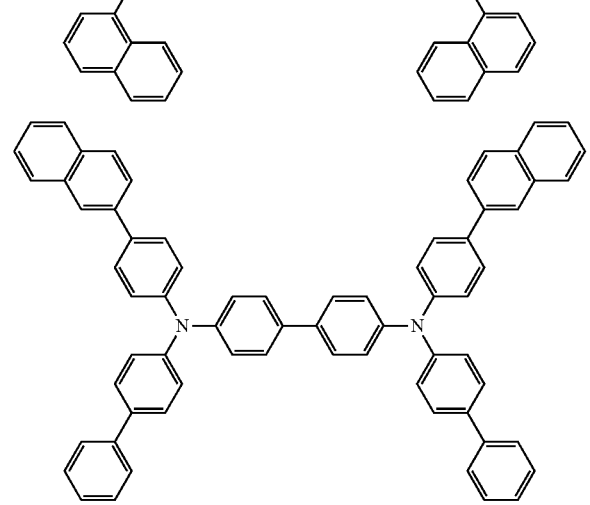

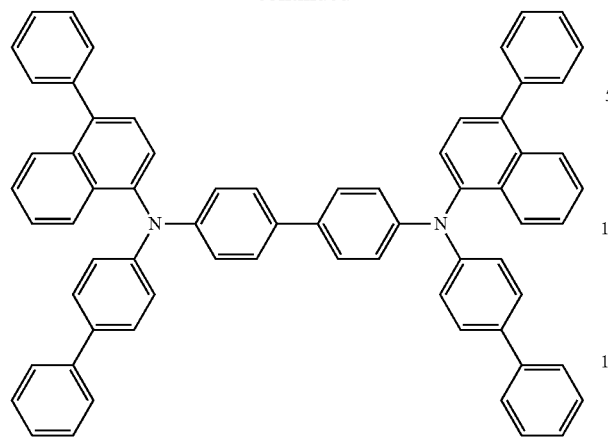
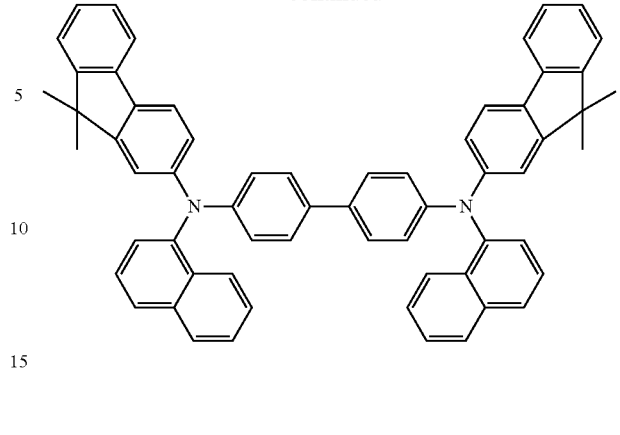
[Chemical Formula 13]
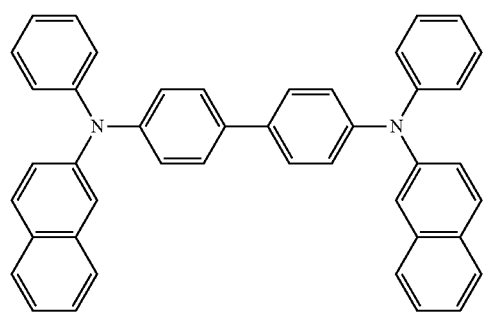
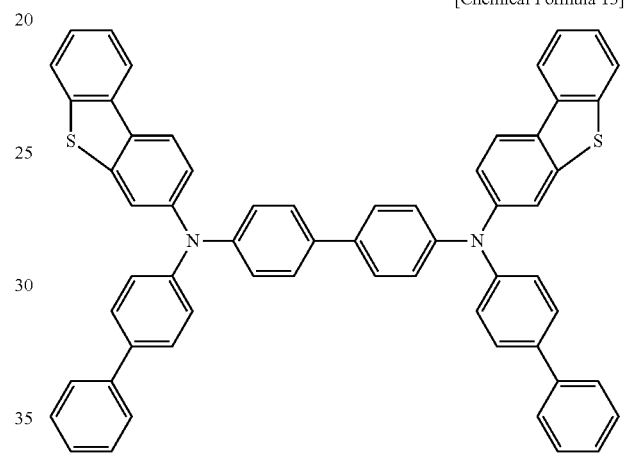
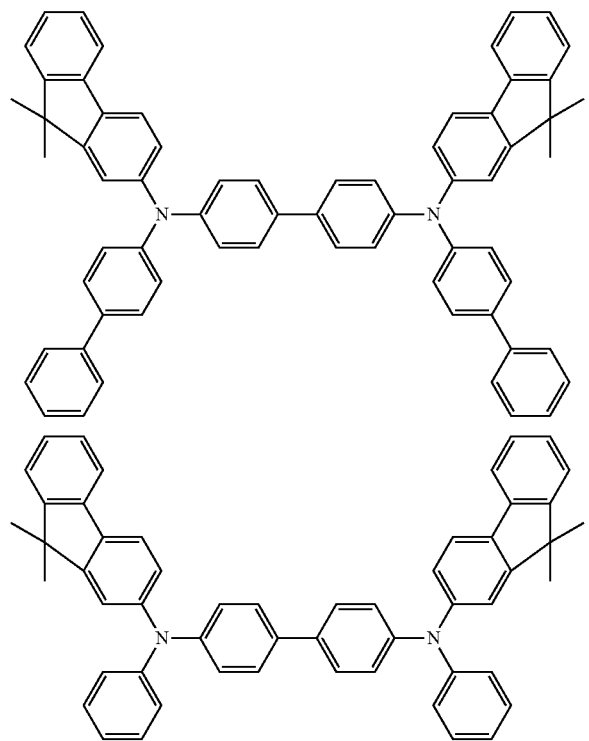
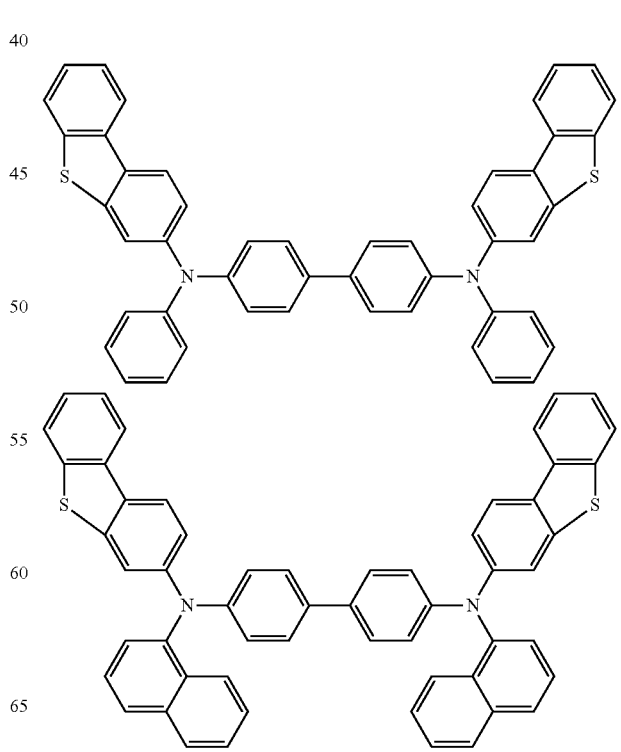

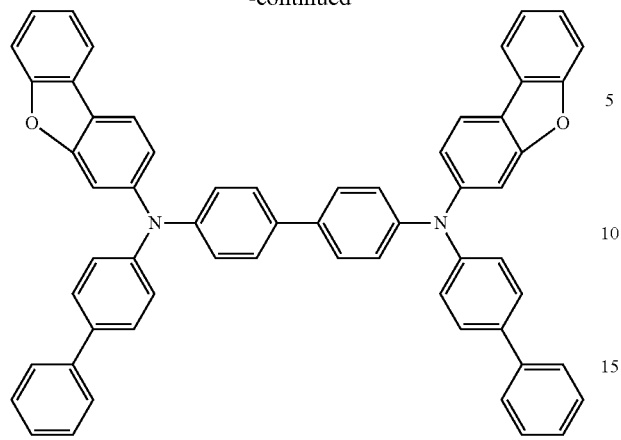
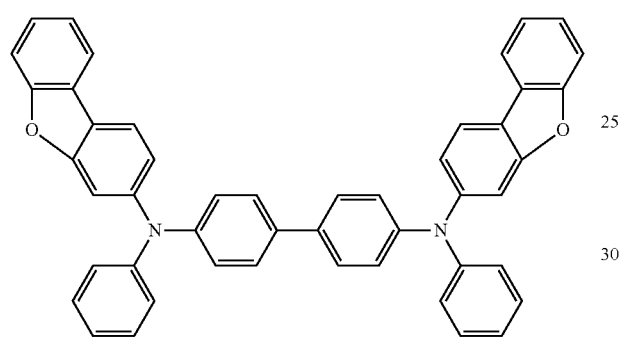
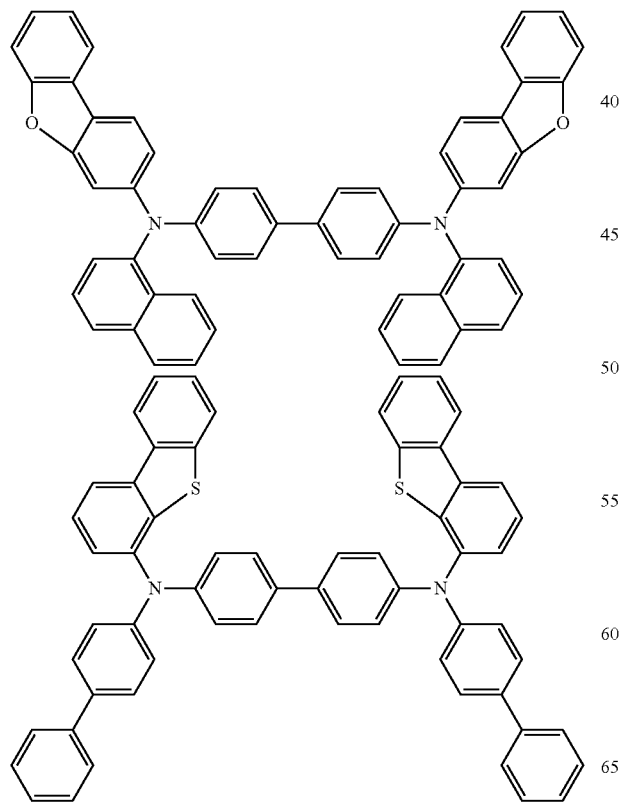
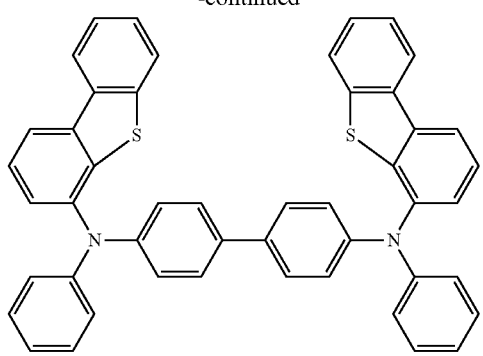
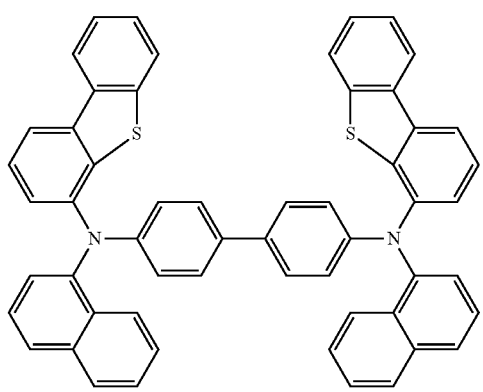
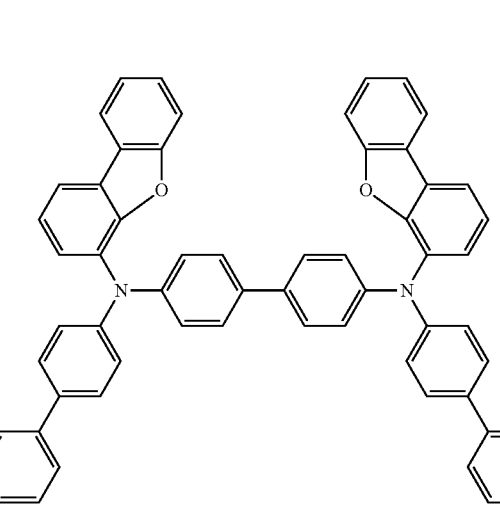
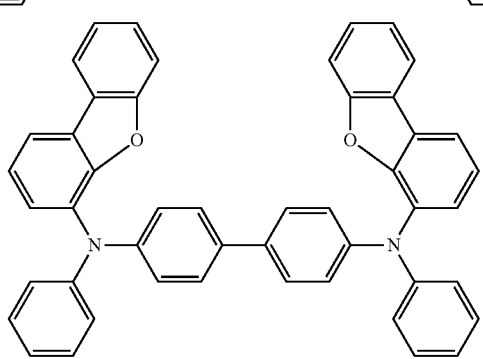

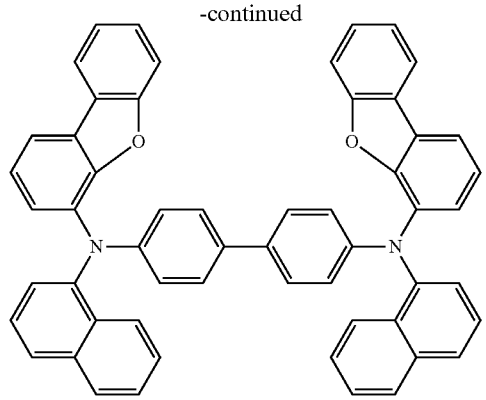
The amine derivative represented by the formula (2) is exemplified by the following compounds.
[Chemical Formula 14]
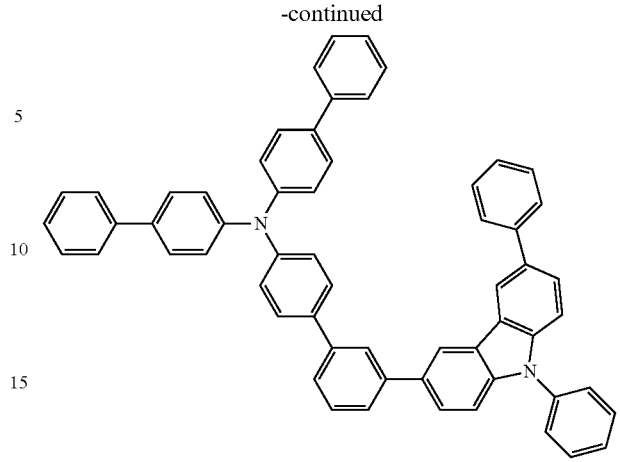
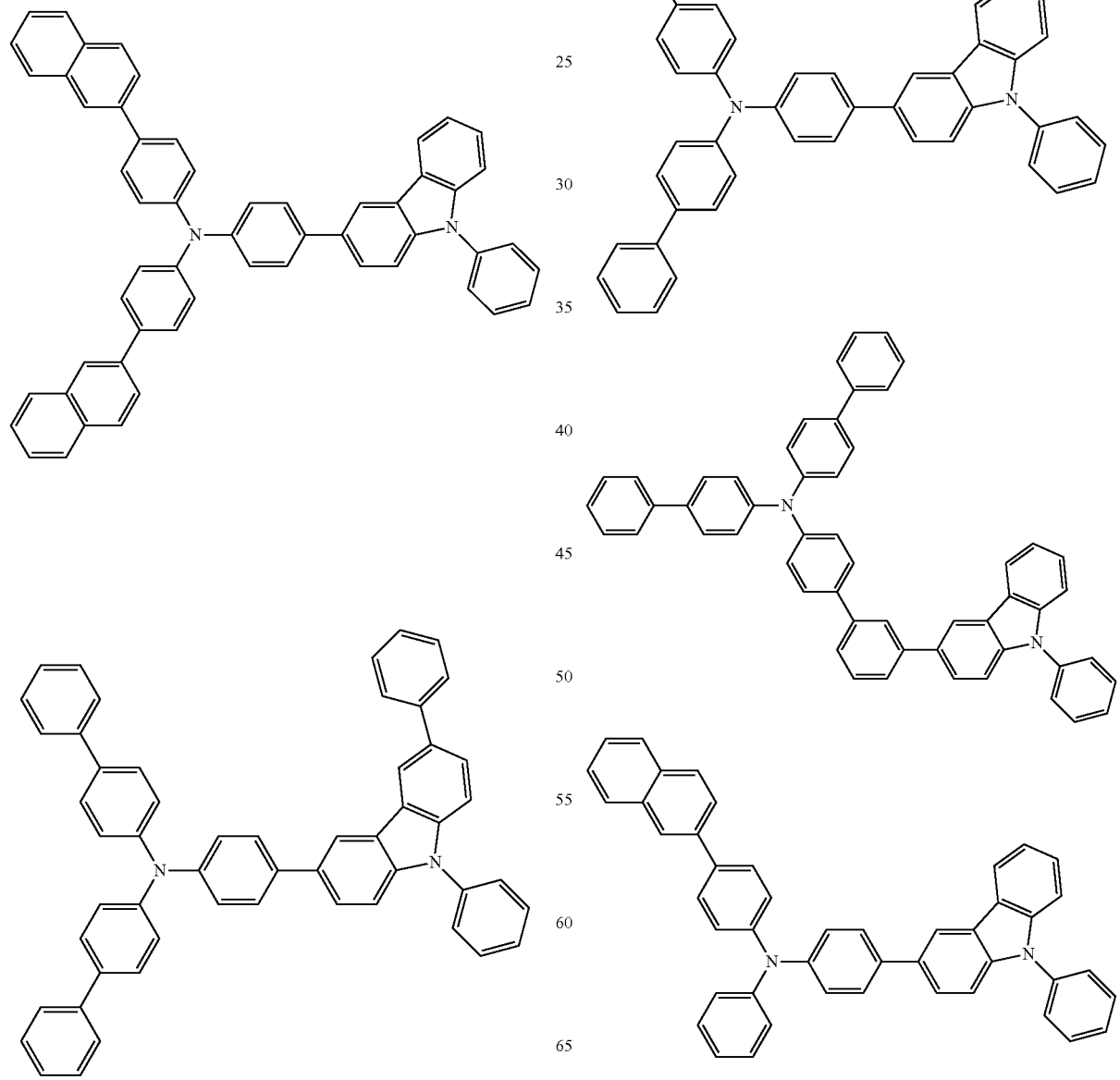

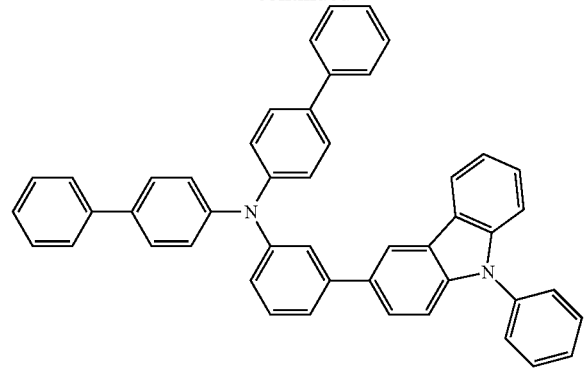
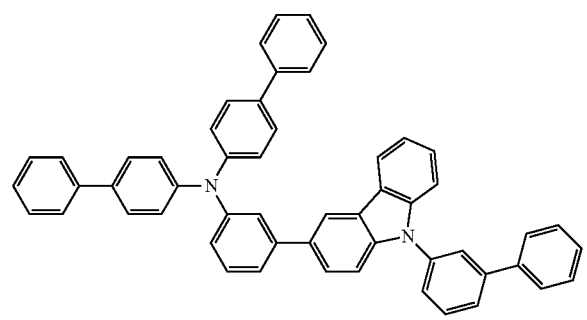
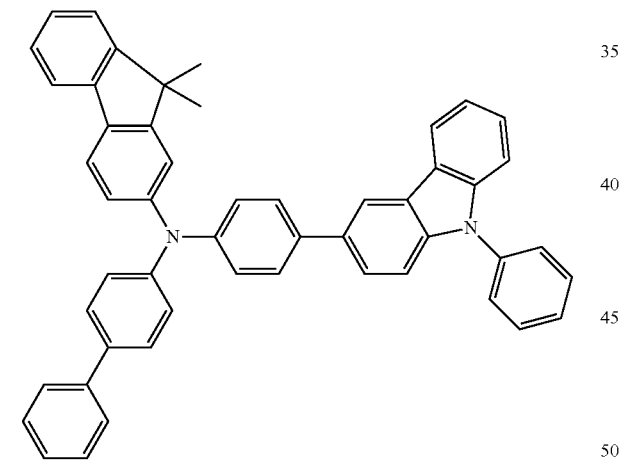
[Chemical Formula 15]
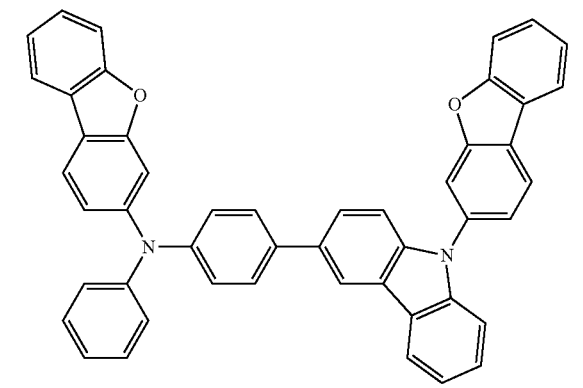
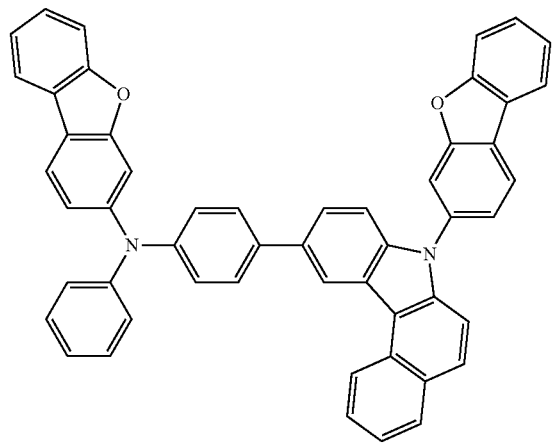
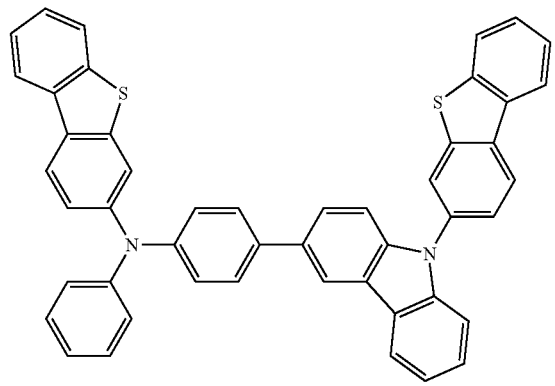
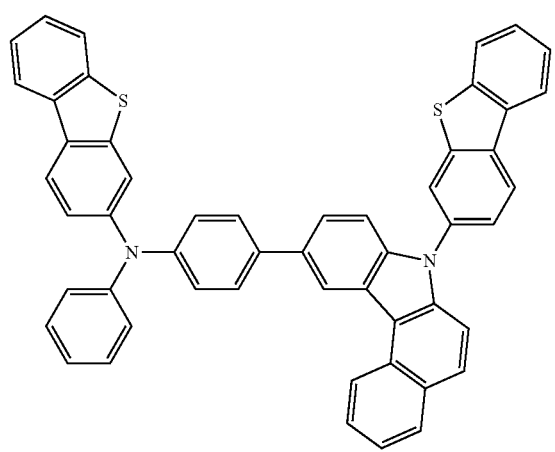

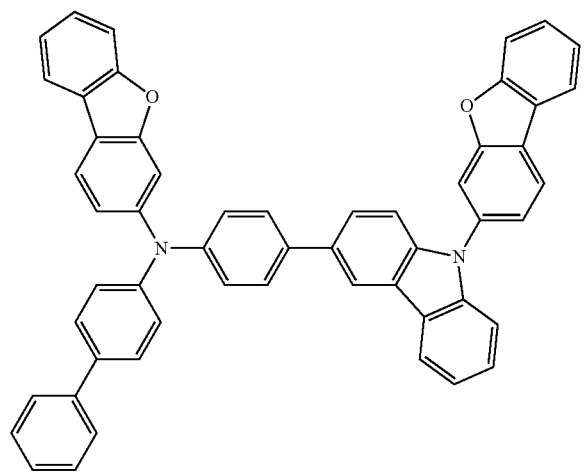
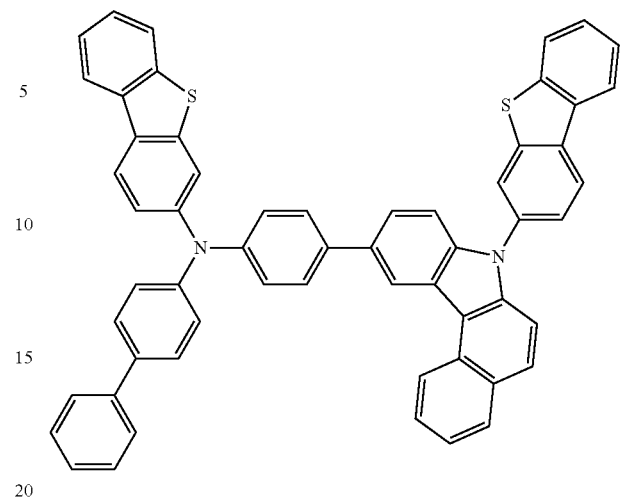
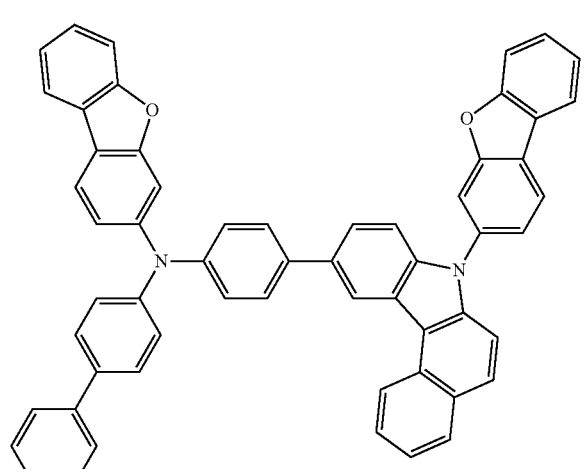
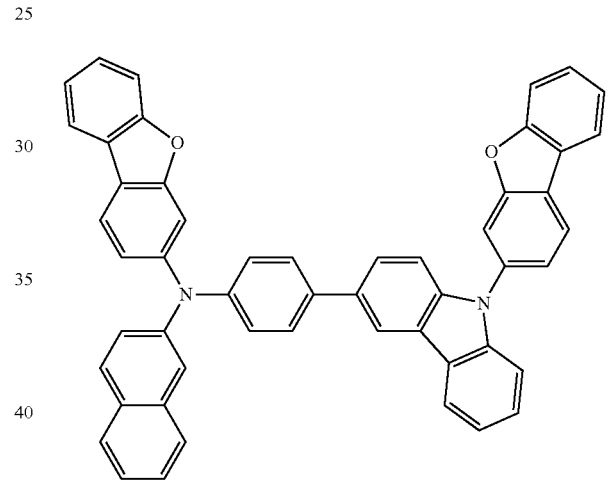
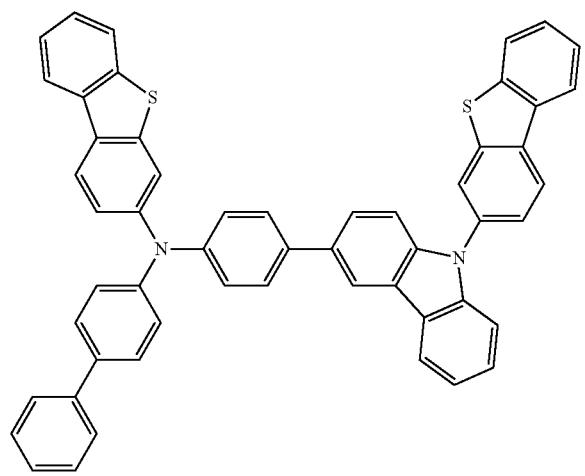
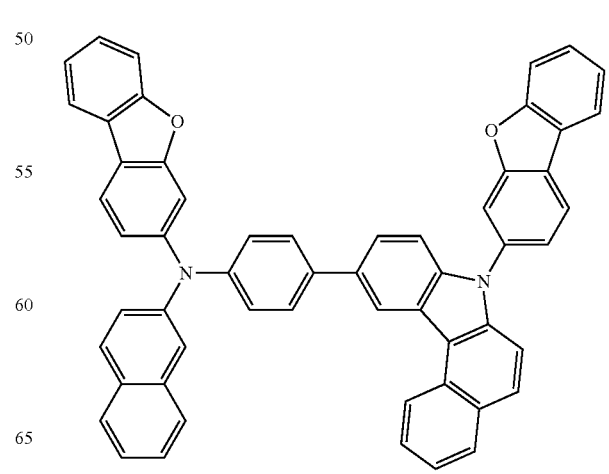

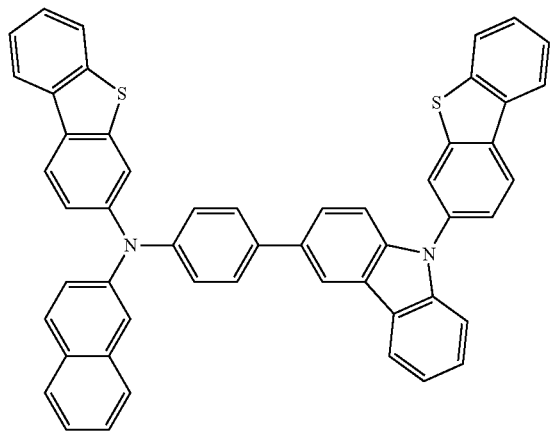
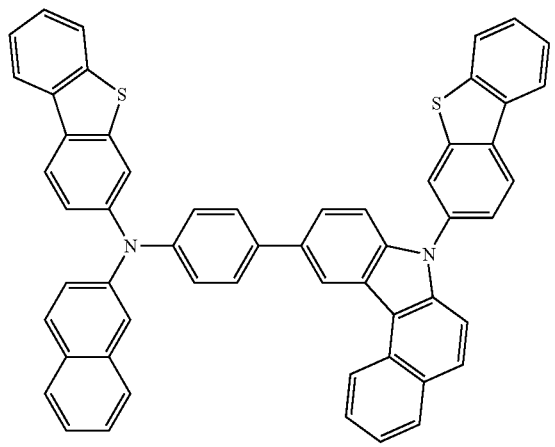
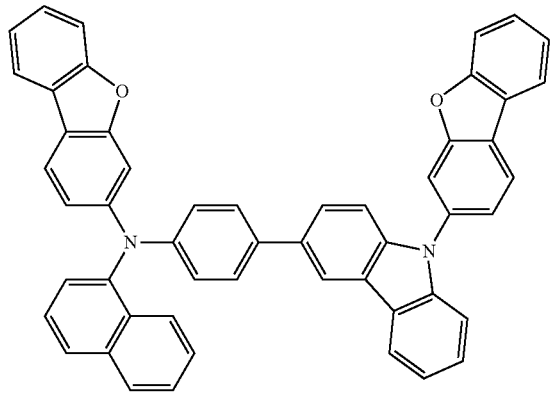
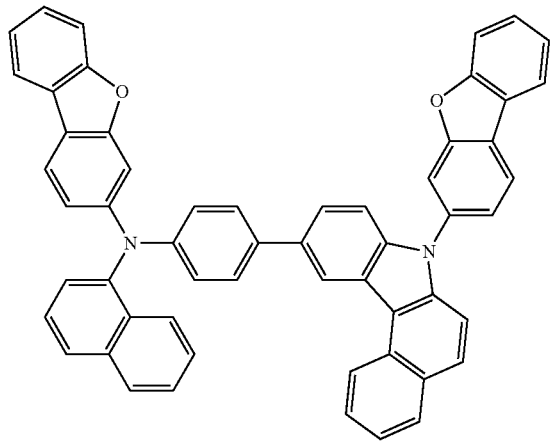
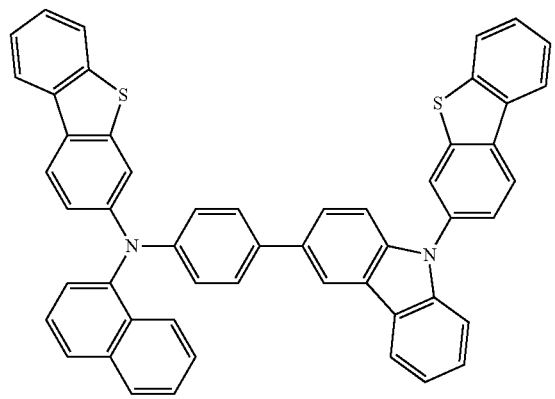
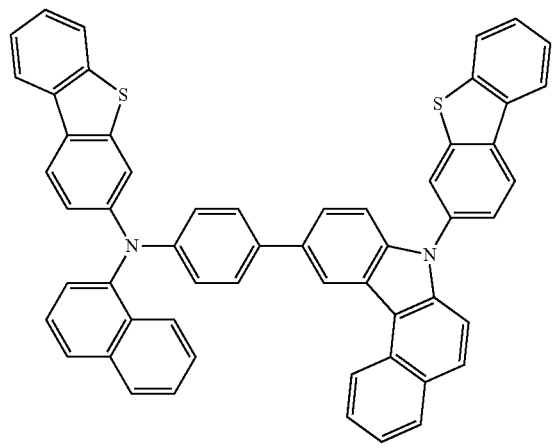
[Chemical Formula 16]
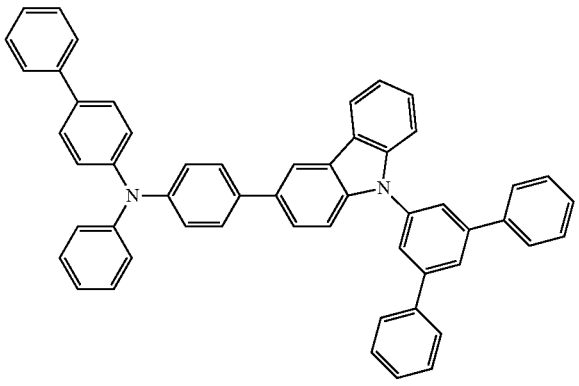
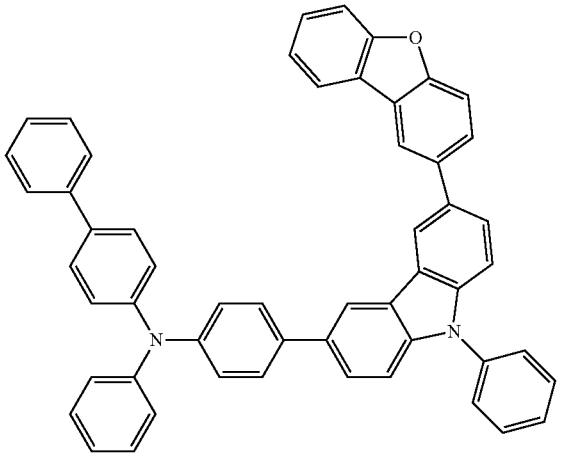

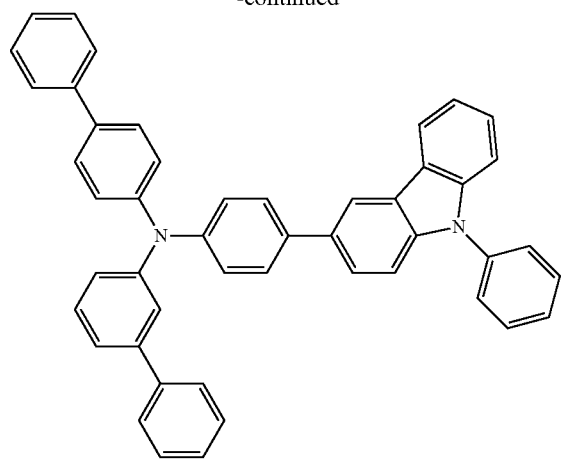
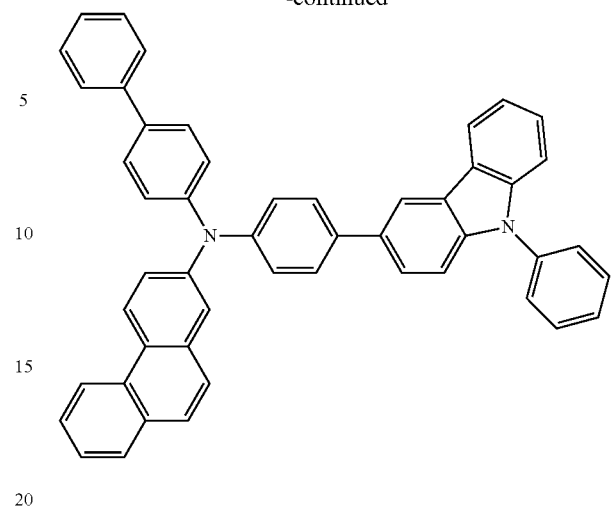
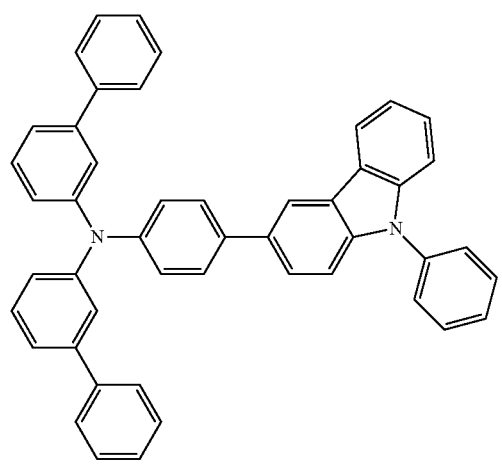
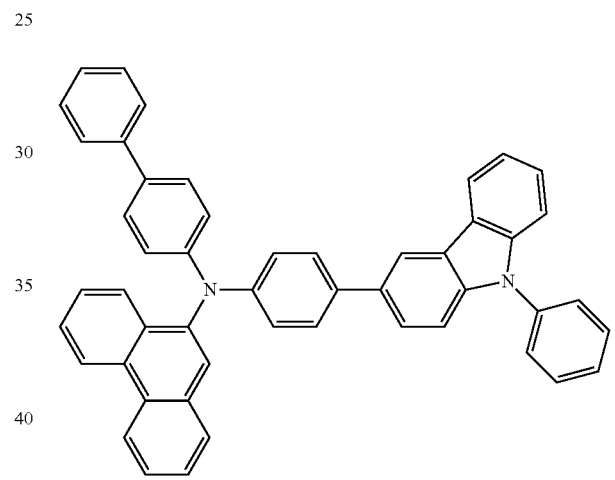
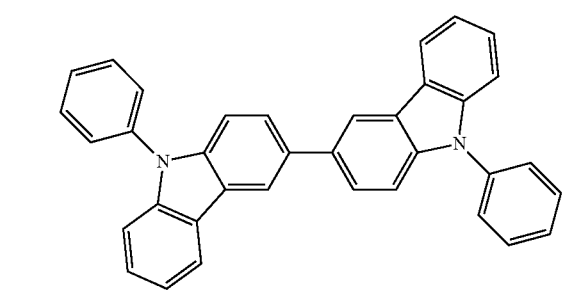
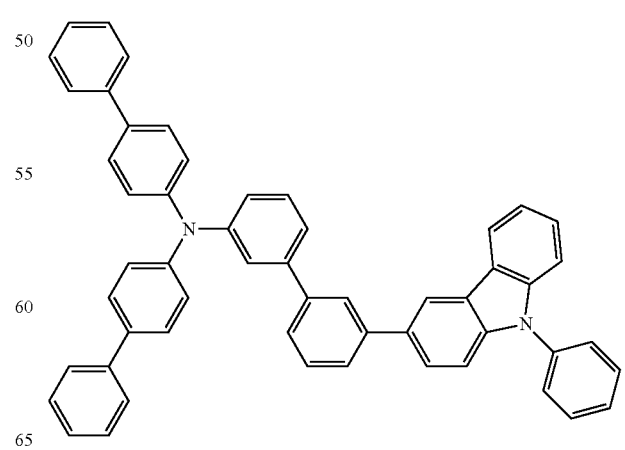
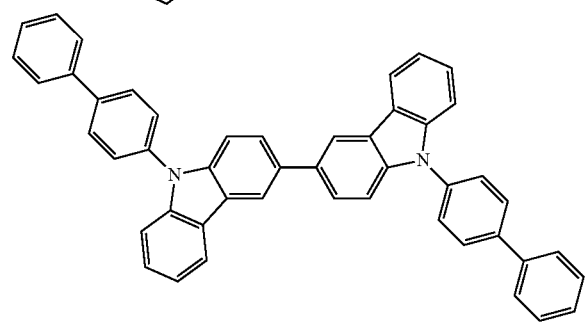

The amine derivative represented by the formula (3) is exemplified by the following compounds.
[Chemical Formula 17]
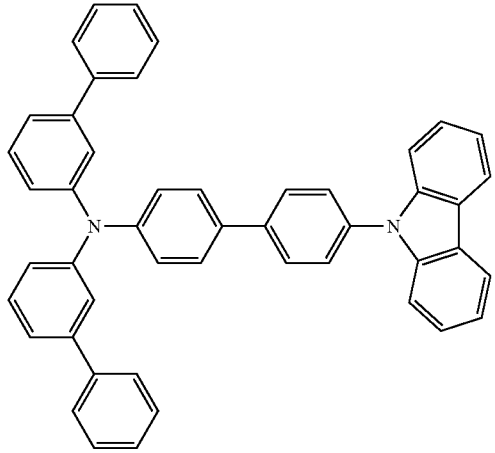
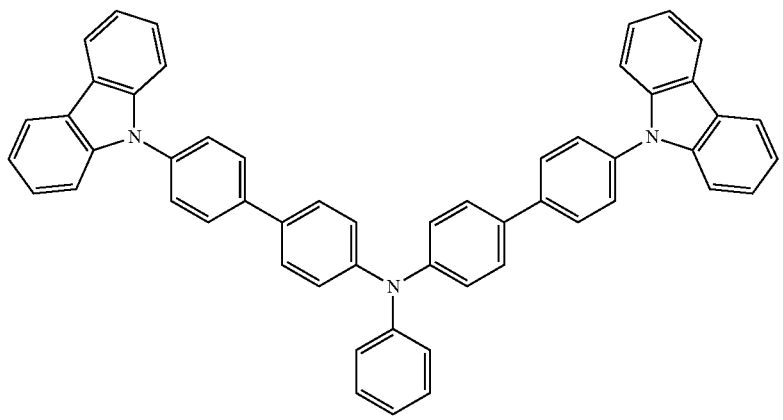
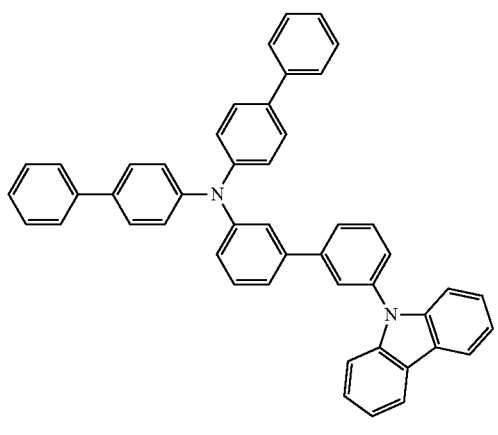
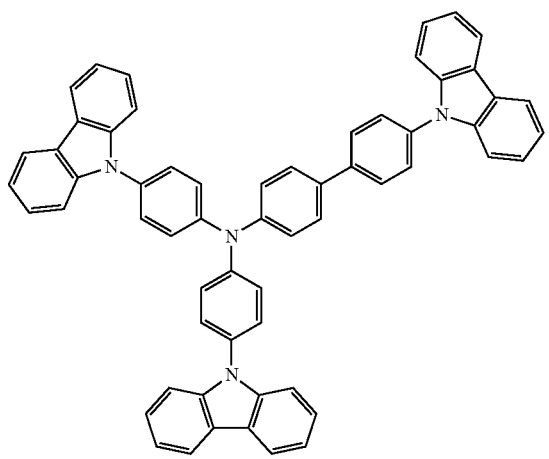

-continued
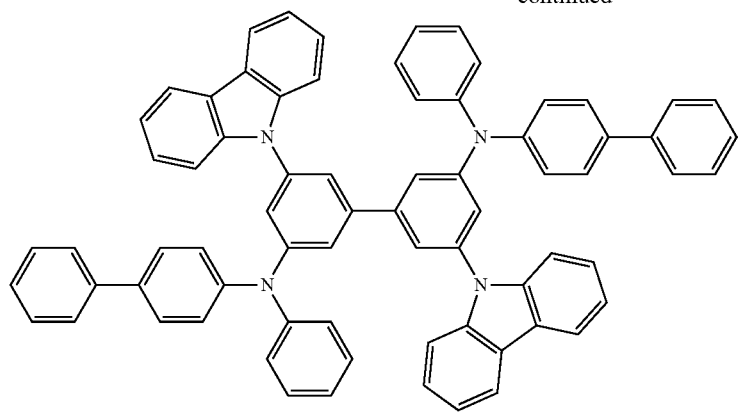
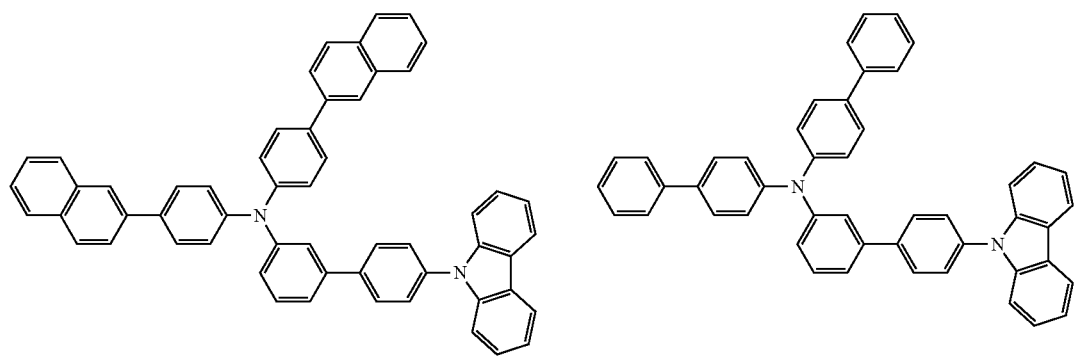
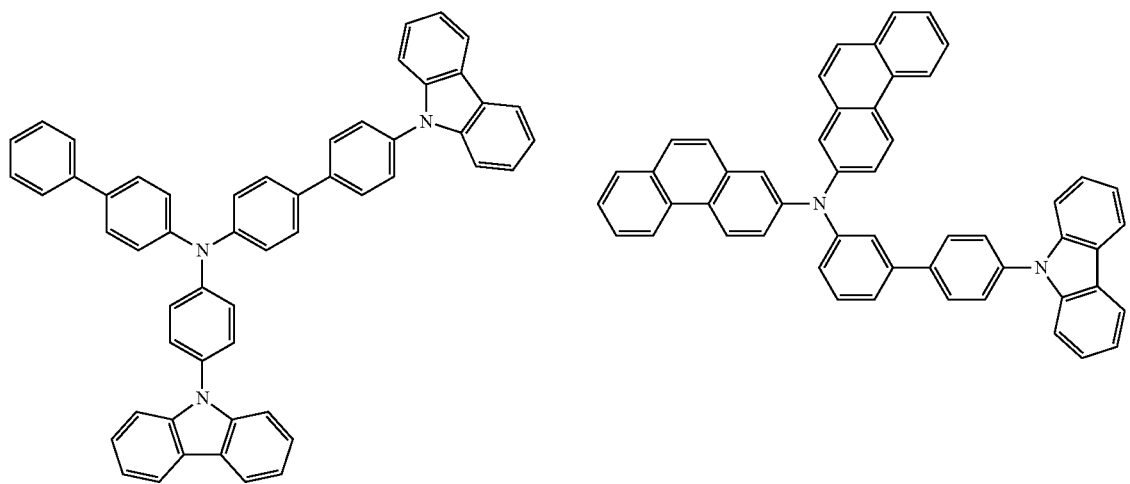

The amine derivative represented by the formula (4) is exemplified by the following compounds.
[Chemical Formula 18]
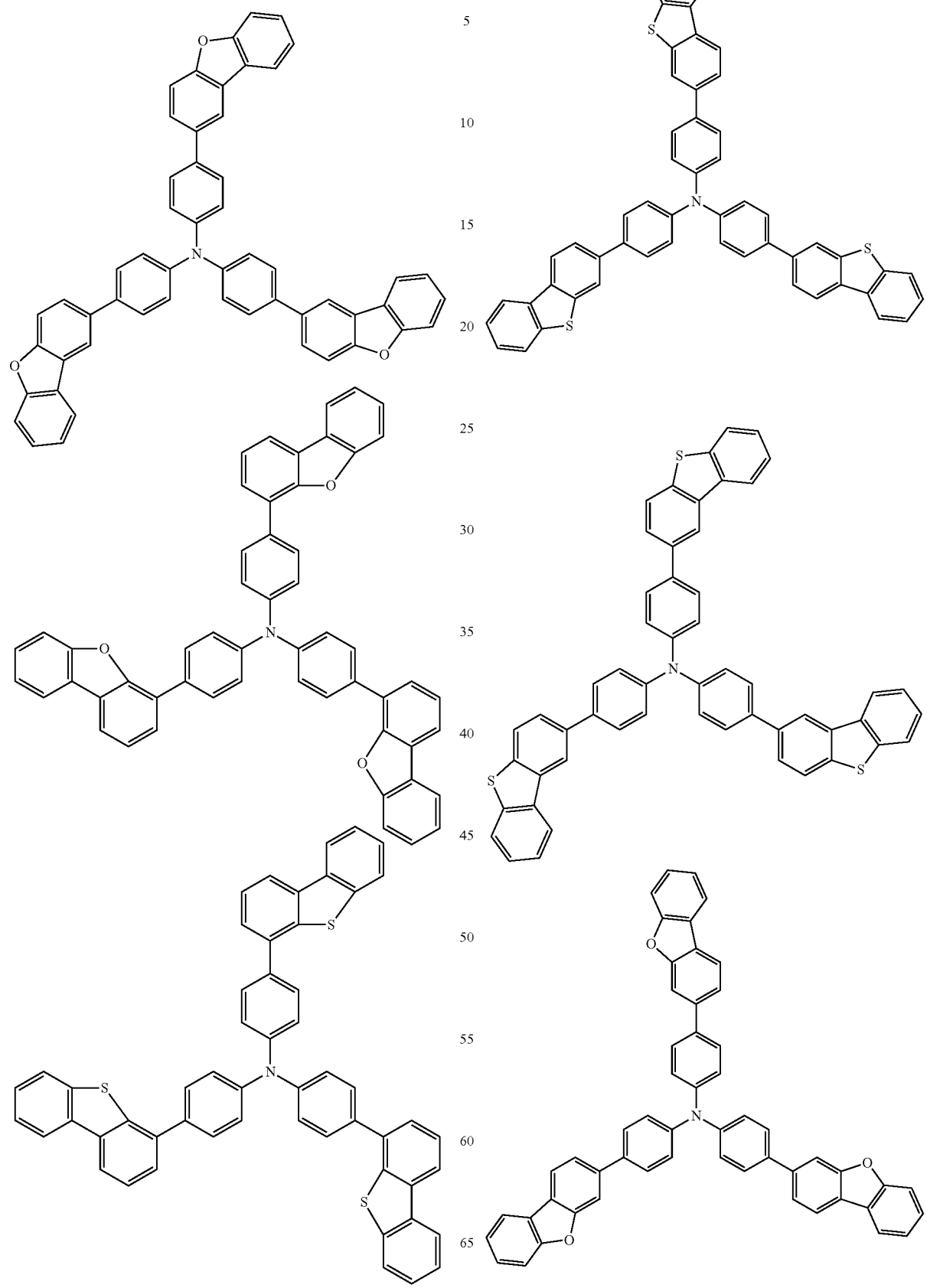

[Chemical Formula 19]
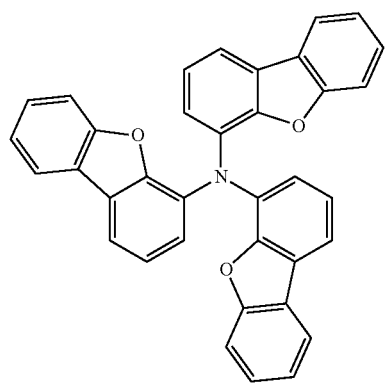
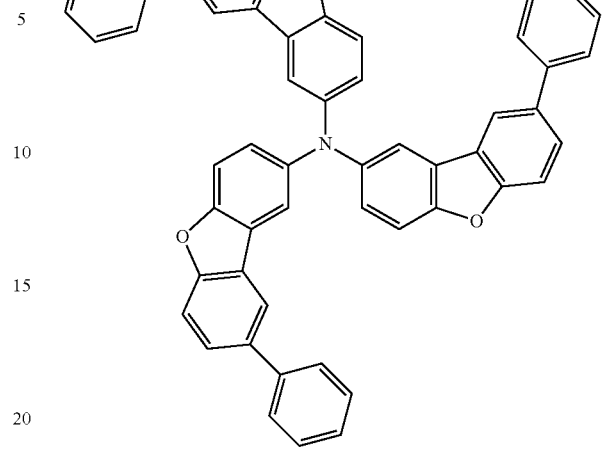
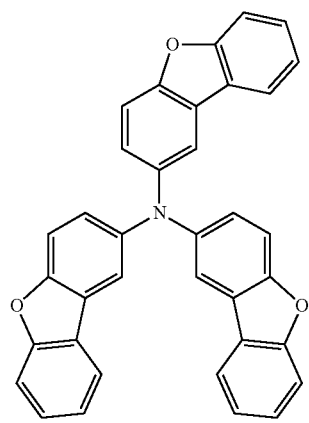
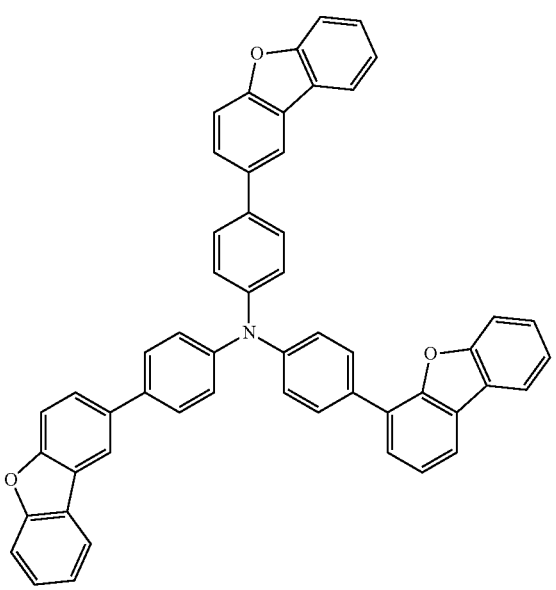
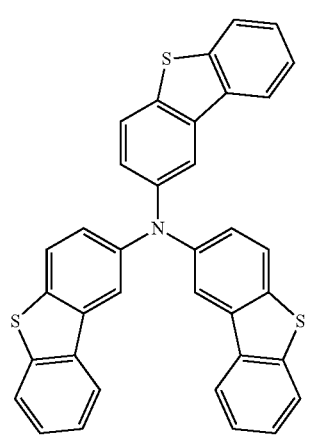
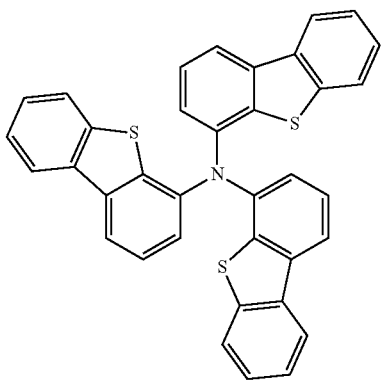

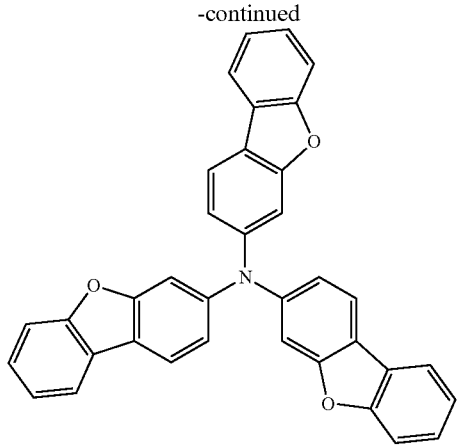
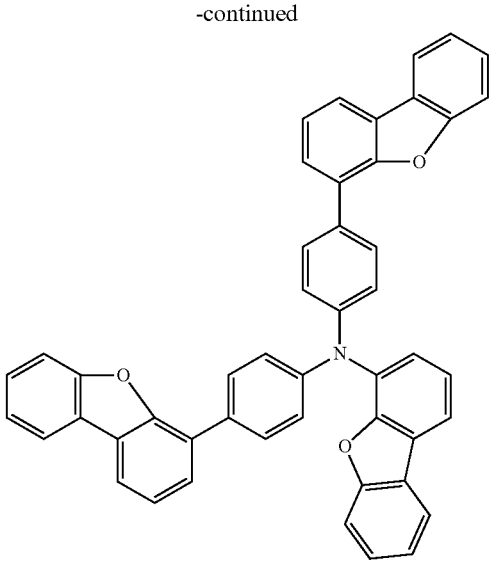
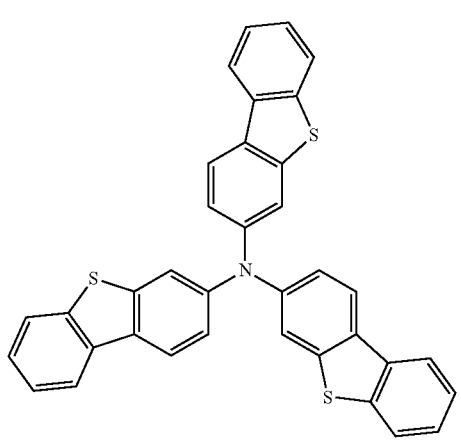
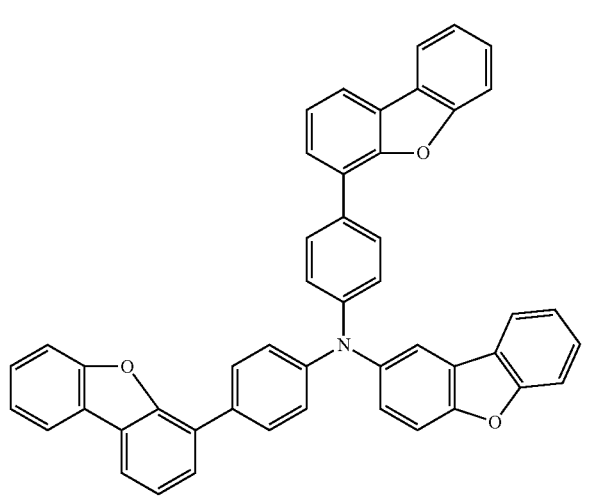
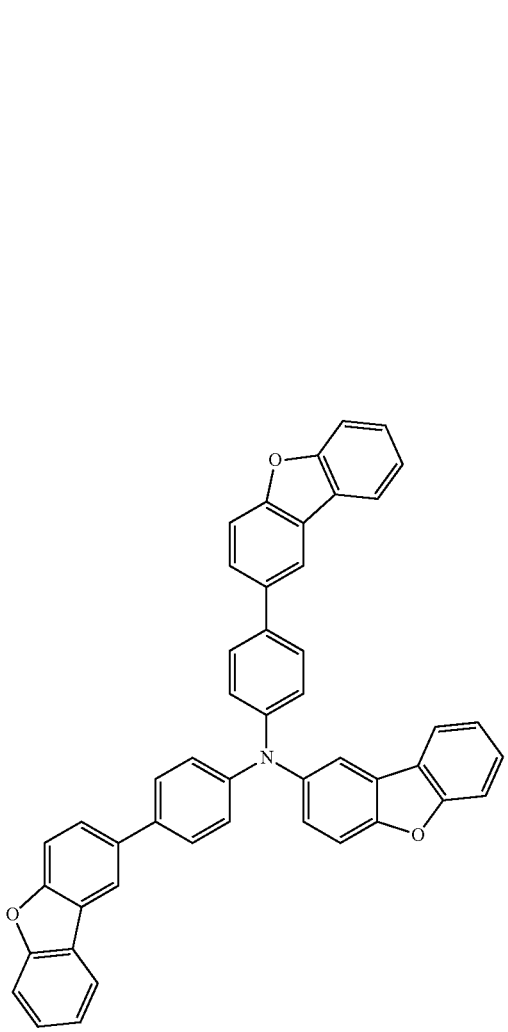
The amine derivative represented by the formula (5) is exemplified by the following compounds.

[Chemical Formula 20]
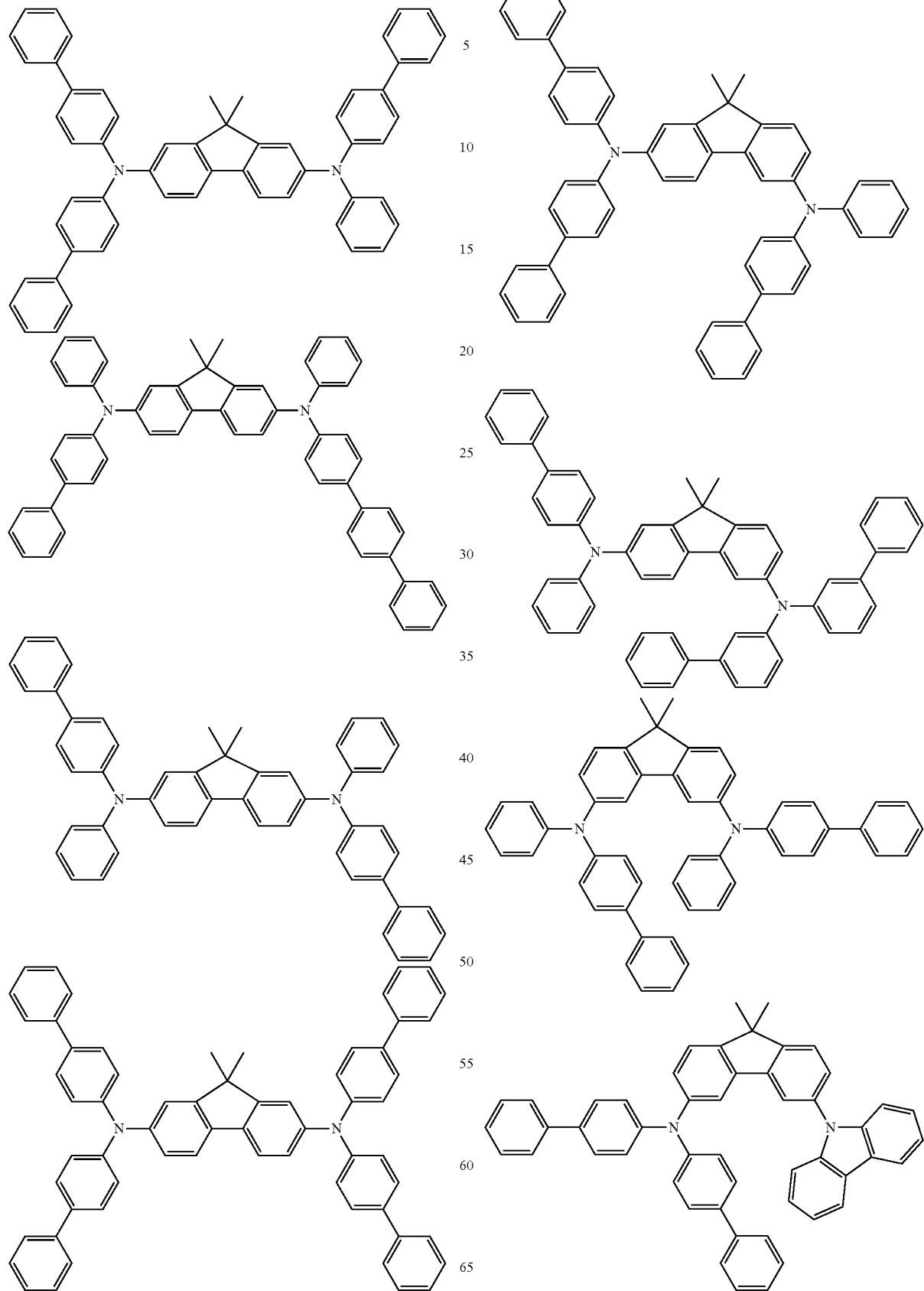

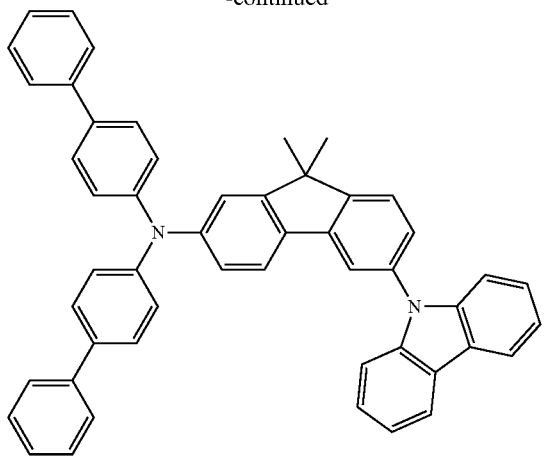
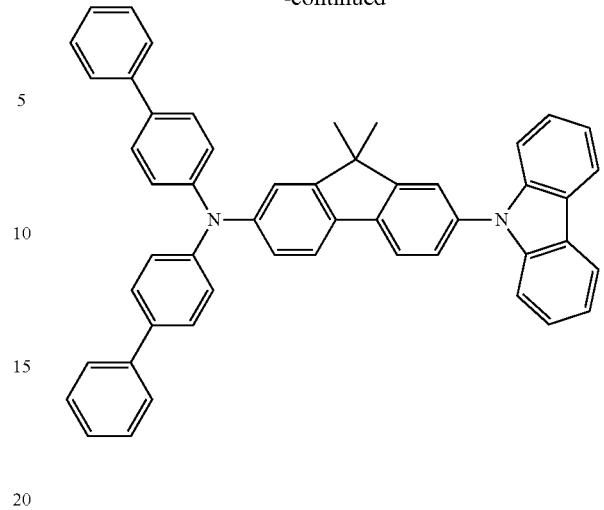
[Chemical Formula 21]
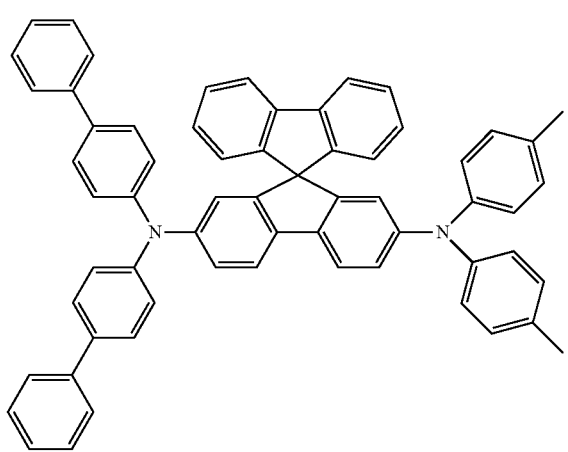
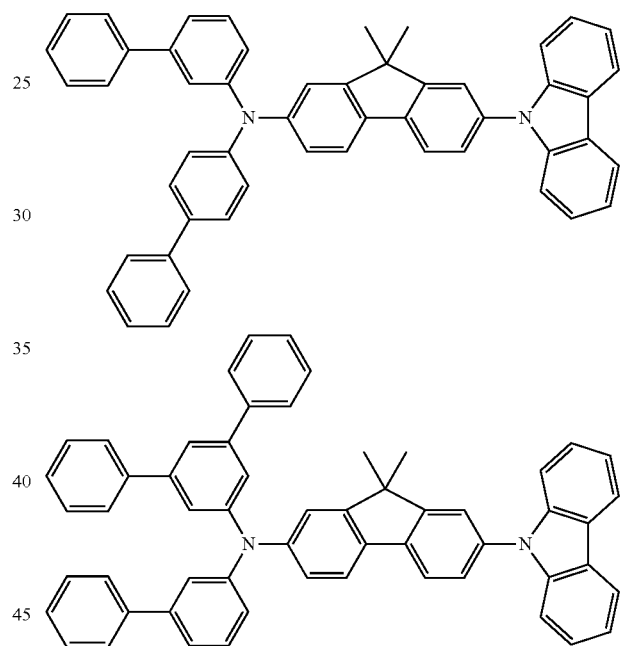
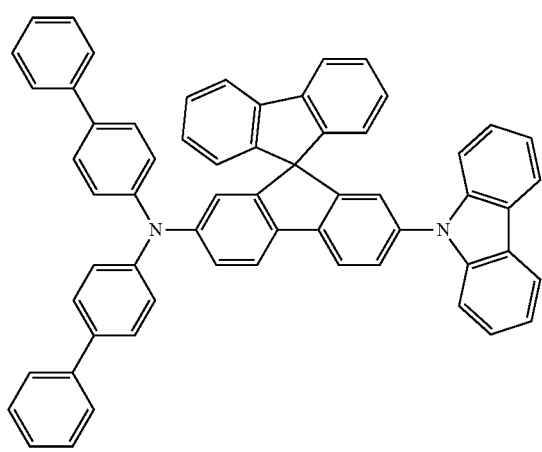

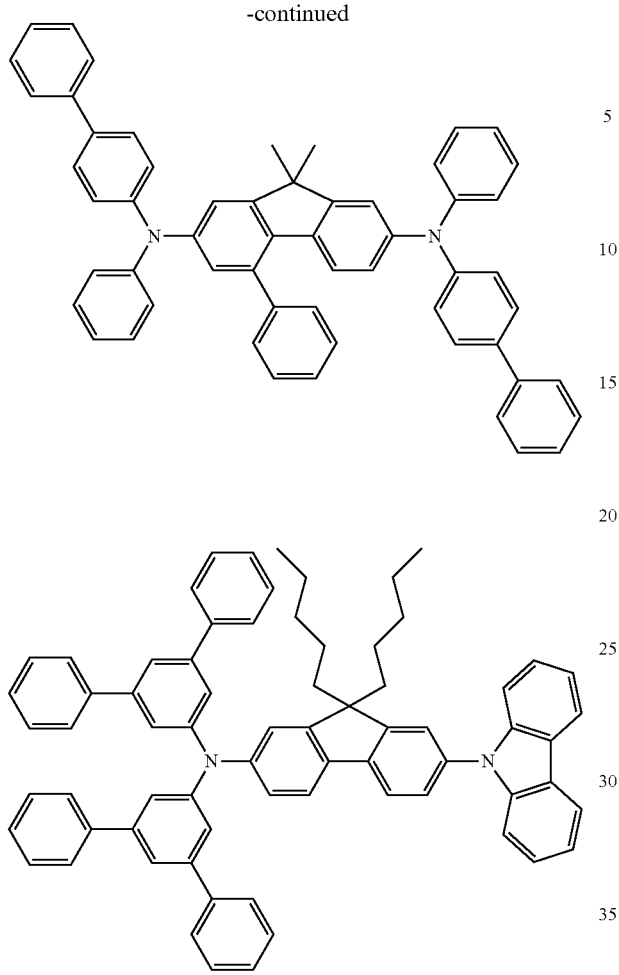
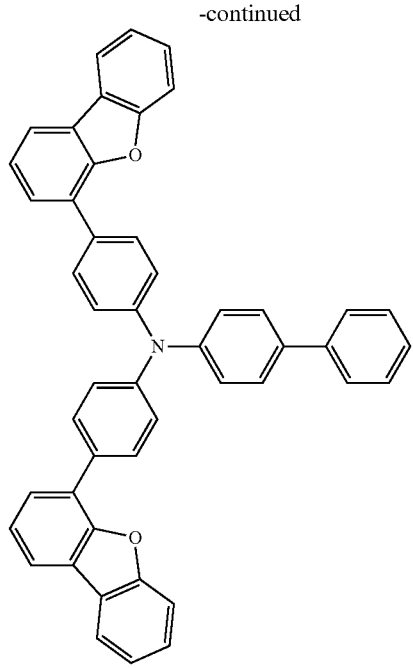
The amine derivative represented by the formula (6) is exemplified by the following compounds.
[Chemical Formula 22]
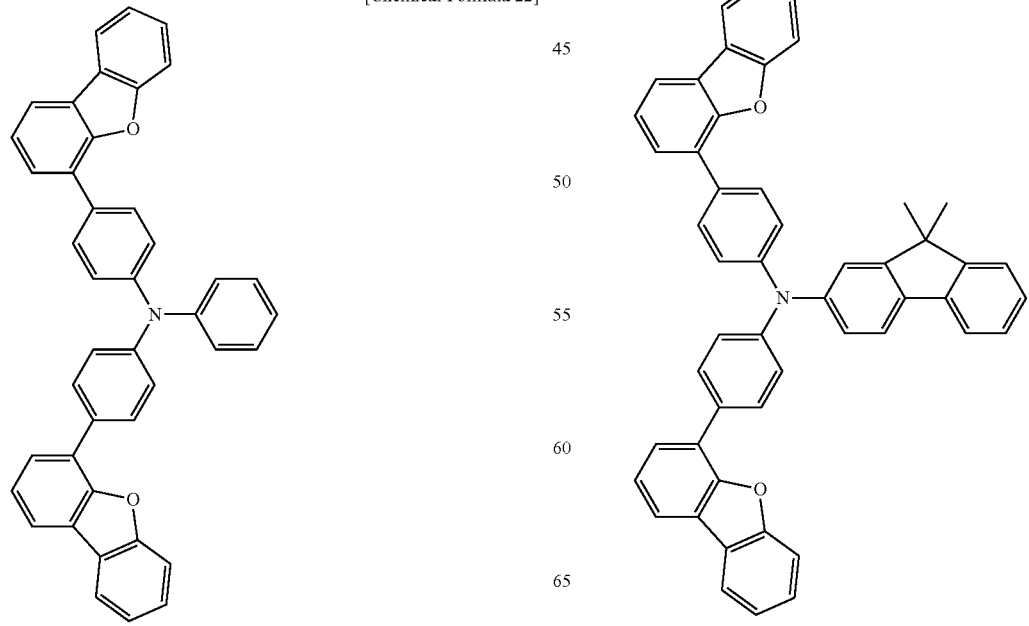

51
-continued
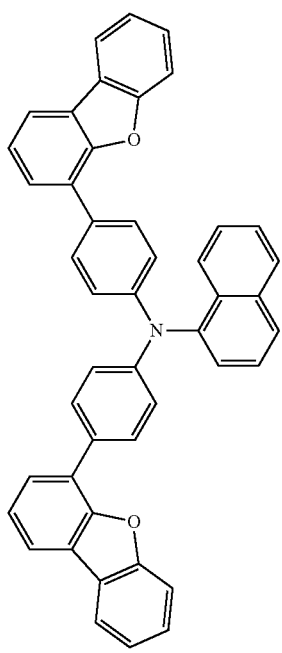
52
-continued
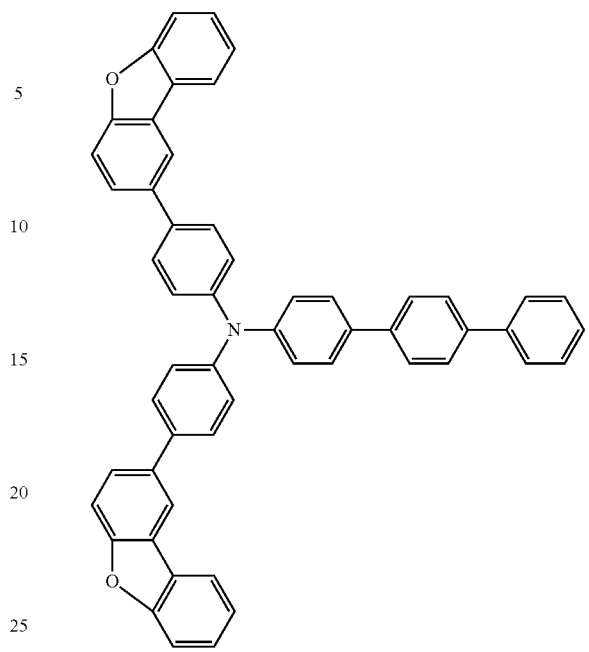
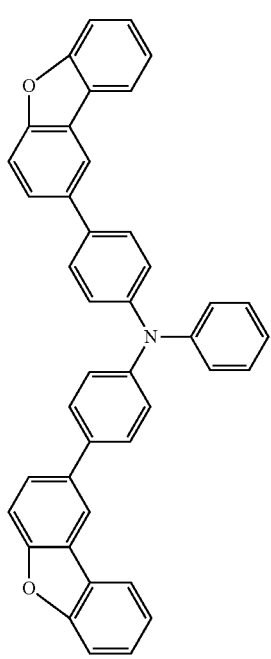
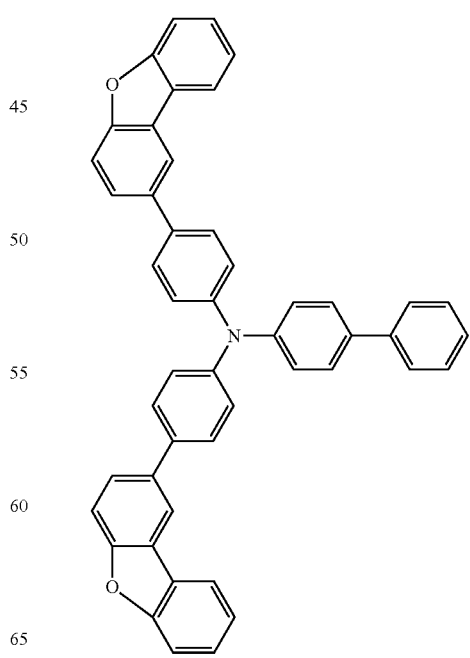

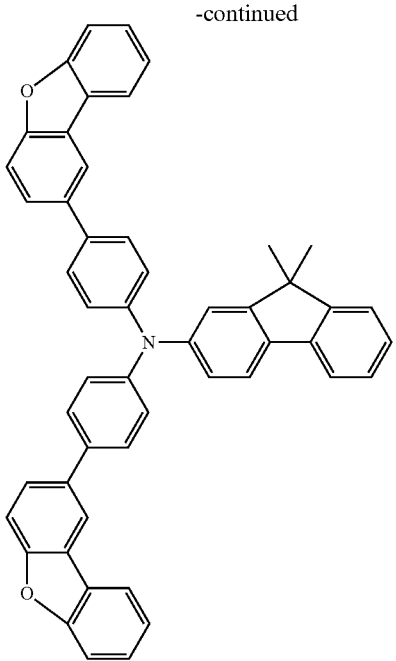
The amine derivative represented by the formula (7) is exemplified by the following compounds.
[Chemical Formula 23]
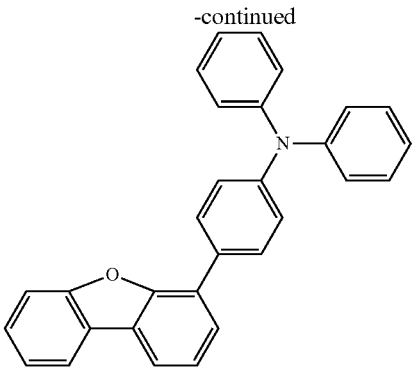
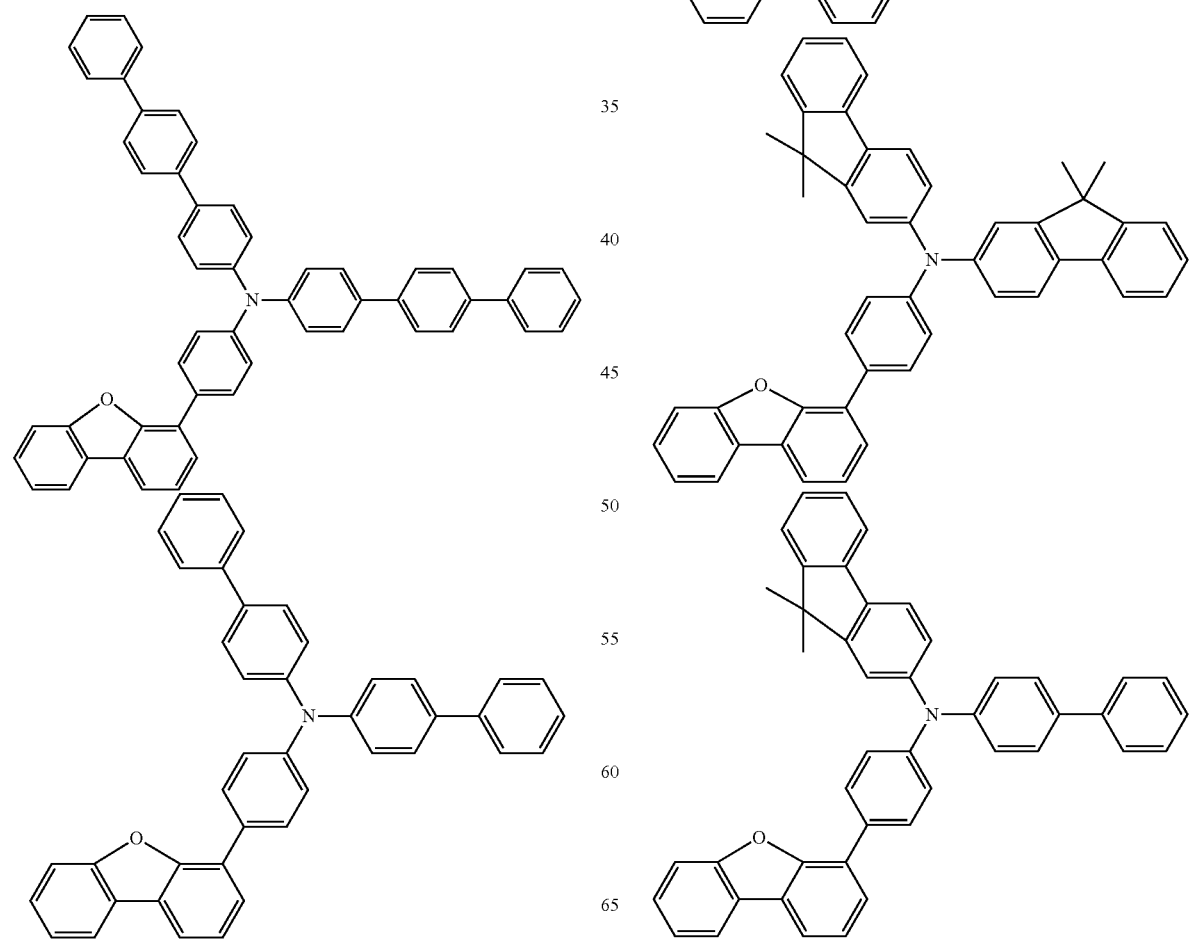

-continued
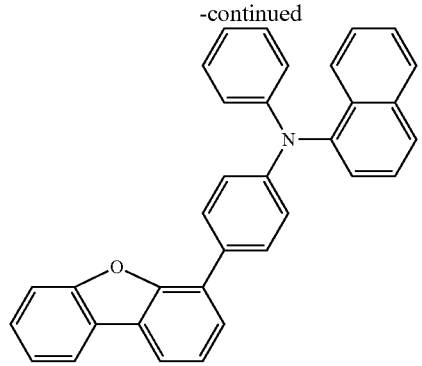
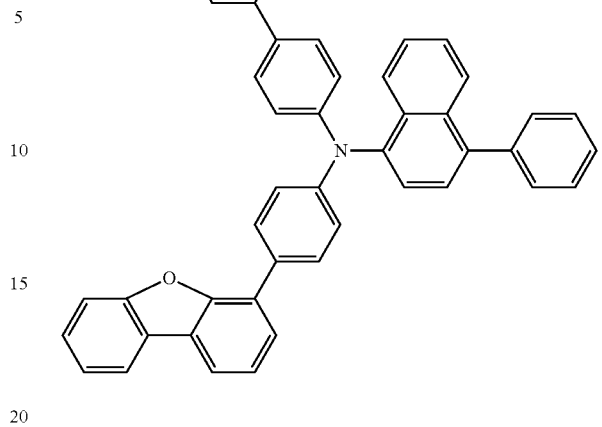
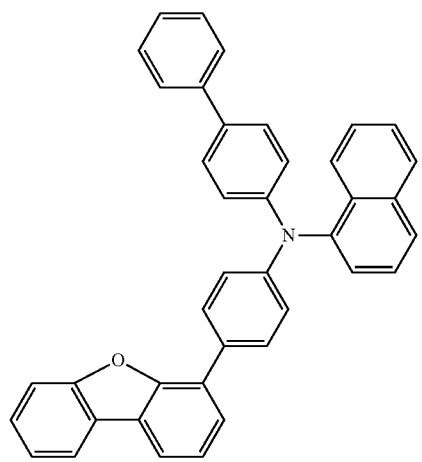
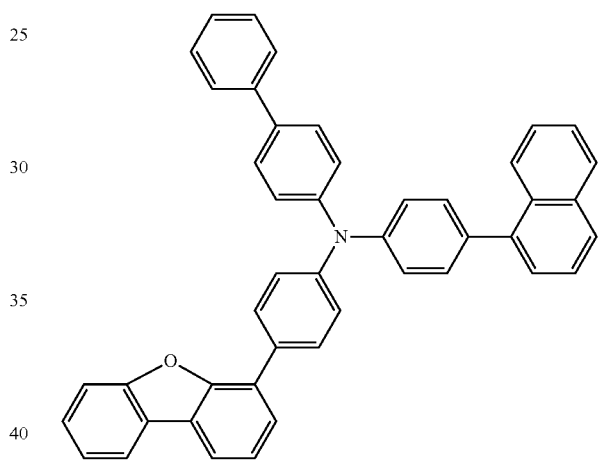
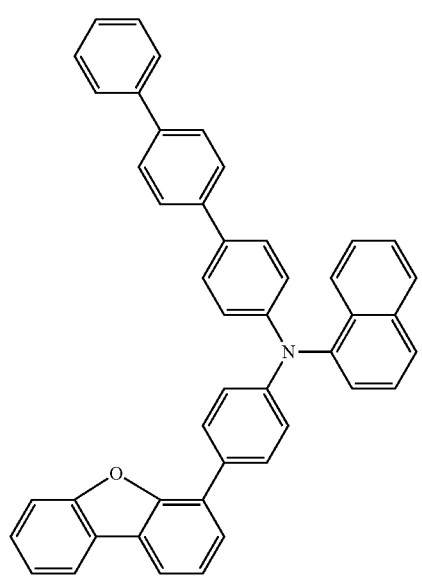

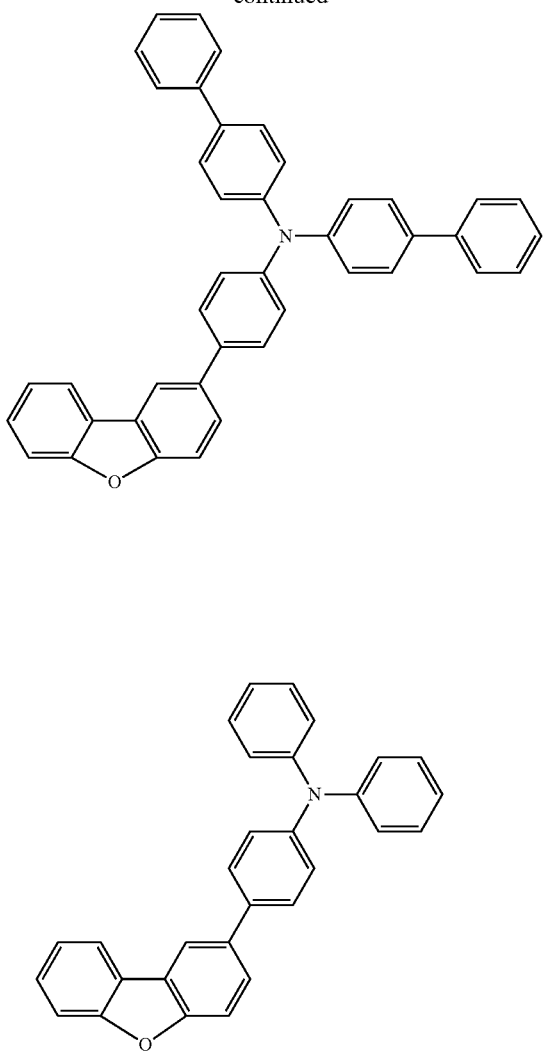
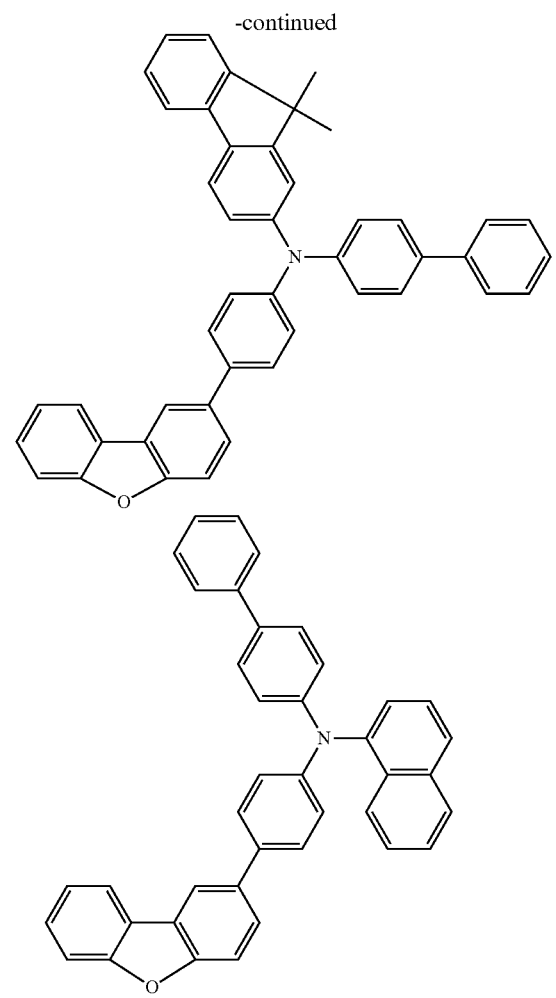

A triplet energy gap (Eg(T)) of the first host material is preferably 2.4 eV or more, more preferably 2.5 eV or more. When the triplet energy gap of the first host material is 2.4 eV or more, the triplet energy of the first host material can be made larger than the triplet energy of the first luminescent material. With this arrangement, the triplet energy of the first luminescent material can be prevented from diffusing over the first host material and the like, thereby improving luminous efficiency and the like.

On the other hand, the triplet energy gap (Eg(T)) of the first host material is preferably smaller than a triplet energy gap (Eg(T)) of a hole transporting material of the hole transporting layer 6 adjacent to the first emitting layer 51. With this arrangement, the triplet energy can be prevented from diffusing over the hole transporting layer 6 adjacent to the first emitting layer 51, thereby improving luminous efficiency and the like.

The second host material is an azine derivative that is one of a monoazine derivative, a diazine derivative and a triazine derivative. The azine derivative means a six-membered ring compound containing one or more nitrogen atoms as atoms for forming a ring.

Since the second host material is one of a monoazine derivative, a diazine derivative and a triazine derivative, the second host material exhibits an excellent electron transporting performance from the electron transporting layer 7 to the first emitting layer 51. Here, the second host material preferably exhibits a higher electron transporting performance than the first host material. With this arrangement, a region where excitons are generated is prevented from shifting from an interface between the first emitting layer 51 and the second emitting layer 52 toward the second emitting layer 52, thereby avoiding color shift.

Moreover, since the second host material is one of a monoazine derivative, a diazine derivative and a triazine derivative, unlike the organic EL device described in non-Patent Literature 1, the second emitting layer is also favorably emittable, so that the first and second emitting layers are emittable in good balance.

Further, a difference between Ip (ionization potential) of the first host material and Ip of the material of the hole transporting layer 6 adjacent to the first emitting layer 51 is preferably 0.2 eV or less, more preferably 0.15 eV or less, further more preferably 0.10 eV or less. When the difference between Ip of the first host material and Ip of the material of the hole transporting layer 6 is 0.2 eV or less, hole transporting performance from the hole transporting layer 6 to the first emitting layer 51 becomes favorable, so that holes flowing into the first emitting layer 51 and the second emitting layer 52 are increased. Accordingly, the first emitting layer 51 and the second emitting layer 52 can emit light in good balance.

The second host material is preferably different from the first host material. When luminance intensity is increased, electron velocity is faster than hole velocity. However, when different materials are used as the first and second host materials in combination, a region where excitons are generated can be prevented from shifting toward the first emitting layer 51, thereby avoiding color shift.

In the organic EL device of this exemplary embodiment, it is preferable that a hole mobility of the first host material is larger than that of the second host material. For instance, when an electrical field of $10^4$ to $10^6$ V/cm is applied, it is preferable that the first host material has a hole mobility of $10^{-5}$ cm²/Vs or more and the second host material has a hole mobility of $10^{-7}$ cm²/Vs or more.

Since the hole mobility of the first host material is made larger than that of the second host material, holes can be concentrated at the interface between the first emitting layer 51 and the second emitting layer 52.

In the organic EL device of this exemplary embodiment, it is preferable that an electron mobility of the first host material is smaller than that of the second host material. For instance, when an electrical field of $10^4$ to $10^6$ V/cm is applied, it is preferable that the first host material has an electron mobility of $10^{-8}$ cm²/Vs or more and the second host material has a hole mobility of $10^{-5}$ cm²/Vs or more.

Since the electron mobility of the first host material is made smaller than that of the second host material, electrons can be concentrated at the interface between the first emitting layer 51 and the second emitting layer 52.

Accordingly, excitons can be favorably generated near the interface between the first emitting layer 51 and the second emitting layer 52.

Moreover, a difference between the triplet energy gap (Eg(T)) of the first host material and a triplet energy gap (Eg(T)) of a second hole material of the second emitting layer 52 is preferably less than 0.1 eV. With this arrangement, triplet energy can be prevented from diffusing from the first emitting layer 51 to the hole transporting layer 6 adjacent to the first emitting layer 51, thereby improving luminous efficiency and the like.

In order to prevent diffusion of triplet energy to at least one of the hole transporting layer 6 adjacent to the first emitting layer 51 and the second emitting layer 52, the triplet energy gap (Eg(T)) of the first host material is preferably 2.5 eV or less. With this arrangement, luminous efficiency and the like can be improved.

The second host material preferably has higher affinity level and ionization potential than the first host material. When the second host material has a higher affinity level than the first host material, the second emitting layer 52 can function as an electron blocking layer due to the difference in affinity level. When the second host material has a higher ionization potential than the first host material, the second emitting layer 52 can also function as a hole blocking layer due to the difference in ionization potential.

Consequently, excitons can be favorably generated near the interface between the first emitting layer 51 and the second emitting layer 52, thereby avoiding color shift even when luminance intensity is increased.

Here, an affinity level (Af: electron affinity) refers to ejected or absorbed energy when an electron is given to a molecule of a host material, which is defined to be positive in the case of ejection and negative in the case of absorption.

The affinity level is defined as follows, with use of ionization potential (Ip) and optical energy gap (Eg(S)).

Af=Ip−Eg(S)

Here, the ionization potential Ip refers to energy necessary for a compound of the host material to remove electrons to ionize, for which a value measured with an ultraviolet ray photoelectron spectrometer (AC-3 manufactured by Riken Keiki Co., Ltd.).

The optical energy gap Eg(S) refers to a difference between conductive level and covalent electron level, which can, for example, be defined by a wavelength value at an intersection of the tangent line adjacent to a long wavelength of an absorption spectrum and a base line (no absorption) in a solution in which each host material is dissolved in toluene being converted into energy value.

The second host material is preferably compounds represented by the following formulae (21) to (26).

[Chemical Formula 24]

(21)

(22)

(23)

(24)

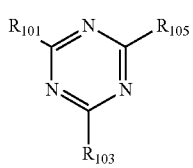

(25)

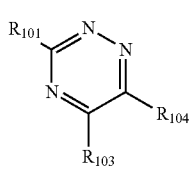

(26)

In the formulae (21) to (26), $R_{101}$ to $R_{105}$ each represent a substituted or unsubstituted aryl group, a substituted or unsubstituted heterocyclic group, or an alkyl group.

Preferable substituents for the aryl group are an aryl group having 6 to 30 carbon atoms, a heterocyclic group having 5 to 30 carbon atoms and an alkyl group having 1 to 20 carbon atoms.

Preferable substituents for the heterocyclic group are an aryl group having 6 to 30 carbon atoms, a heterocyclic group having 5 to 30 carbon atoms and an alkyl group having 1 to 20 carbon atoms.

Each compound as the second host material preferably has a carbazole skeleton. With the second host material having a carbazole skeleton, the organic EL device 1 exhibiting an excellent durability without color shift can be obtained.

On the other hand, when, for instance, TPBIP having no carbazole group (represented by a formula (40)), is used as the second host material, durability of the organic EL device is decreased.

[Chemical Formula 25]

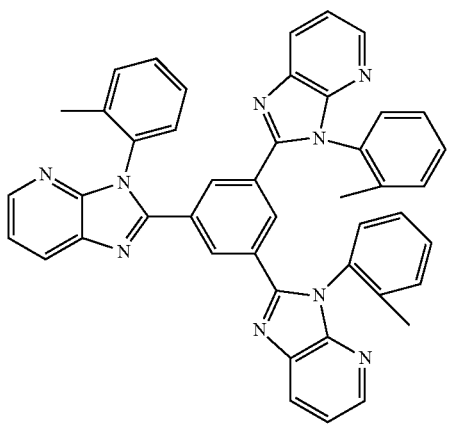

(40)

When CBP (4,4'-bis[9-dicarbazolyl]-2,2'-biphenyl) is used as the second host material, electron injectability to the second emitting layer 52 becomes insufficient. Accordingly, luminous efficiency may not be maintained unless an electron injecting layer is provided between the second emitting layer 52 and the electron transporting layer 7.

The second host material having a carbazole skeleton is exemplified by a compound (carbazole azine compound) represented by the following general formula (BL-9) or (BL-10).

[Chemical Formula 26]

$$(Cz-)_m A \qquad (BL-9)$$

In the formula (BL-9), Cz is a substituted or unsubstituted carbazolyl group or a substituted or unsubstituted azacarbazolyl group. A is a group of one of a monoazine derivative, a diazine derivative and a triazine derivative. m is an integer of 1 to 3.

[Chemical Formula 27]

$$Cz-A_n \qquad (BL-10)$$

In the formula (BL-10), Cz is a substituted or unsubstituted carbazolyl group or a substituted or unsubstituted azacarbazolyl group. A is a group of one of a monoazine derivative, a diazine derivative and a triazine derivative. n is an integer of 1 to 3.

The second host material having a carbazole skeleton is preferably a compound represented by the following formula (27).

[Chemical Formula 28]

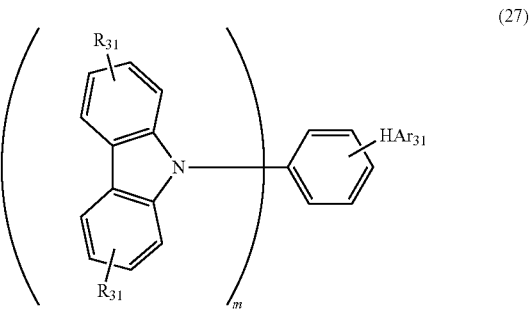

(27)

In the formula (27), $HAr_{31}$ is a substituted or unsubstituted nitrogen-containing six-membered heterocyclic group. m is an integer of 1 to 4, preferably 1 to 3, more preferably 1 or 2. $R_{31}$ is a substituted or unsubstituted alkyl group or aryl group. $R_{31}$ may be bonded to each other to form a cyclic structure in which benzene rings are fused.

Specifically, the second host material having a carbazole skeleton is preferably compounds represented by the following formulae (8) to (12A).

[Chemical Formula 29]

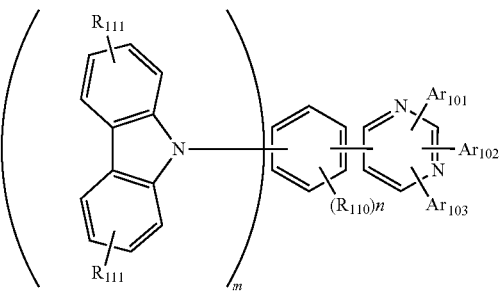

(8)

-continued

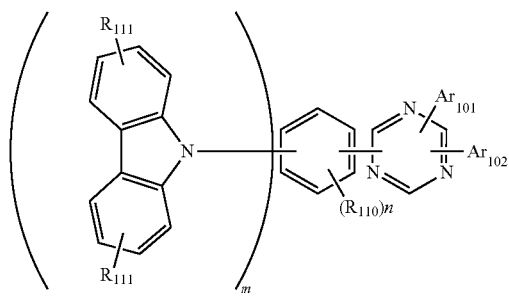
(9)

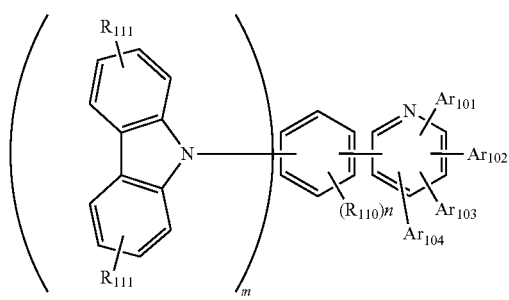
(10)

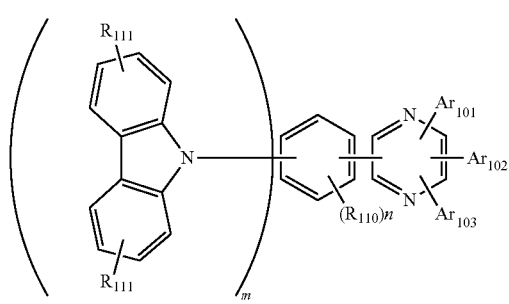
(11)

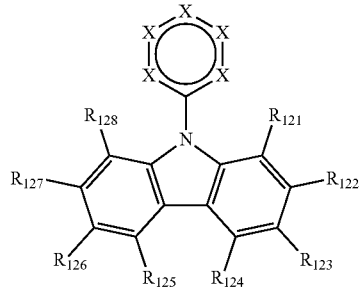
(12)

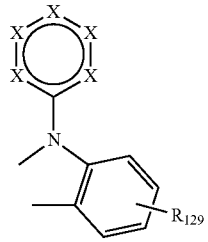
(12A)

In the formulae (8) to (11), $Ar_{101}$ to $Ar_{104}$ each represent a substituted or unsubstituted aryl group having 6 to 60 carbon atoms, or a substituted or =substituted heterocyclic group having 3 to 60 carbon atoms. $R_{110}$ and $R_{111}$ represent the same as $R_1$.

n is an integer of 1 to 4. m is an integer of 1 to 4. m is preferably an integer of 1 to 3, more preferably 1 or 2. The sum (n+m) of n and m satisfies a relationship of $2 \leq (n+m) \leq 5$.

In the formulae (12) and (12A), X is N or CH, in which the number of N is from 1 to 4.

In the formula (12), $R_{121}$ to $R_{128}$ each represent a hydrogen atom, an aryl group or an alkyl group, or $R_{121}$ to $R_{128}$ are bonded with a skeleton represented by the formula (12A).

$R_{121}$ to $R_{128}$ are bonded with the skeleton represented by the formula (12A) such that at least one of combinations of $R_{121}$ and $R_{122}$, $R_{122}$ and $R_{123}$, $R_{123}$ and $R_{124}$, $R_{125}$ and $R_{126}$, $R_{126}$ and $R_{127}$, and $R_{127}$ and $R_{128}$ is bonded with the skeleton represented by the formula (12A).

In the formula (12A), $R_{129}$ is a hydrogen atom, an aryl group or an alkyl group.

The second host material represented by the formulae (8) to (12A) is exemplified by the following compounds.

[Chemical Formula 30]

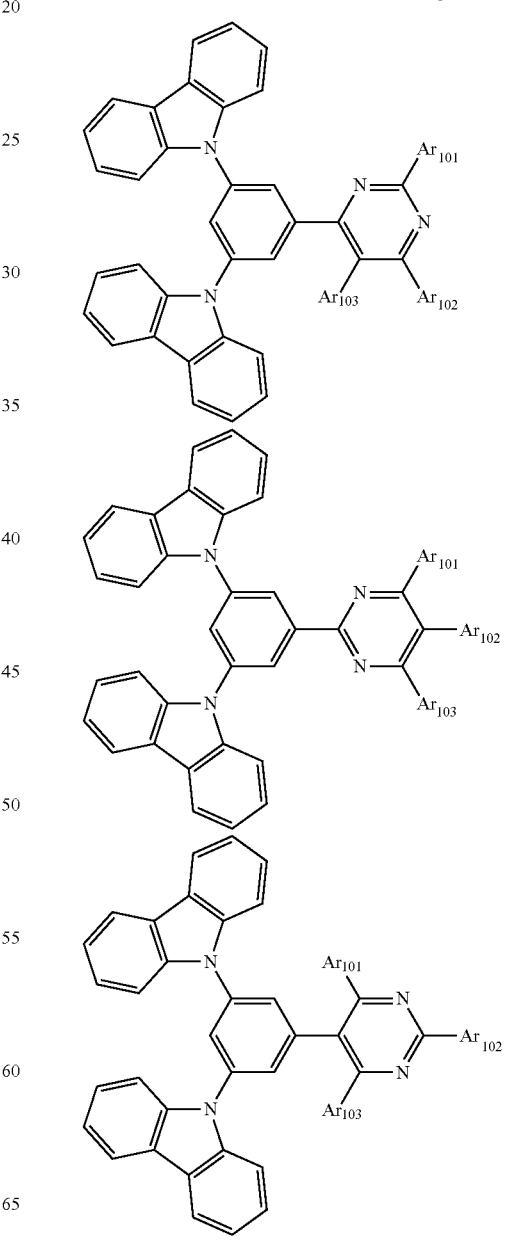

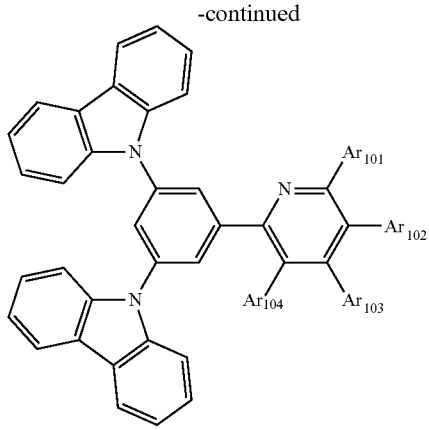

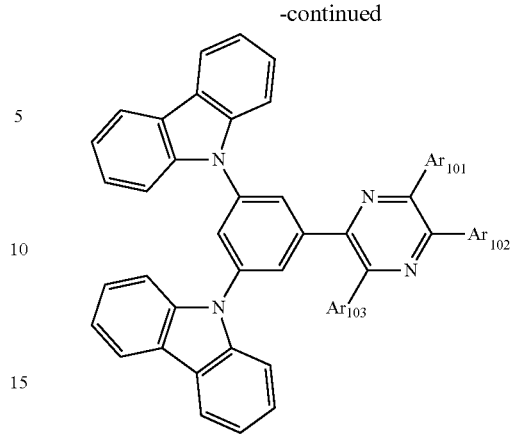

The second host material having a carbazole skeleton may alternatively be a compound represented by the following formula (28).

[Chemical Formula 31]

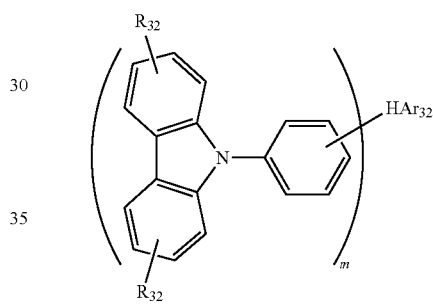

(28)

In the formula (28), $HAr_{32}$ is a substituted or unsubstituted nitrogen-containing six-membered heterocyclic group. m is an integer of 1 to 4, preferably 1 to 3, more preferably 1 or 2. $R_{32}$ is a substituted or unsubstituted alkyl group or aryl group. $R_{32}$ may be bonded to each other to form a cyclic structure in which benzene rings are fused.

The second host material having a carbazole skeleton may alternatively be compounds represented by the following formulae (29) to (32).

[Chemical Formula 32]

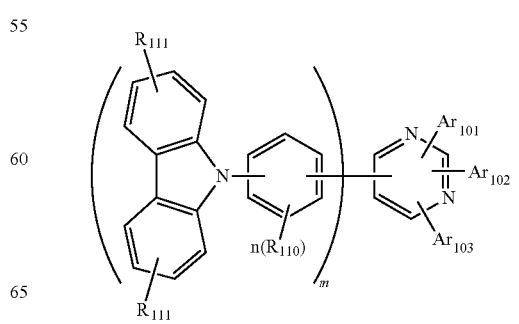

(29)

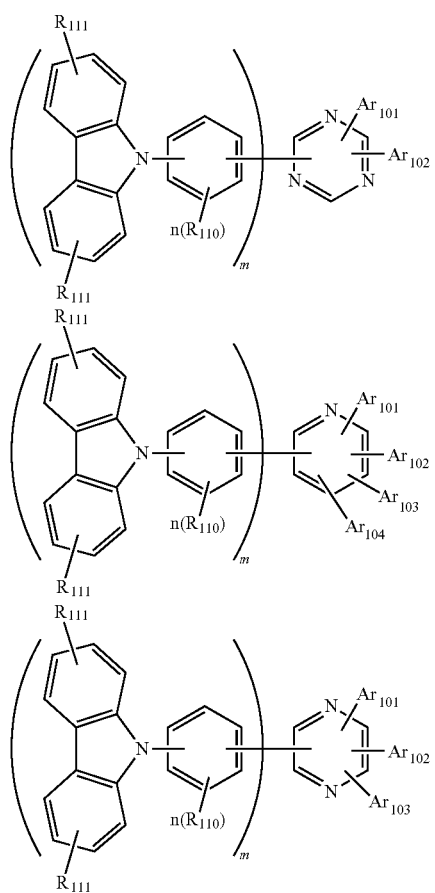
(30)
(31)
(32)
In the formulae (29) to (32), $Ar_{101}$ to $Ar_{103}$, $R_{110}$ and $R_{111}$ are the same groups as those in the formulae (8) to (11).
The second host material represented by the formulae (29) to (32) is exemplified by the following compounds.
[Chemical Formula 33]
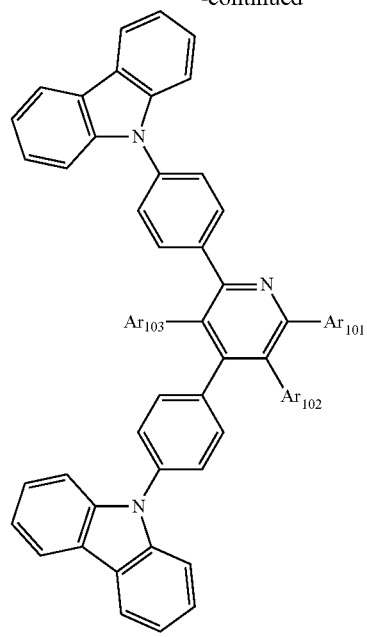
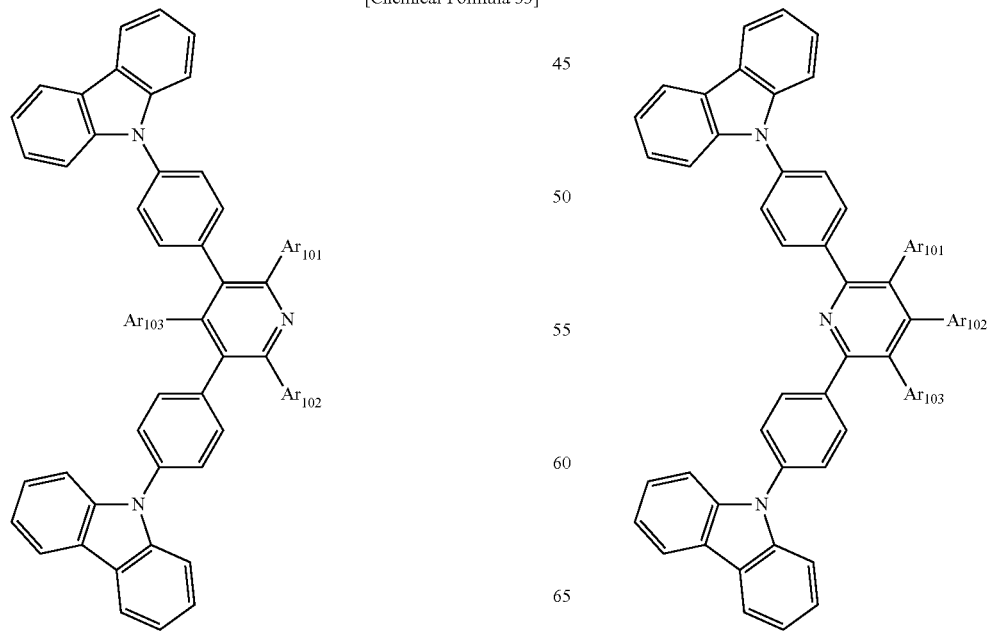

-continued
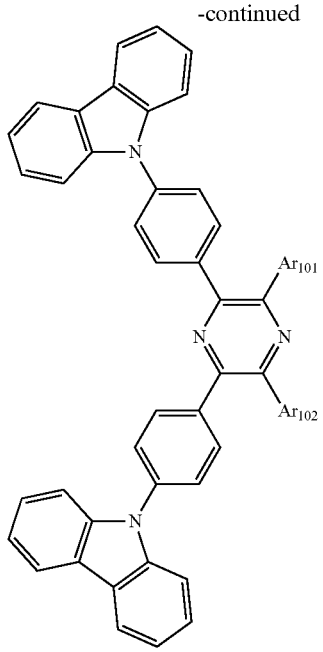
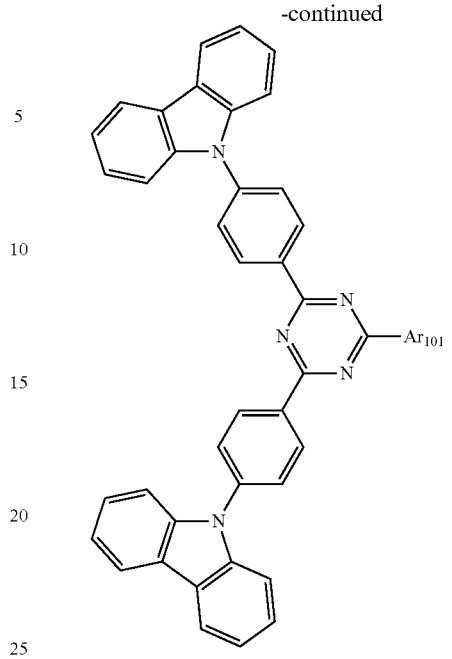
Specific examples of the second host material are the following compounds.
[Chemical Formula 34]
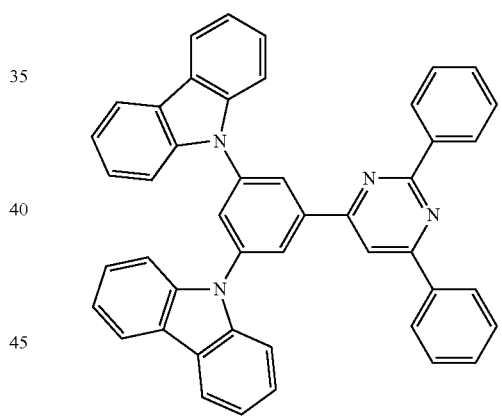
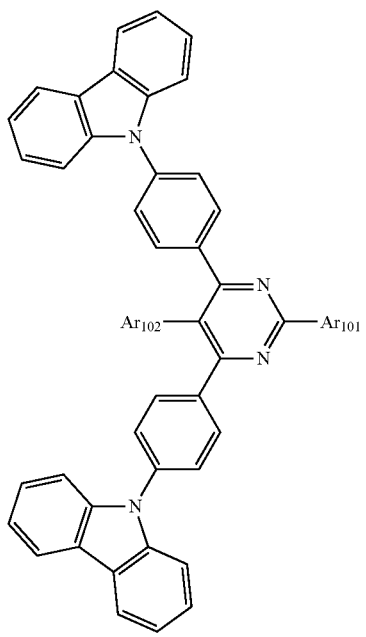
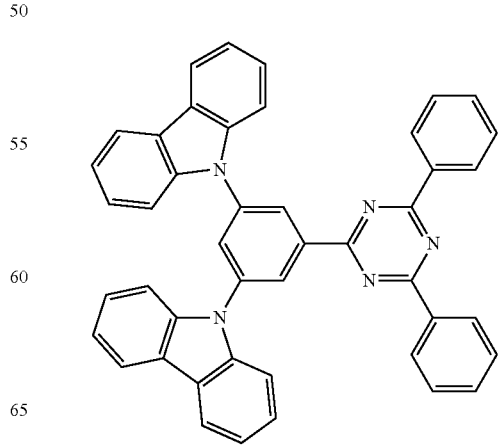

71
-continued
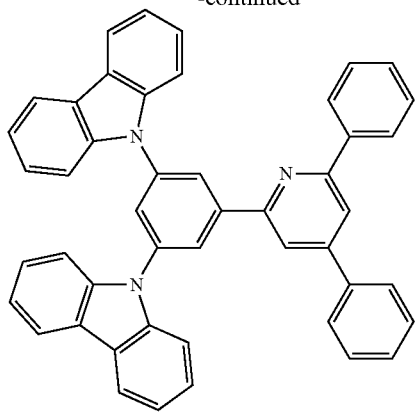
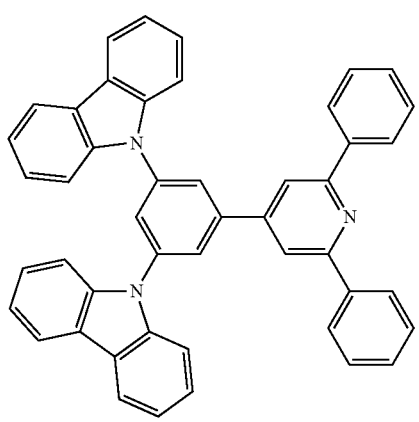
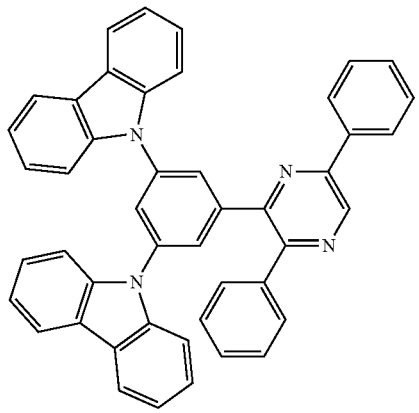
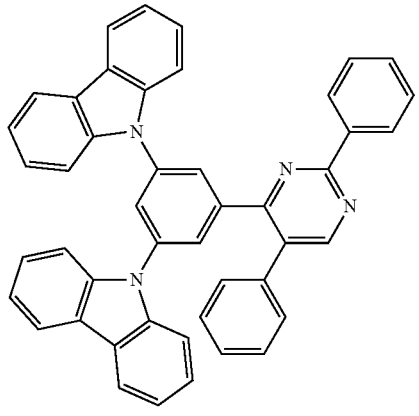
72
-continued
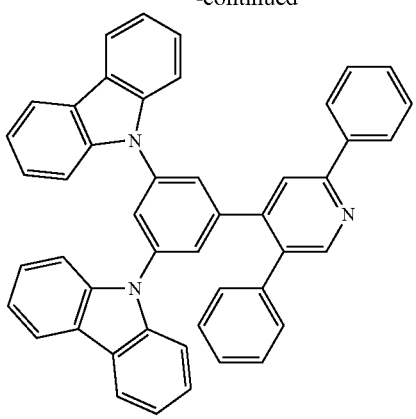
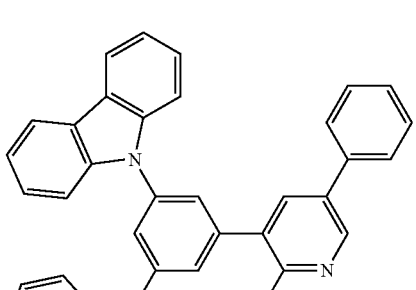
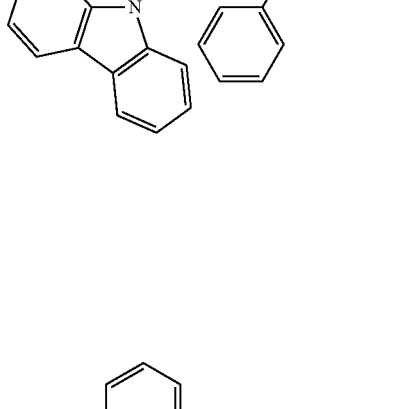
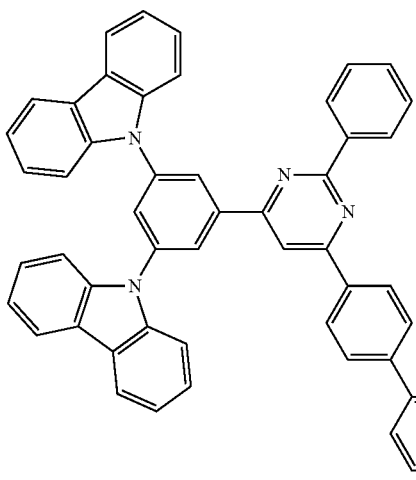

73
-continued
74
-continued
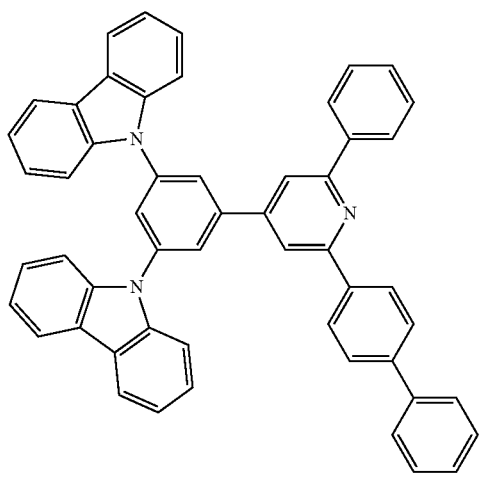
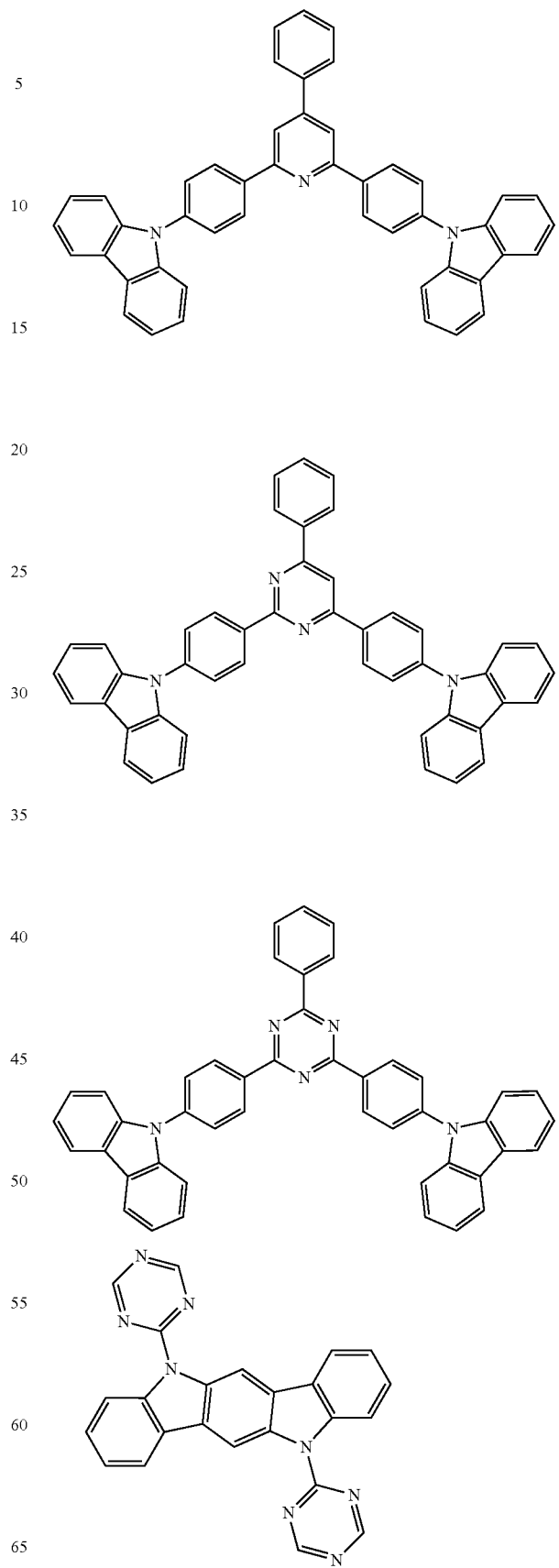

-continued

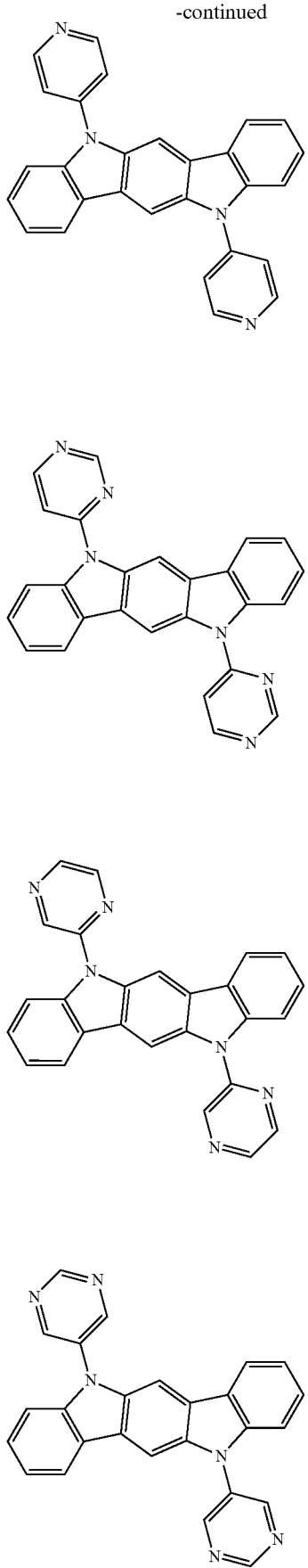

The second host material may alternatively be compounds represented by the following formulae (8A) to (11A).

[Chemical Formula 35]

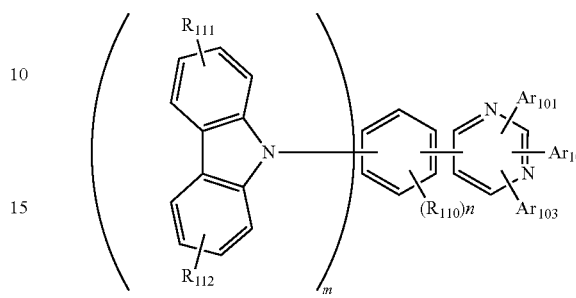

(8A)

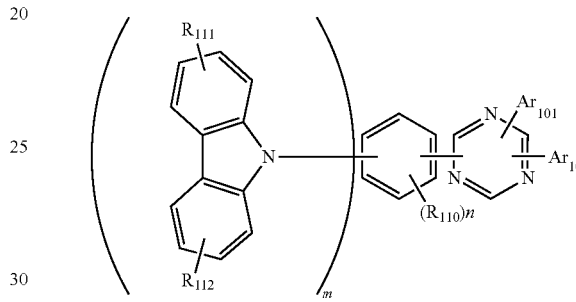

(9A)

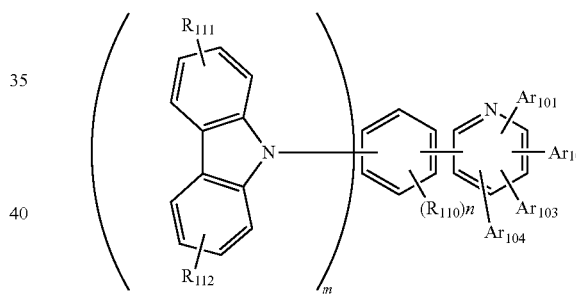

(10A)

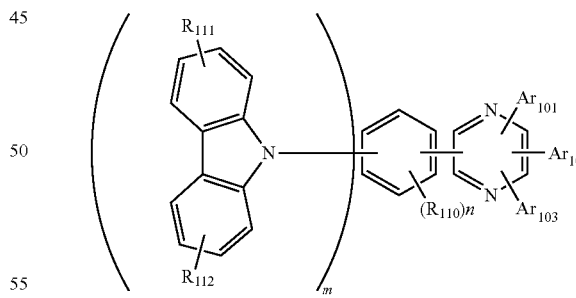

(11A)

In the formulae (8A) to (11A), $Ar_{101}$ to $Ar_{104}$ each represent a hydrogen atom, a substituted or unsubstituted aryl group having 6 to 60 carbon atoms, or a substituted or unsubstituted heterocyclic group having 3 to 60 carbon atoms. In the formulae (8A), (9A) and (11A), all of $Ar_{101}$ to $Ar_{103}$ are not a hydrogen atom at the same time. In the formula (10A), all of $Ar_{101}$ to $Ar_{104}$ are not a hydrogen atom at the same time.

In the formulae (8A) to (11A), $R_{110}$ to $R_{112}$ each represent a hydrogen atom, a halogen atom, a substituted or unsubstituted alkyl group having 1 to 40 carbon atoms, a substituted or unsubstituted heterocyclic group having 3 to 20 carbon atoms, a substituted or unsubstituted non-fused aryl group having 6 to 40 carbon atoms, a substituted or unsubstituted fused aryl group having 6 to 12 carbon atoms, a substituted or unsubstituted fused/non-fused-mixed aryl group having 12 to 40 carbon atoms, a substituted or unsubstituted aralkyl group having 7 to 20 carbon atoms, a substituted or unsubstituted alkenyl group having 2 to 40 carbon atoms, a substituted or unsubstituted alkyl amino group having 1 to 40 carbon atoms, a substituted or unsubstituted aralkyl amino group having 7 to 60 carbon atoms, a substituted or unsubstituted alkylsilyl group having 3 to 20 carbon atoms, a substituted or unsubstituted arylsilyl group having 8 to 40 carbon atoms, a substituted or unsubstituted aralkylsilyl group having 8 to 40 carbon atoms, or a substituted or unsubstituted halogenated alkyl group having 1 to 40 carbon atoms.

In the formulae (8A) to (11A), n is an integer of 1 to 4 and m is an integer of 1 to 4. The sum (n+m) of n and m satisfies a relationship of 2≤(n+m)≤5.

The second host material may alternatively be a compound represented by the following formula (13).

[Chemical Formula 36]

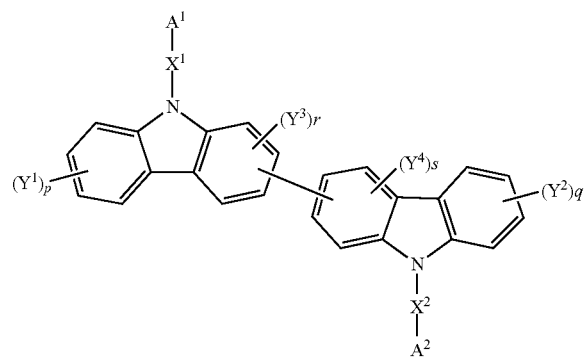

(13)

In the formula (13), $A^1$ represents a substituted or unsubstituted nitrogen-containing heterocyclic group having 1 to 30 ring carbon atoms (except for a substituted or unsubstituted carbazolyl group and a substituted or unsubstituted indolyl group).

$A^2$ represents a substituted or unsubstituted aromatic hydrocarbon group having 6 to 30 ring carbon atoms, or a substituted or unsubstituted nitrogen-containing heterocyclic group having 1 to 30 ring carbon atoms.

$X^1$ and $X^2$ each independently represent a single bond, a substituted or unsubstituted aromatic hydrocarbon group having 6 to 30 ring carbon atoms, a substituted or unsubstituted fused aromatic hydrocarbon group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms.

When $X^1$ is a single bond, $A^1$ and N, which are adjacent to $X^1$, are directly bonded to each other. When $X^2$ is a single bond, $A^2$ and N, which are adjacent to $X^2$, are directly bonded to each other.

$Y^1$ to $Y^4$ each independently represent a hydrogen atom, a deuterium atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, a substituted or unsubstituted fused aromatic hydrocarbon group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms. Adjacent ones of $Y^1$ to $Y^4$ may be bonded to each other to form a cyclic structure.

p and q each are an integer of 1 to 4, and r and s each are an integer of 1 to 3.

When p and q each are an integer of 2 to 4 and r and s each are an integer of 2 to 3, a plurality of $Y^1$ to $Y^4$ may be the same or different.

At least one of $A^1$, $A^2$, $X^2$, and $Y^1$ to $Y^4$ is a group derived from a monoazine derivative, a diazine derivative or a triazine derivative.

Preferably, the formula (13) is shown as the following formula (13A).

[Chemical Formula 37]

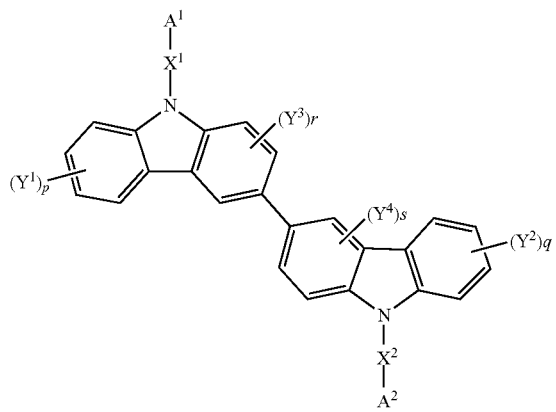

(13A)

In the formula (13A), $A^1$, $A^2$, $X^1$, $X^2$, $Y^1$ to $Y^4$, p, q, r and s are the same as those of the formula (13).

Preferably, the formula (13A) is shown as the following formula (13B).

[Chemical Formula 38]

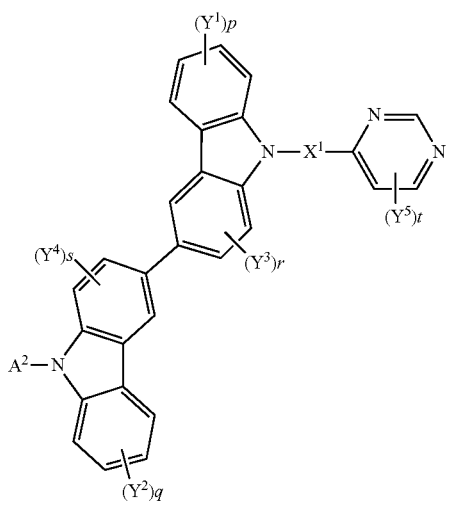

(13B)

In the formula (13B), $A^2$, $X^1$, $Y^1$ to $Y^4$, p, q, r and s are the same as those of the formula (13). $Y^5$ is the same as $Y^1$ to $Y^4$ of the formula (13). t is an integer of 1 to 3. When t is 2 or 3, a plurality of $Y^5$ may be the same or different.

Preferably, the formula (13) is shown as the following formula (13C).

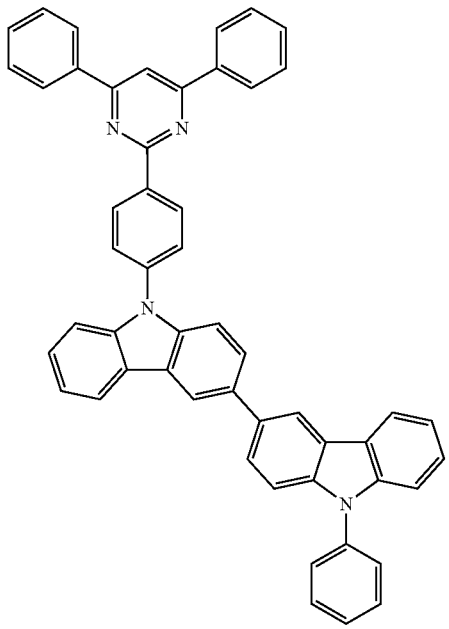

[Chemical Formula 39]

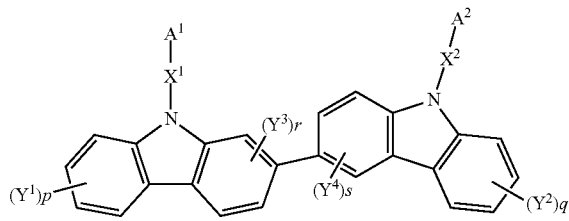

(13C)

In the formula (13C), $A^1$, $A^2$, $X^1$, $X^2$, $Y^1$ to $Y^4$, p, q, r and s are the same as those of the formula (13).

Preferably, the formula (13) is shown as the following formula (13D).

[Chemical Formula 40]

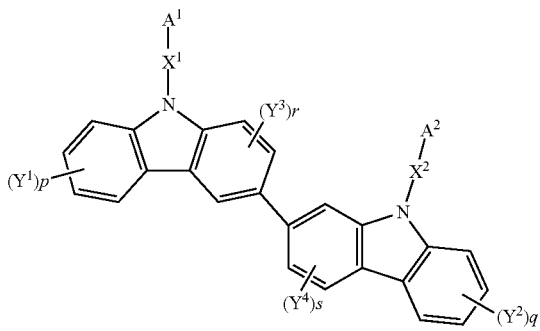

(13D)

In the formula (13D), $A^1$, $A^2$, $X^1$, $X^2$, $Y^1$ to $Y^4$, p, q, r and s are the same as those of the formula (13).

The second host material of the formula (13A) is exemplified by the following compounds. The second host material of the formula (13A) includes the following exemplified compounds represented by the formula (13B) as the second host material.

[Chemical Formula 41]

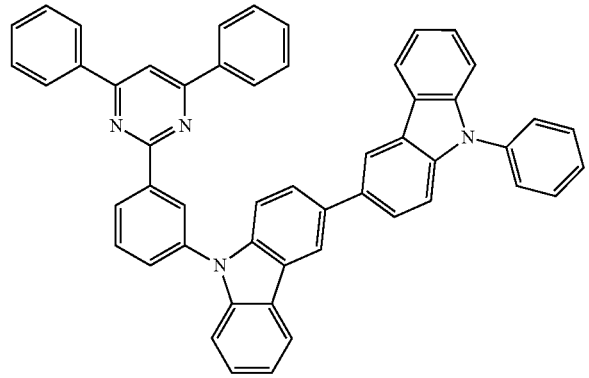

-continued
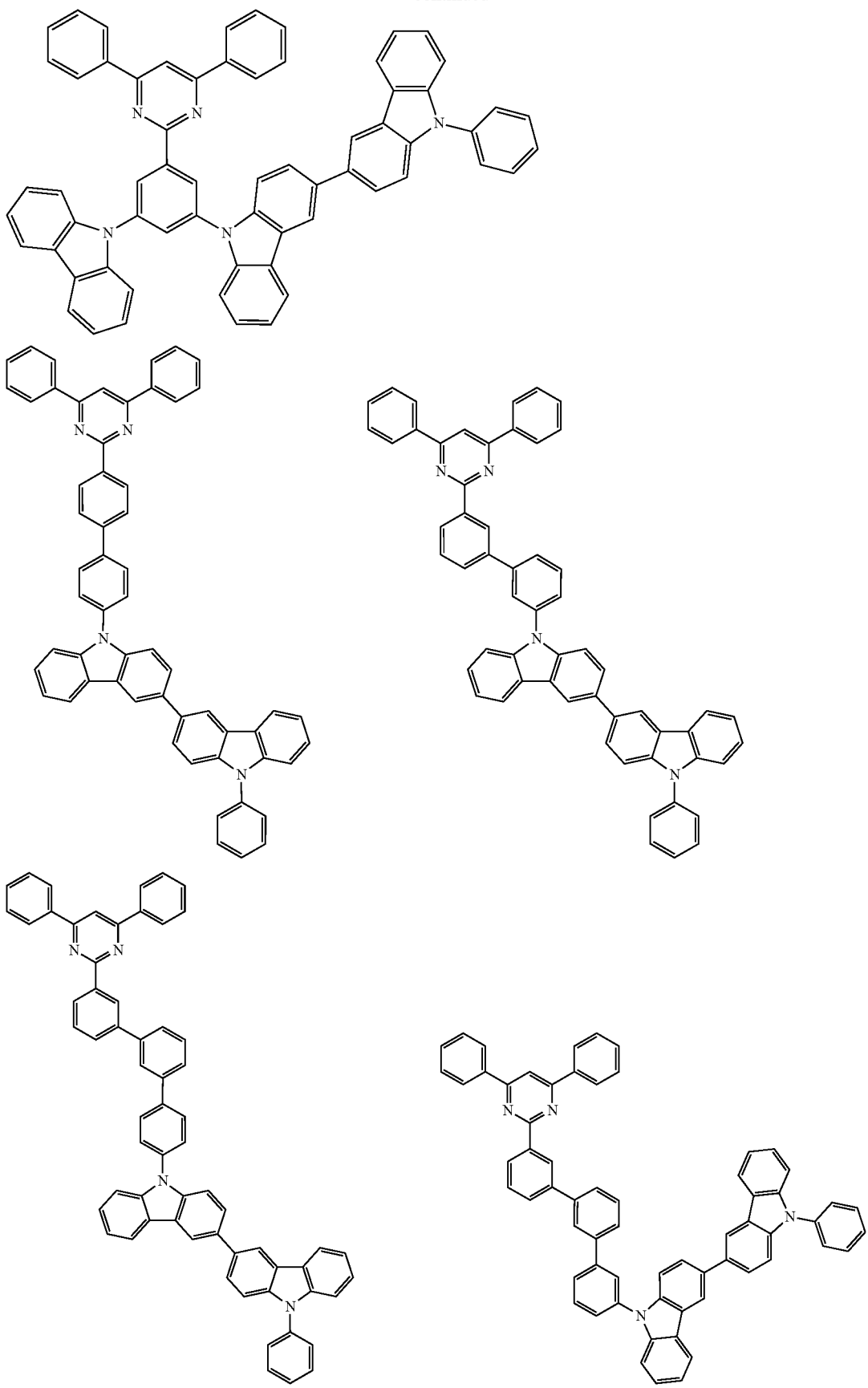

-continued
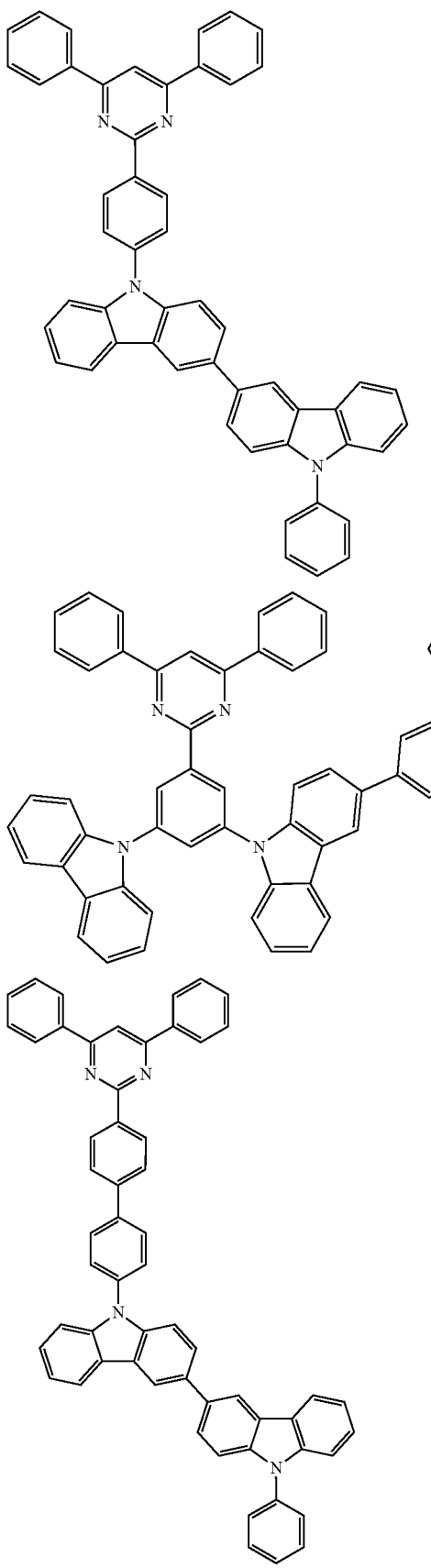
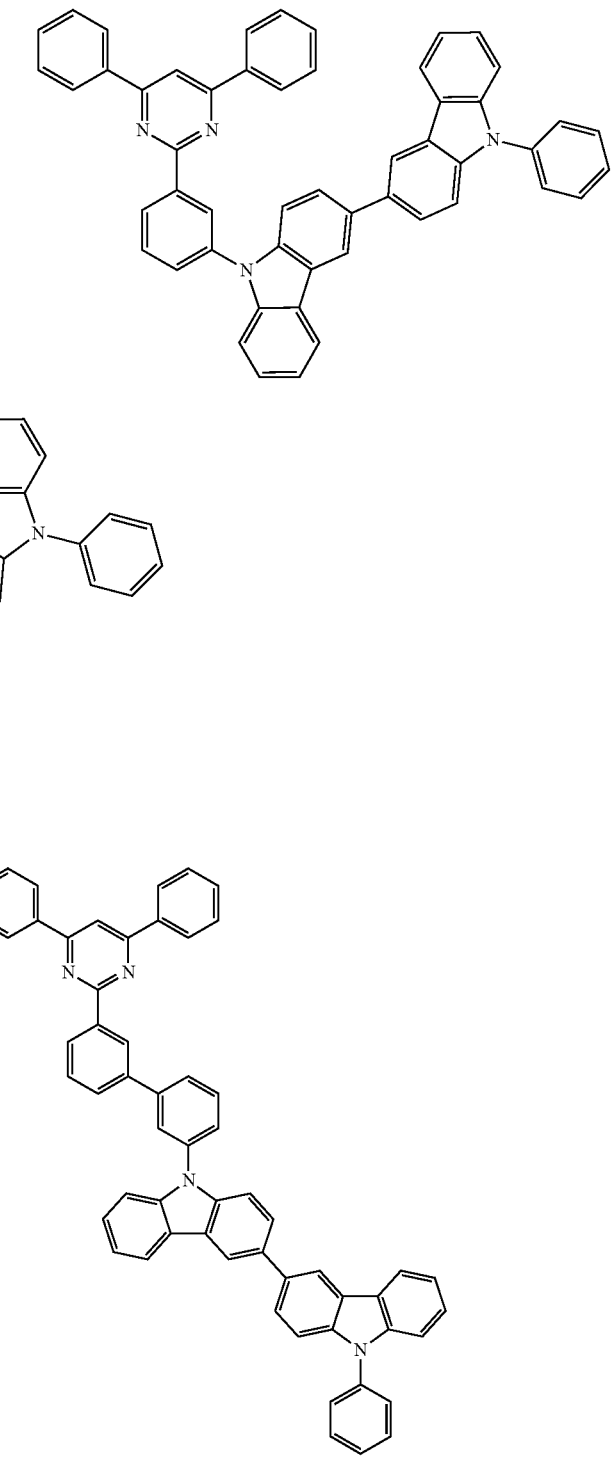

-continued
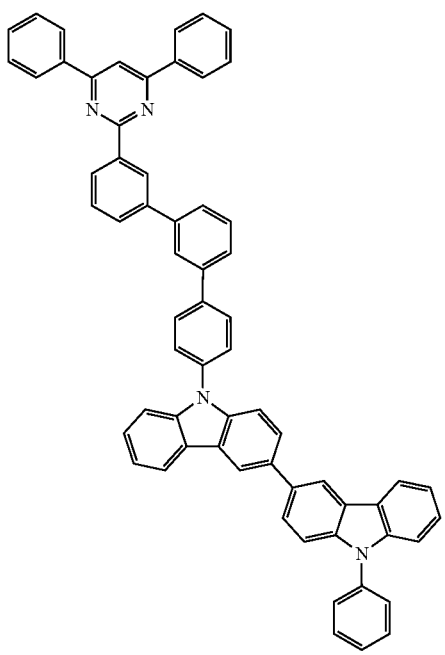
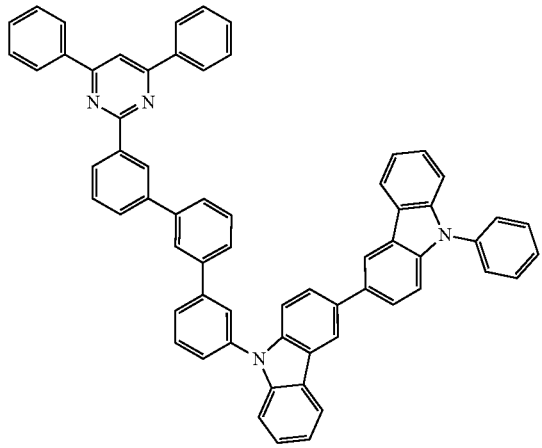
[Chemical Formula 42]
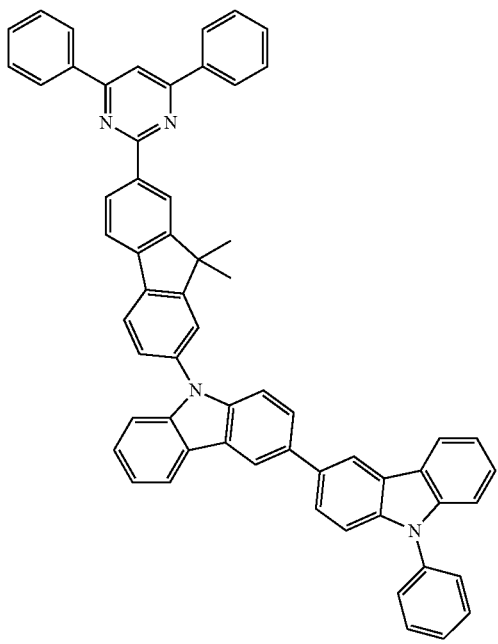
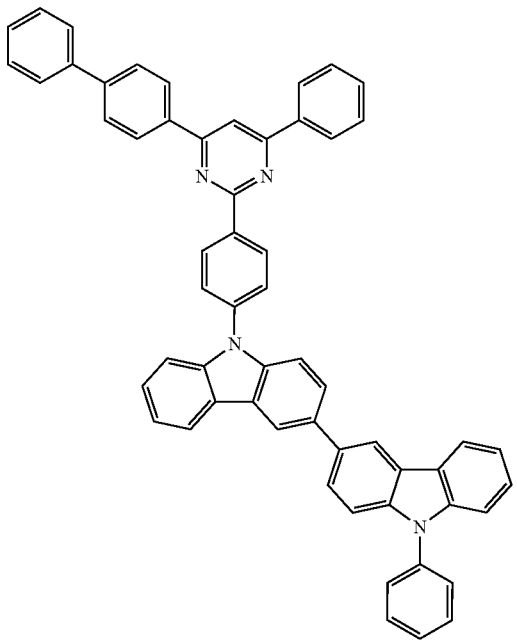

-continued
87
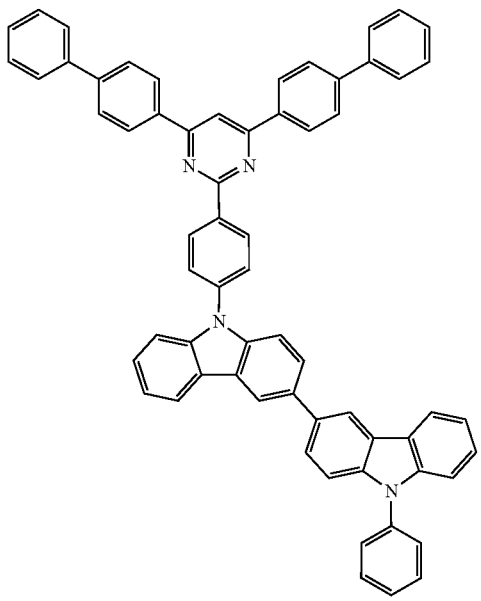
88
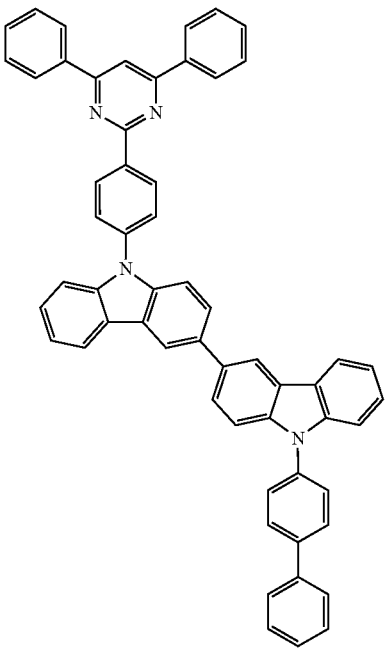
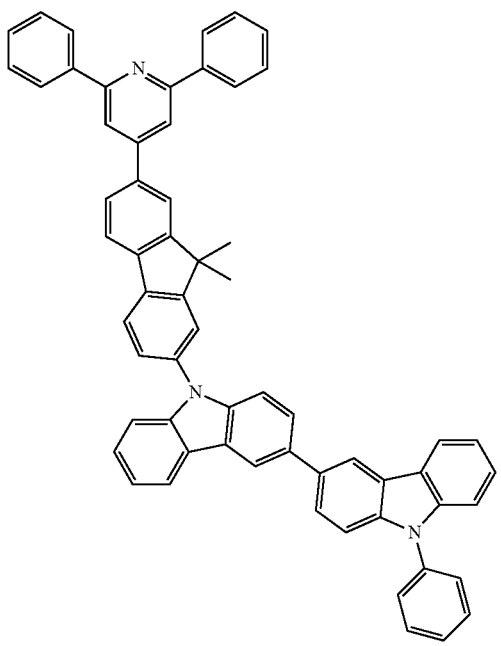
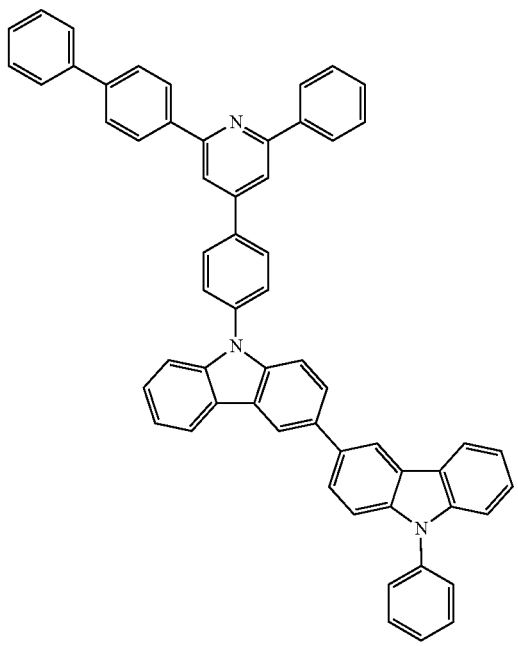

-continued
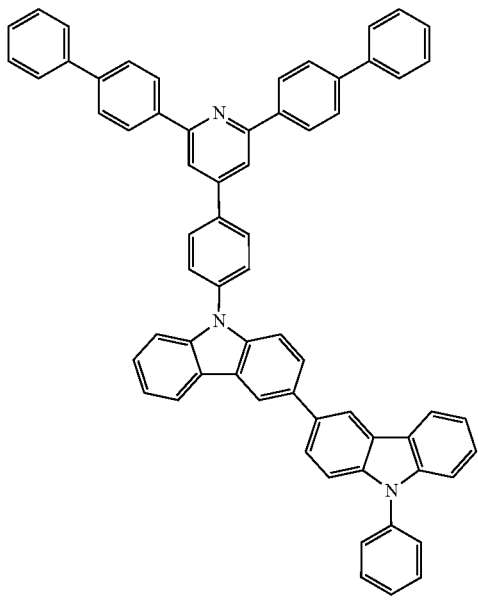
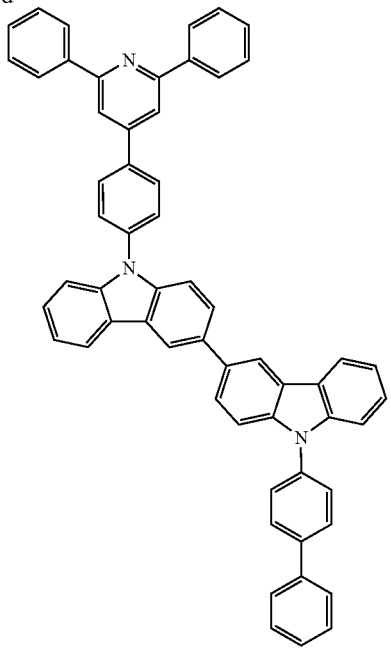
[Chemical Formula 43]
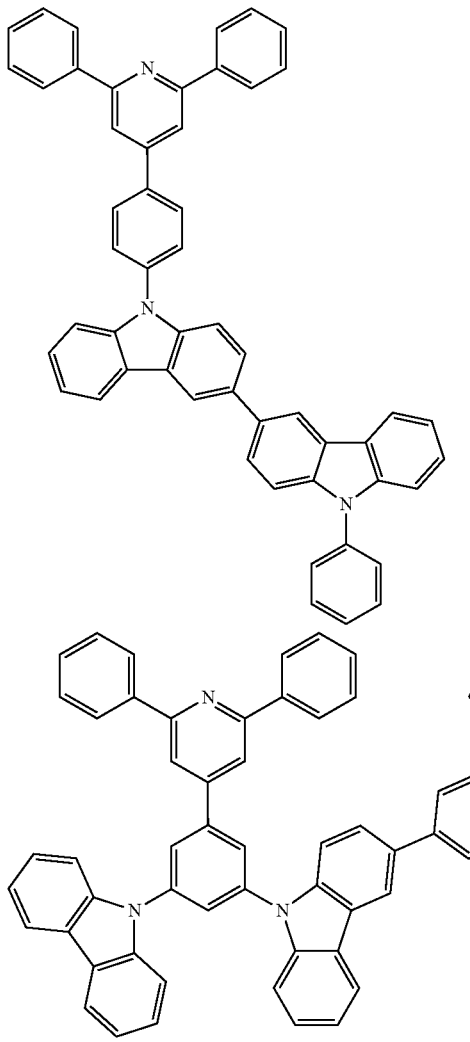
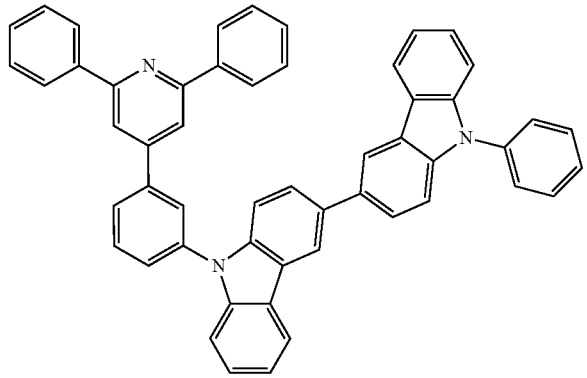
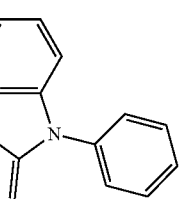
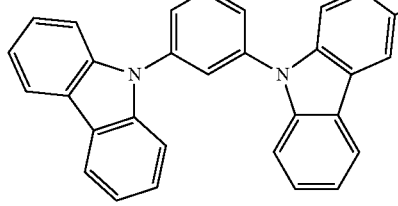

-continued
91
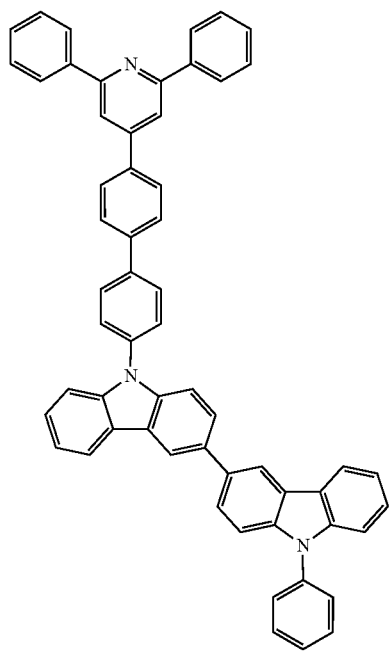
92
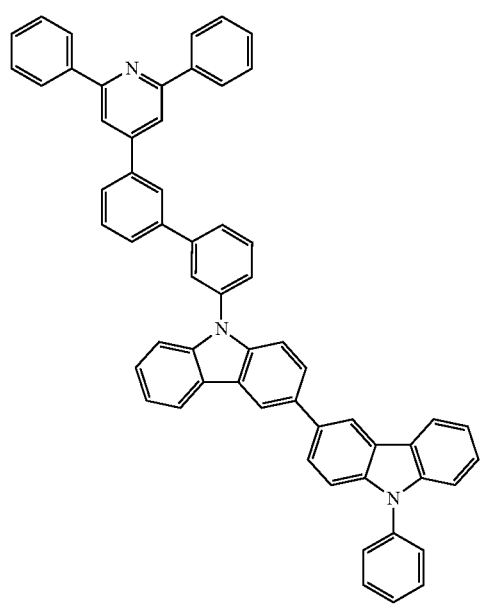
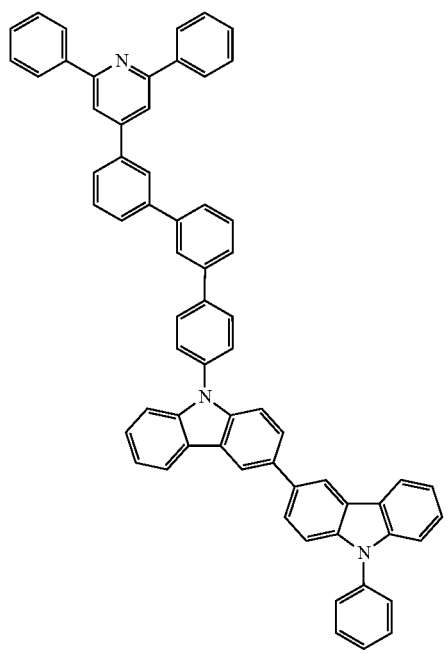
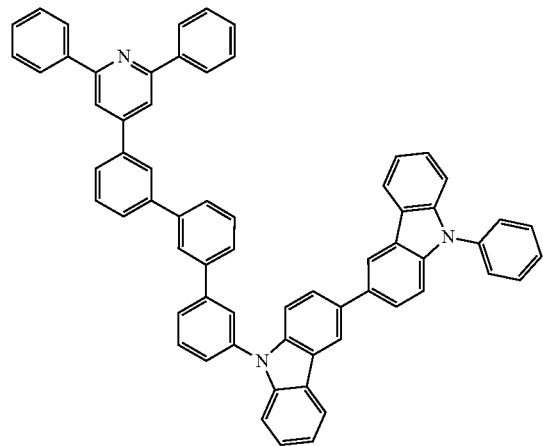

93
94
-continued
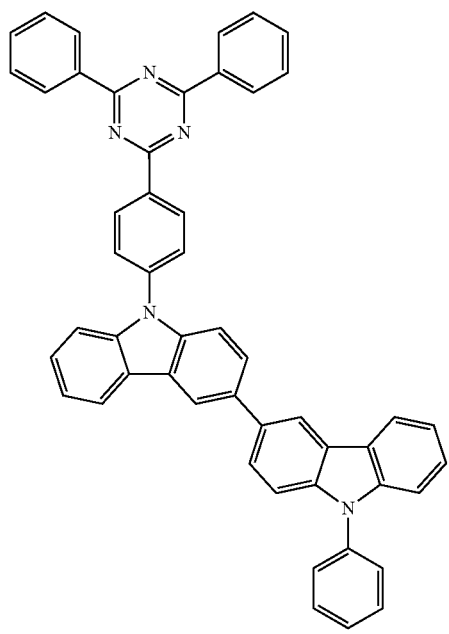
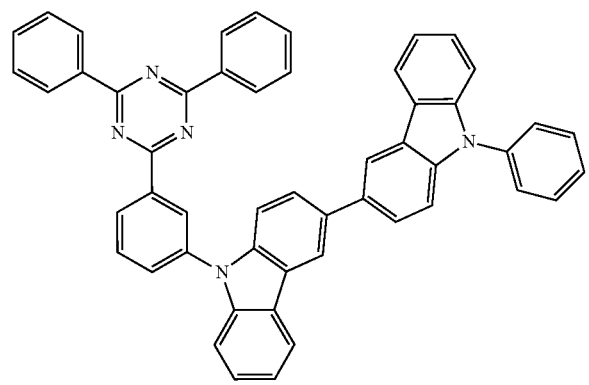
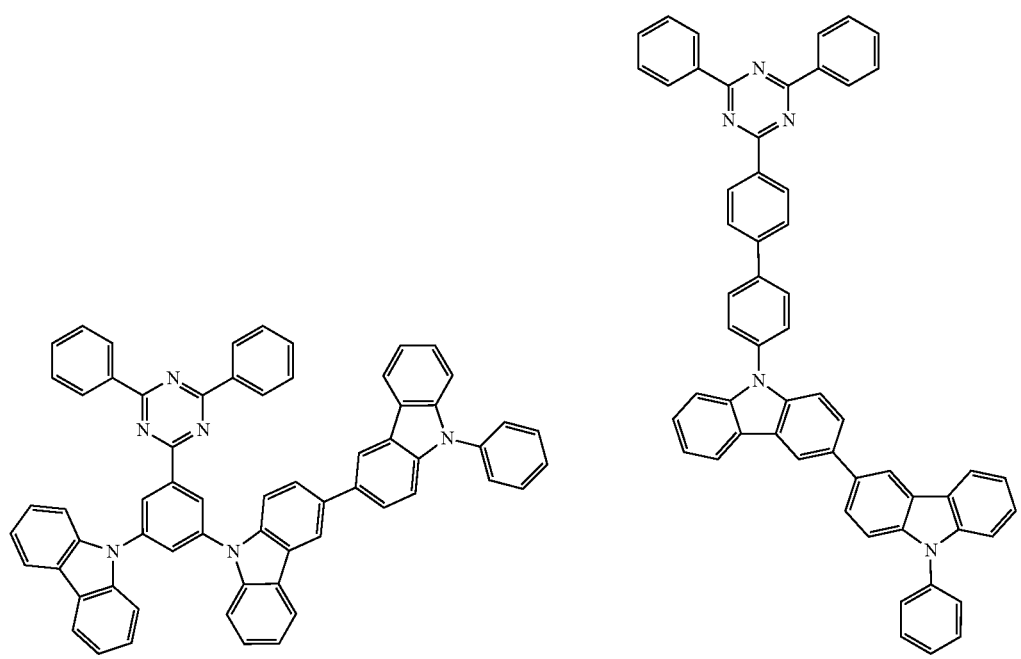

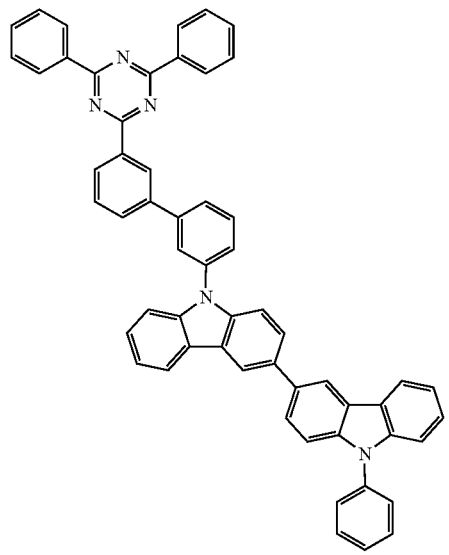
-continued
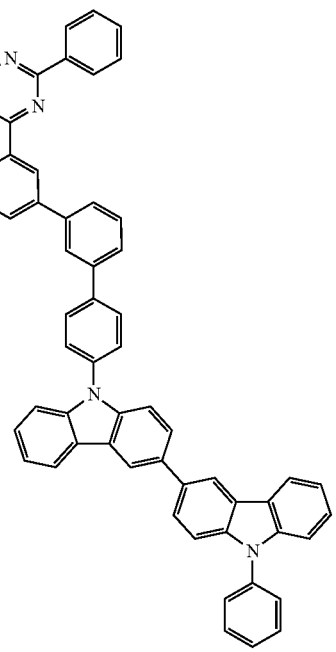
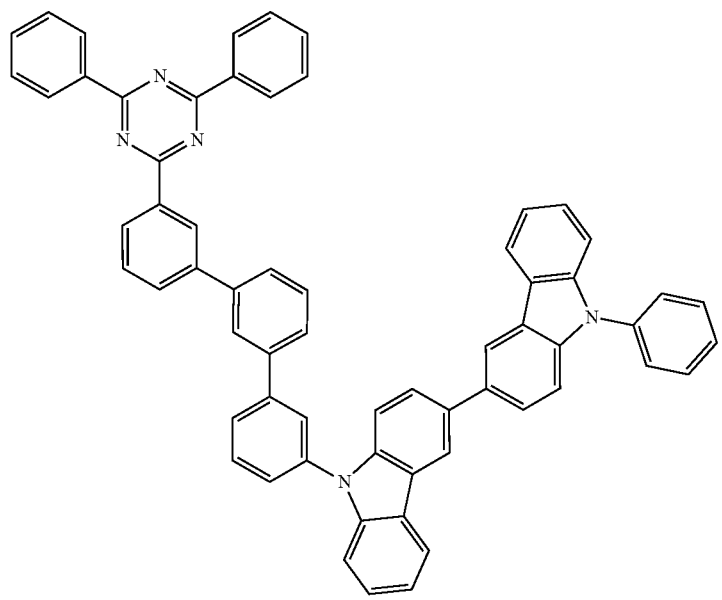

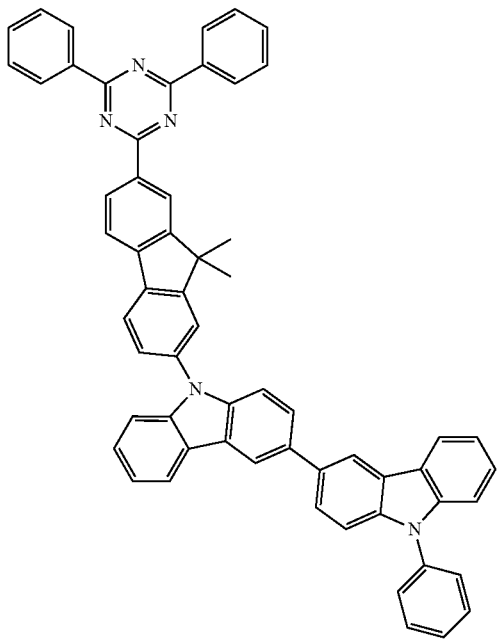
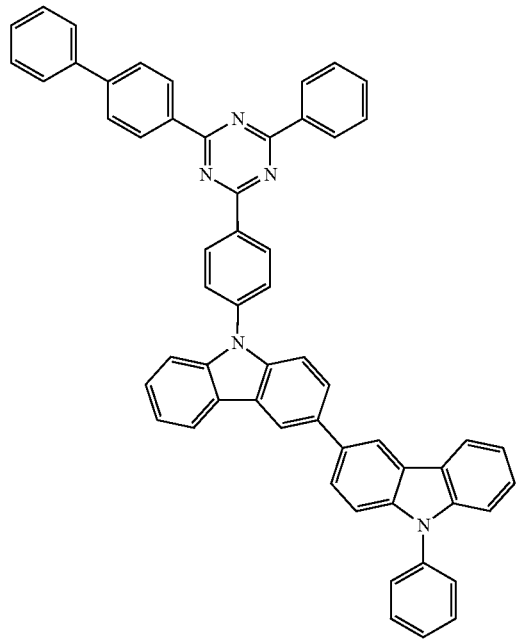
[Chemical Formula 44]
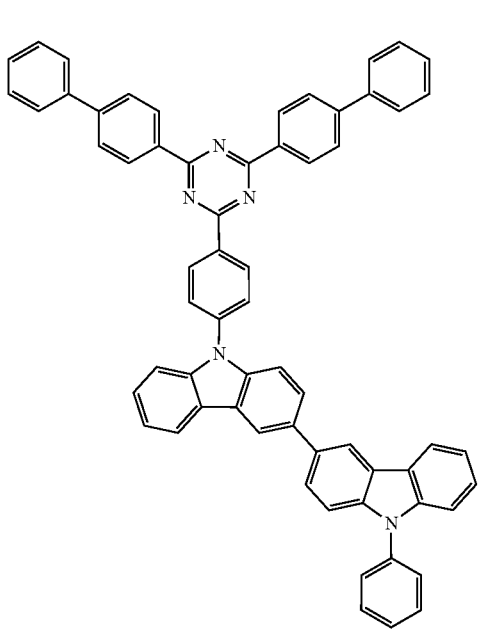
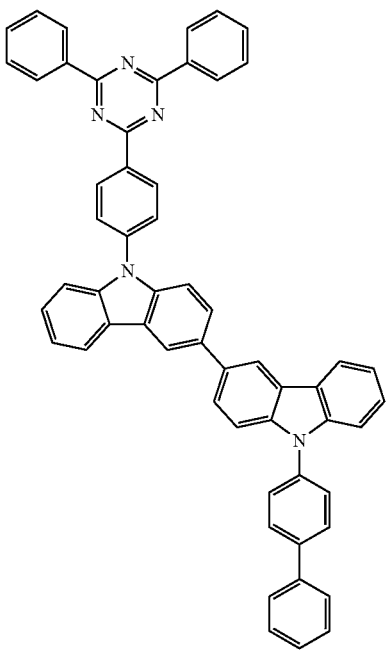

-continued
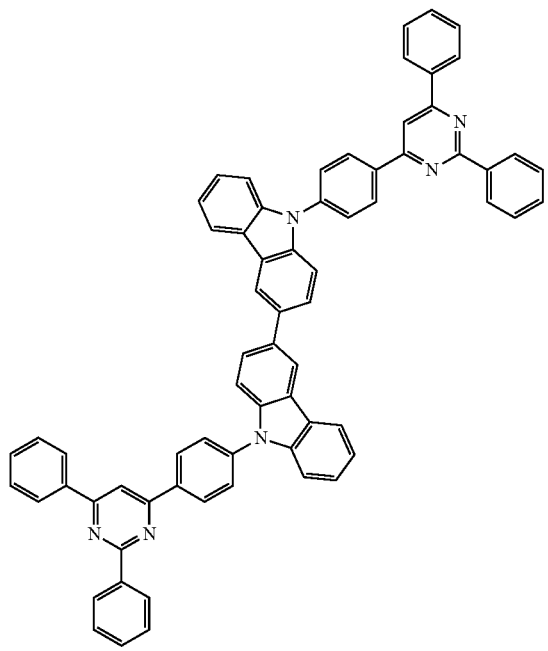
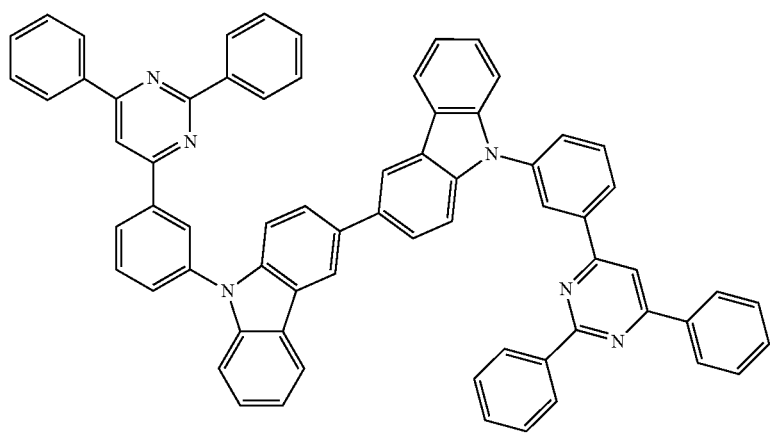
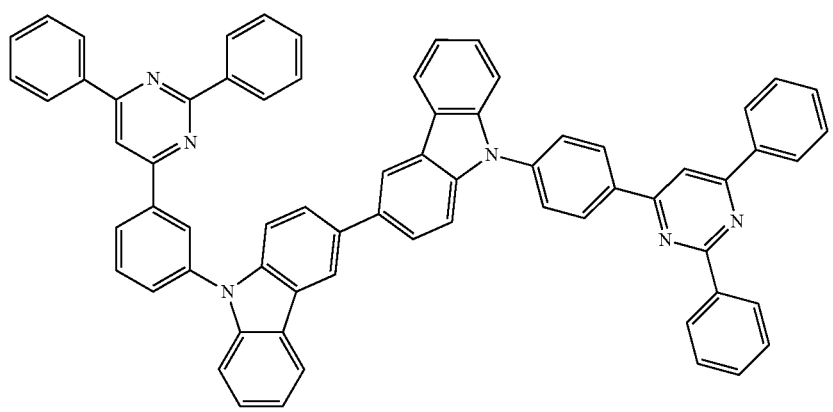

-continued
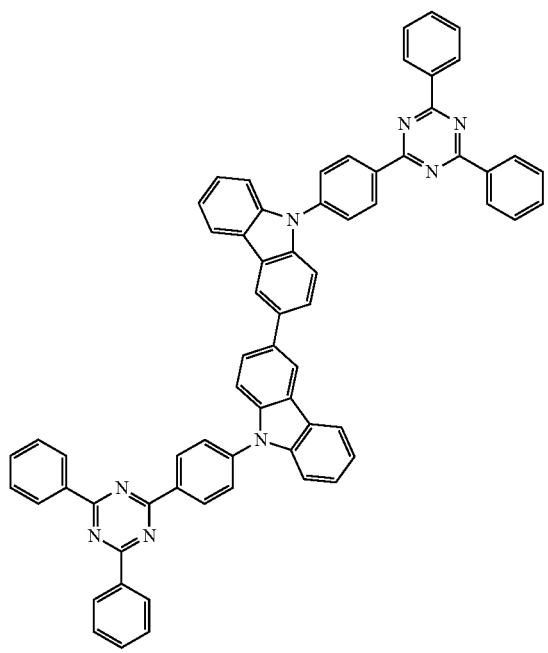
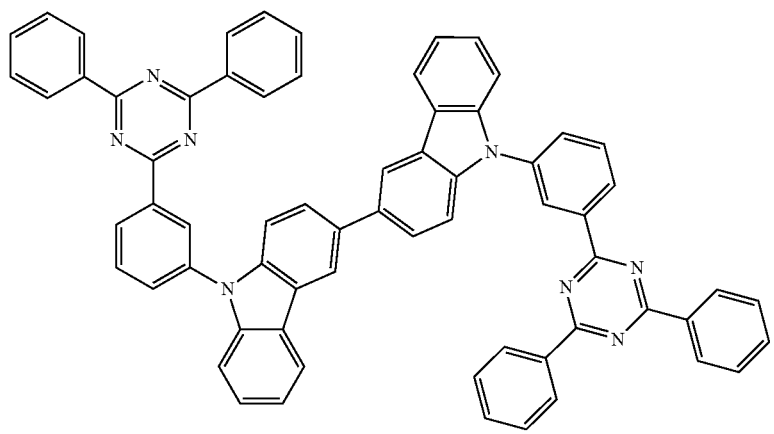
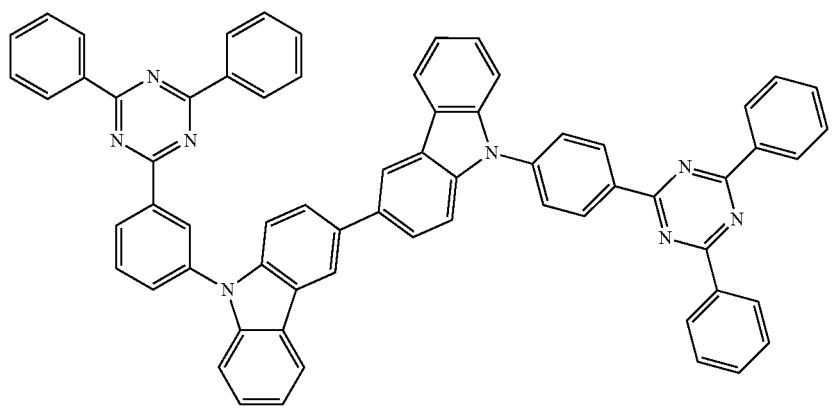

-continued
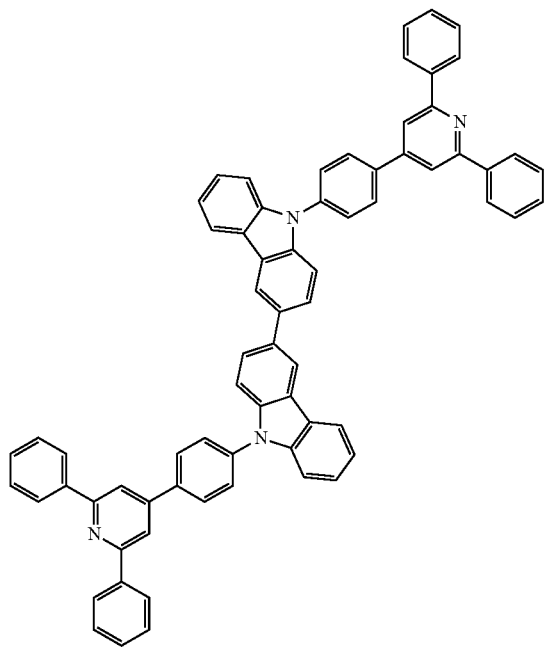
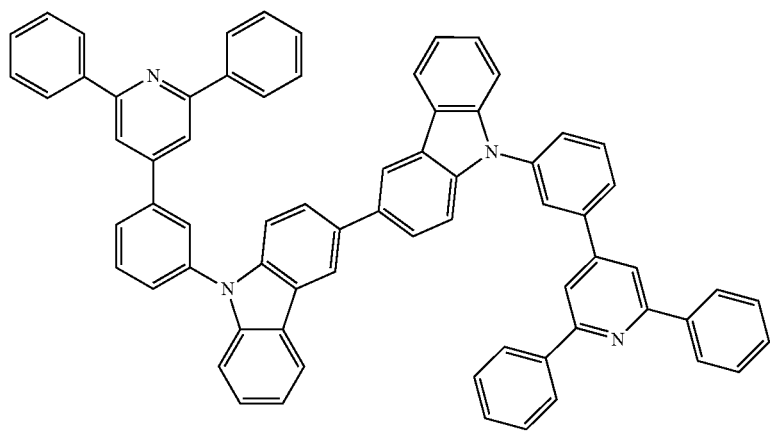
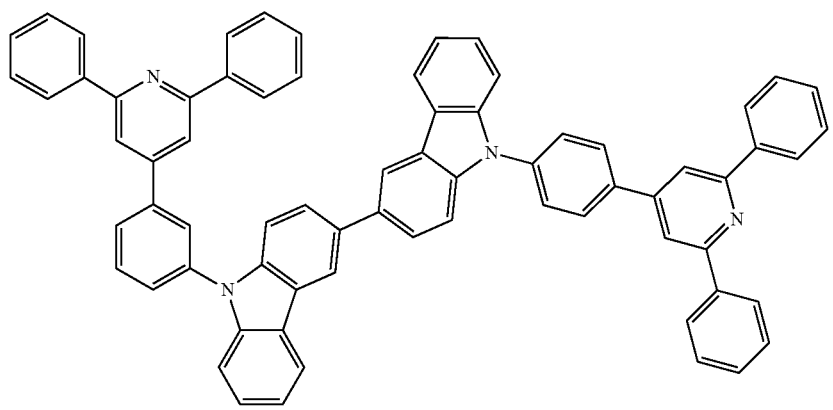

-continued
[Chemical Formula 45]
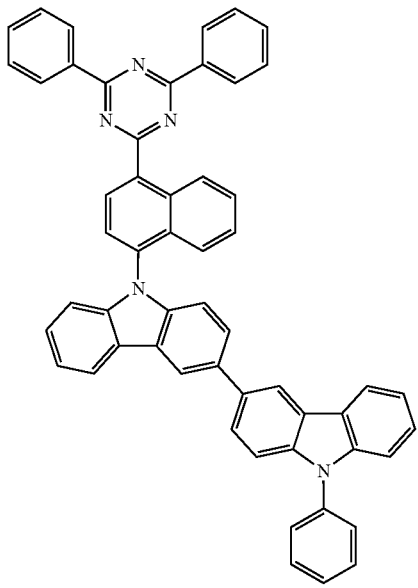
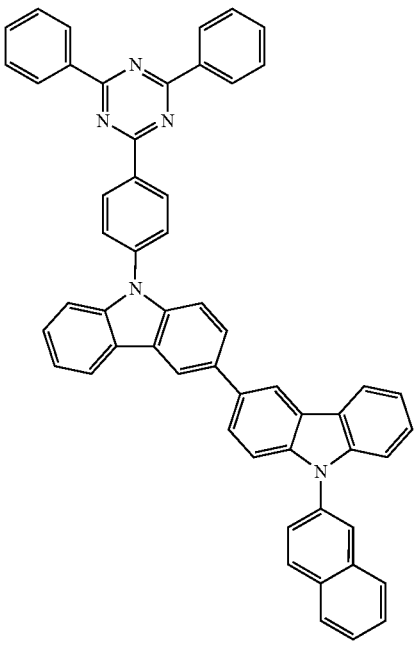
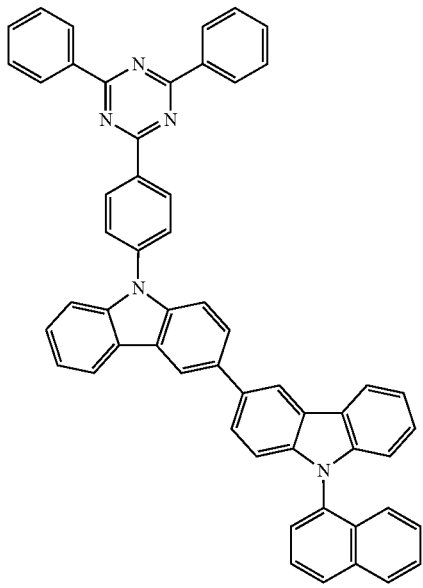
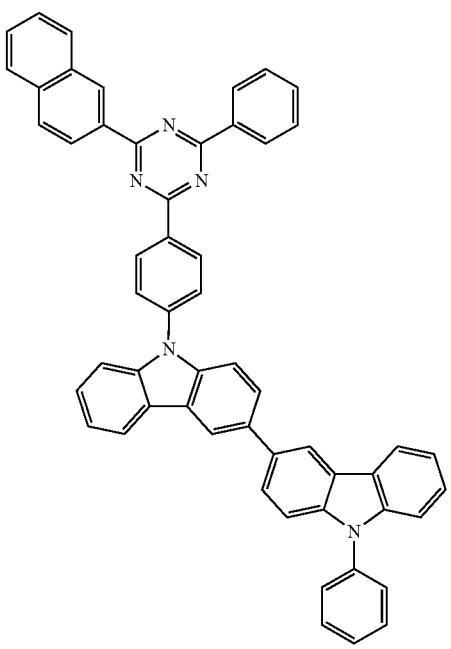

-continued
| 107 | 108 |
|---|---|
| 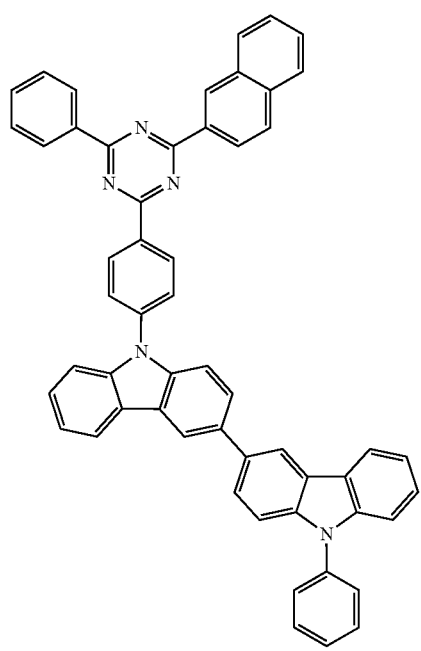 | 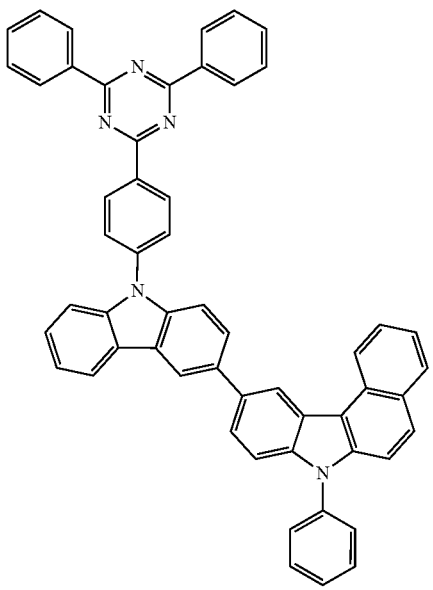 |
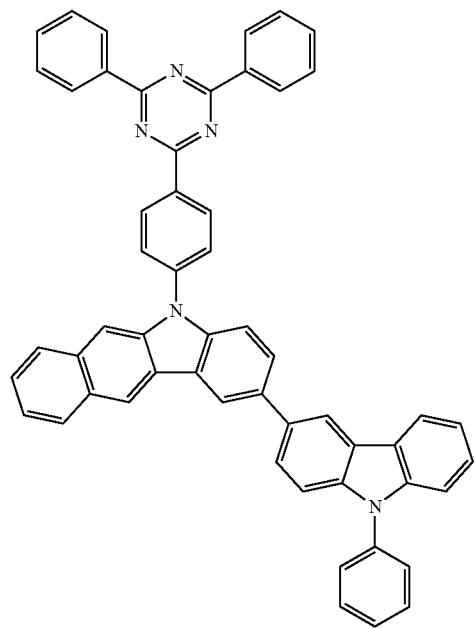 [SMILES: c1ccc(-c2cc(-c3ccc(-n4c5ccc(-c6ccc7c(c6)c6ccccc6n7-c6ccccc6)cc5c5cc6ccccc6cc54)cc3)nc(-c3ccccc3)n2)cc1]

[Chemical Formula 46]
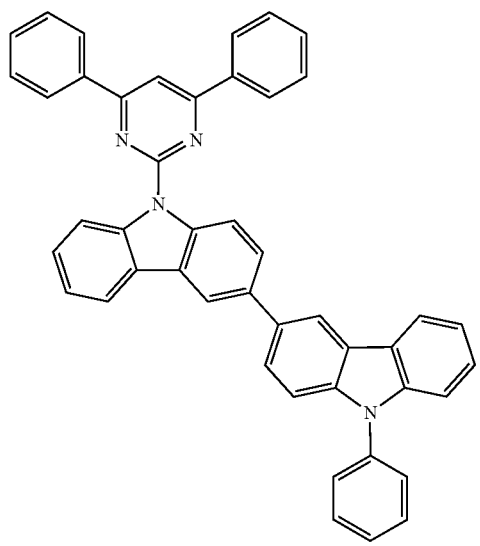
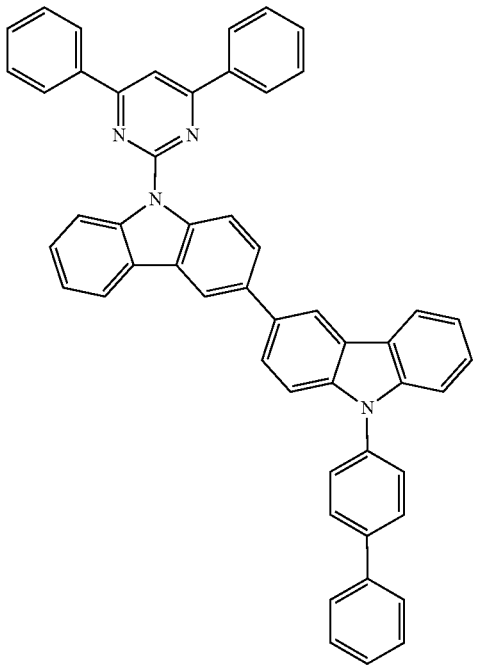
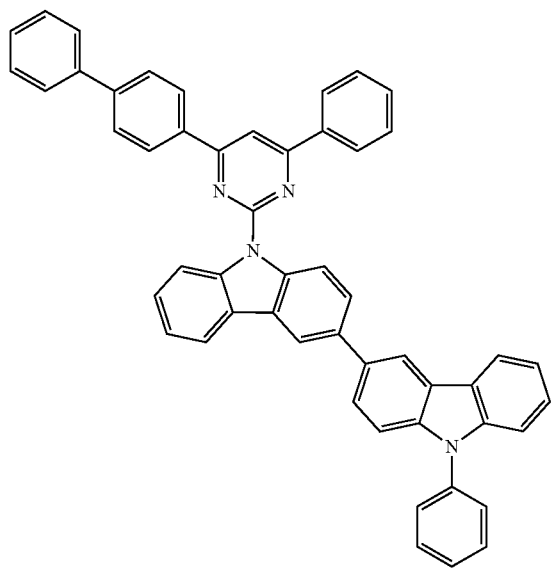
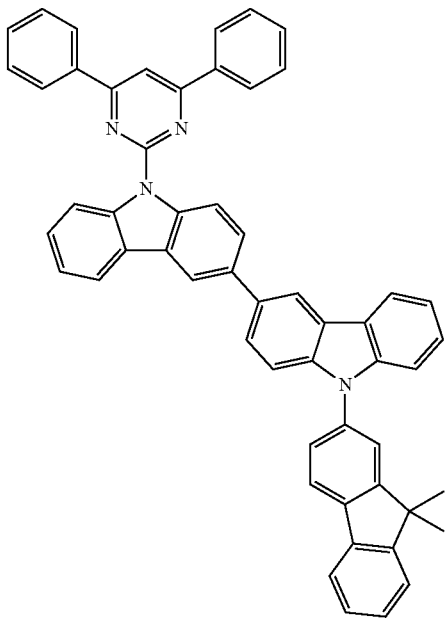

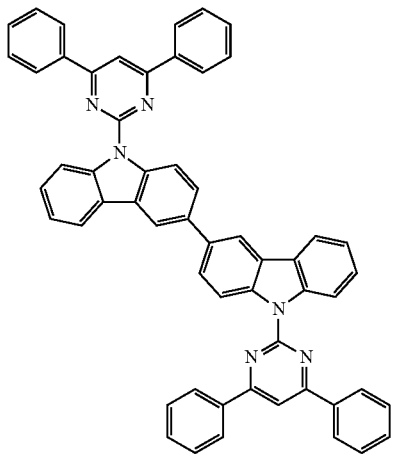
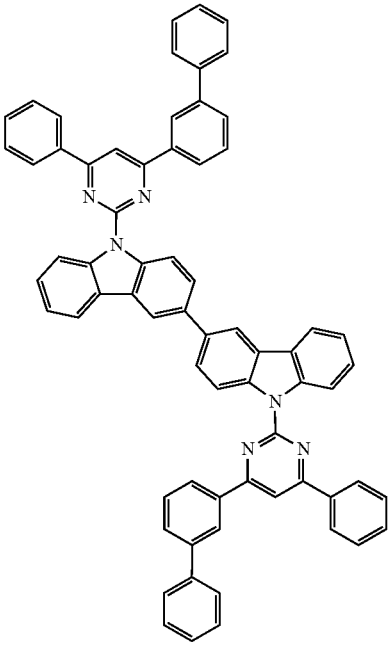
The second host material of the formula (13B) is exemplified by the following compounds.
[Chemical Formula 47]
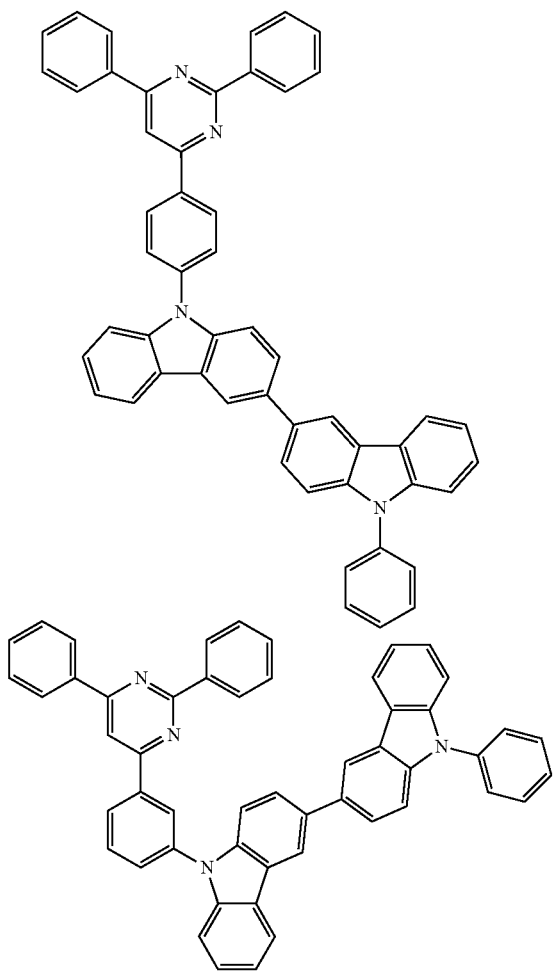
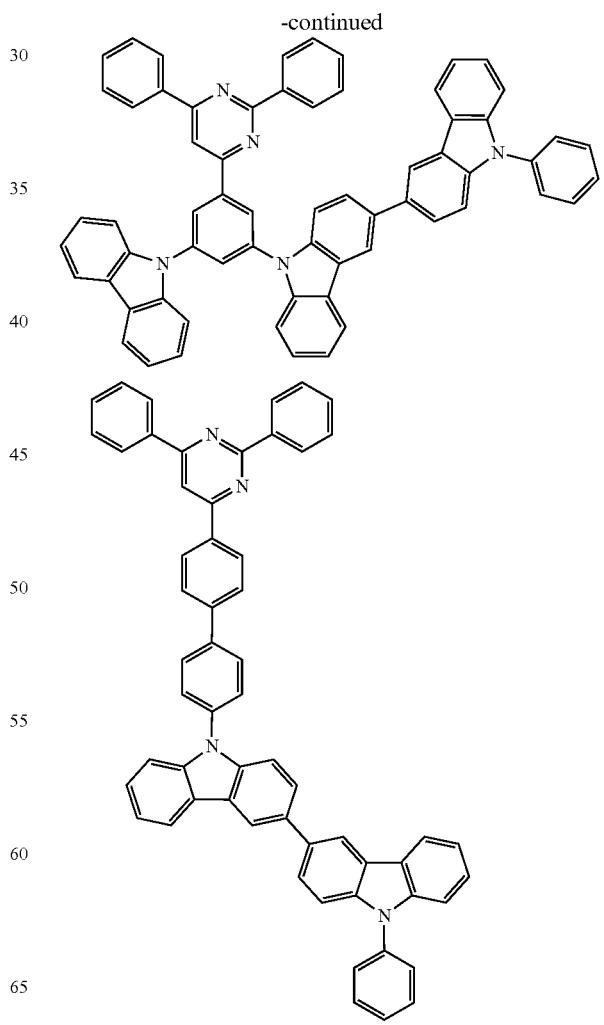

113
-continued
114
-continued
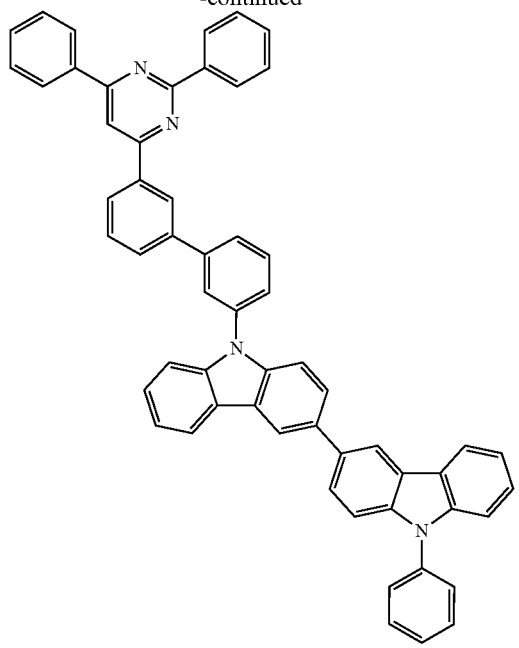
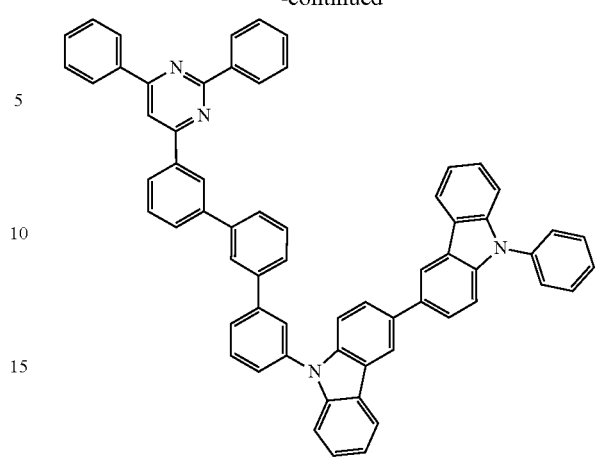
[Chemical Formula 48]
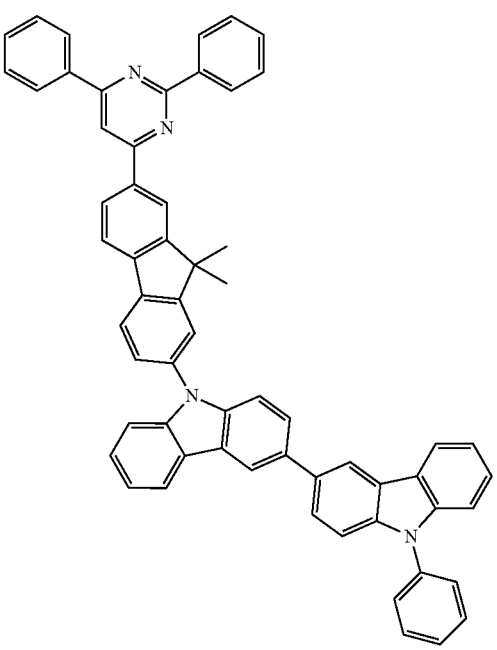

115
-continued
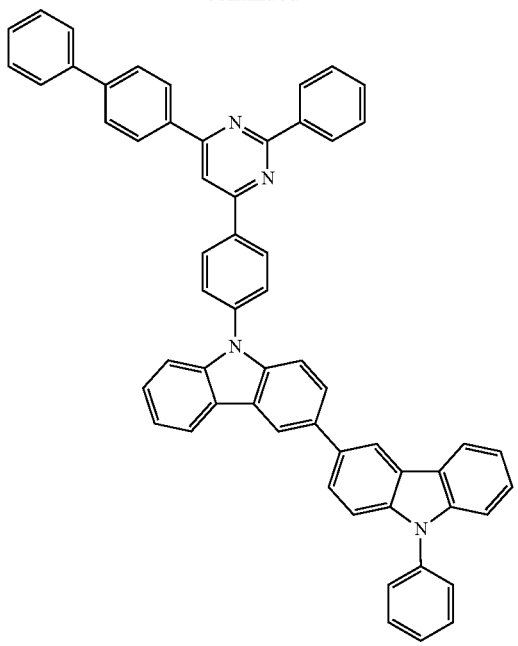
116
-continued
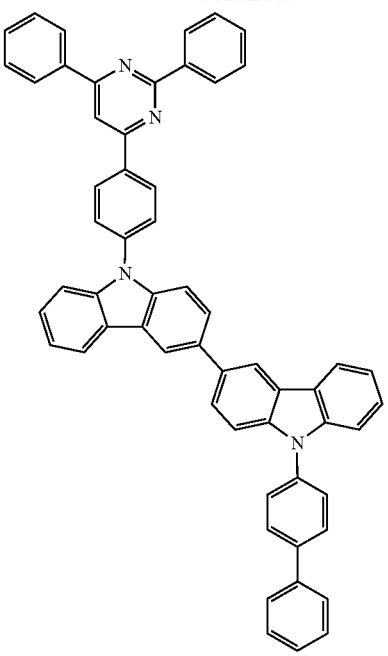
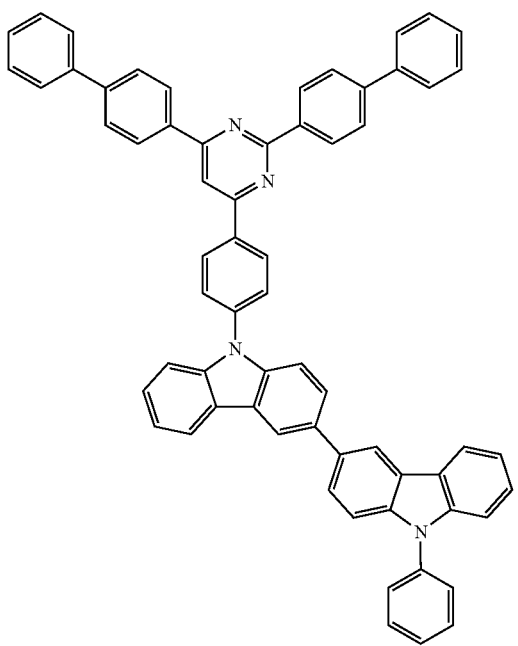
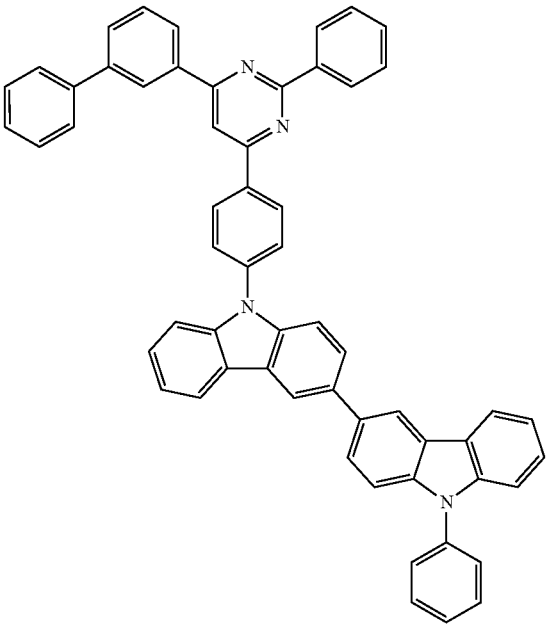

117
-continued
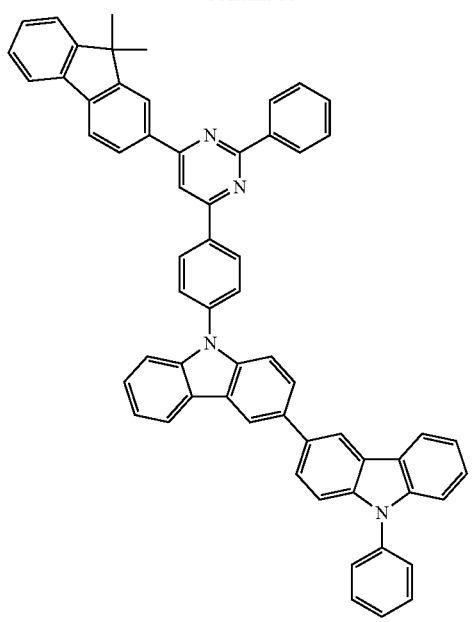
118
-continued
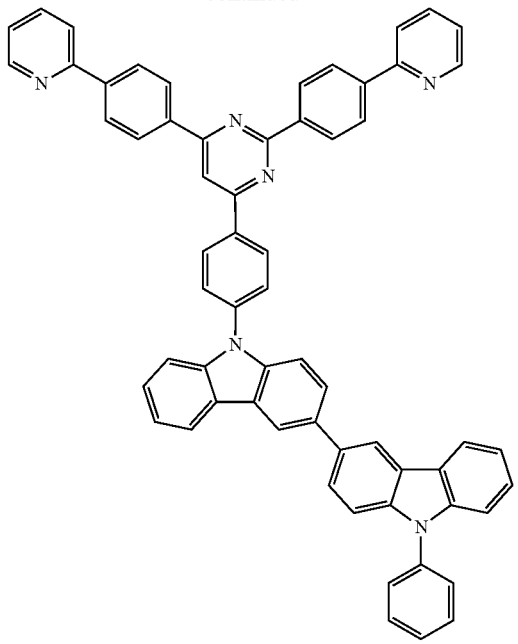
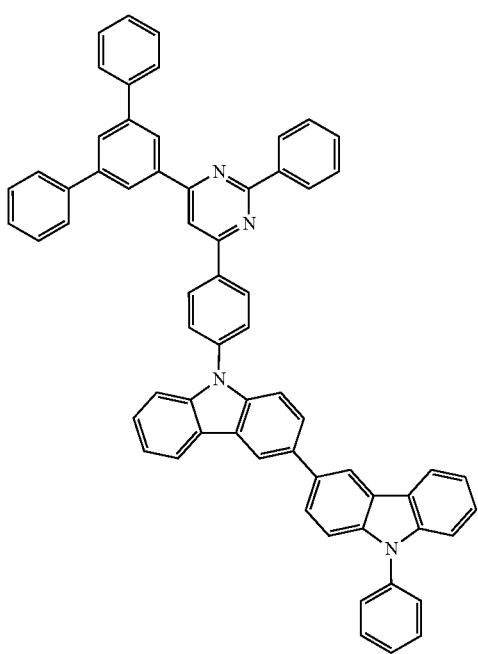
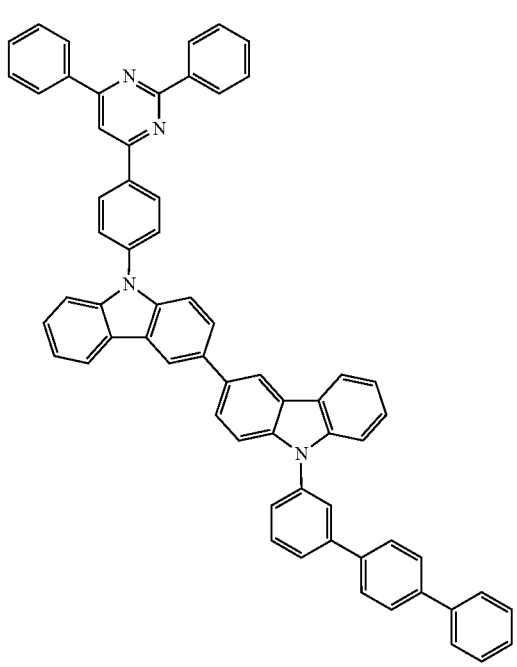

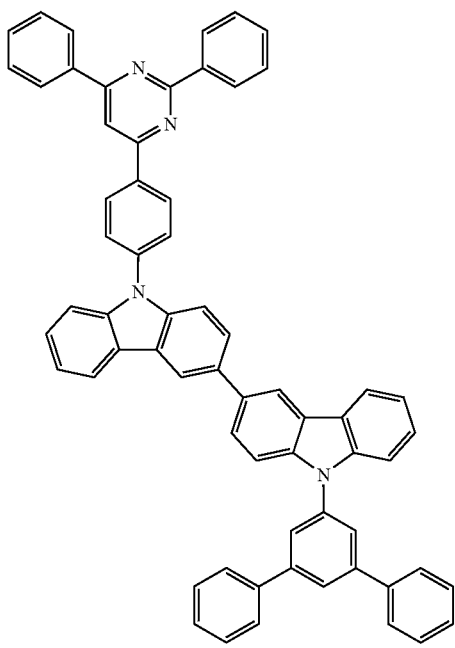
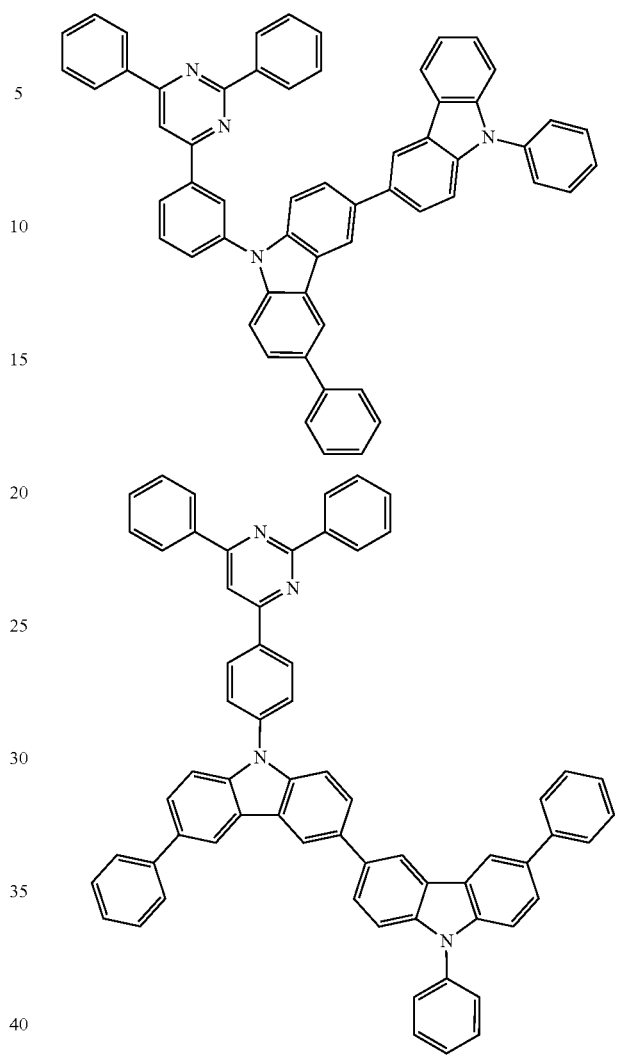
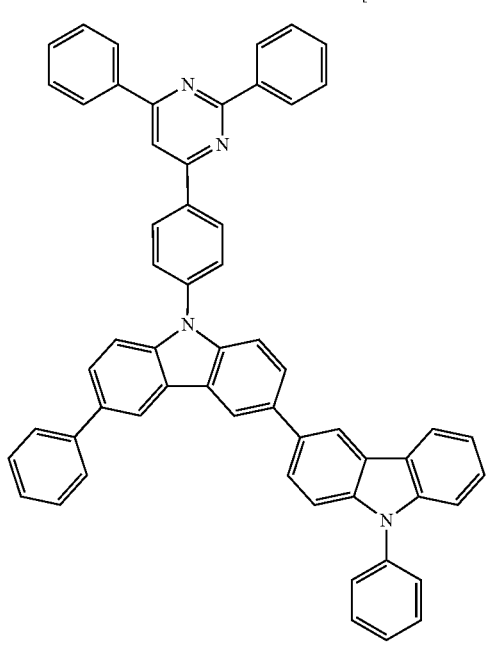
[Chemical Formula 49]

121
-continued
122
-continued
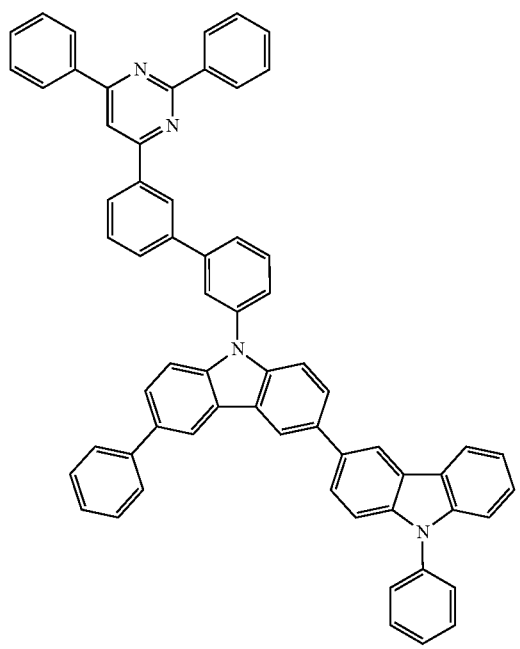
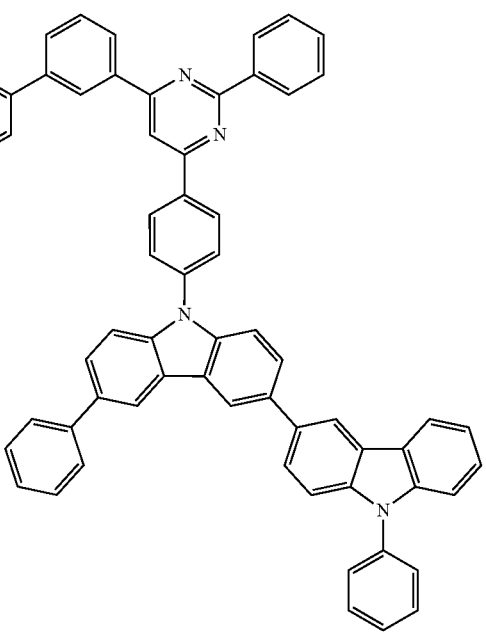

123
-continued
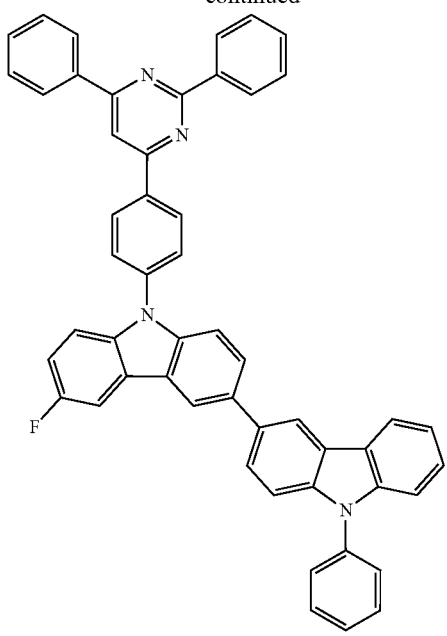
124
-continued
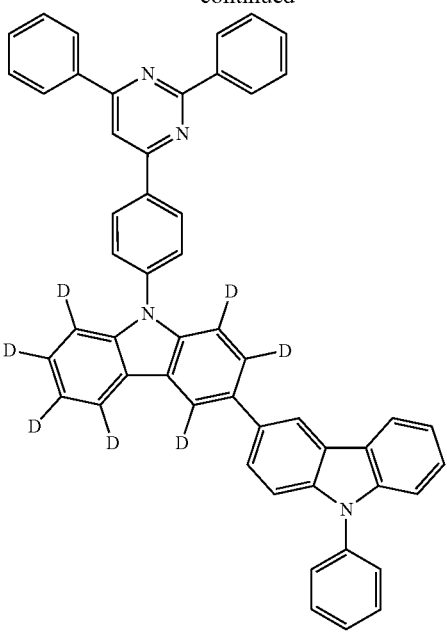
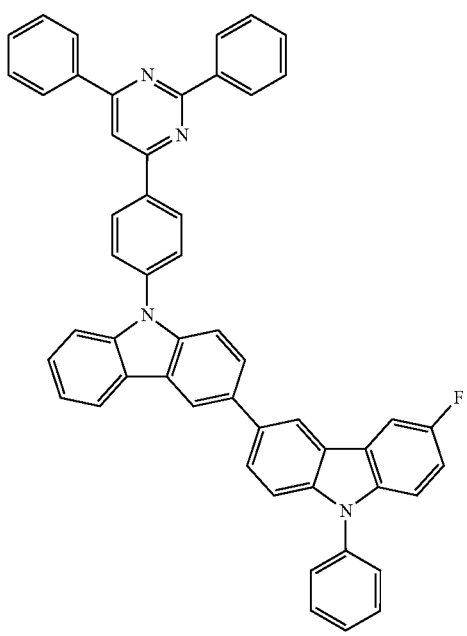
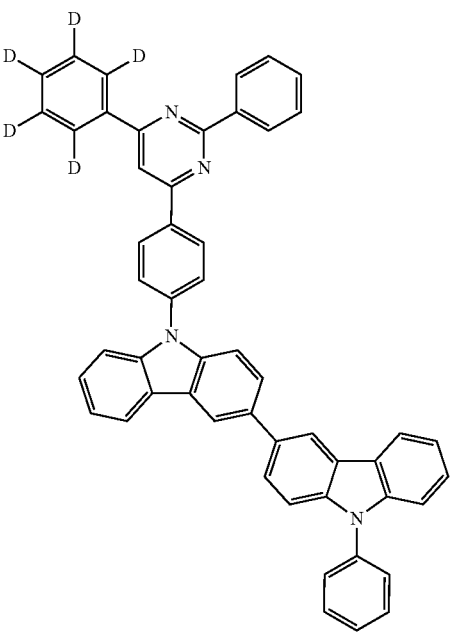

125
-continued
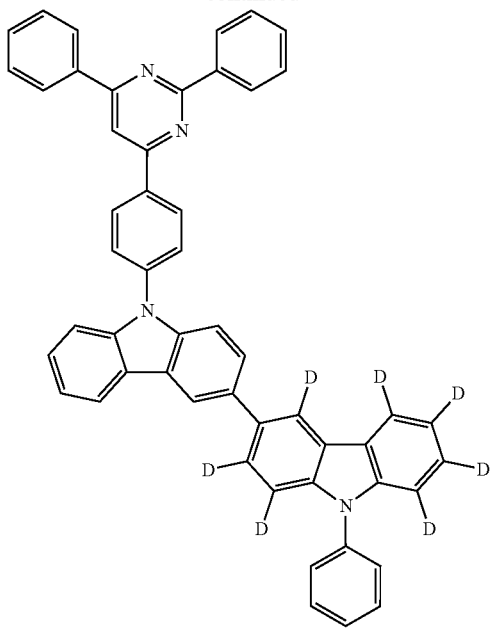
126
-continued
[Chemical Formula 50]
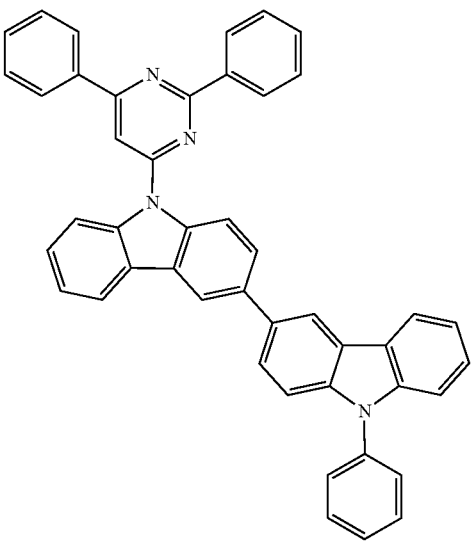
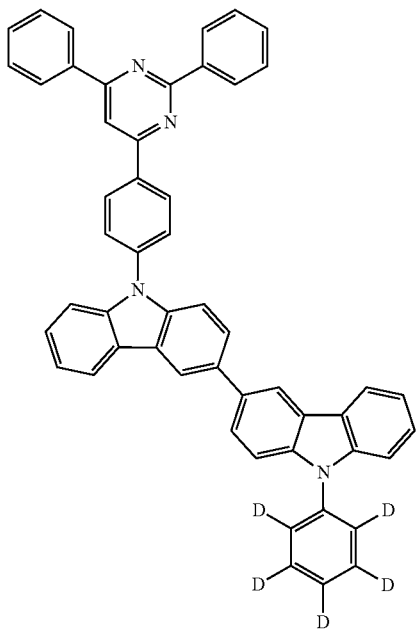
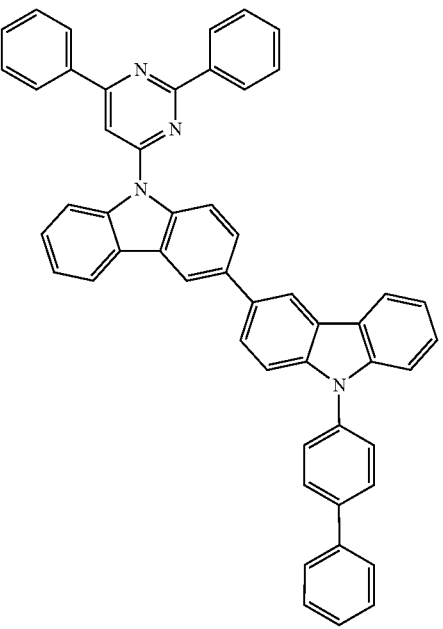

127
-continued
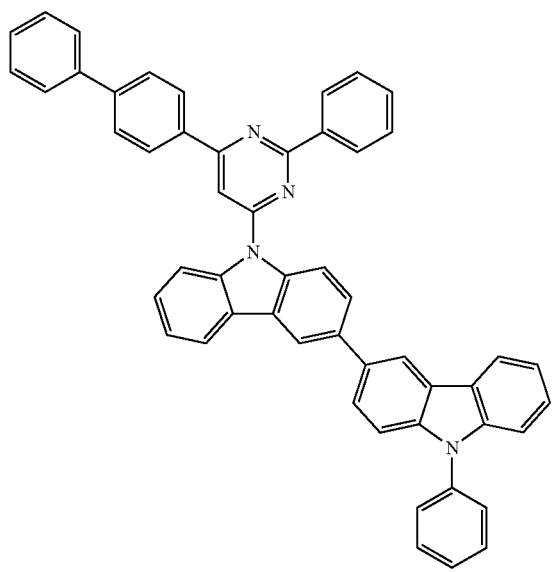
128
-continued
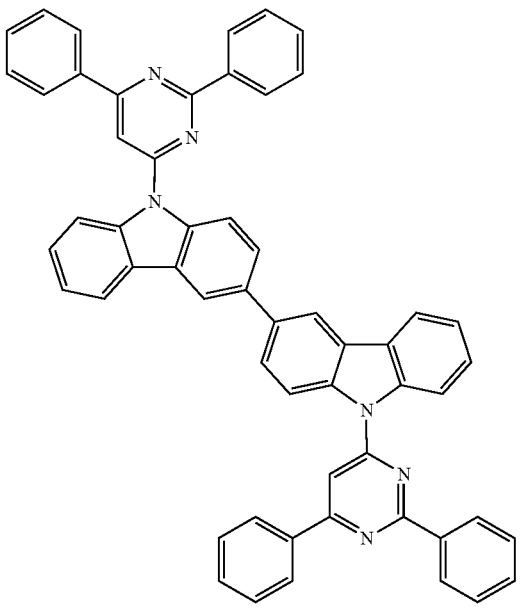
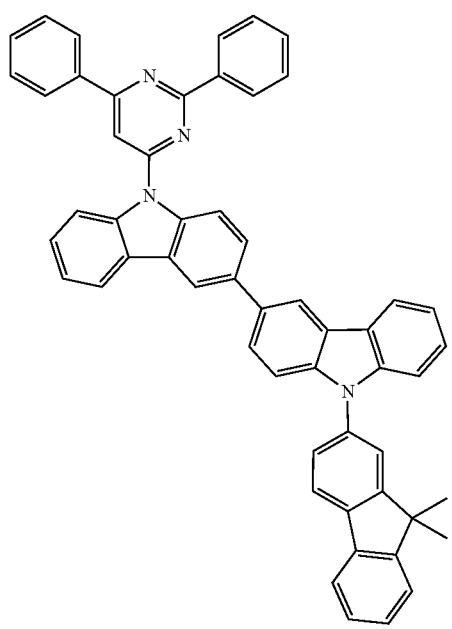
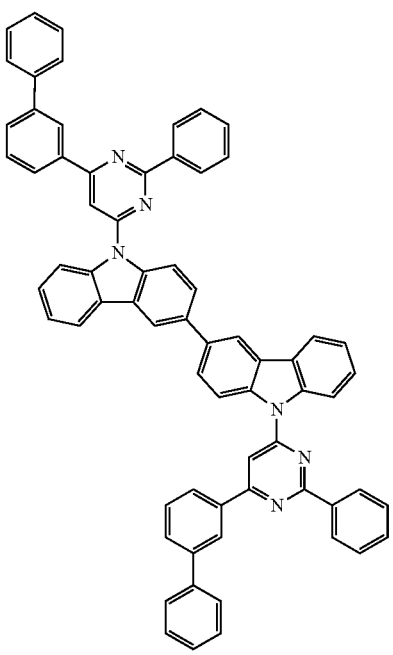

129
-continued
[Chemical Formula 51]
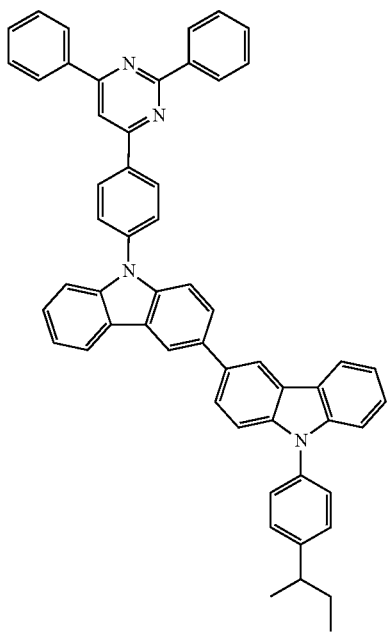
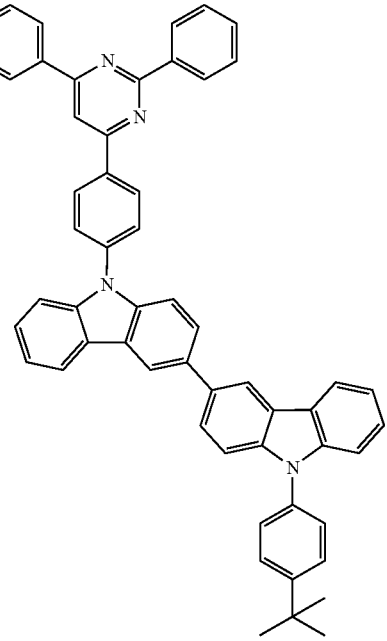
130
-continued
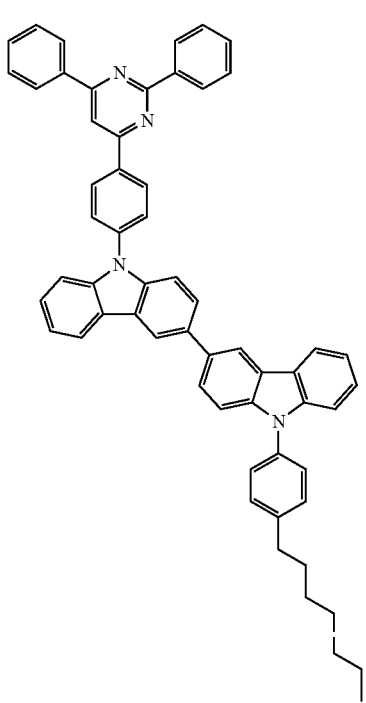
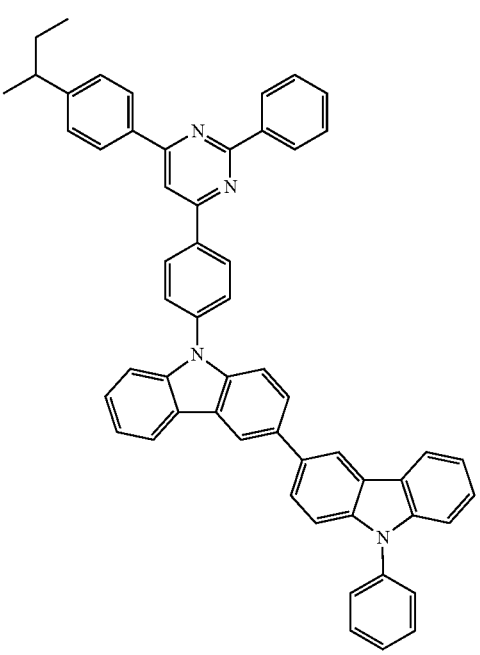

131
-continued
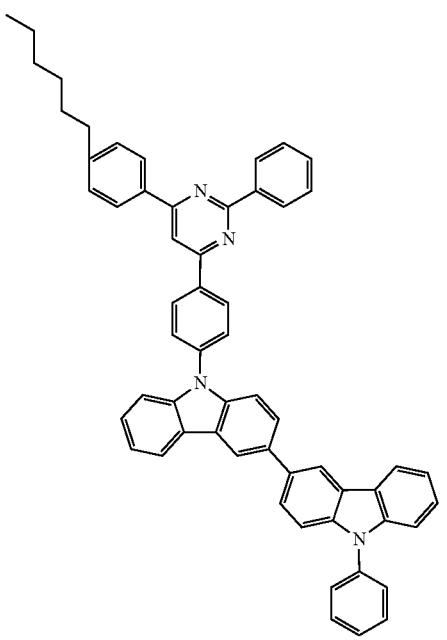
132
-continued
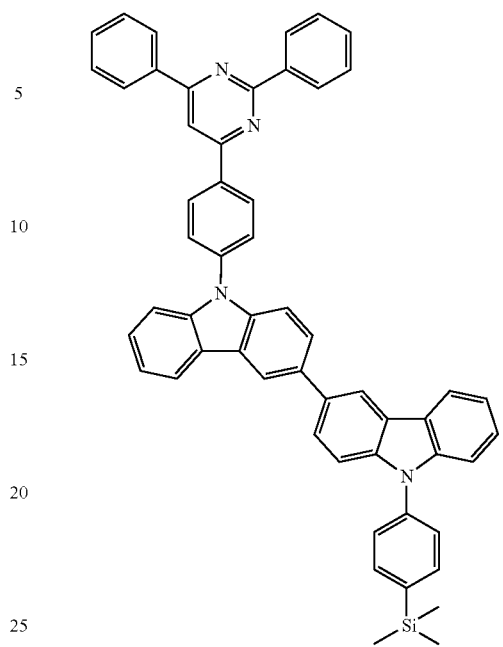
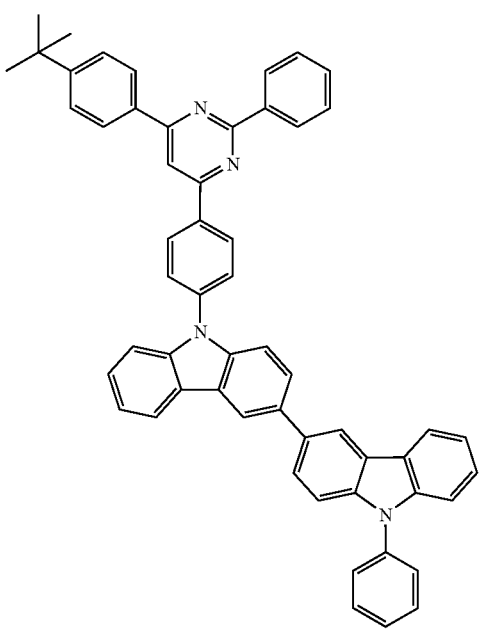
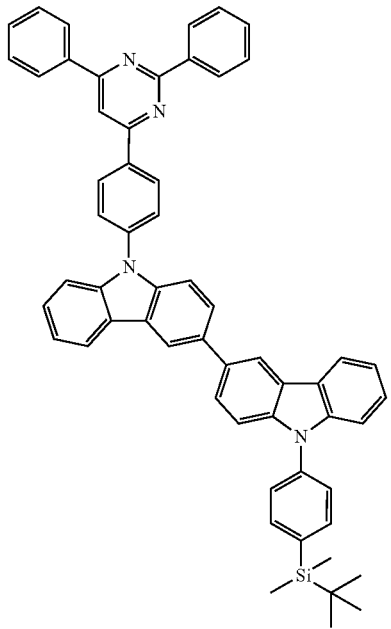

-continued
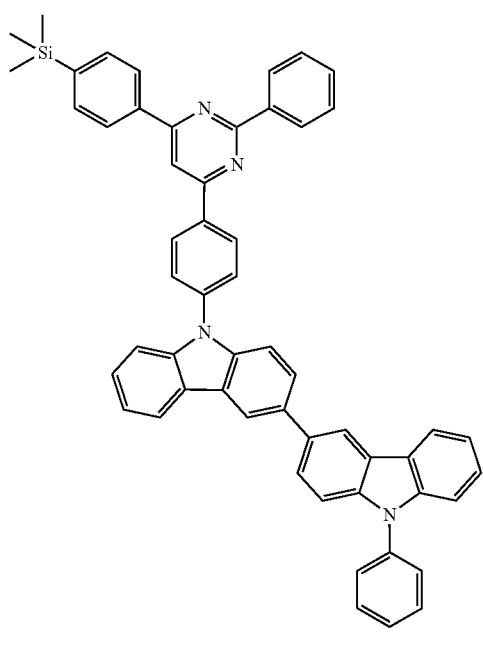
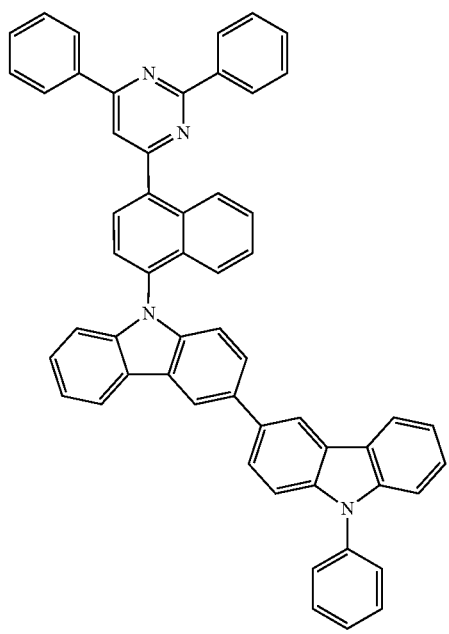
[Chemical Formula 52]
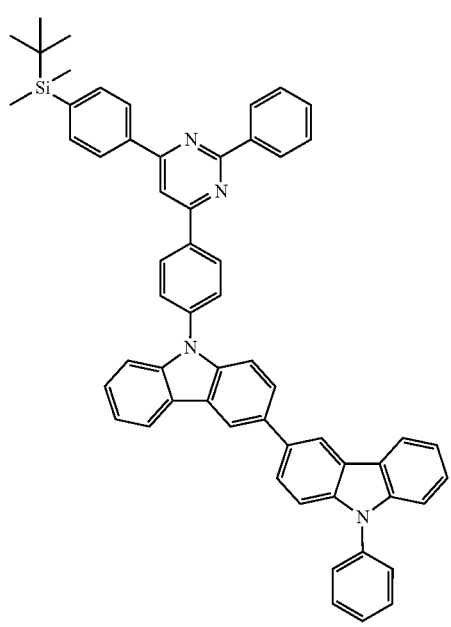
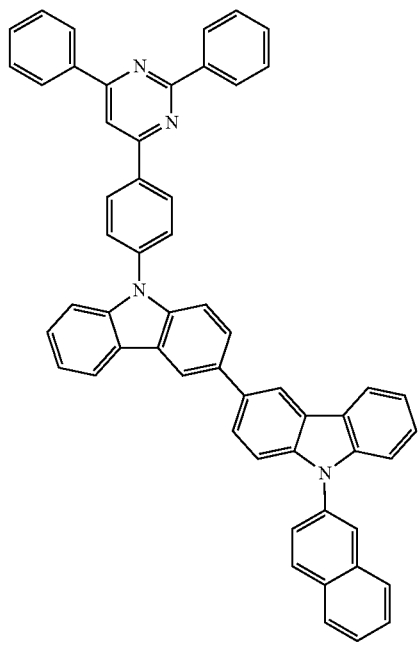

135
-continued
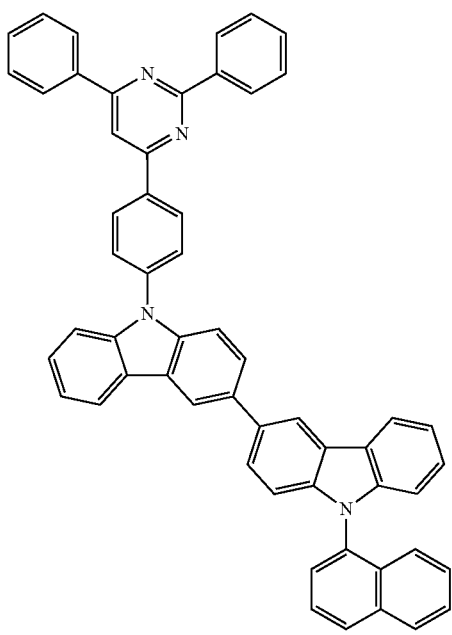
136
-continued
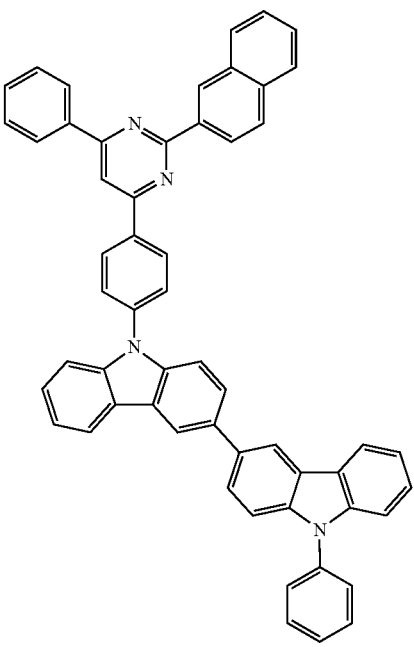
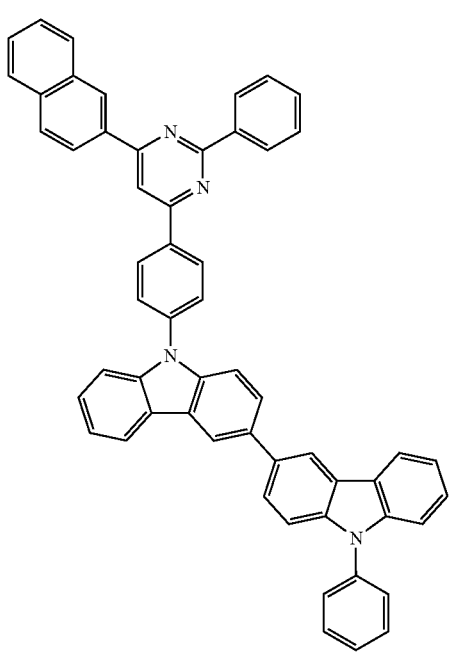
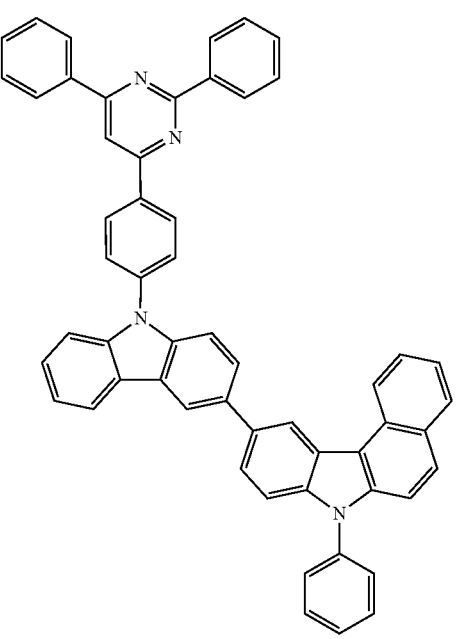

137
-continued
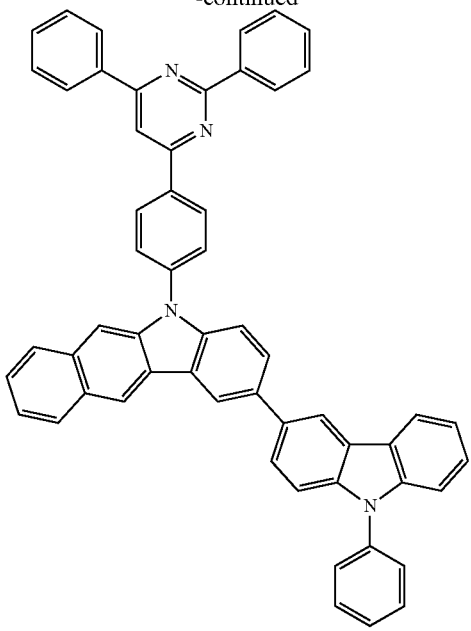
The second host material of the formula (13C) is exemplified by the following compounds.
[Chemical Formula 53]
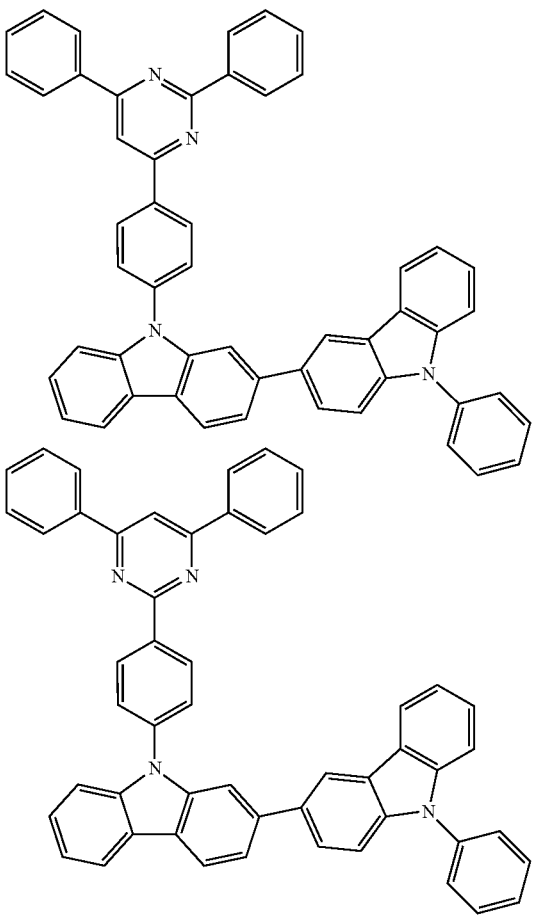
138
-continued
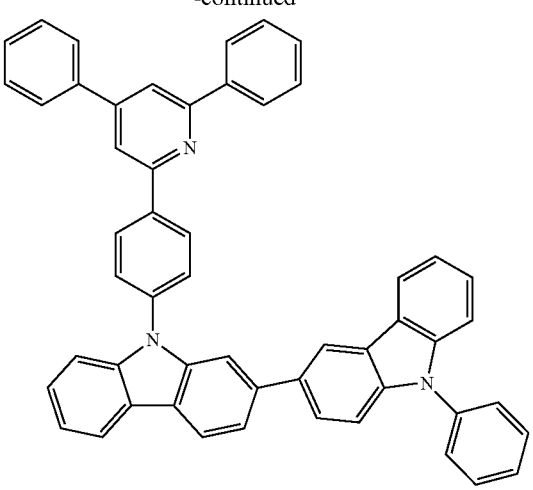
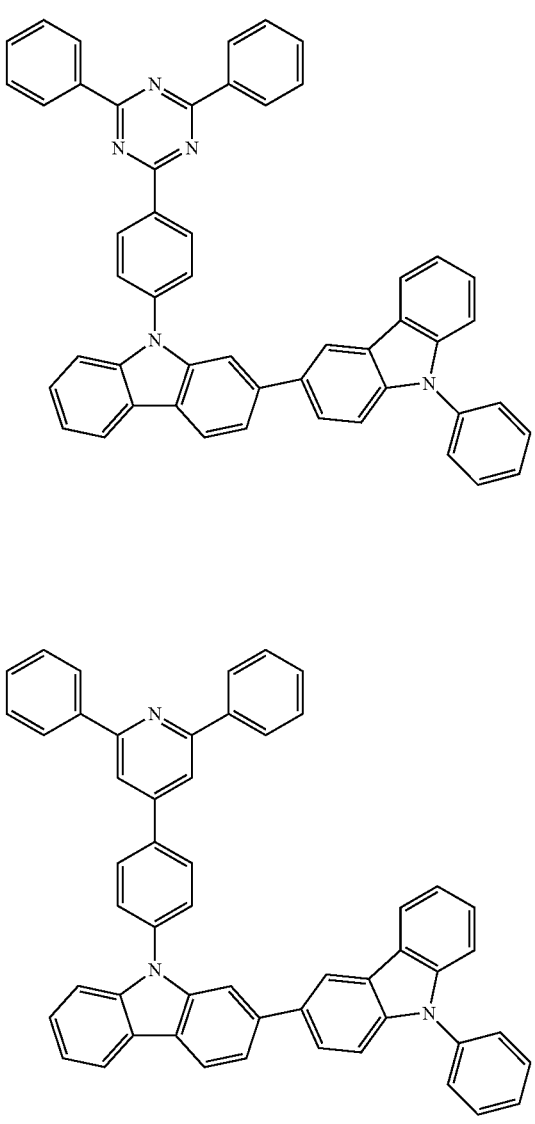

-continued
[Chemical Formula 54]
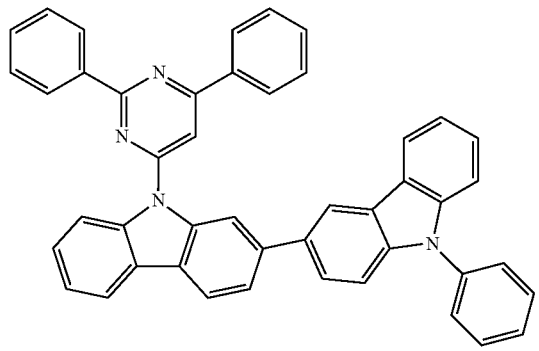
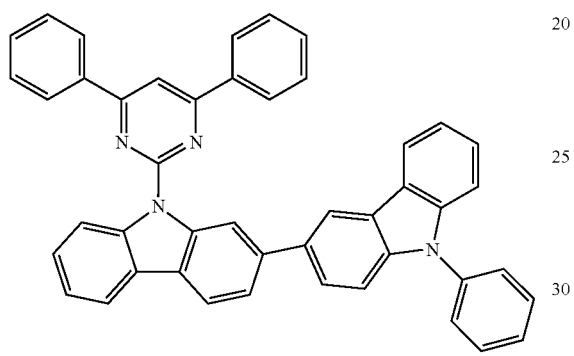
-continued
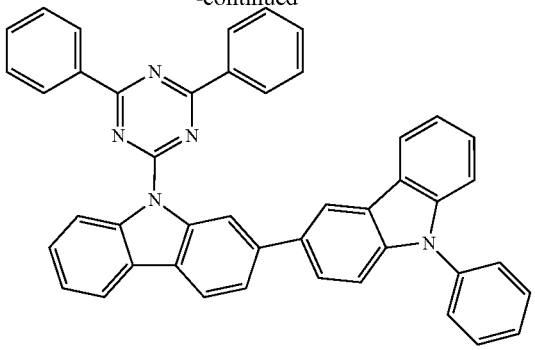
[Chemical Formula 55]
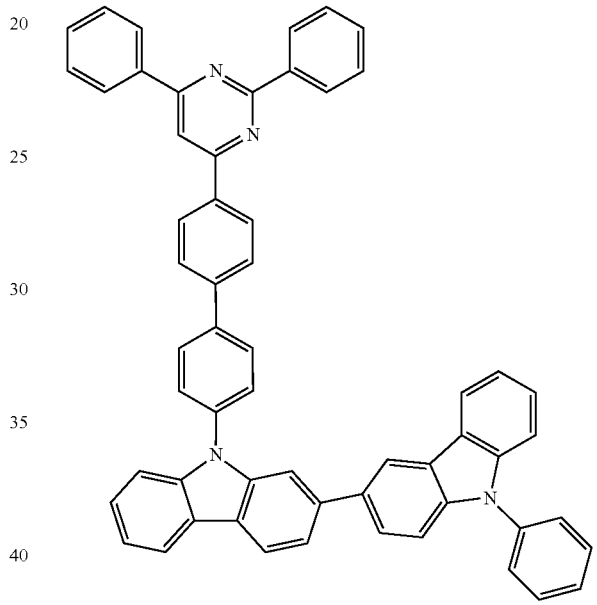
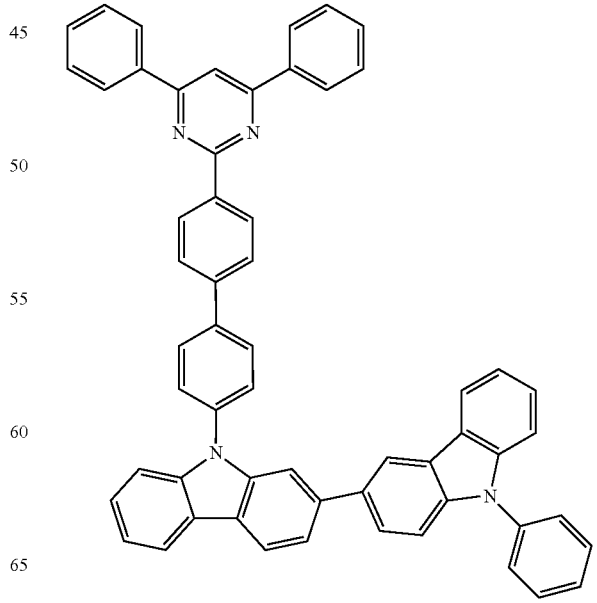

-continued
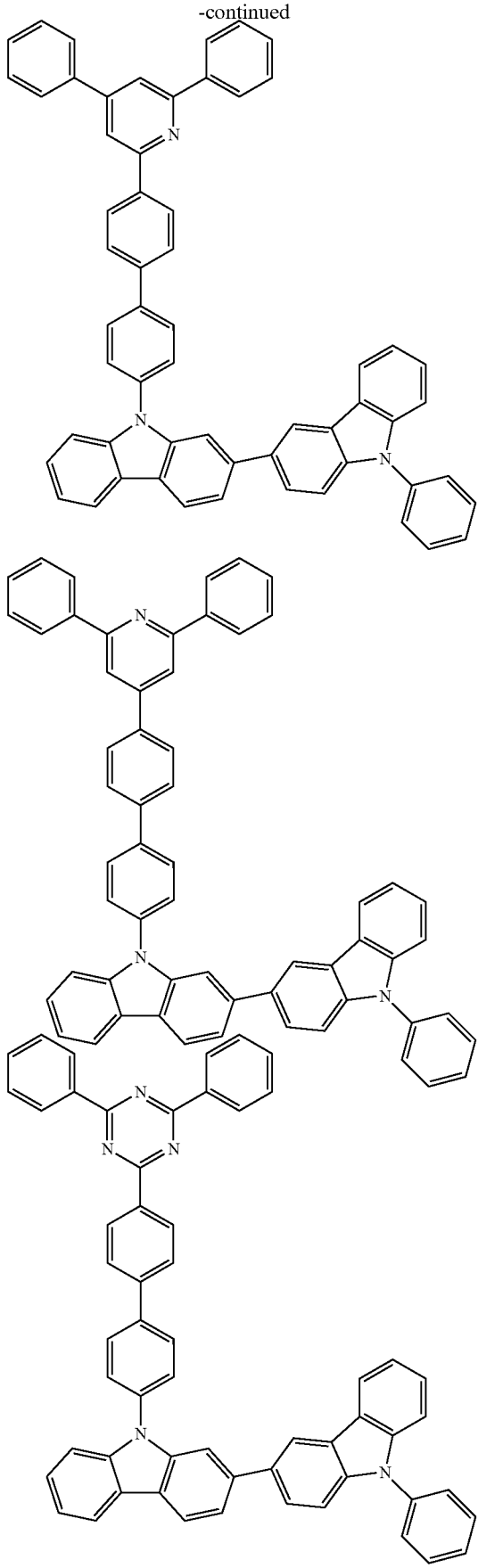
-continued
[Chemical Formula 56]
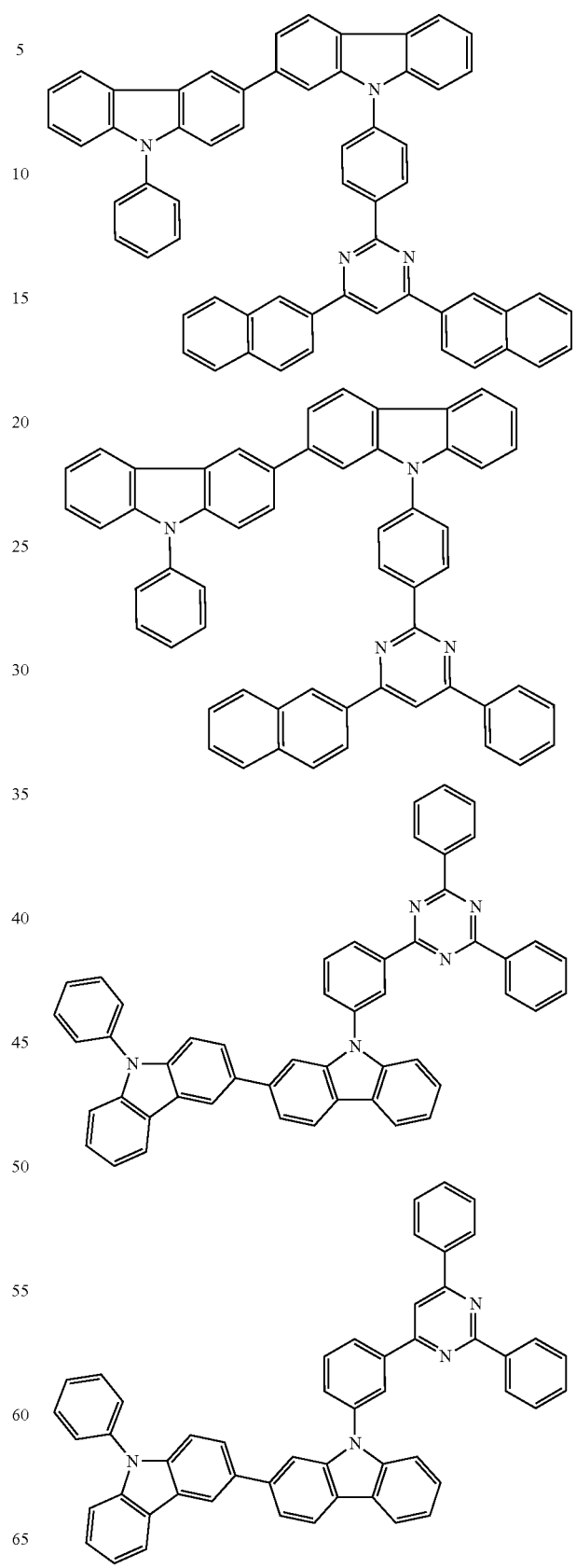

[Chemical Formula 57]
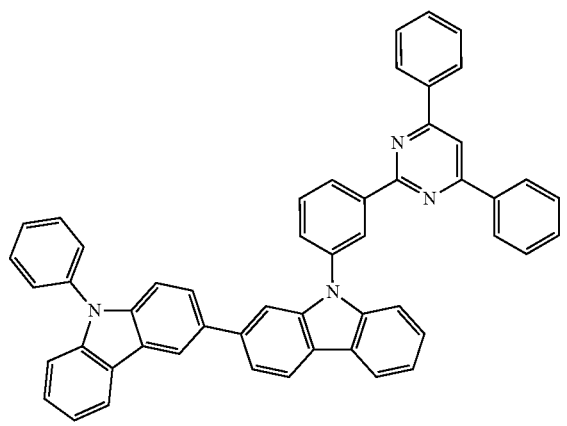
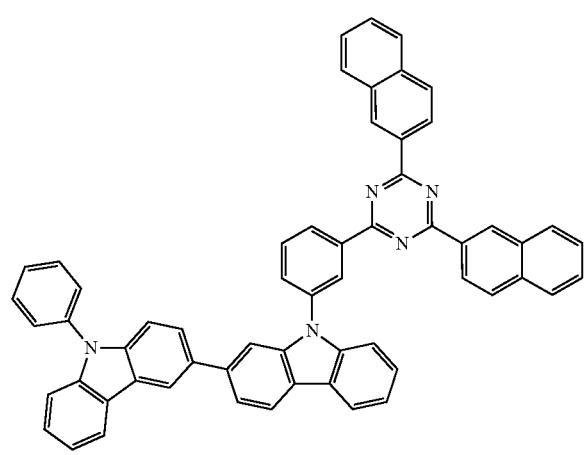
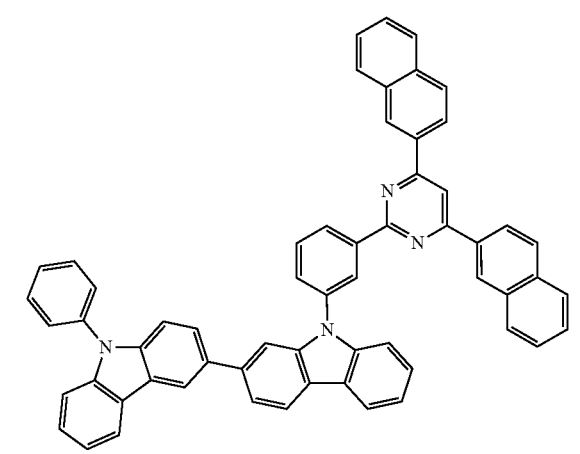
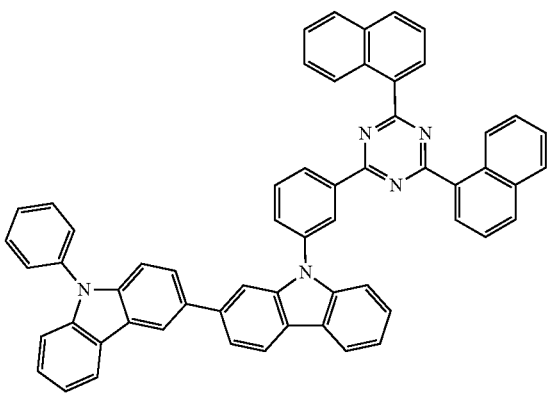
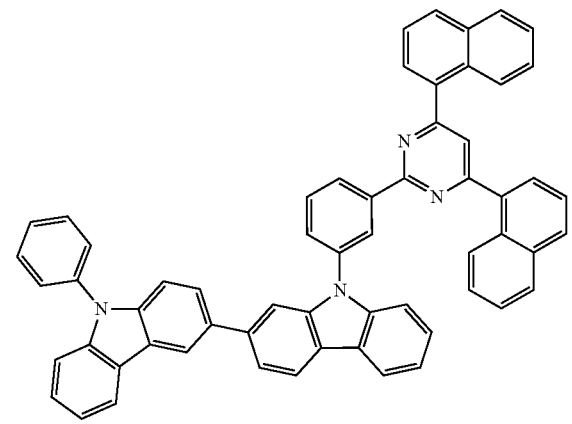
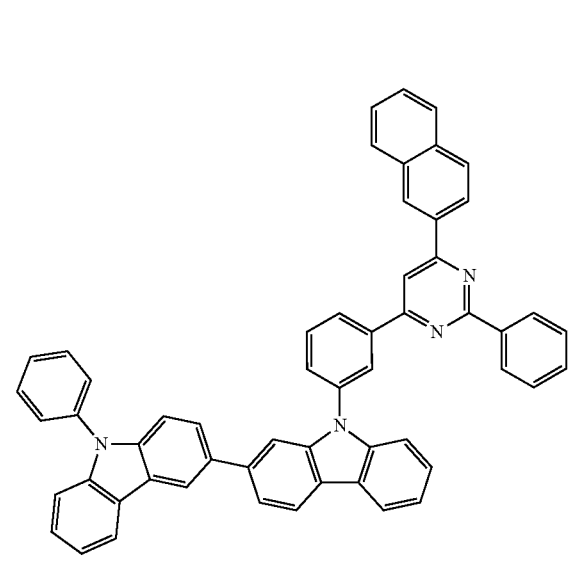

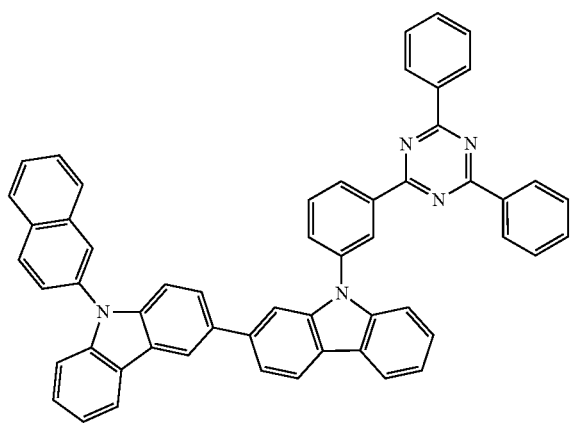
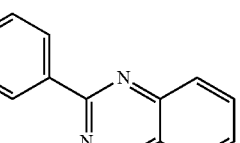
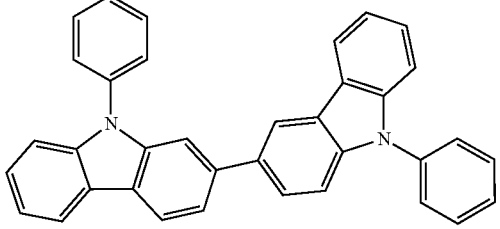
[Chemical Formula 58]
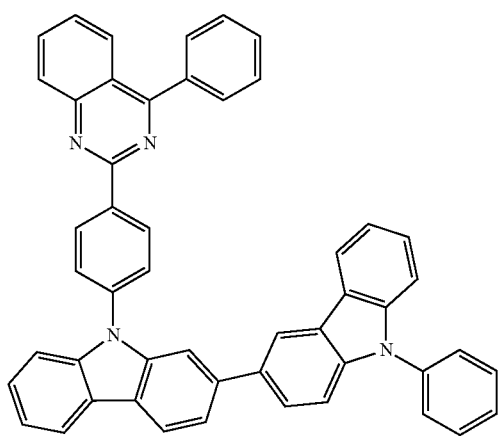
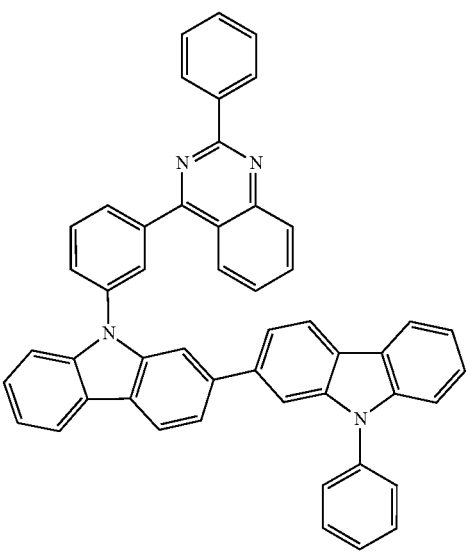
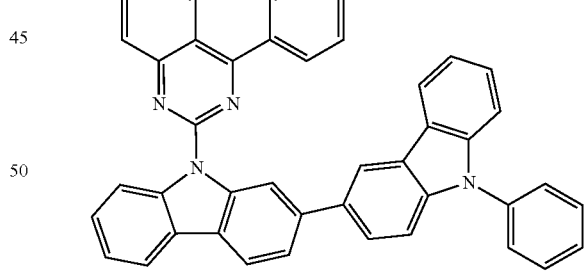
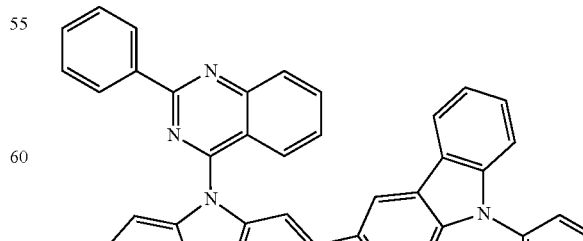
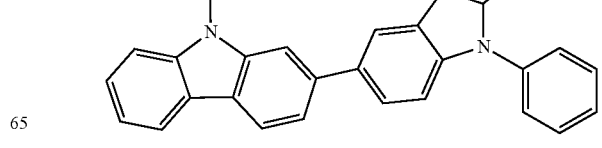

[Chemical Formula 59]
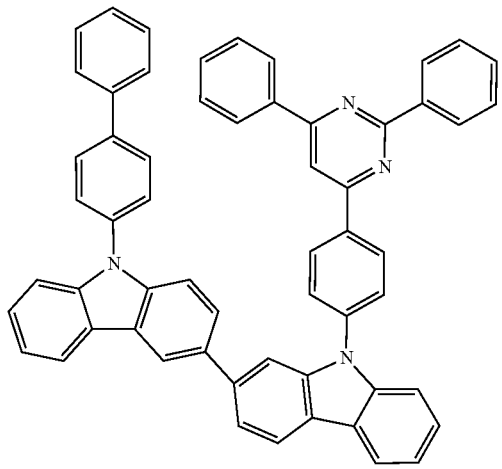
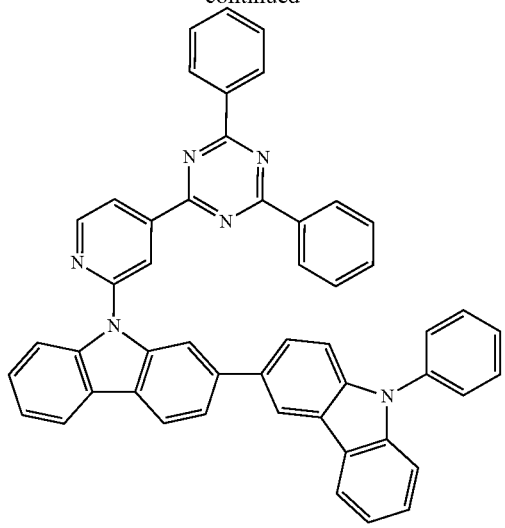
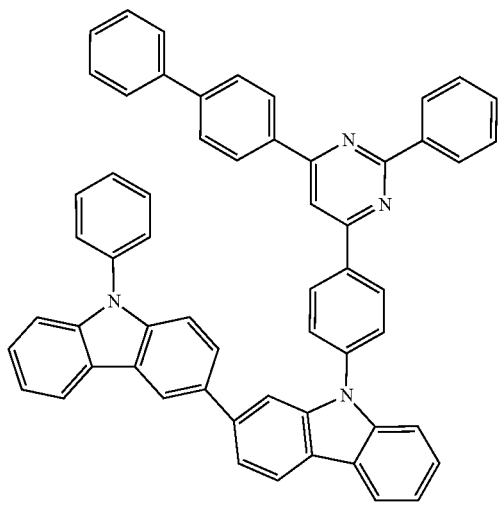
The second host material of the formula (13D) is exemplified by the following compounds.
[Chemical Formula 60]
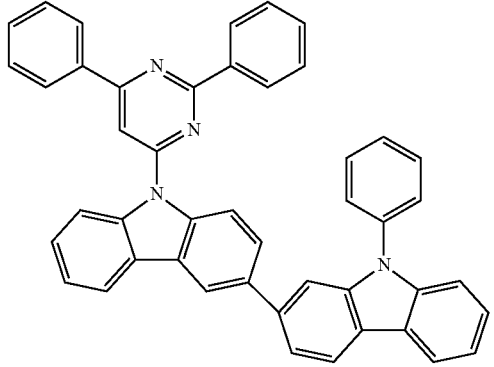
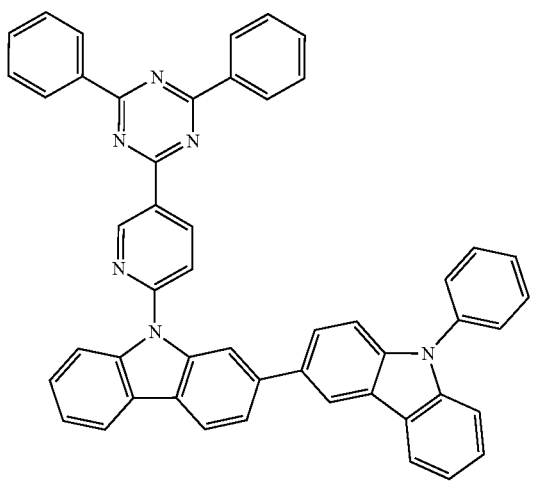
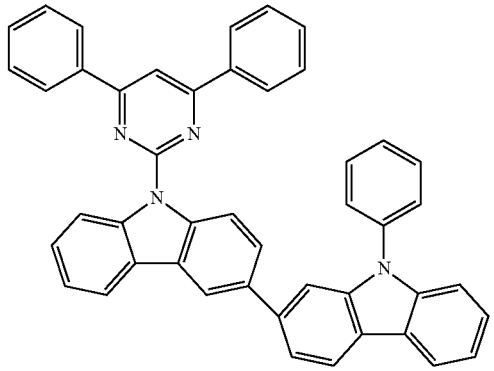

149
-continued
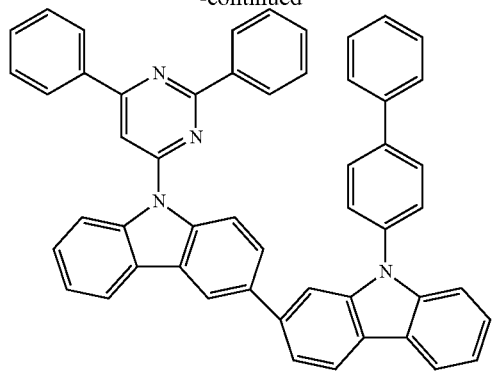
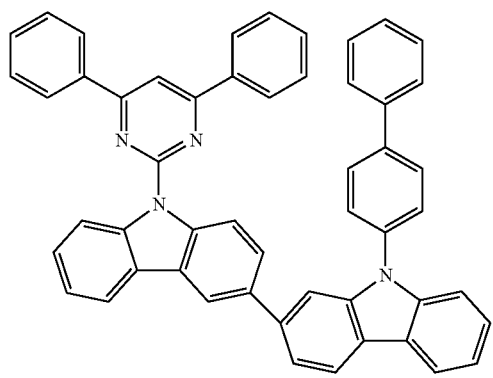
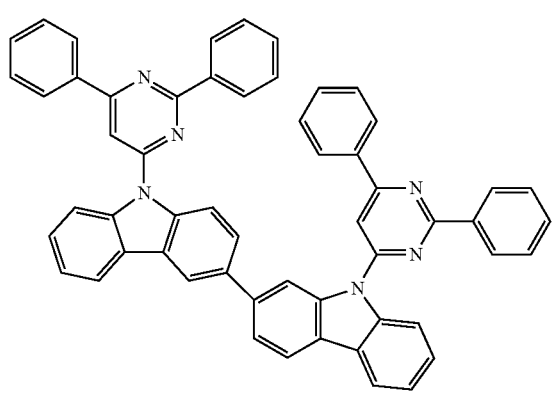
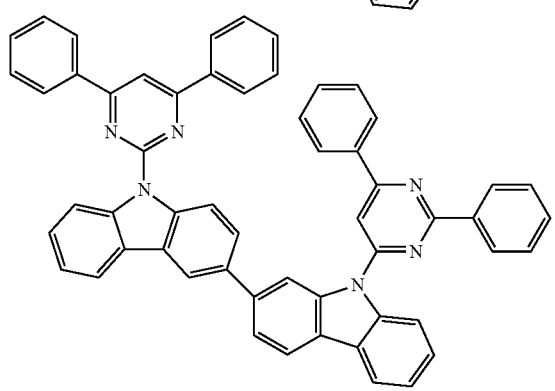
150
-continued
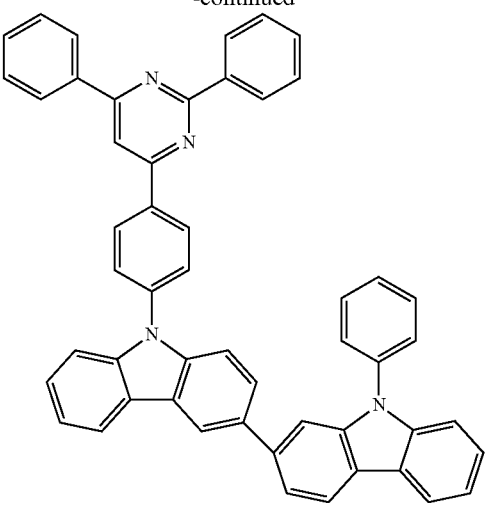
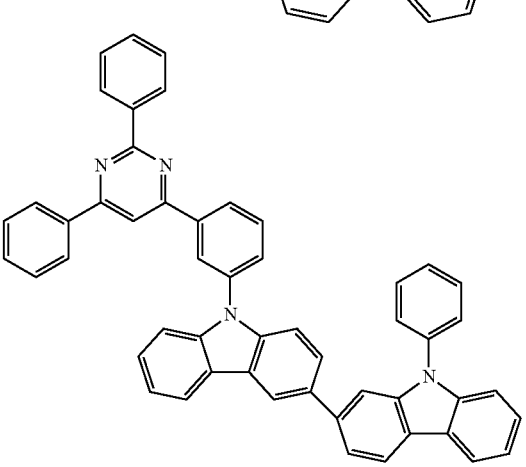
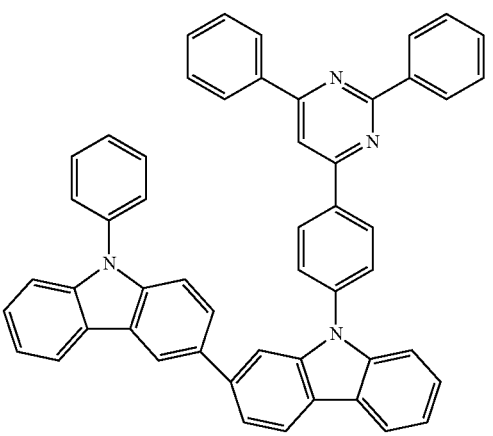
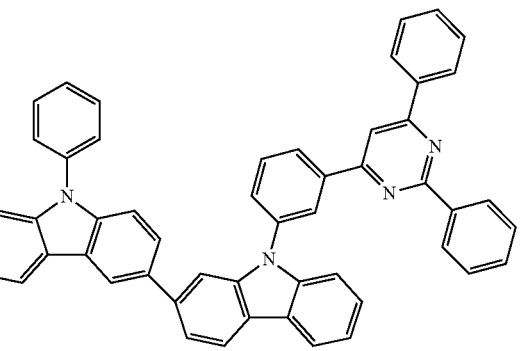

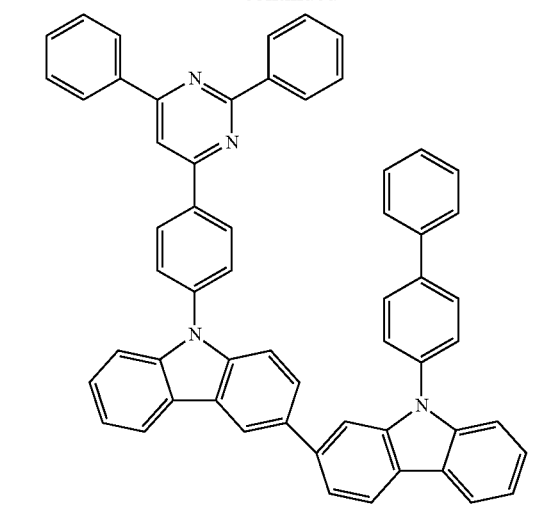
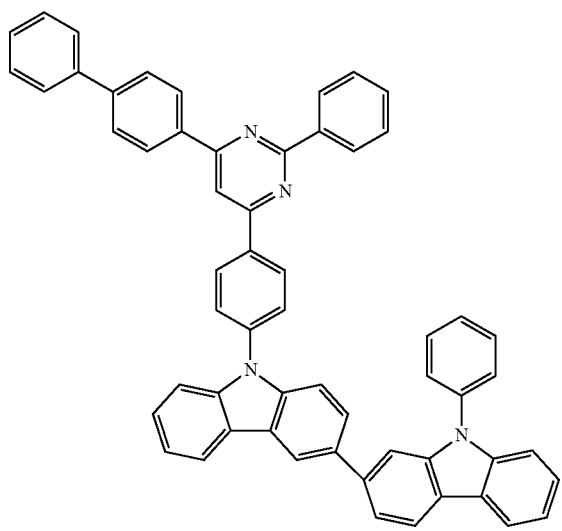
[Chemical Formula 61]
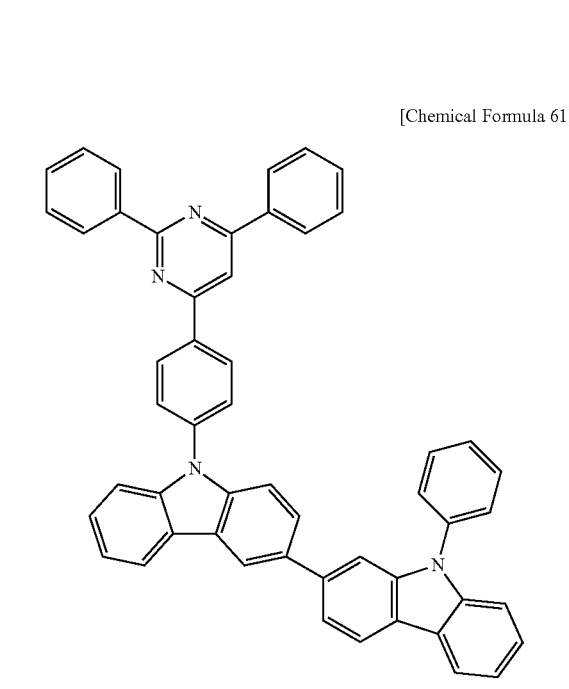
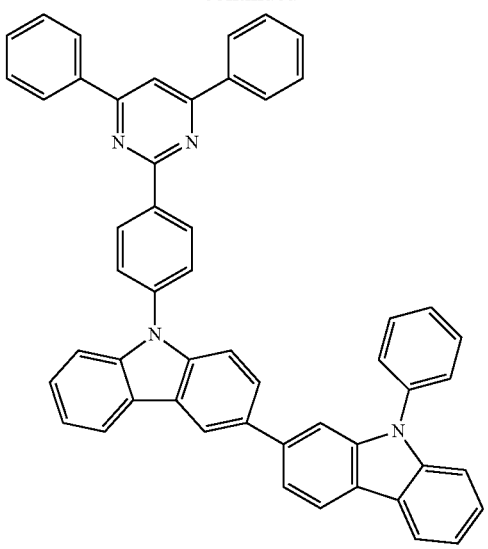
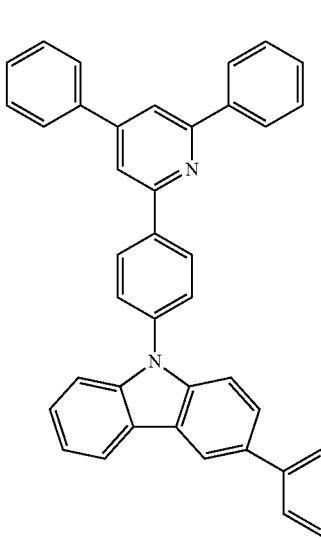
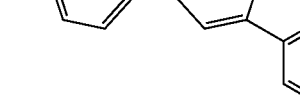

153
-continued
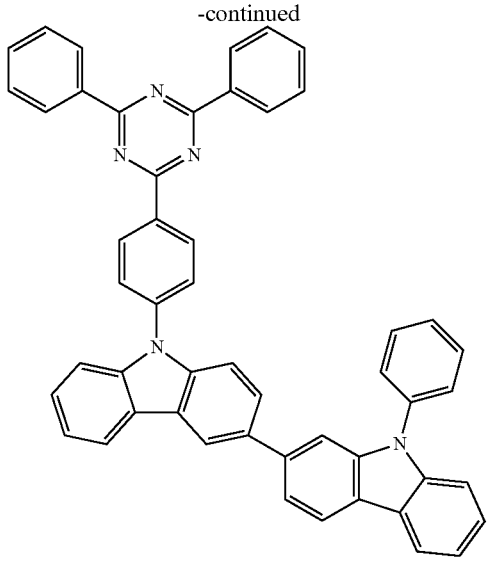
154
-continued
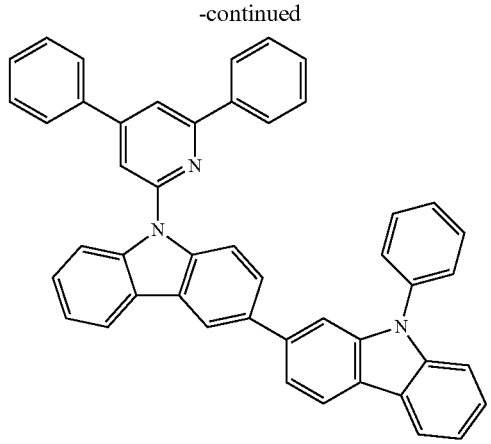
[Chemical Formula 62]
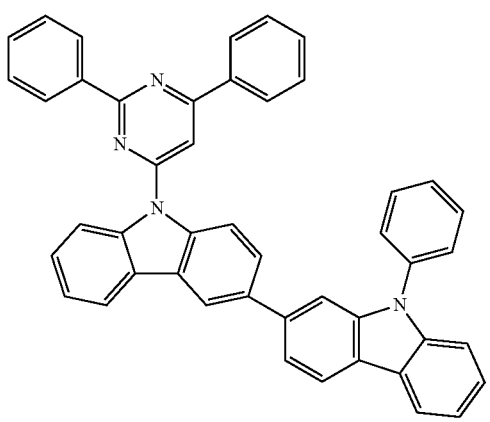
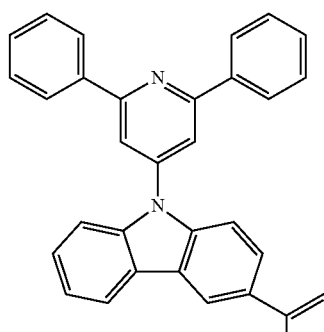
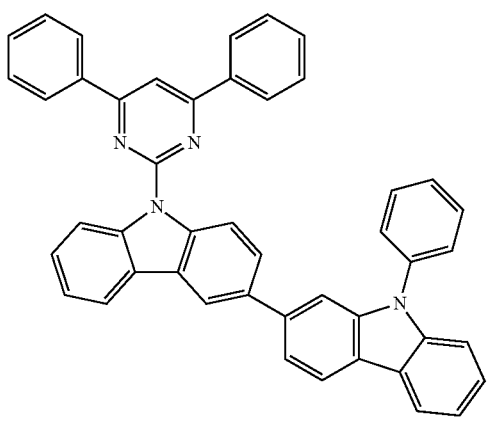
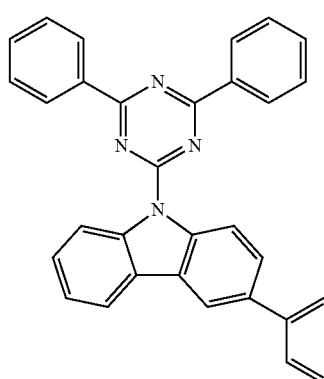

155
-continued
[Chemical Formula 63]
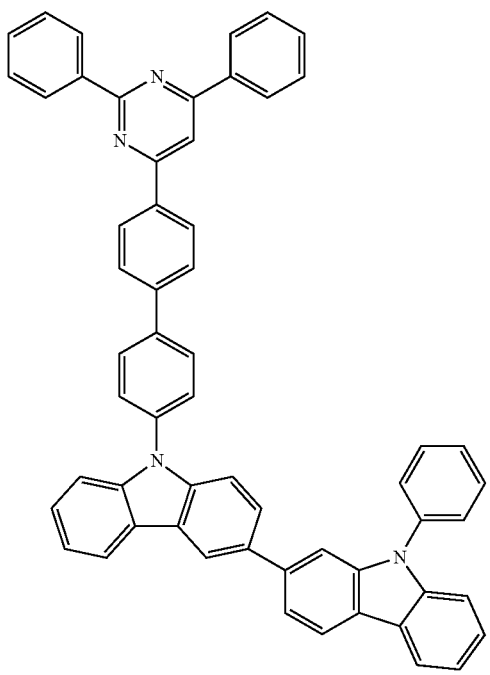
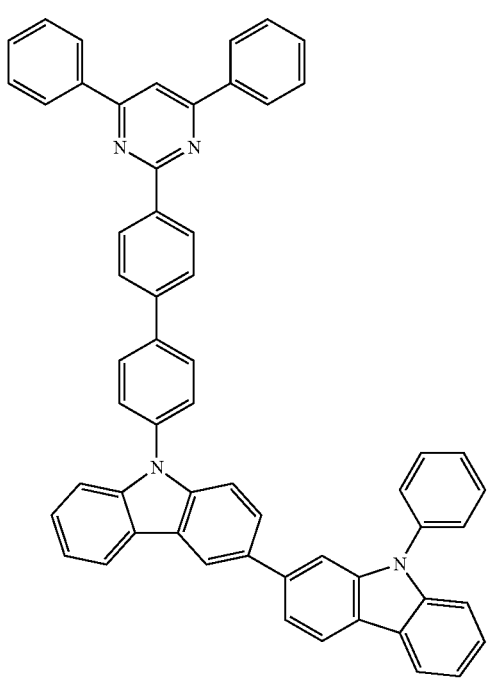
156
-continued
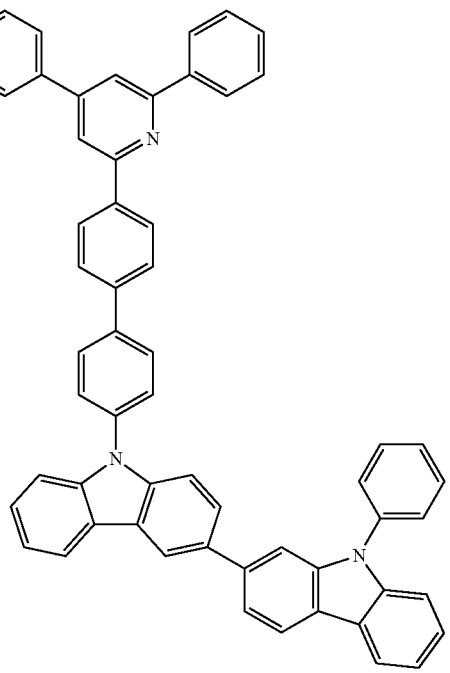
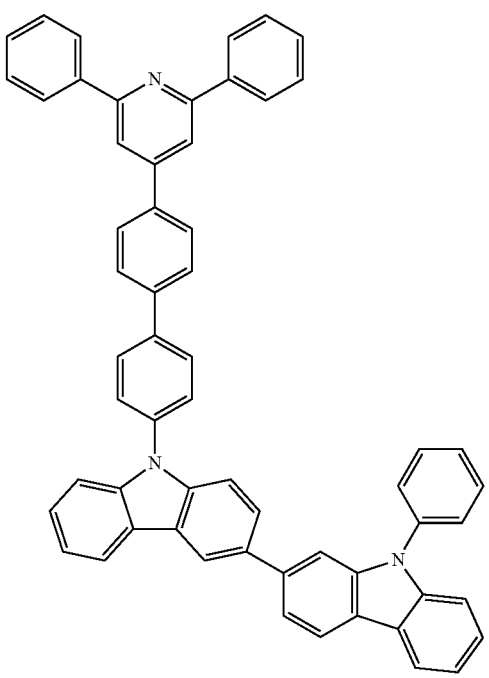

157
-continued
158
-continued
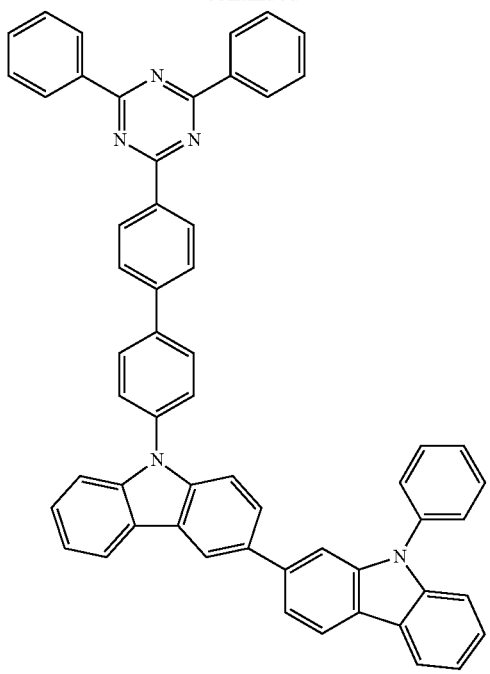
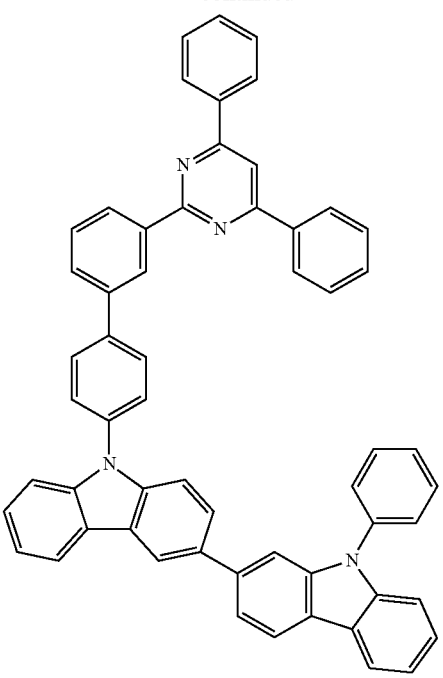
[Chmeical Formula 64]
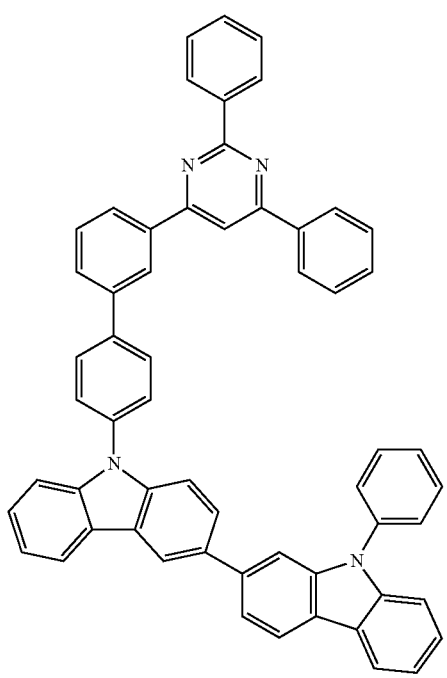

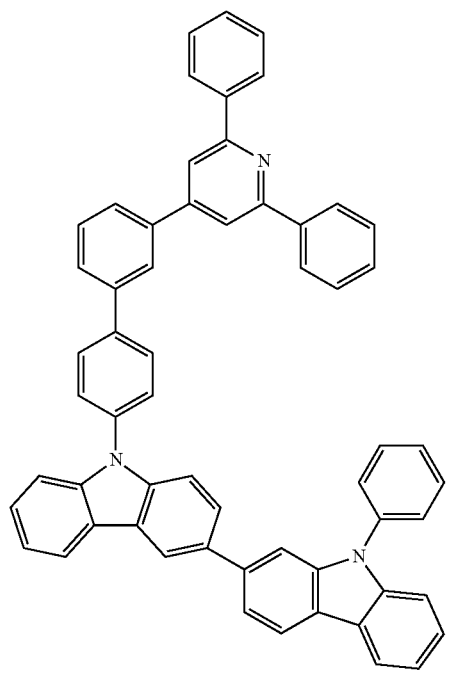
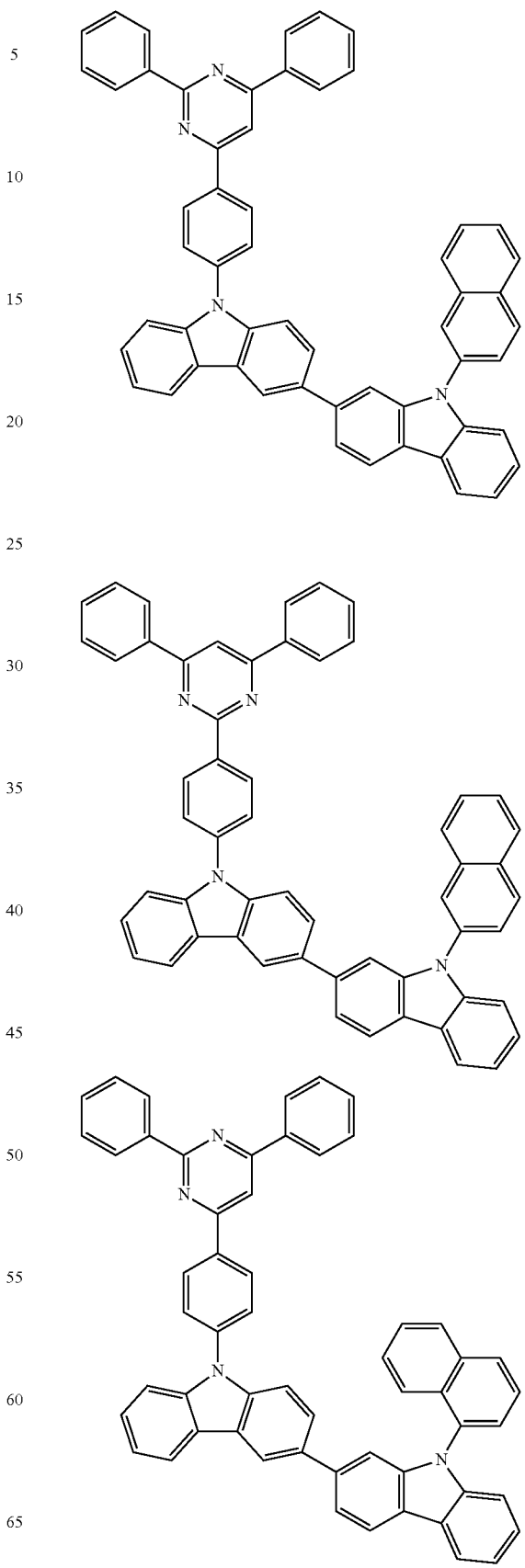

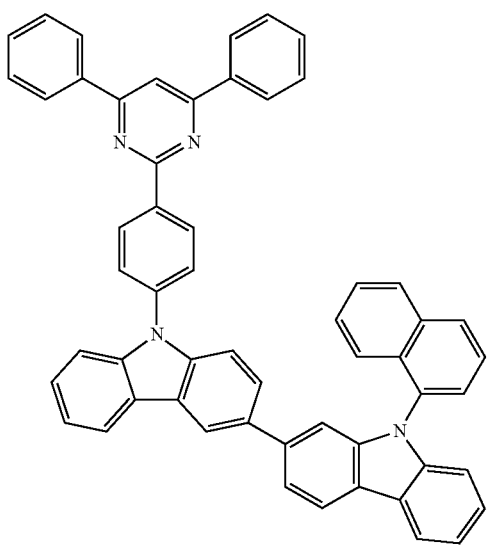
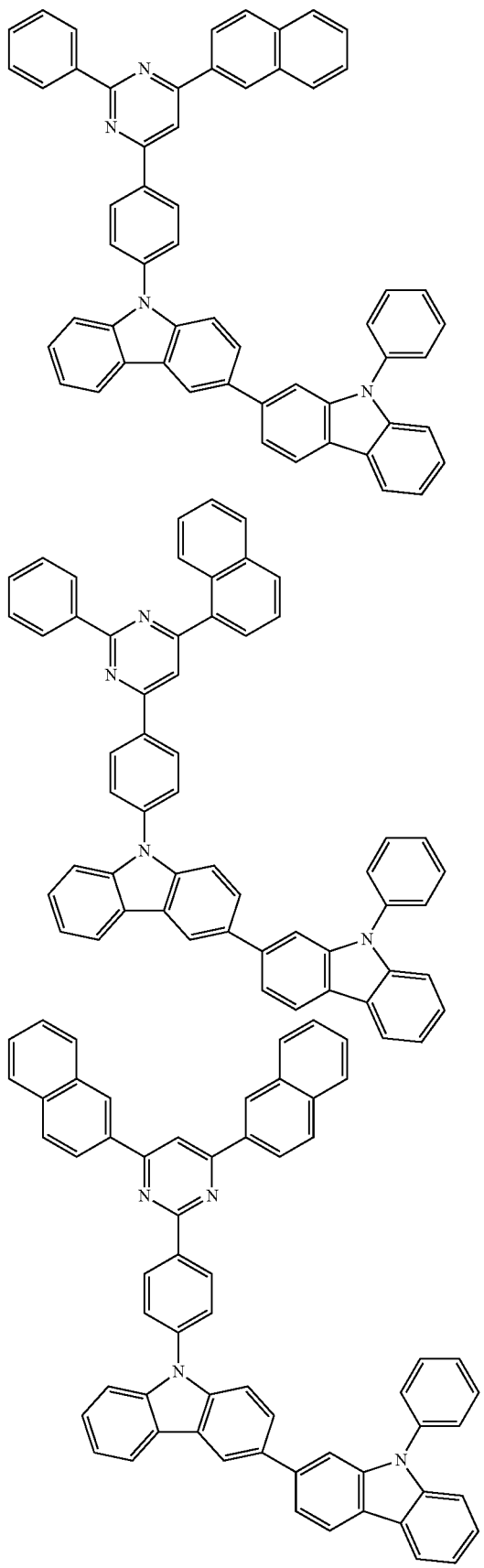

163
-continued
164
-continued
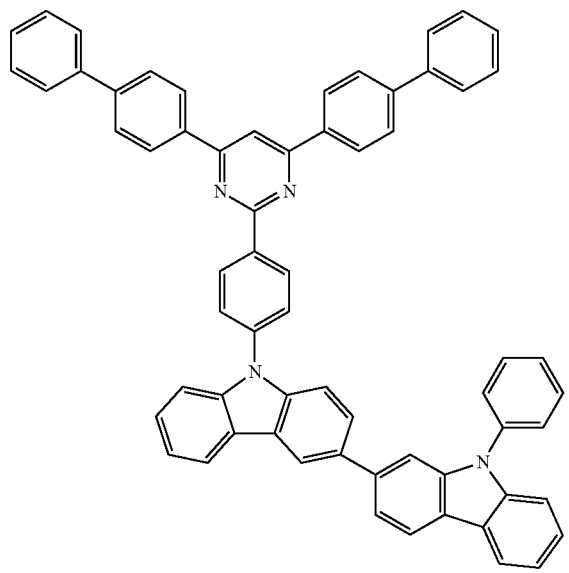
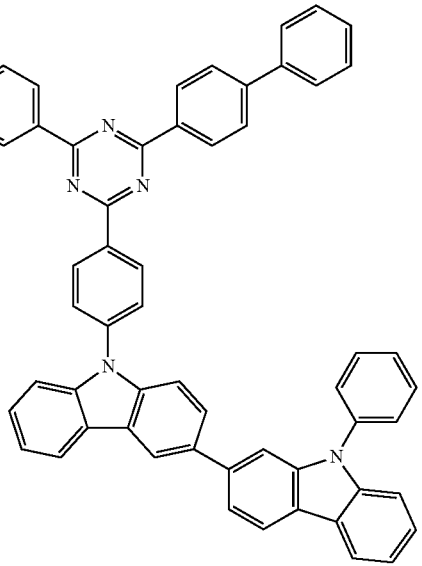
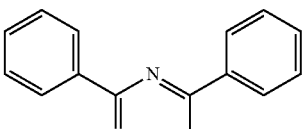
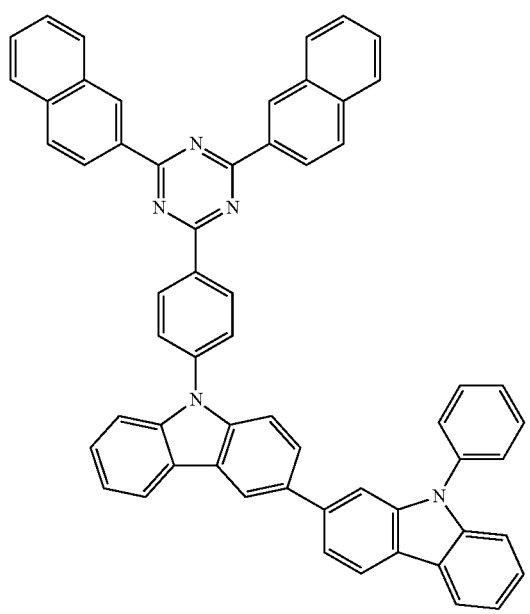
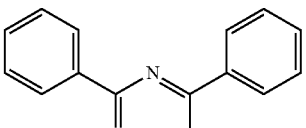
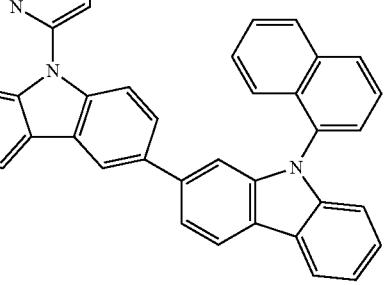

165
-continued
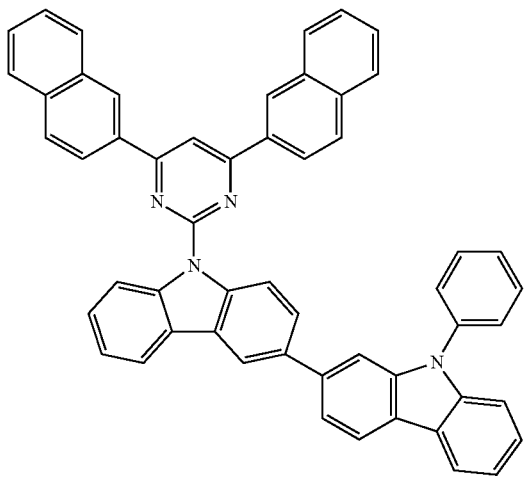
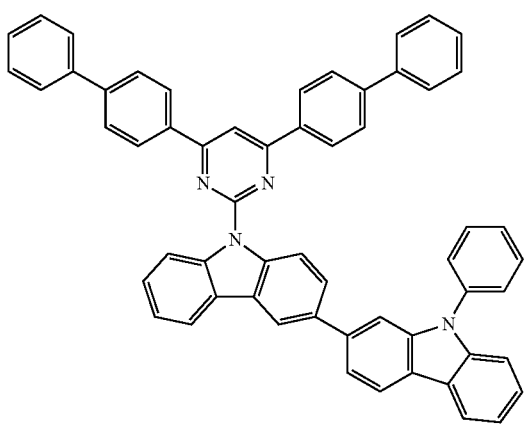
[Chemical Formula 67]
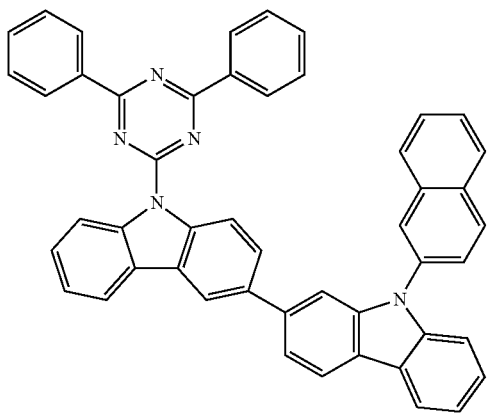
166
-continued
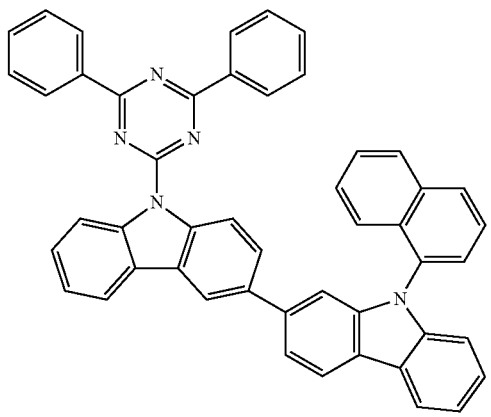
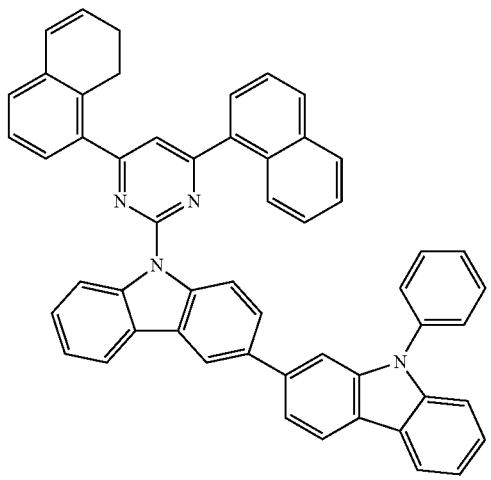
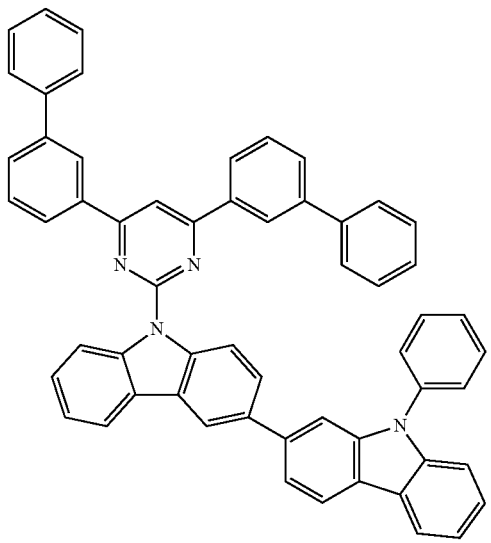

167
-continued
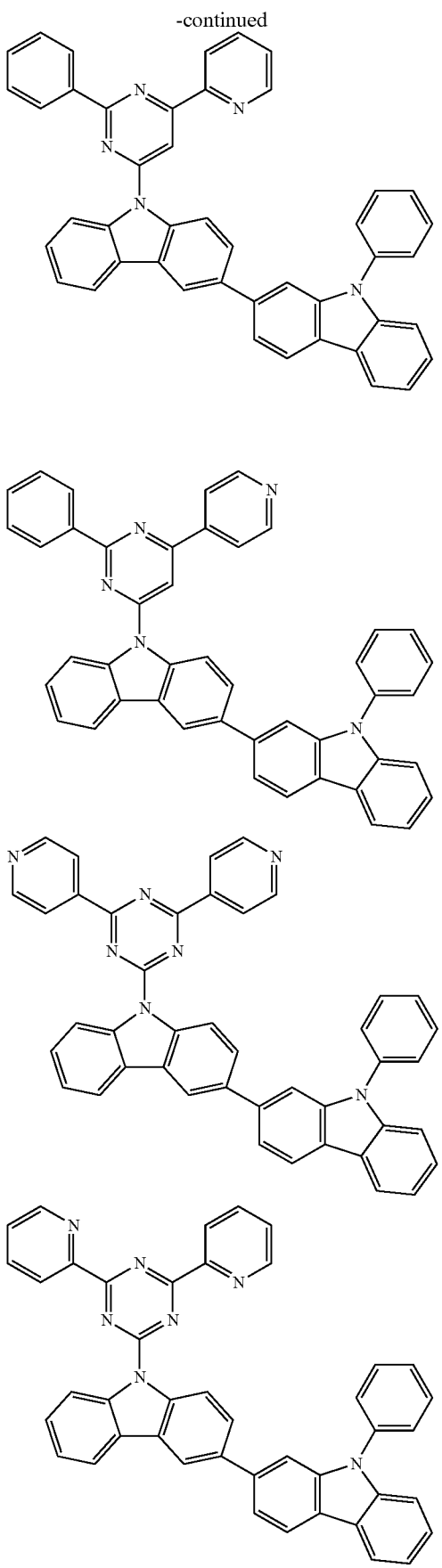
168
-continued
[Chemical Formula 68]
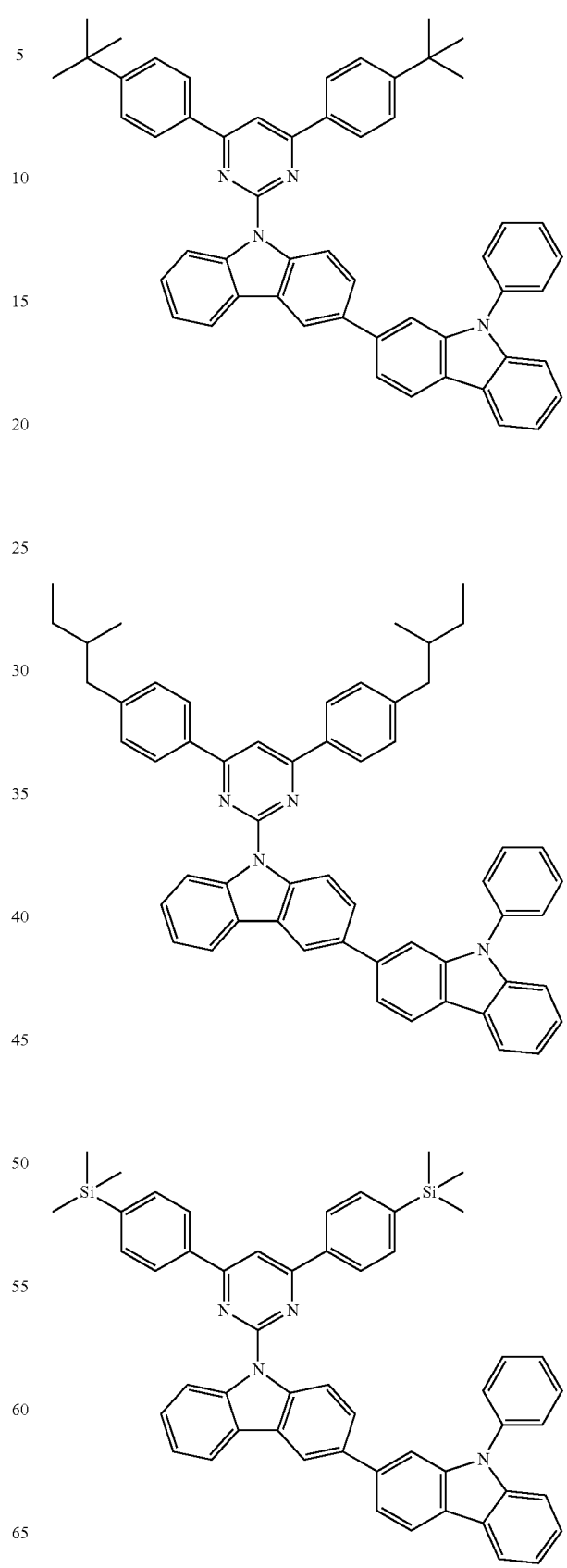

169
-continued
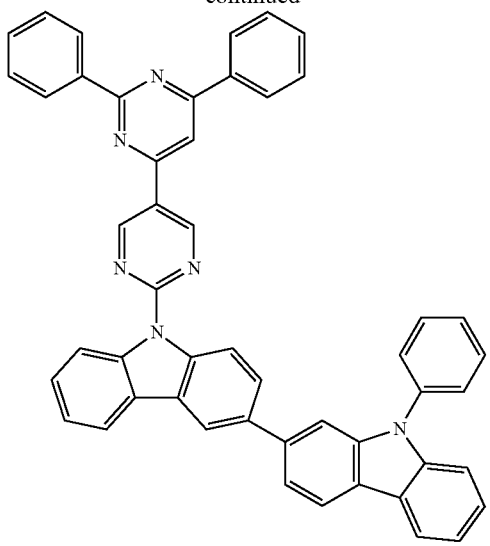
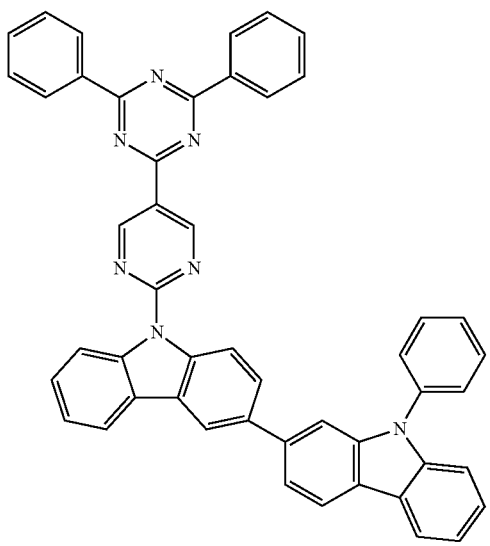
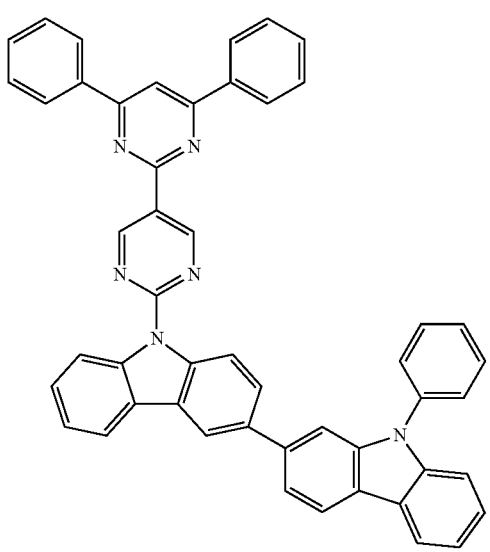
170
-continued
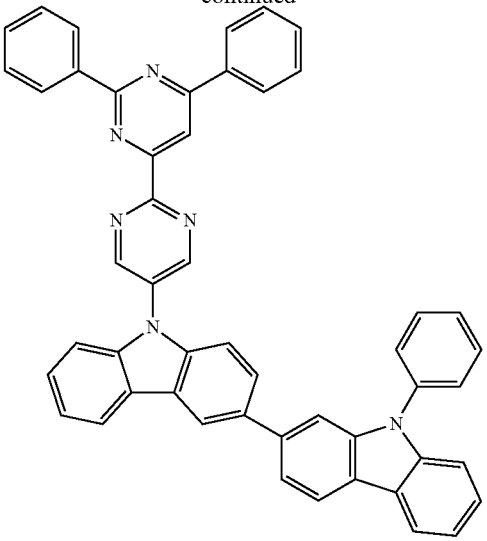
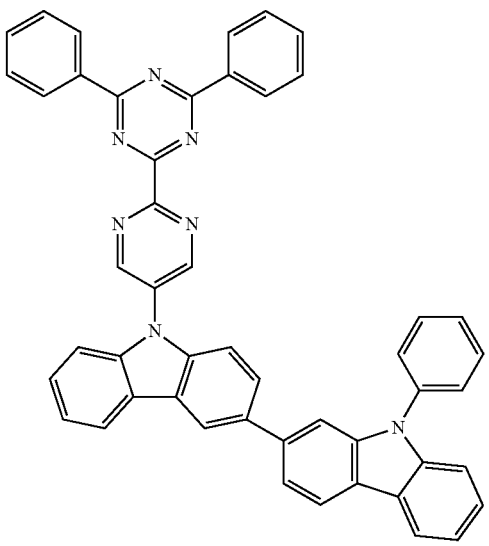
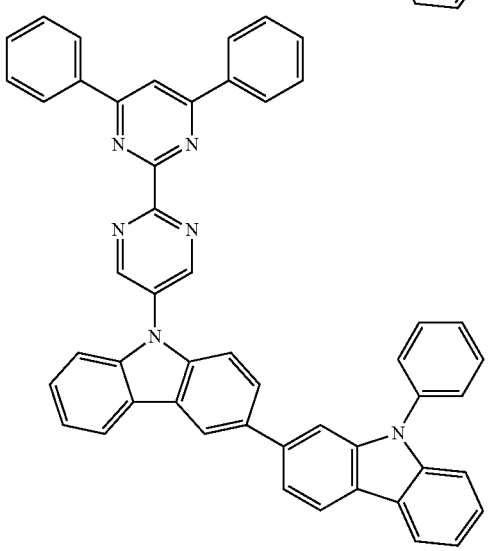

[Chemical Formula 69]
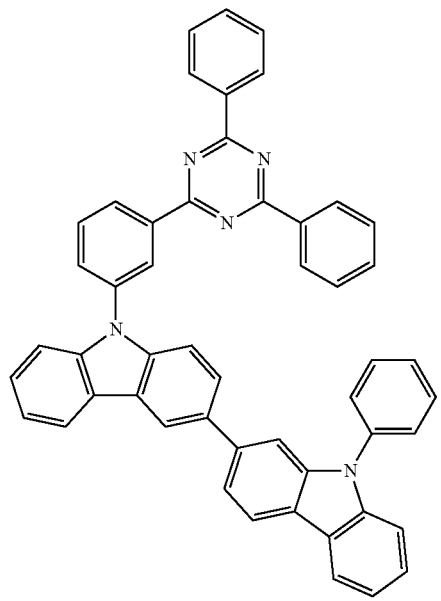
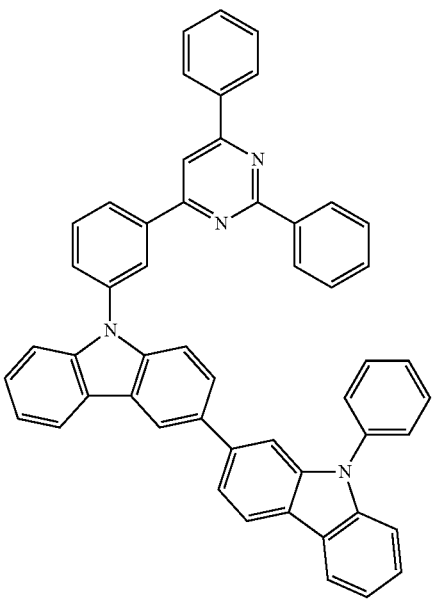
[Chemical Formula 70]
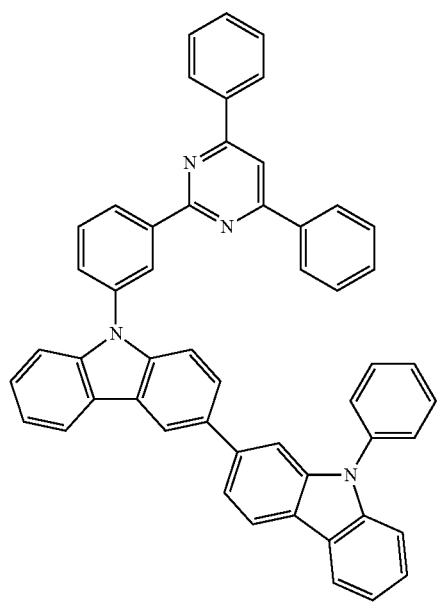
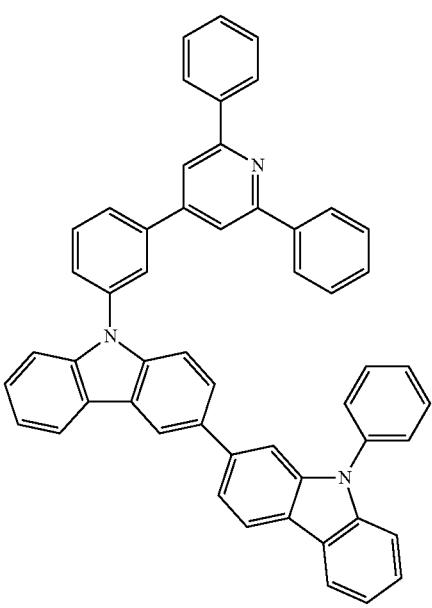

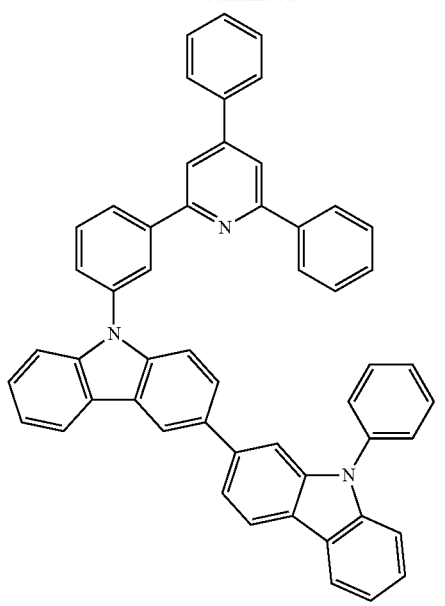

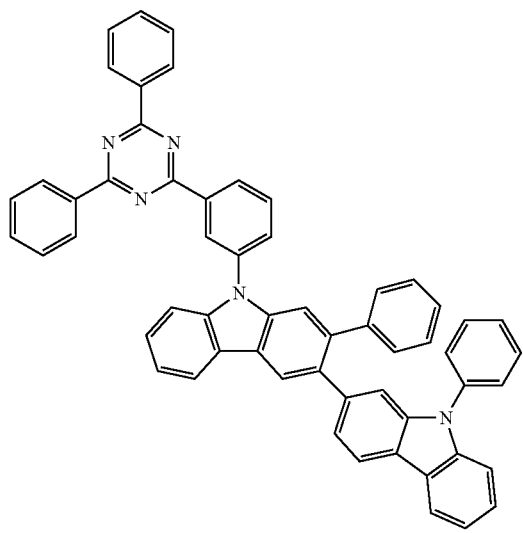 [SMILES: c1ccc(-c2nc(-c3ccccc3)nc(-c3cccc(-n4c5ccccc5c5cc(-c6ccc7c8ccccc8n(-c8ccccc8)c7c6)c(-c6ccccc6)cc54)c3)n2)cc1]

The second host material may alternatively be a compound represented by the following formula (14) or (15).

[Chemical Formula 71]

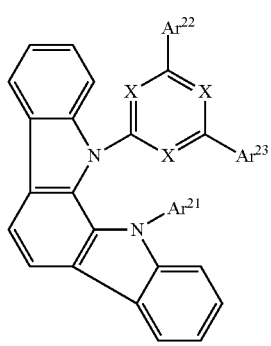

(14)

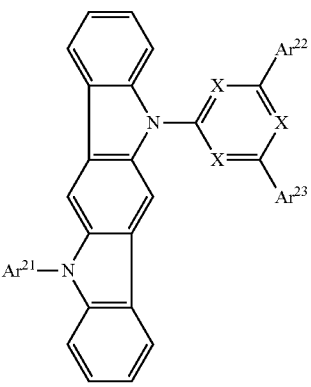

(15)

In the formulae (14) and (15), X is CH or N, in which at least one of X is N. $Ar^{21}$ to $Ar^{23}$ each independently are a substituted or unsubstituted non-fused aromatic hydrocarbon group or aromatic heterocyclic ring.

$Ar^{22}$ or $Ar^{23}$ may form a fused ring with a ring including X.

The second host material represented by the formula (14) or (15) is exemplified by the following compounds.

[Chemical Formula 72]

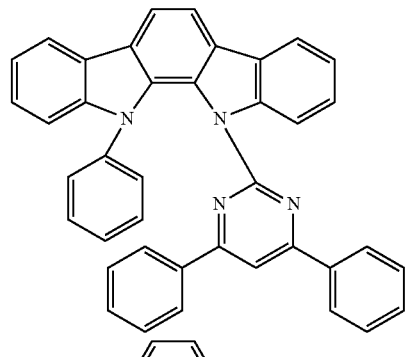

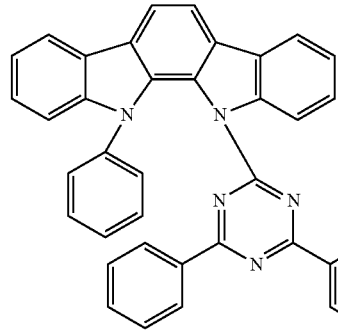

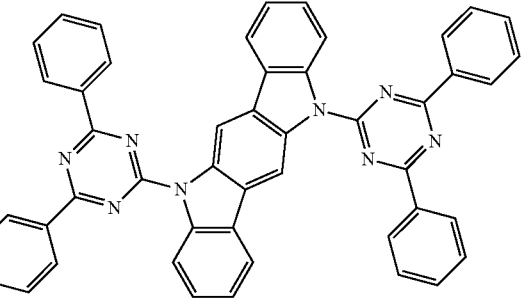

-continued

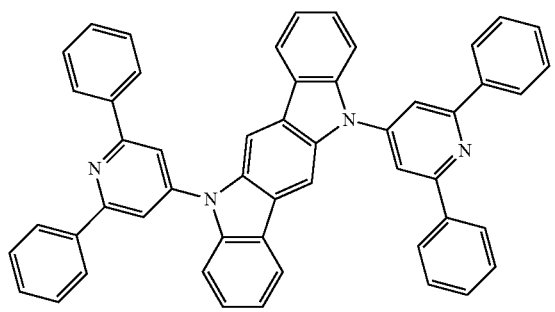

The second host material may alternatively be a compound represented by the following formula (16) or (17).

[Chemical Formula 73]

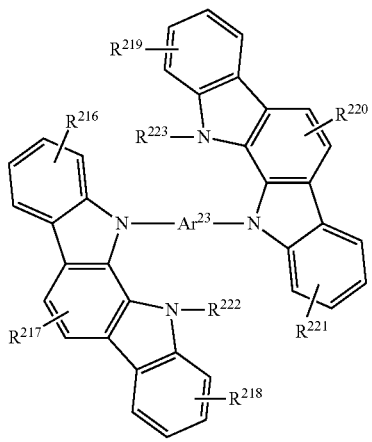

(16)

In the formula (16), $Ar^{23}$ is a divalent bonding group including a substituted or unsubstituted non-fused aromatic hydrocarbon group or aromatic heterocyclic group.

$R^{217}$ and $R^{220}$ are a hydrogen atom, a substituted or unsubstituted non-fused aromatic hydrocarbon group or an aromatic heterocyclic ring.

$R^{222}$ and $R^{223}$ are a substituted or unsubstituted non-fused aromatic hydrocarbon group or an aromatic heterocyclic group. $R^{216}$, $R^{218}$, $R^{219}$ and $R^{221}$ are a hydrogen atom, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amido group, substituted or unsubstituted aromatic hydrocarbon group, or substituted or unsubstituted aromatic heterocyclic group.

In the formula (16), one of $Ar^{23}$ and $R^{216}$ to $R^{223}$ is a group derived from a monoazine derivative, a diazine derivative or a triazine derivative,

[Chemical Formula 74]

(17)

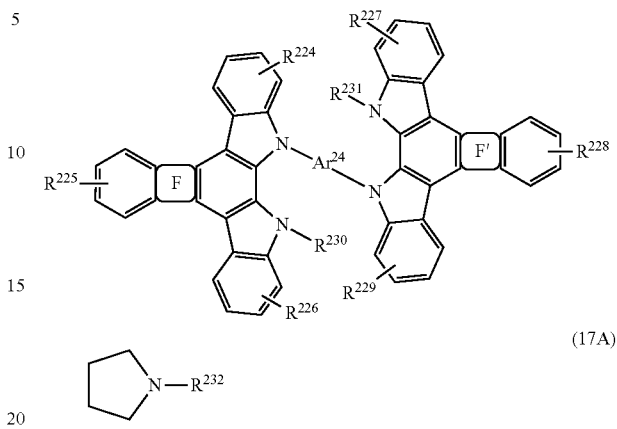

(17A)

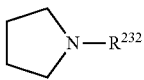

In the formulae (17) and (17A), rings F and F' are a heterocyclic ring fused to adjacent rings and represented by the formula (17A). $Ar^{24}$ represents the same as $Ar^{23}$.

$R^{230}$ to $R^{232}$ each independently represent the same as $R^{222}$.

$R^{224}$ to $R^{229}$ each independently represent the same as $R^{216}$.

In the formula (17), one of $Ar^{24}$ and $R^{224}$ to $R^{231}$ in the formula (17) and $R^{232}$ in the formula (17A) is a group derived from a monoazine derivative, a diazine derivative or a triazine derivative.

The second host material represented by the formulae (16) and (17) is exemplified by the following compound.

[Chemical Formula 75]

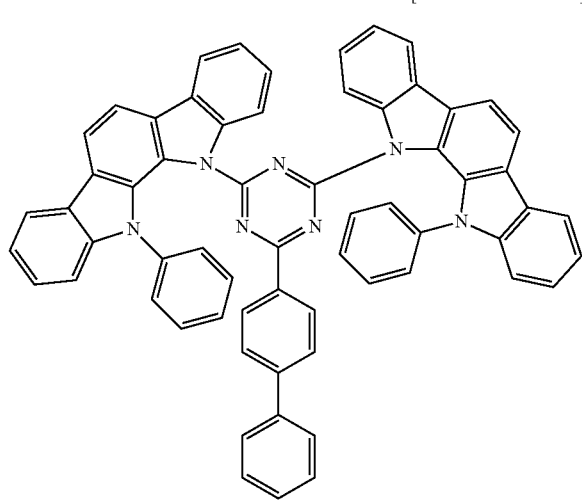

Luminescent Material

The first and second luminescent materials are different metal complexes. Each of the metal complexes preferably contains at least one metal selected from iridium (Ir), palladium (Pd) and platinum (Pt). Each of the metal complexes is preferably an ortho-metalated complex represented by the following formula (20).

[Chemical Formula 76]

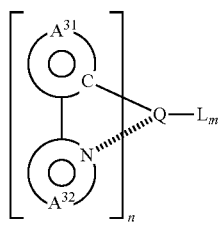

(20)

In the formula (20), Ar$^{31}$, which is a ring bonded to Ar$^{32}$ and Q, represents a substituted or unsubstituted aromatic hydrocarbon ring group or a substituted or unsubstituted aromatic heterocyclic group.

Preferable examples of the aromatic hydrocarbon ring group are a phenyl group, a biphenyl group, a naphthyl group and an anthryl group.

Preferable examples of the aromatic heterocyclic group are a thienyl group, a pyridyl group, a quinolyl group and an isoquinolyl group.

Preferable examples of a substituent for the aromatic hydrocarbon ring group or the aromatic heterocyclic group are a halogen atom, an alkyl group having 1 to 30 carbon atoms, an alkenyl group, an alkoxycarbonyl group having 1 to 30 carbon atoms, an alkoxy group having 1 to 30 carbon atoms, an aryloxy group, a dialkylamino group, a haloalkyl group and a cyano group.

A preferable example of the halogen atom is a fluorine atom.

Preferable examples of the alkyl group having 1 to 30 carbon atoms are a methyl group and an ethyl group.

A preferable example of the alkenyl group is a vinyl group.

Preferable examples of the alkoxycarbonyl group having 1 to 30 carbon atoms are a methoxycarbonyl group and an ethoxycarbonyl group.

Preferable examples of the alkoxy group having 1 to 30 carbon atoms are a methoxy group and an ethoxy group.

Preferable examples of the aryloxy group are a phenoxy group and a benzyloxy group.

Preferable examples of the dialkylamino group are a dimethylamino group and a diethylamino group.

A preferable example of the acyl group is an acetyl group.

A preferable example of the haloalkyl group is a trifluoromethyl group.

A$^{32}$ is an aromatic heterocyclic group bonded to A$^{31}$. Specifically, A$^{32}$ is a substituted or unsubstituted aromatic heterocyclic group containing nitrogen as an atom for forming an aromatic hetero ring.

Preferable examples of the aromatic heterocyclic group are a pyridyl group, pyrimidyl group, pyrazine group, triazine group, benzothiazole group, benzooxazole group, benzimidazole group, quinolyl group, isoquinolyl group, quinoxaline group and phenanthridine group.

Substituents for A$^{32}$ are the same as those for A$^{31}$.

A ring including A$^{31}$ and a ring including A$^{32}$ may be bonded to each other at portions other than A$^{31}$ and A$^{32}$ to form a fused ring or an unsaturated ring. Such a fused ring is exemplified by a 7,8-benzoquinoline group.

Q is one of palladium (Pd), illidium (Ir) and platinum (Pt).

L is a bidentate ligand. Preferable examples of the bidentate ligand are a β-diketo ligand such as acetylacetonato and pyromellitic acid.

In the formula (20), m and n represent an integer. When Q is a divalent metal, n=2 and m=0. When Q is a trivalent metal, n=3 and m=0, or n=2 and m=1.

The ortho-metalated complex represented by the formula (20) is exemplified by the following compounds.

[Chemical Formula 77]

(K-1)

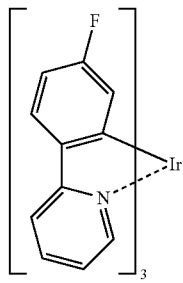

(K-2)

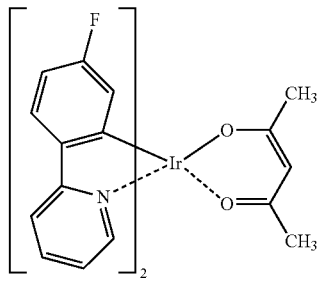

(K-3)

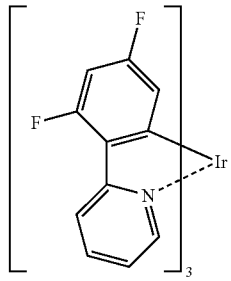

(K-4)

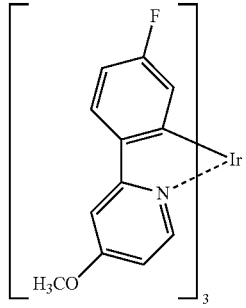

(K-5)

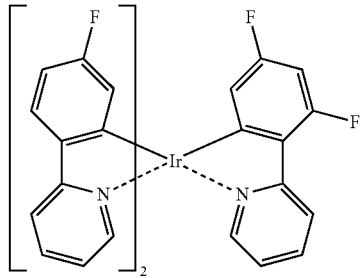

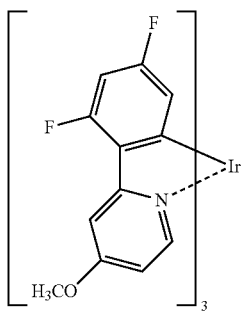
(K-6)
[Chemical Formula 78]
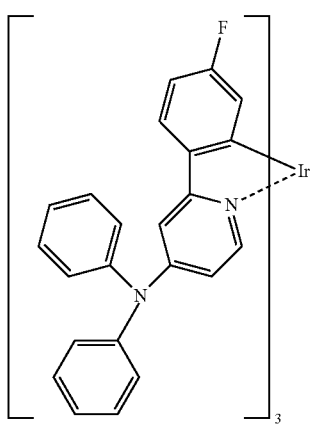
(K-7)
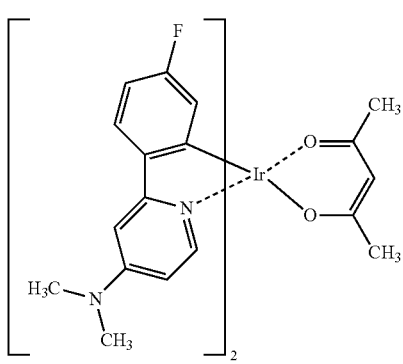
(K-8)
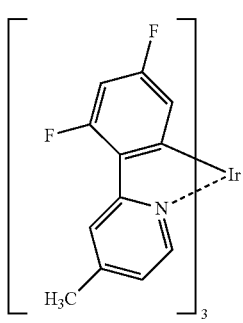
(K-9)
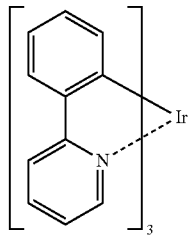
(K-10)
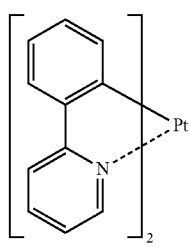
(K-11)
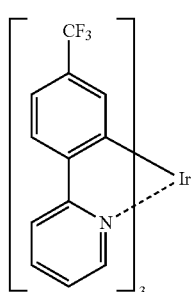
(K-12)
[Chemical Formula 79]
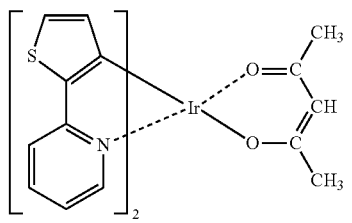
(K-13)
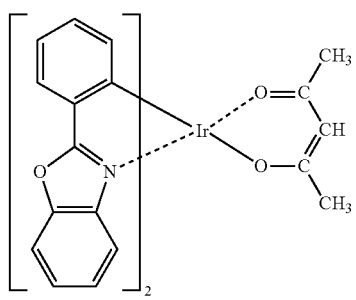
(K-14)
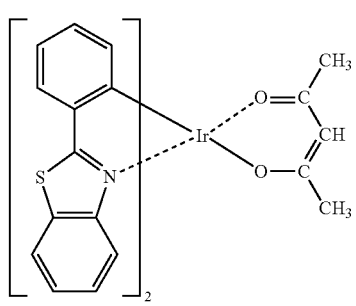
(K-15)

(K-16) 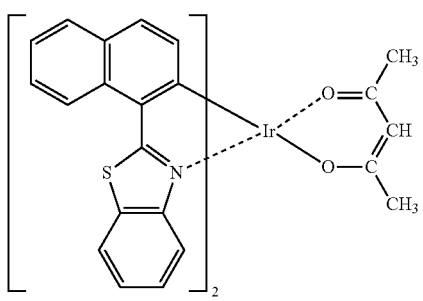
(K-17) 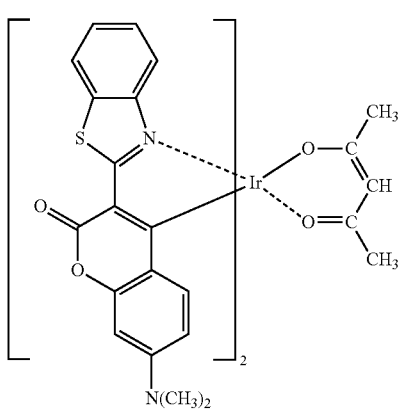
[Chemical Formula 80]
(K-18) 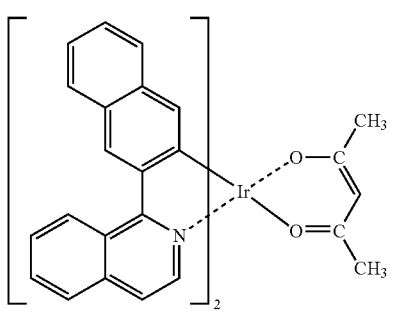
(K-19) 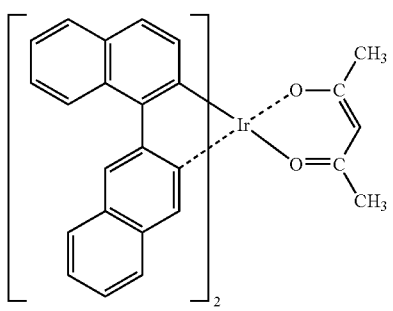
(K-20) 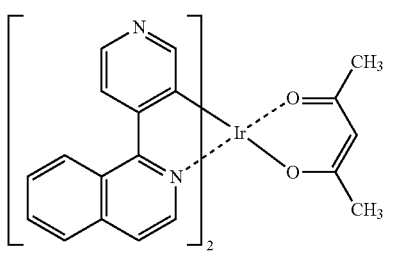
(K-21) 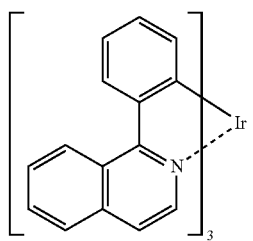
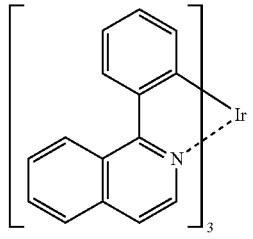
(K-22) 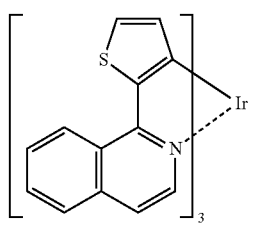
(K-23) 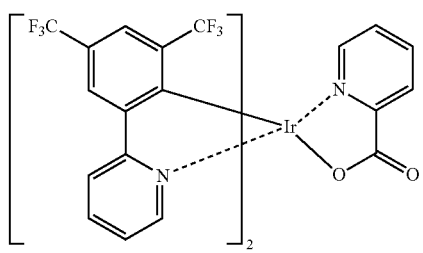
(K-24) 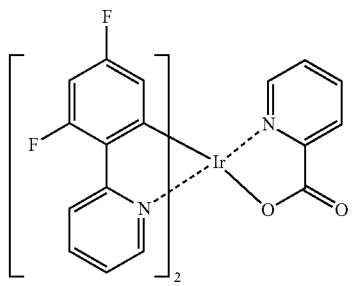
(K-25) 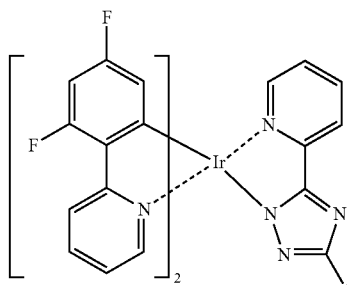

[Chemical Formula 81]

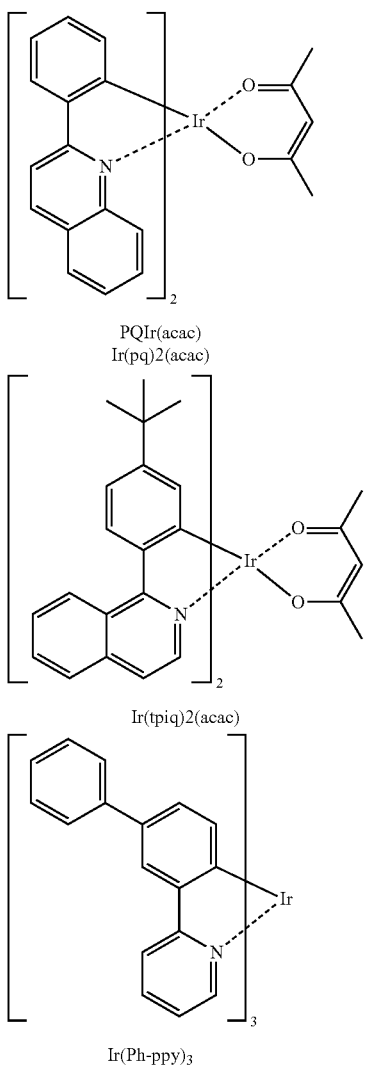

PQIr(acac)
Ir(pq)2(acac)

Ir(tpiq)2(acac)

Ir(Ph-ppy)₃

The first luminescent material preferably exhibits a luminescence peak of 570 nm or more. The second luminescent material preferably exhibits a luminescence peak of 569 nm or less, more preferably of 565 nm or less.

The luminescence peak of 570 nm or more is shown by, for instance, red emission. The luminescence peak of 569 nm or less is shown by, for instance, green emission.

Hole Transporting Layer

The hole transporting layer 6 aids transportation of holes into the first emitting layer 51.

Examples of a material of the hole transporting layer 6 are as follows.

Specifically, examples of the material are triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, polysilane copolymers, aniline copolymers and conductive polymer oligomers.

Preferable material of the hole transporting layer 6 includes compounds represented by the following formulae (1) to (7).

Electron Transporting Layer

The electron transporting layer 7 aids transportation of electrons into the second emitting layer 52.

When an electric field of $10^4$ to $10^6$V/cm is applied, a material of the electron transporting layer 7 preferably has an electron mobility of $10^{-7}$ cm²/Vs or more, more preferably $10^{-6}$ cm²/Vs or more, further more preferably $10^{-5}$ cm²/Vs or more. When the electron mobility is $10^{-7}$ cm²/Vs or more, electron transportation performance into the second emitting layer 52 is improved to raise luminous efficiency and the like.

Specifically, examples of the material of the electron transporting layer 7 are compounds represented by the following formulae.

[Chemical Formula 82]

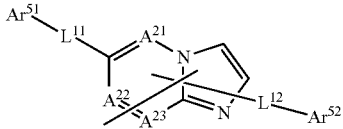
(50)

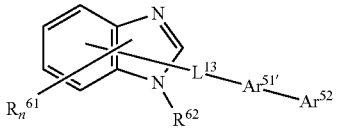
(51)

In the formulae (50) and (51), $A^{21}$ to $A^{23}$ are a nitrogen atom or a carbon atom. $R^{61}$ and $R^{62}$ each are a substituted or unsubstituted aryl group having 6 to 60 carbon atoms, a substituted or unsubstituted heteroaryl group having 3 to 60 carbon atoms, an alkyl group having 1 to 20 carbon atoms, an haloalkyl group having 1 to 20 carbon atoms or an alkoxy group having 1 to 20 carbon atoms.

n is an integer of 0 to 5. When n is an integer of 2 or more, a plurality of $R^{61}$ may be mutually the same or different.

In addition, adjacent ones among the plurality of $R^{61}$ may be bonded to each other to form a substituted or unsubstituted carbocyclic aliphatic ring or a substituted or unsubstituted carbocyclic aromatic ring.

$Ar^{51}$ is a substituted or unsubstituted aryl group having 6 to 60 carbon atoms or a substituted or unsubstituted heteroaryl group having 3 to 60 carbon atoms.

$Ar^{51'}$ is a substituted or unsubstituted arylene group having 6 to 60 carbon atoms or a substituted or unsubstituted heteroarylene group having 3 to 60 carbon atoms.

$Ar^{52}$ is a hydrogen atom, an alkyl group having 1 to 20 carbon atoms, a haloalkyl group having 1 to 20 carbon atoms, an alkoxy group having 1 to 20 carbon atoms, a substituted or unsubstituted aryl group having 6 to 60 carbon atoms, or a substituted or unsubstituted heteroaryl group having 3 to 60 carbon atoms.

$L^{11}$ to $L^{13}$ each are a single bond, a substituted or unsubstituted fused ring having 6 to 60 carbon atoms, a substituted or unsubstituted fused heterocycle having 3 to 60 carbon atoms, or a substituted or unsubstituted fluorenylene group.

The electron transporting layer may be formed of a plurality of layers, e.g., two layers including first and second electron transporting layers.

Second Exemplary Embodiment

Next, an organic EL device according to a second exemplary embodiment will be described below.

Figure 2:
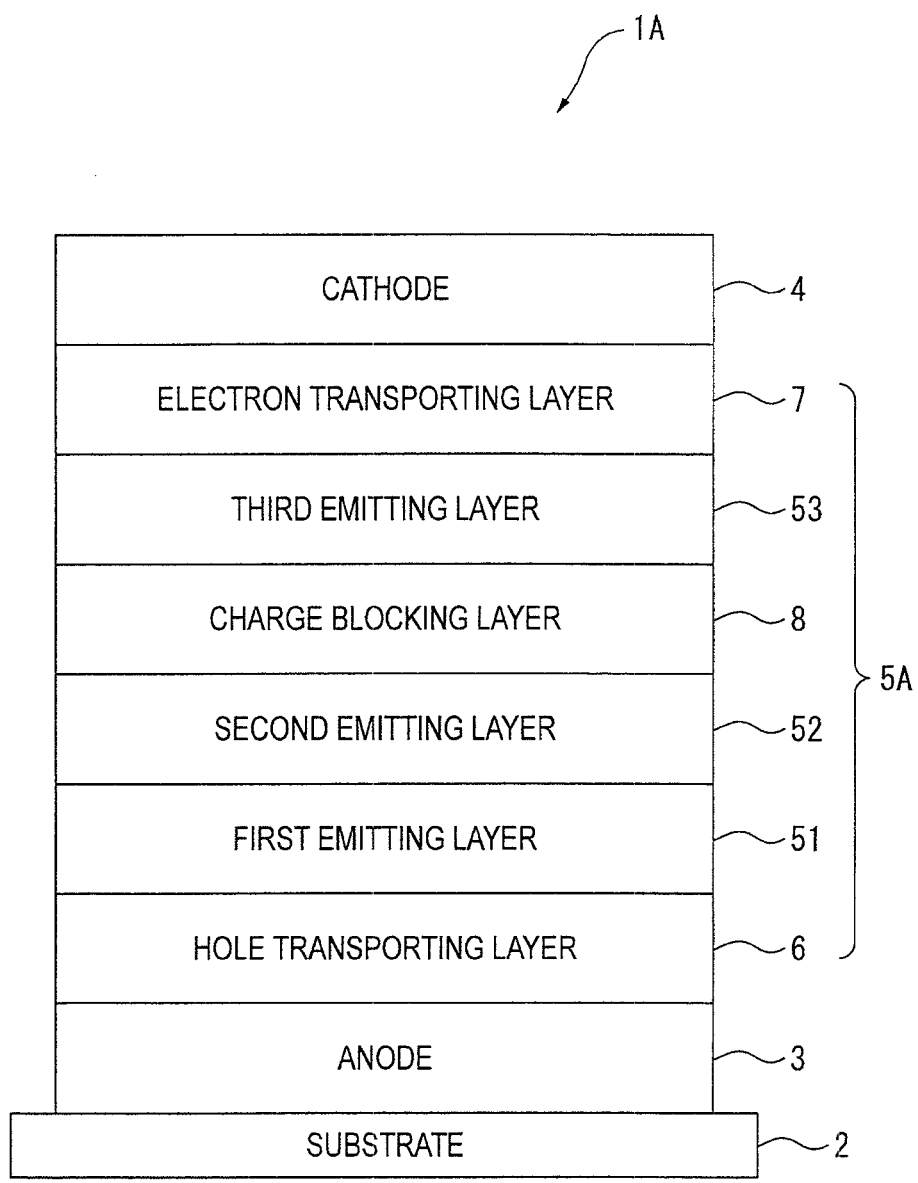
FIG. 2 schematically shows an exemplary arrangement of an organic EL device according to a second exemplary embodiment.

As shown in FIG. 2, an organic EL device 1A according to the second exemplary embodiment is different from the first exemplary embodiment in that the organic EL device 1A further includes a charge blocking layer 8 and a third emitting layer 53 between the second emitting layer 52 and the electron transporting layer 7 in an emitting unit 5A.

The charge blocking layer 8 is continuously formed on the second emitting layer 52 near the cathode 4. The third emitting layer 53 is continuously formed between the charge blocking layer 8 and the electron transporting layer 7.

Provided as an energy barrier of an HOMO level or an LUMO level between the second emitting layer 52 and the third emitting layer 53 adjacent thereto, the charge blocking layer 8 controls injection of charge (holes or electrons) into the second emitting layer 52 and the third emitting layer 53 and controls balance of charge injected thereinto.

The third emitting layer 53 is, for instance, a blue fluorescent emitting layer having a peak wavelength of 450 to 500 nm. The third emitting layer 53 includes a third host material and a third luminescent material.

Examples of the third host material are a compound having a central anthracene skeleton which is represented by the following formula (41).

[Chemical Formula 83]

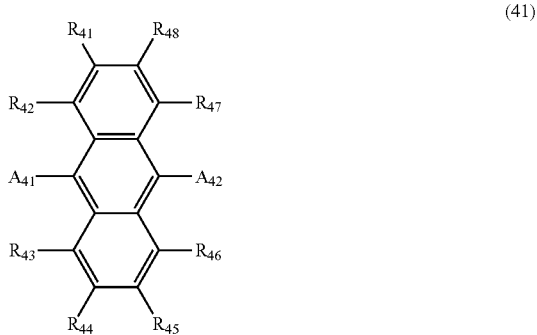

(41)

In the formula (41), $Ar_{41}$ and $Ar_{42}$ each are a group derived from a substituted or unsubstituted aromatic ring having 6 to 20 ring carbon atoms.

$R_{41}$ to $R_{48}$ each are a hydrogen atom, a substituted or unsubstituted aryl group having 6 to 50 ring carbon atoms, a substituted or unsubstituted heteroaryl group having 5 to 50 atoms for forming a ring (hereinafter referred to as ring atoms), a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Examples of a substituent for the aromatic ring of each of $Ar_{41}$ and $Ar_{42}$ are a substituted or unsubstituted aryl group having 6 to 50 ring carbon atoms, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxy group.

Examples of the third luminescent material are an arylamine compound, a styrylamine compound, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumaline, oxadiazole, aldazine, bisbenzoxazoline, bisstyryl, pyrazine, cyclopentadiene, a metal complex of quinoline, a metal complex of aminoquinoline, a metal complex of benzoquinoline, imine, diphenylethylene, vinylanthracene, diaminocarbazole, pyrane, thiopyrane, polymethine, merocyanin, an imidazole chelated oxinoid compound, quinacridone, rubrene and a fluorescent dye.

Since the organic EL device 1A includes the third emitting layer 53 exhibiting blue emission in addition to the first emitting layer 51 exhibiting red emission and the second emitting layer 52 exhibiting green emission, the organic EL device 1A can exhibit white emission as a whole.

Accordingly, the organic EL device 1A is suitably applicable as a surface light source for an illumination unit, a backlight and the like.

Third Exemplary Embodiment

An organic EL device according to this exemplary embodiment may have a tandem device structure in which at least two emitting units are provided. In such a tandem device structure, an intermediate layer is interposed between the two emitting units.

The intermediate layer, which is a layer as a supply source for injecting electrons or holes into the emitting units, is provided by an intermediate electroconductive layer or a charge generating layer. In addition to charge injected from a pair of electrodes, charge supplied from the intermediate layer is injected into the emitting unit. Accordingly, by providing the intermediate layer, luminous efficiency (current efficiency) relative to injected current is improved.

Among at least two emitting units according to this exemplary embodiment, at least one emitting unit at least includes the hole transporting layer, the first and second emitting layers of the invention and the electron transporting layer. Among at least two emitting units, an emitting unit(s) other than the emitting unit including the first and second emitting layers of the invention may be subject to no limitation as long as the emitting unit(s) includes at least one emitting layer.

Specific examples of the organic EL device of this exemplary embodiment are shown below.

(14) anode/first emitting unit/intermediate layer/second emitting unit/cathode

Figure 3:
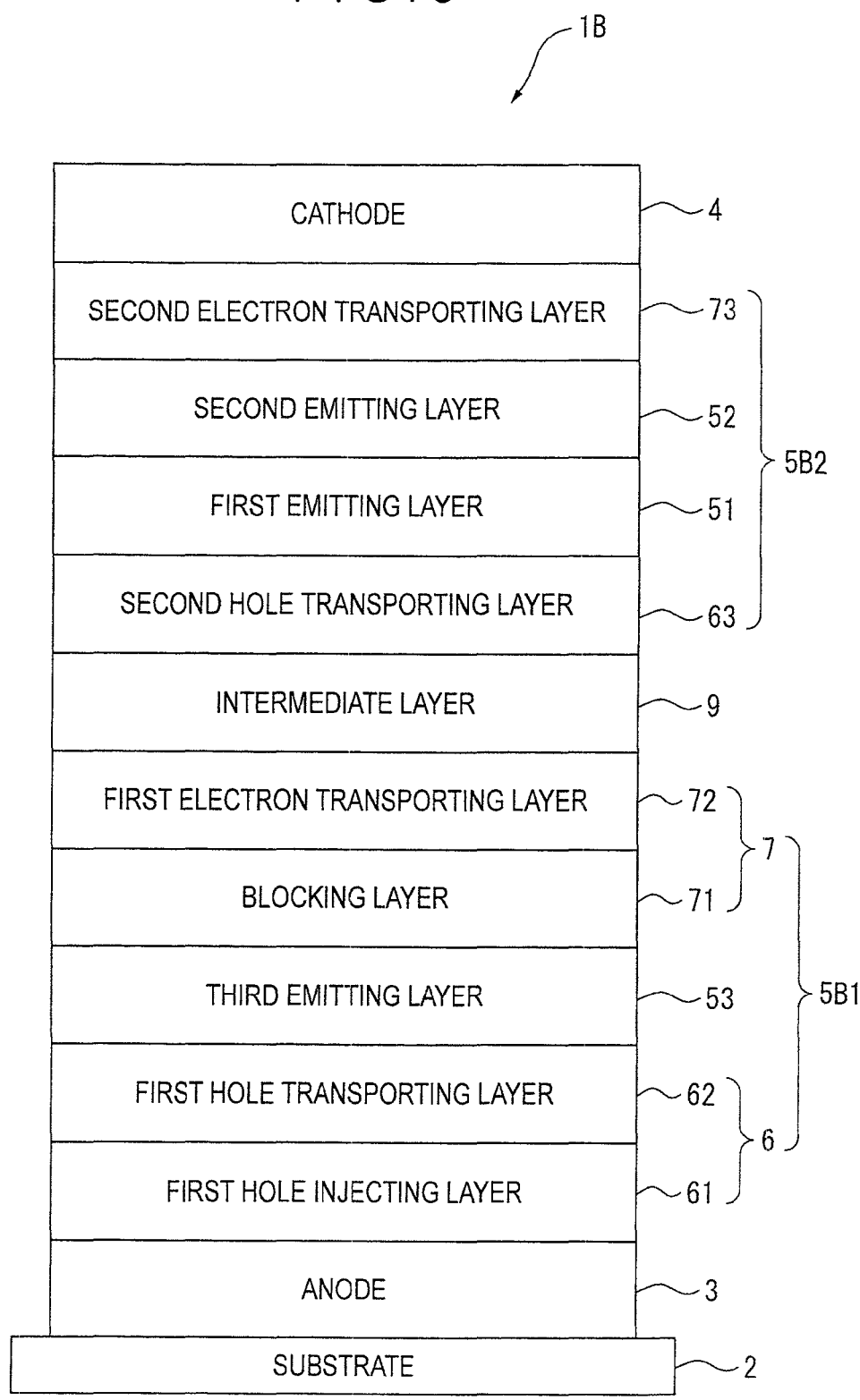
FIG. 3 schematically shows an exemplary arrangement of an organic EL device according to a third exemplary embodiment.

(15) anode/first emitting unit/intermediate layer/second emitting unit/intermediate layer/third emitting unit/cathode FIG. 3 shows one example of the organic EL device according to the third exemplary embodiment.

An organic EL device 1B includes the anode 3, a first emitting unit 5B1, the intermediate layer 9, a second emitting unit 5B2 and the cathode 4 in sequential order.

The first emitting unit 5B1 includes a hole transporting zone 6, the third emitting layer 53, and an electron transporting zone 7 in sequential order starting from the anode 3.

The hole transporting zone 6 includes a first hole injecting layer 61 and a first hole transporting layer 62.

The third emitting layer 53 includes a host material and a luminescent material exhibiting fluorescent emission of a main peak wavelength of 550 nm or less.

The electron transporting zone 7 includes a blocking layer 71 adjacent to the third emitting layer 53 and a first electron transporting layer 72. The second emitting unit 5B2 is structured in the same manner as the emitting unit of the first exemplary embodiment. The second emitting unit 5B2 includes a second hole transporting layer 63, the first emitting layer 51, the second emitting layer 52 and a second electron transporting layer 73 in sequential order starting from the anode 2.

Triplet energy (ETd) of the luminescent material of the third emitting layer 53 is preferably larger than triplet energy (ETh) of the host material. Triplet energy (ETb) of the blocking layer 71 is preferably larger than ETh. Accordingly, triplet excitons are trapped in the third emitting layer 53 to effectively cause a TTF phenomenon (a phenomenon where singlet excitons are generated by collision and fusion of two triplet excitons), thereby providing a fluorescent device with high efficiency.

Herein, the blocking layer 71 means a layer functioning as a barrier against the triplet energy. Accordingly, the blocking layer functions differently from a hole blocking layer and a charge blocking layer.

A commercially-available measuring machine F-4500 (manufactured by Hitachi, Ltd.) was used for measuring triplet energy. The conversion equation of triplet energy $E^T$ is as follows.

$$\text{The conversion equation: } E^T(\text{eV}) = 1239.85/\lambda_{edge}$$

When the phosphorescence spectrum is expressed in coordinates of which the ordinate axis indicates the phosphorescence intensity and of which the abscissa axis indicates the wavelength, and a tangent is drawn to the rise of the phosphorescence spectrum on the shorter wavelength side, "$\lambda_{edge}$" is a wavelength value (unit: nm) at the intersection of the tangent and the abscissa axis.

Examples of the intermediate layer 9 include a metal, metal oxide, mixture of metal oxides, composite oxide, and electron-accepting organic compound. Examples of the metal are preferably Mg, Al, and a film formed by co-evaporating Mg and Al. Examples of the metal oxide include ZnO, WO₃, MoO₃ and MoO₂. Examples of the mixture of the metal oxides include ITO, IZO, and ZnO:Al. Examples of the electron-accepting organic compound include an organic compound having a CN group as a substituent. The organic compound having a CN group is preferably a triphenylene derivative, tetracyanoquinodimethane derivative and indenofluorene derivative. The triphenylene derivative is preferably hexacyanohexaazatriphenylene (HAT). The tetracyanoquinodimethane derivative is preferably tetrafluoroquinodimethane and dicyanoquinodimethane. The indenofluorene derivative is preferably a compound disclosed in International Publication WO2009/011327, WO2009/069717, or WO2010/064655. The electron accepting substance may be a single substance, or a mixture with other organic compounds.

Examples of the compounds usable for the electron transporting zone, host material, luminescent material and blocking layer in the tandem device structure of this exemplary embodiment are compounds disclosed in Patent Application Number PCT/JP2010/003431. The compounds usable for the hole transporting zone are the same as those for the material of the hole transporting layer of the first exemplary embodiment.

When the intermediate layer 9 is a charge generating layer, the electron transporting zone 7 near an interface with the charge generating layer is preferably doped with a donor (e.g., an alkali metal) in order that the third emitting layer 53 can easily accept electrons from the charge generating layer. As the donor, at least one of a donor metal, donor metal compound and donor metal complex can be used. Examples of the compounds usable for the donor metal, donor metal compound and donor metal complex are compounds disclosed in Patent Application Number PCT/JP2010/003434.

Modifications

In the first and second exemplary embodiments, the anode and the hole transporting layer are continuously formed to each other. However, the hole injecting layer may be further formed between the anode and the hole transporting layer.

Preferable examples of a material of the hole injecting layer are a porphyrin compound, an aromatic tertiary amine compound, or a styrylamine compound. Particularly preferable examples include an aromatic tertiary amine compound such as hexacyanohexaazatriphenylene (HAT). With use of hexacyanohexaazatriphenylene, adherence between the anode and the hole transporting layer is improved to increase durability.

Further, the hole transporting performance can be enhanced in a structure where the hole injecting layer and the hole transporting layer are provided between the anode and the first emitting layer, as compared with a structure where holes are directly transported from the anode to the first emitting layer.

In other words, provision of the hole injecting layer and the hole transporting layer can reduce an energy difference in ionization potential between the anode and the hole injecting layer, an energy difference in ionization potential between the hole injecting layer and the hole transporting layer, and an energy difference in ionization potential between the hole transporting layer and the first emitting layer. Accordingly, since energy barrier can be reduced when holes are transferred to each layer, hole transporting performance can be improved and consequently luminous efficiency and the like can be improved.

In the first to third exemplary embodiments, the cathode and the electron transporting layer are continuously formed to each other. However, the electron injecting layer may be further formed between the cathode and the electron transporting layer.

Although two emitting units are formed in the third exemplary embodiments, three or more emitting units may be formed. In this arrangement, a charge generating layer may be provided each between the emitting units.

The organic EL device in the first to third exemplary embodiments may be used as a display device in addition to a surface light source for an illumination unit, a backlight and the like.

EXAMPLES

Examples of the invention will be described below. However, the invention is not limited by these Examples.

Example 1

In Example 1, an organic EL device was manufactured as follows.

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for 30 minutes. After the glass substrate having the transparent electrode line was cleaned, the glass substrate was mounted on a substrate holder of a vacuum deposition apparatus, so that a compound HI001 was initially laminated onto a surface of the glass substrate where the transparent electrode line was provided so as to cover the transparent electrode. Thus, a 40-nm thick hole transporting layer was formed.

On the hole transporting layer, PR001 as the first host material and Ir(tpiq)$_2$(acac) as the first luminescent material were co-evaporated. Thus, a 20-nm thick first emitting layer exhibiting red emission was formed. A concentration of the first luminescent material was 10 mass %.

On the first emitting layer, PGH001 as the second host material and Ir(Ph-ppy)$_3$ as the second luminescent material were co-evaporated. Thus, a 40-nm thick second emitting layer exhibiting green emission was formed. A concentration of the second luminescent material was 20 mass %.

A compound ET001 was laminated on the second emitting layer to form a 30-nm thick electron transporting layer.

LiF was deposited at a rate of 1 Å/min on the electron transporting layer to form a 1-nm electron injecting cathode. A metal Al was deposited on the electron injecting cathode to form an 80-nm thick cathode.

Examples 2 to 9 and 11 to 13 and Comparatives 1 to 3

The organic EL devices according respectively to Examples 2 to 9 and 11 to 13 and Comparatives 1 to 3 were formed in the same manner as in Example 1 except that the materials, a thickness of each of the layers and a concentration of each of the emitting materials were changed as shown in Table 1.

In Example 8, the organic EL device was manufactured in the same manner as in Example 2 except that the hole injecting layer was formed of the compound HI001 and the hole transporting layer was formed of a compound PR003.

The numerals in parentheses in Table 1 indicate a thickness of each layer (unit: nm).

Examples 14 and 15

In Example 14, an organic EL device was manufactured as follows.

The compound HI001 was laminated on a glass substrate having an ITO transparent electrode (anode) of Example 1 to form a 50-nm thick first hole injecting layer.

A compound HT001 was laminated on the first hole injecting layer to form a 45-nm thick first hole transporting layer.

BH001 (the host material) and BD001 (the luminescent material) were co-evaporated on the first hole transporting layer to form a 25-nm thick third emitting layer exhibiting blue emission. A concentration of the luminescent material was 5 mass %.

A compound TB001 was laminated on the third emitting layer to form a 20-nm thick blocking layer.

A compound ET003 and LiF were co-evaporated on the blocking layer to laminate a 10-nm thick first electron transporting layer thereon.

HAT (hexacyanohexaazatriphenylene) was laminated on the first electron transporting layer to form a 20-nm thick intermediate layer.

The compound HT001 was laminated on the intermediate layer to form a 30-nm thick second hole transporting layer.

PR004 (the first host material) and Ir(piq)$_2$(acac) (the first luminescent material) were co-evaporated on the second hole transporting layer to form a 10-nm thick first emitting layer exhibiting red emission. A concentration of the first luminescent material was 2 mass %.

PGH002 (the second host material) and Ir(ppy)$_3$ (the second luminescent material) were co-evaporated on the first emitting layer to form a 30-nm thick second emitting layer exhibiting green emission. A concentration of the second luminescent material was 10 mass %.

The compound ET001 was laminated on the second emitting layer to form a 35-nm thick second electron transporting layer.

LiF was deposited at a rate of 1 Å/min on the second electron transporting layer to form a 1-nm electron injecting cathode. A metal Al was deposited on the electron injecting cathode to form an 80-nm thick cathode.

In Example 15, the organic EL devices was formed in the same manner as in Example 14 except that the materials of the second emitting layer in Example 14 were replaced as shown in Table 1.

Examples 16 to 20

In Example 16, an organic EL device was manufactured as follows.

A glass substrate (manufactured by Geomatec Co., Ltd.) having a 130-nm thick ITO transparent electrode (anode) of the same size as that in Example 1 was ultrasonic-cleaned in isopropyl alcohol for five minutes, and then UV/ozone-cleaned for 30 minutes. After the glass substrate having the transparent electrode line was cleaned, the glass substrate was mounted on a substrate holder of a vacuum deposition apparatus, so that the compound HAT (hexacyanohexaazatriphenylene) was initially laminated onto a surface of the glass substrate where the transparent electrode line was provided so as to cover the transparent electrode. Thus, a 5-nm thick hole injecting layer was formed. The compound HI001 was laminated on the hole injecting layer. Thus, a 35-nm thick hole transporting layer was formed.

On the hole transporting layer, PR004 as the first host material and Ir(pq)$_2$(acac) as the first luminescent material were co-evaporated. Thus, a 10-nm thick first emitting layer exhibiting red emission was formed. A concentration of the first luminescent material was 6 mass %.

On the first emitting layer, PGH007 as the second host material and Ir(ppy)$_3$ as the second luminescent material were co-evaporated. Thus, a 30-nm thick second emitting layer exhibiting green emission was formed. A concentration of the second luminescent material was 15 mass %.

A compound ET004 was laminated on the second emitting layer to form a 20-nm thick first electron transporting layer. A compound ET002 was laminated on the first electron transporting layer to form a 10-nm thick second electron transporting layer.

Moreover, LiF was deposited at a rate of 1 Å/min on the second electron transporting layer to form a 1-nm electron injecting cathode. A metal Al was deposited on the electron injecting cathode to form an 80-nm thick cathode.

In Examples 17 to 20, organic EL devices were formed in the same manner as in Example 16 except that the materials of the second emitting layer in Example 16 were replaced as shown in Table 1.

The first host material, the second host material, the material of the hole transporting layer and the material of the electron transporting layer, which were used in Examples 1 to 9 and 11 to 20 and Comparatives 1 to 3, are represented by the following formulae.
First Host Material
[Chemical Formula 84]
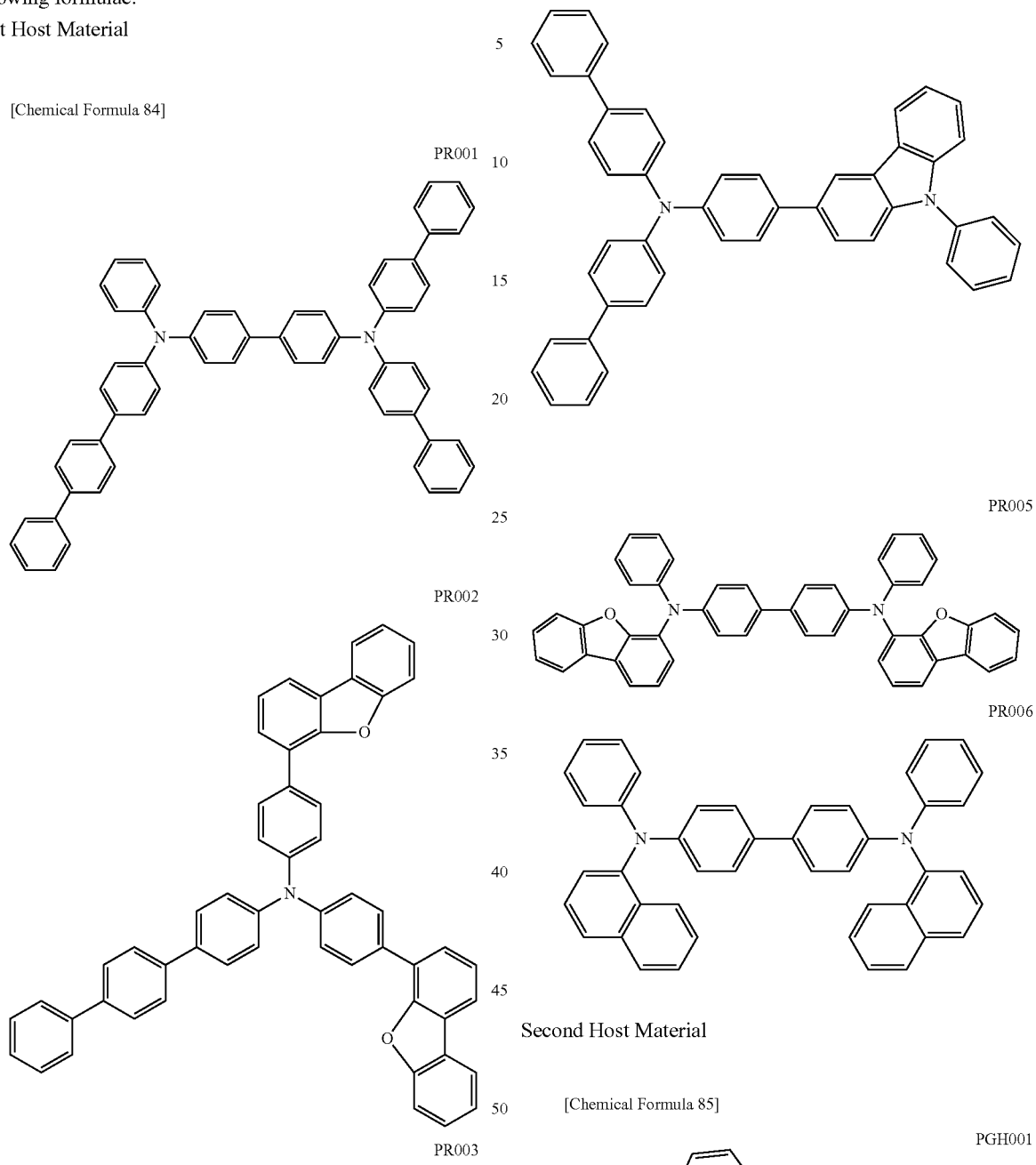
Second Host Material
[Chemical Formula 85]
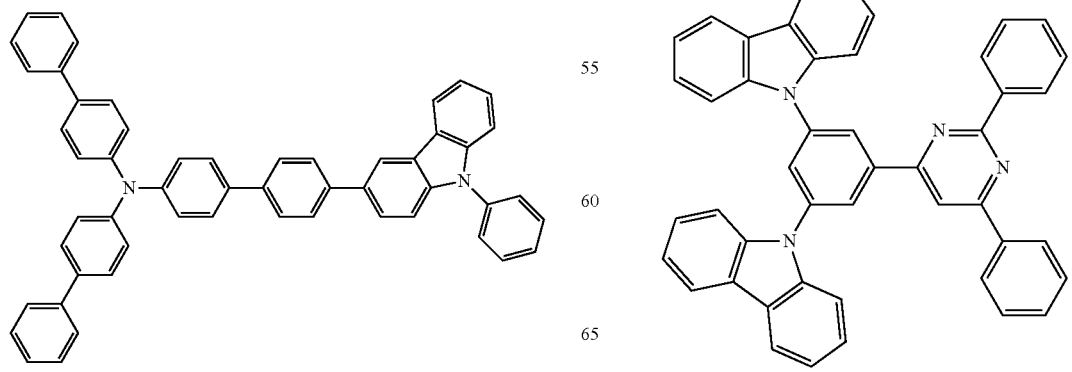

PGH002
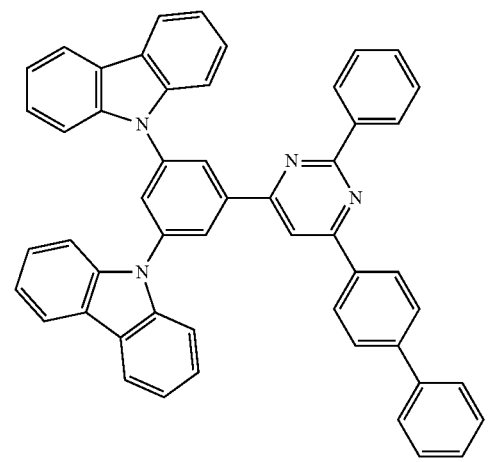
PGH003
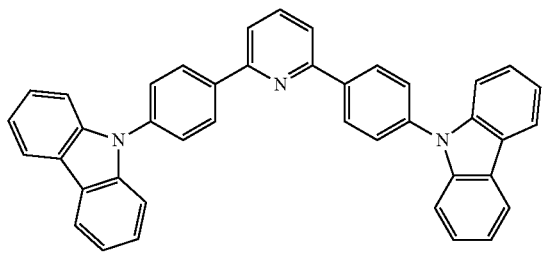
PGH005
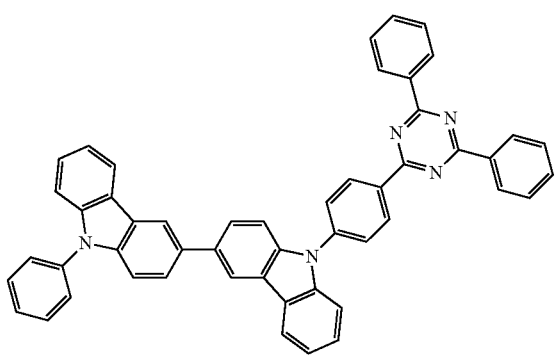
PGH006
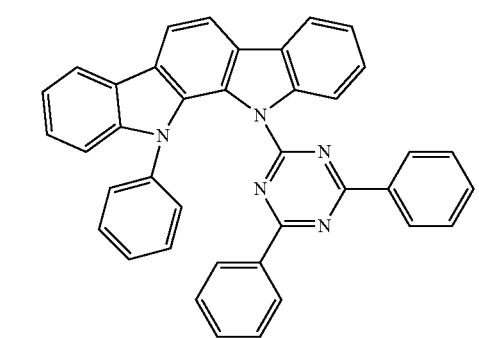
[Chemical Formula 86]
PGH007
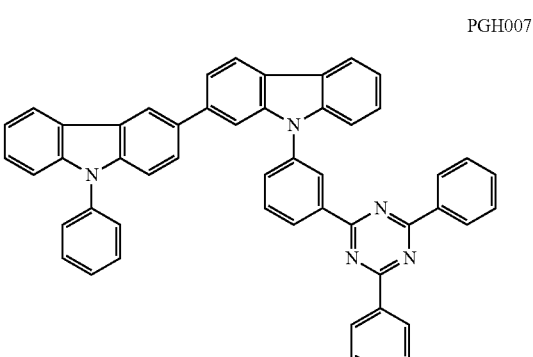
PGH008
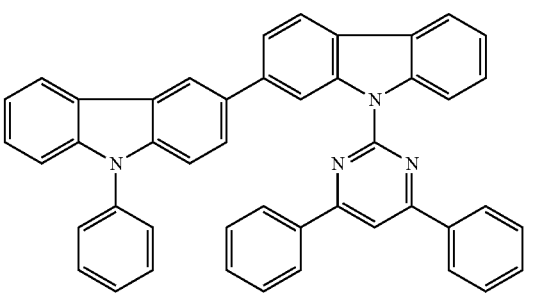
PGH009
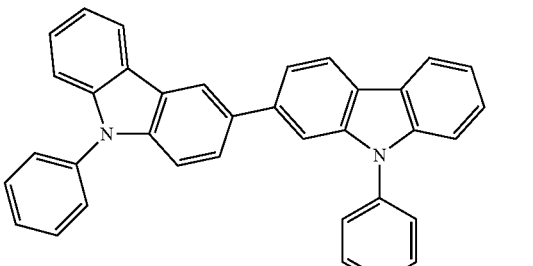
PGH010
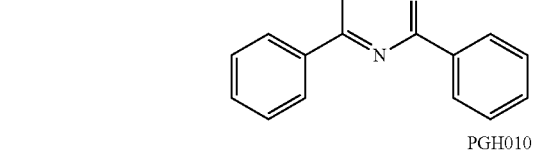

-continued
PGH011
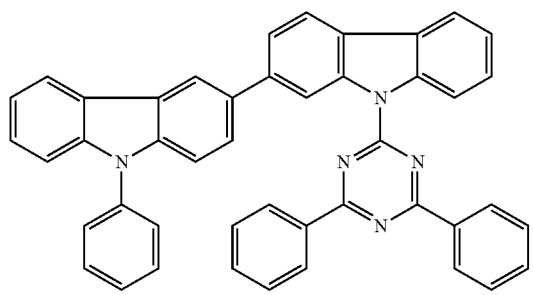
Host Material and Luminescent Material of Third Emitting Layer, and Material of Blocking Layer
[Chemical Formula 87]
BD001
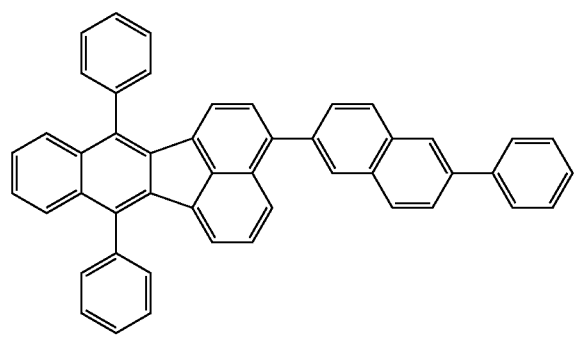
TB001
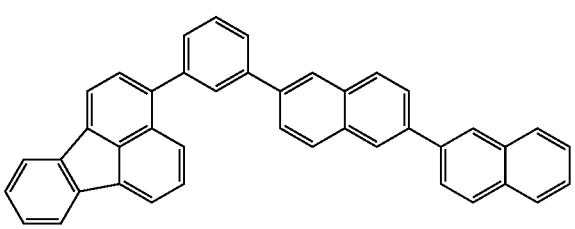
BH001
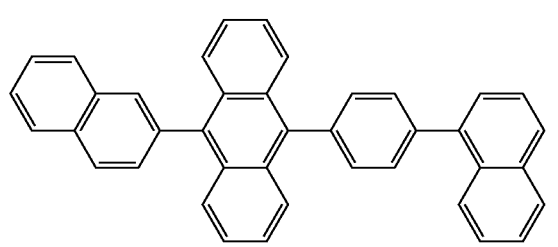
Materials of Hole Transporting Layer and Electron Transporting Layer
[Chemical Formula 88]
HI001
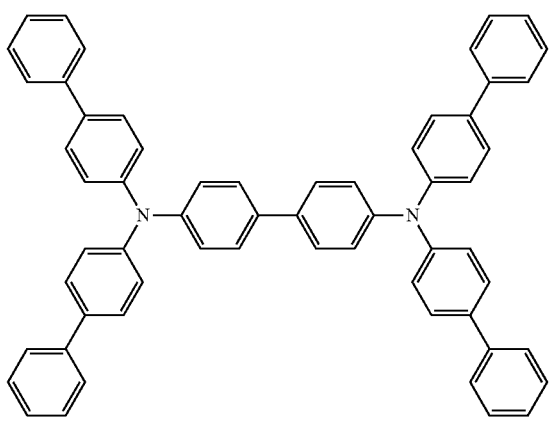
ET001
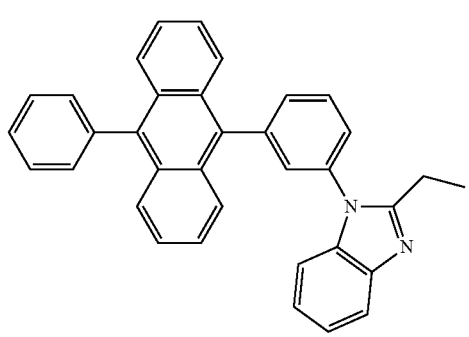
HT001
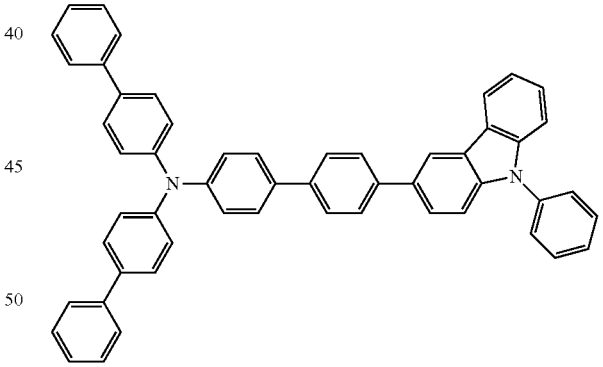
ET002
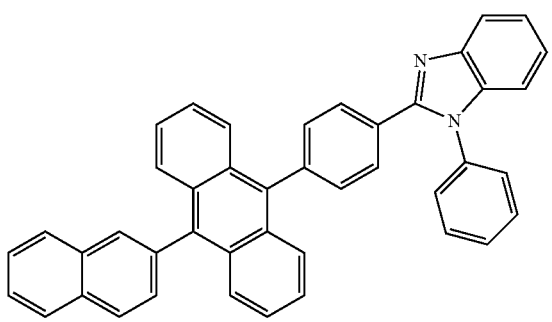

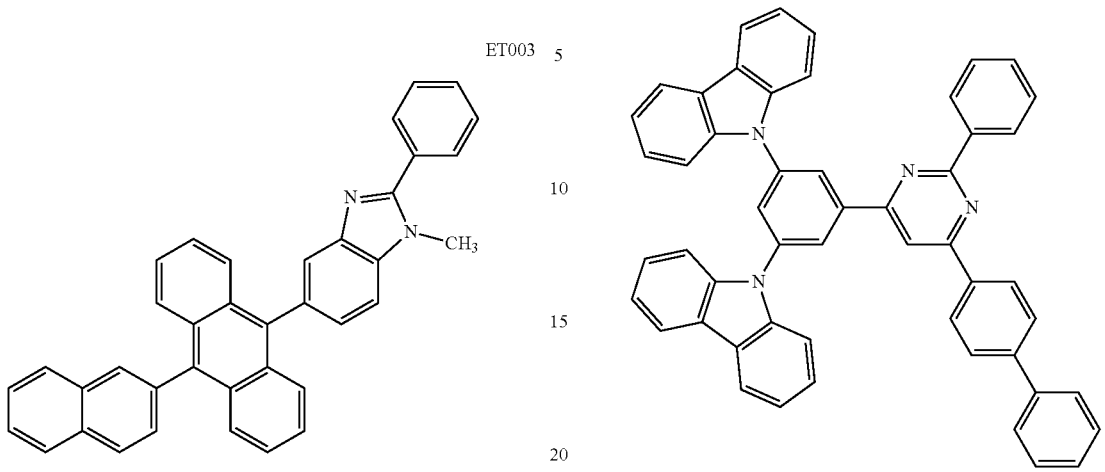

TABLE 1

| | Arrangement of Organic EL Device |
|---|---|
| Example 1 | ITO/HI001(40)/PR001:Ir(tpiq)$_2$(acac)(20:10%)/PGH001:Ir(Ph-ppy)$_3$(40:20%)/ET001(30)/LiF(1)/Al(80) |
| Example 2 | ITO/HI001(40)/PR002:Ir(tpiq)$_2$(acac)(20:10%)/PGH001:Ir(Ph-ppy)$_3$(40:20%)/ET001(30)/LiF(1)/Al(80) |
| Example 3 | ITO/HI001(40)/PR003:Ir(tpiq)$_2$(acac)(20:10%)/PGH001:Ir(Ph-ppy)$_3$(40:20%)/ET001(30)/LiF(1)/Al(80) |
| Example 4 | ITO/HI001(40)/PR004:Ir(tpiq)$_2$(acac)(20:10%)/PGH001:Ir(Ph-ppy)$_3$(40:20%/ET001(30)/LiF(1)/Al(80) |
| Example 5 | ITO/HI001(40)/PR006:Ir(tpiq)$_2$(acac)(20:10%)/PGH001:Ir(Ph-ppy)$_3$(40:20%)/ET001(30)/LiF(1)/Al(80) |
| Example 6 | ITO/HI001(50)/PR006:Ir(tpiq)$_2$(acac)(20:10%)/PGH002:Ir(ppy)$_3$(50:10%)/ET002(30)/LiF(1)/Al(80) |
| Example 7 | ITO/HI001(30)/PR005:Ir(tpiq)$_2$(acac)(20:10%)/PGH002:Ir(ppy)$_3$(50:10%)/ET002(30)/LiF(1)/Al(80) |
| Example 8 | ITO/HI001(30)/PR003(20)/PR003:Ir(tpiq)$_2$(acac)(10:10%)/PGH001:Ir(ppy)$_3$(40:20%)/ET002(30)/LiF(1)/Al(80) |
| Example 9 | ITO/HI001(40)/PR004:Ir(tpiq)$_2$(acac)(20:10%)/PGH003:Ir(Ph-ppy)$_3$(40:20%)/ET001(30)/LiF(1)/Al(80) |
| Example 11 | ITO/HI001(50)/PR004:Ir(piq)$_2$(acac)(10:8%)/PGH002:Ir(ppy)$_3$(30:10%)/ET001(35)/LiF(1)/Al(80) |
| Example 12 | ITO/HI001(50)/PR004:Ir(piq)$_2$(acac)(10:8%)/PGH005:Ir(ppy)$_3$(30:10%)/ET001(35)/LiF(1)/Al(80) |
| Example 13 | ITO/HI001(50)/PR004:Ir(piq)$_2$(acac)(10:8%)/PGH006:Ir(ppy)$_3$(30:10%)/ET001(35)/LiF(1)/Al(80) |
| Example 14 | ITO(130 nm)/HI001(50)/HT001(45)/BH001:BD001(25:5%)/TB001(20)/ET003:Li(10:4%)/HAT(20)/HI001(30)/ PR004:Ir(piq)$_2$(acac)(10:2%)/PGH002:Ir(ppy)$_3$(30:10%/ET001(35)/LiF(1)/Al(80) |
| Example 15 | ITO(130 nm)/HI001(50)/HT001(45)/BH001:BD001(25:5%)/TB001(20)/ET003:Li(10:4%)/HAT(20)/HI001(30)/ PR004:Ir(piq)$_2$(aoac)(10:2%)/PGH005:Ir(ppy)$_3$(30:10%)/ET001(35)/LiF(1)/Al(80) |
| Example 16 | ITO(130)/HAT(5)/HI001(35)/PR004:Ir(pq)$_2$(acac)(10:6%)/PGH007:Ir(ppy)$_3$(30:15%)/ET004(20)/ET002(10)/LiF(1)/Al(80) |
| Example 17 | ITO(130)/HAT(5)/HI001(35)/PR004:Ir(pq)$_2$(acac)(10:6%)/PGH008:Ir(ppy)$_3$(30:15%)/ET004(20)/ET002(10)/LiF(1)/Al(80) |
| Example 18 | ITO(130)/HAT(5)/HI001(35)/PR004:Ir(pq)$_2$(acac)(10:6%)/PGH009:Ir(ppy)$_3$(30:15%)/ET004(20)/ET002(10)/LiF(1)/Al(80) |
| Example 19 | ITO(130)/HAT(5)/HI001(35)/PR004:Ir(pq)$_2$(acac)(10:6%)/PGH010:Ir(ppy)$_3$(30:15%)/ET004(20)/ET002(10)/LiF(1)/Al(80) |
| Example 20 | ITO(130)/HAT(5)/HI001(35)/PR004:Ir(pq)$_2$(acac)(10:6%)/PGH011:Ir(ppy)$_3$(30:15%)/ET004(20)/ET002(10)/LiF(1)/Al(80) |
| Comparative 1 | ITO/NPD(40)/TPD:Ir(phq)$_3$(20:10%)/TPBIP:Ir(ppy)$_3$(40:10%)/TPBIP(30)/LiF(1)/Al(80) |
| Comparative 2 | ITO/NPD(40)/TPD:Ir(tpiq)$_2$(acac)(20:10%)/TPBIP:Ir(ppy)$_3$(40:10%)/TPBIP(30)/LiF(1)/Al(80) |
| Comparative 3 | ITO/NPD(40)/CBP:PQIr(acac)(18:4%)/CBP:Ir(ppy)$_3$(12:5%)/BCP(40)/LiF(1)/Al(150) |

The first host material, the second host material, the host material and the luminescent material of the third emitting layer and the material of the blocking layer, which were used in Examples 1 to 9 and 11 to 20 and Comparatives 1 to 3, were measured for affinity levels and ionization potentials. The results are shown in Table 2. Triplet energy (ETh) of the second host material of the third emitting layer was 1.83 eV. Triplet energy (ETd) of the luminescent material of the third emitting layer was 2.13 eV. Triplet energy (ET) of the material of the blocking layer was 2.27 eV. A measurement method is as shown above.

TABLE 2

| | | Affinity Level (Af) (ev) | Ionization Potential (Ip) (ev) |
|---|---|---|---|
| First Host Material | PR001 | 2.43 | 5.51 |
| | PR002 | 2.47 | 5.60 |
| | PR003 | 2.43 | 5.60 |
| | PR004 | 2.28 | 5.50 |
| | PR005 | 2.35 | 5.54 |
| | PR006 | 2.50 | 5.50 |
| | TPD | 2.4 | 5.4 |
| | CBP | 2.4 | 6.0 |
| Second Host Material | PGH001 | 2.50 | 6.05 |
| | PGH002 | 2.62 | 6.13 |
| | PGH003 | 2.52 | 6.01 |
| | PGH005 | 2.70 | 5.68 |
| | PGH006 | 2.72 | 5.89 |
| | PGH007 | 2.17 | 5.58 |
| | PGH008 | 2.07 | 5.48 |
| | PGH009 | 2.51 | 5.81 |
| | PGH010 | 2.56 | 5.70 |
| | PGH011 | 2.18 | 5.55 |
| | TPBIP | 2.5 | 6.0 |
| | CBP | 2.4 | 6.0 |
| Host Material of Third Emitting Layer | BH001 | 3.0 | 6.0 |
| Luminescent Material of Third Emitting Layer | BD001 | 3.1 | 6.0 |
| Material of Blocking Layer | TB001 | 3.0 | 6.1 |
| Material of Hole Transporting Layer | HI001 | — | 5.5 |
| | NPD | — | 5.49 |

Next, the organic EL devices of Examples 1 to 9 and 11 to 20 and Comparatives 1 to 3 were measured and evaluated in terms of voltage, chromaticity, color shift, current efficiency, luminous efficiency, emission wavelength and durability (lifetime) at current densities shown in Table 3. The results are shown in Tables 3 and 4.

Chromaticity (CIE(x),(y)) was measured when driven at current densities of 1 mA/cm$^2$ and 10 mA/cm$^2$. Color shift was evaluated using a difference in chromaticity.

TABLE 3

| | Voltage (V) | Current Density (mA/cm$^2$) | Chromaticity (CIE) x | y |
|---|---|---|---|---|
| Example 1 | 4.2 | 1 | 0.43 | 0.55 |
| | 4.8 | 10 | 0.42 | 0.56 |
| Example 2 | 4.4 | 1 | 0.45 | 0.52 |
| | 5.1 | 10 | 0.43 | 0.55 |
| Example 3 | 4.2 | 1 | 0.44 | 0.54 |
| | 4.9 | 10 | 0.42 | 0.55 |
| Example 4 | 4.3 | 1 | 0.44 | 0.54 |
| | 5.0 | 10 | 0.42 | 0.55 |
| Example 5 | 4.4 | 1 | 0.43 | 0.54 |
| | 5.0 | 10 | 0.42 | 0.55 |
| Example 6 | 3.5 | 1 | 0.50 | 0.48 |
| | 4.5 | 10 | 0.47 | 0.50 |
| Example 7 | 3.4 | 1 | 0.45 | 0.52 |
| | 4.4 | 10 | 0.43 | 0.54 |
| Example 8 | 3.1 | 1 | 0.46 | 0.51 |
| | 3.9 | 10 | 0.42 | 0.54 |
| Example 9 | 4.5 | 1 | 0.38 | 0.54 |
| | 5.2 | 10 | 0.40 | 0.56 |
| Example 11 | 2.73 | 1 | 0.55 | 0.43 |
| | 3.38 | 10 | 0.54 | 0.44 |
| Example 12 | 2.71 | 1 | 0.50 | 0.47 |
| | 3.38 | 10 | 0.49 | 0.48 |
| Example 13 | 2.61 | 1 | 0.45 | 0.52 |
| | 3.27 | 10 | 0.47 | 0.50 |
| Example 14 | 5.63 | 1 | 0.33 | 0.32 |
| | 6.86 | 10 | 0.30 | 0.29 |
| Example 15 | 5.61 | 1 | 0.30 | 0.34 |
| | 6.83 | 10 | 0.28 | 0.31 |
| Example 16 | 2.94 | 1 | 0.49 | 0.49 |
| | 3.64 | 10 | 0.48 | 0.49 |
| Example 17 | 2.82 | 1 | 0.36 | 0.60 |
| | 3.58 | 10 | 0.36 | 0.59 |
| Example 18 | 3.24 | 1 | 0.47 | 0.51 |
| | 3.77 | 10 | 0.47 | 0.51 |
| Example 19 | 2.68 | 1 | 0.50 | 0.48 |
| | 3.20 | 10 | 0.49 | 0.49 |
| Example 20 | 2.83 | 1 | 0.38 | 0.58 |
| | 3.46 | 10 | 0.39 | 0.57 |
| Comparative 1 | 6.4 | 1 | 0.58 | 0.42 |
| | 7.5 | 10 | 0.58 | 0.42 |
| Comparative 2 | 6.7 | 1 | 0.46 | 0.53 |
| | 7.9 | 10 | 0.44 | 0.55 |
| Comparative 3 | 5.5 | 1 | 0.50 | 0.47 |
| | 7.0 | 10 | 0.58 | 0.40 |

TABLE 4

| | Current Density (mA/cm$^2$) | Current Efficiency (L/J) (cd/A) | Luminous Efficiency ($\eta$) (lm/W) | Wavelength ($\lambda_p$) (nm) | Durability (Lifetime) @10000 nits |
|---|---|---|---|---|---|
| Example 1 | 1 | 24.0 | 18.1 | 526 | 3000 |
| | 10 | 34.4 | 22.5 | 526 | |
| Example 2 | 1 | 21.8 | 15.4 | 634 | 3500 |
| | 10 | 32.6 | 20.2 | 527 | |
| Example 3 | 1 | 25.2 | 18.7 | 527 | 5000 |
| | 10 | 35.4 | 22.8 | 527 | |
| Example 4 | 1 | 26.5 | 19.3 | 527 | 5000 |
| | 10 | 37.1 | 23.4 | 527 | |
| Example 5 | 1 | 27.7 | 19.9 | 527 | 3000 |
| | 10 | 37.4 | 23.4 | 527 | |
| Example 6 | 1 | 28.6 | 25.4 | 631 | 3500 |
| | 10 | 31.8 | 22.1 | 631 | |
| Example 7 | 1 | 34.5 | 31.4 | 631 | 4500 |
| | 10 | 36.1 | 25.8 | 525 | |
| Example 8 | 1 | 34.4 | 35.4 | 630 | 2500 |
| | 10 | 38.8 | 31.0 | 524 | |
| Example 9 | 1 | 37.5 | 26.2 | 527 | 4000 |
| | 10 | 35.6 | 21.5 | 527 | |
| Example 11 | 1 | 32.6 | 37.5 | 614 | 1300 |
| | 10 | 30.4 | 28.2 | 613 | |
| Example 12 | 1 | 37.9 | 43.8 | 613 | 2000 |
| | 10 | 35.4 | 32.9 | 612 | |
| Example 13 | 1 | 41.8 | 50.3 | 611 | 1800 |
| | 10 | 31.8 | 30.6 | 611 | |
| Example 14 | 1 | 53.4 | 29.8 | — | 23000 @1000 nits |
| | 10 | 48.1 | 22.0 | — | |
| Example 15 | 1 | 54.8 | 30.7 | — | 32000 @1000 nits |
| | 10 | 49.7 | 22.9 | — | |
| Example 16 | 1 | 48.7 | 52.1 | 598 | 4000 |
| | 10 | 42.8 | 37.0 | 598 | |
| Example 17 | 1 | 62.0 | 68.9 | 522 | 2000 |
| | 10 | 51.3 | 44.9 | 522 | |

TABLE 4-continued

|  | Current Density (mA/cm$^2$) | Current Efficiency (L/J) (cd/A) | Luminous Efficiency ($\eta$) (lm/W) | Wavelength ($\lambda_p$) (nm) | Durability (Lifetime) @10000 nits |
|---|---|---|---|---|---|
| Example 18 | 1 | 44.8 | 43.4 | 597 | 2000 |
|  | 10 | 44.3 | 36.9 | 596 |  |
| Example 19 | 1 | 42.6 | 49.9 | 598 | 2000 |
|  | 10 | 39.9 | 39.2 | 598 |  |
| Example 20 | 1 | 53.1 | 58.9 | 521 | 1000 |
|  | 10 | 49.6 | 45.1 | 520 |  |
| Comparative 1 | 1 | 24.4 | 12.0 | 592 | 500 |
|  | 10 | 23.5 | 9.8 | 592 |  |
| Comparative 2 | 1 | 26.8 | 12.6 | 527 | 650 |
|  | 10 | 27.1 | 10.8 | 527 |  |
| Comparative 3 | 1 | 35.6 | 20.4 | 598 | 50 |
|  | 10 | 16.3 | 13.1 | 598 |  |

Next, a triplet energy gap (Eg(T)) of each of the first and second host materials was measured. A commercially-available measuring machine F-4500 (manufactured by Hitachi, Ltd.) was used for the measurement. The (Eg(T)) conversion equation is as follows.

The conversion equation: $(Eg(T))(eV)=1239.85/\lambda_{edge}$

When the phosphorescence spectrum is expressed in coordinates of which the ordinate axis indicates the phosphorescence intensity and of which the abscissa axis indicates the wavelength, and a tangent is drawn to the rise of the phosphorescence spectrum on the shorter wavelength side, "$\lambda_{edge}$" is a wavelength value at the intersection of the tangent and the abscissa axis. The unit is "nm."

TABLE 5

|  |  | Triplet Energy Gap (Eg(T)) |
|---|---|---|
| First Host Material | PR001 | 2.49eV |
|  | PR002 | 2.58eV |
|  | PR003 | 2.60eV |
|  | PR004 | 2.60eV |
|  | PR005 | 2.61eV |
|  | PR006 | 2.46eV |
|  | TPD | 2.5eV |
|  | CBP | 2.7eV |
| Second Host Material | PGH001 | 2.90eV |
|  | PGH002 | 2.65eV |
|  | PGH003 | 2.75eV |
|  | PGH005 | 2.77eV |
|  | PGH006 | 2.77eV |
|  | PGH007 | 2.73eV |
|  | PGH008 | 2.74eV |
|  | PGH009 | 2.76eV |
|  | PGH010 | 2.72eV |
|  | PGH011 | 2.70eV |

Next, an electron mobility of the material of the electron transporting layer was measured. The electron mobility was evaluated using the impedance spectrometry. Al as the anode, the material of the electron transporting layer, LiF, and Al as the cathode were sequentially laminated on the substrate to prepare an electron-only device. DC voltage on which AC voltage of 100 mV was placed was applied thereon, and their complex modulus values were measured. When the frequency at which the imaginary part of the modulus was maximum was set to fmax (Hz), a response time T(sec.) was calculated based on the equation $T=1/2/\pi/fmax$. Using this value, the dependence property of electron mobility on electric field intensity was determined.

TABLE 6

|  |  | Electron Mobility (cm$^2$/Vs) |
|---|---|---|
| Material of Electron Transporting Layer | ET001 | $2.0 \times 10^{-4}$ |
|  | ET002 | $2.0 \times 10^{-4}$ |
|  | ET004 | $6.0 \times 10^{-6}$ |

In Examples 1 to 9 and 11 to 20, the first and second luminescent materials were different ortho-metalated complexes and the second host material was a monoazine derivative, a diazine derivative or a triazine derivative. Accordingly, it was found that the organic EL devices exhibited excellent current efficiency, luminous efficiency and durability (lifetime) with less color shift irrespective of a difference in current density.

In Examples 1 to 9 and 11 to 20, the first luminescent material was an amine derivative. Accordingly, it was found that, because of a low electron mobility of the first emitting layer, holes and electrons were recombinable in both the first emitting layer and the second emitting layer to emit light therefrom in good balance.

In Examples 14 and 15, the organic EL device exhibiting white emission was obtained by combining the first to third emitting layers. It was found that such an organic EL device was excellent particularly in current efficiency. In Examples 14 and 15, since triplet energy (ETd) of the luminescent material of the third emitting layer was larger than triplet energy (ETh) of the host material and triplet energy (ETb) of the material of the blocking layer was larger than Eth, the third emitting layer 53 can emit light efficiently.

In Examples 1 to 9 and 11 to 20, it was found that color shift generated when luminance intensity was increased was small since the second host material was a specific azine derivative.

On the other hand, in Comparative 1, it was found that current efficiency, luminous efficiency and durability (lifetime) were low since the first and second luminescent materials were the same ortho-metalated complex.

Also in Comparative 2, it was found that current efficiency, luminous efficiency and durability (lifetime) were low since a material having no carbazole skeleton was used as the second host material.

In Comparative 3, the second host material used was not an azine derivative. The first and second host materials were the same CBP. The first and second host materials were formed using the same CBP to exhibit equivalent affinity level and ionization potential.

As a result, it was found that color shift was large due to current density, and current efficiency, luminous efficiency and durability were low particularly at high current density.

In Comparatives 1 to 3, it was found that the second emitting layer was less likely to exhibit favorable emission since the second host material was not an azine derivative.

The invention claimed is:
1. An organic electroluminescence device comprising:
an anode,
a cathode; and
layers between the anode and the cathode, the layers comprising a hole transporting layer, a first emitting layer, a second emitting layer, and an electron transporting layer, wherein
the first emitting layer comprises a first host material and a first luminescent material,
the second emitting layer is continuously formed on the first emitting layer near the cathode and comprises a second host material and a second luminescent material, the second host material is a monoazine derivative, a diazine derivative, or a triazine derivative, wherein a monoazine ring of the monoazine derivative, a diazine ring of the diazine derivative and a triazine ring of the triazine derivative are optionally fused with a ring structure except for a nitrogen-containing five-membered ring structure, and the first and second luminescent materials are different metal complexes.

2. The organic electroluminescence device of claim 1, wherein the first and second host materials are different from each other.

3. The organic electroluminescence device according to claim 1, wherein the first host material is an amine derivative.

4. The organic electroluminescence device of claim 3, wherein the amine derivative comprises a compound of at least one formula selected from the group consisting of formulae (1), (2), (3), (4), (5), (6), and (7):

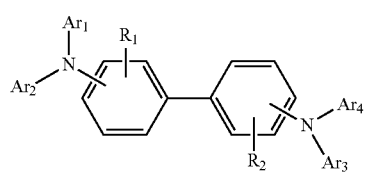
(1)

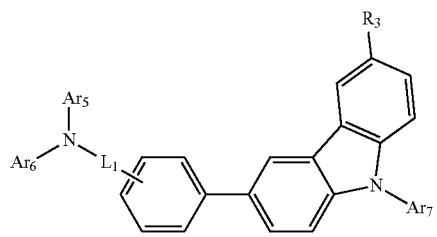
(2)

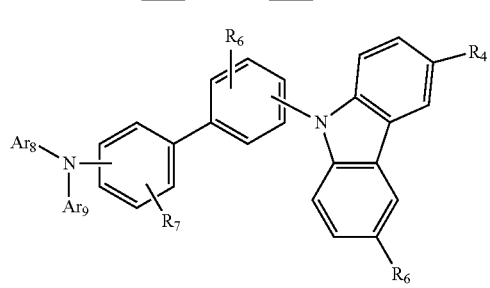
(3)

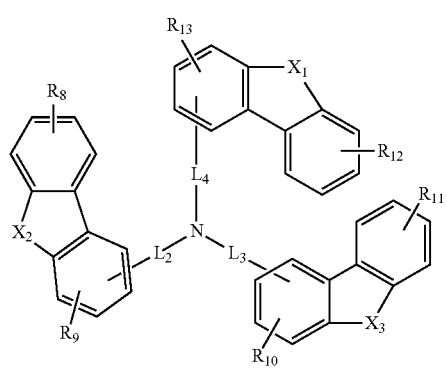
(4)

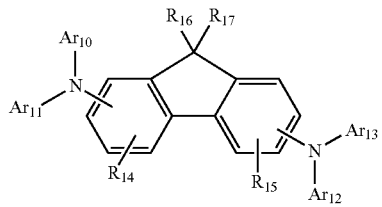
(5)

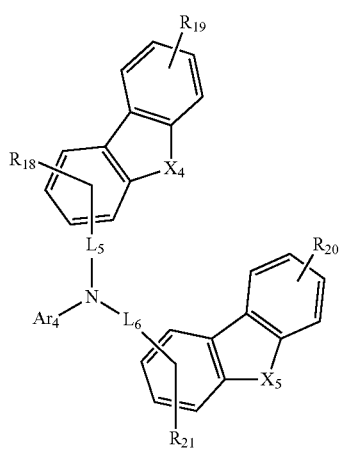
(6)

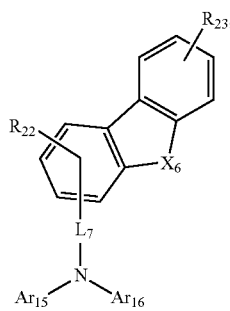
(7)

wherein in formula (1), $Ar_1$ to $Ar_4$ are each independently a substituted or unsubstituted aryl group having 6 to 30 carbon atoms or a substituted or unsubstituted aromatic heterocyclic group having 5 to 40 carbon atoms;

in formulae (2) to (7), $Ar_5$ to $Ar_{16}$ are each independently a substituted or unsubstituted aryl group having 6 to 40 carbon atoms, a substituted or unsubstituted aromatic heterocyclic group having 5 to 40 carbon atoms, a substituted or unsubstituted aryl group having 8 to 40 carbon atoms bonded with an aromatic amino group, or a substituted or unsubstituted aryl group having 8 to 40 carbon atoms bonded with an aromatic heterocyclic group;

in formulae (1) to (7), each of $Ar_1$ to $Ar_{16}$ is independently optionally a ladder-type furan;

in formulae (1) to (7), $Ar_1$, $Ar_3$, $Ar_5$, $Ar_8$, $Ar_{10}$, $Ar_{12}$, and $Ar_{15}$ are each independently optionally respectively bonded to $Ar_2$, $Ar_4$, $Ar_6$, $Ar_9$, $Ar_{11}$, $Ar_{13}$, and $Ar_{16}$ to form a ring;

in formulae (2), (4), (6), and (7), $L_1$ to $L_7$ are each independently a direct bond or a bonding group having 1 to 30 carbon atoms;

in formulae (1) to (7), $R_1$ to $R_{23}$ are each independently a hydrogen atom, a halogen atom, a substituted or unsubstituted alkyl group having 1 to 40 carbon atoms, a substituted or unsubstituted heterocyclic group having 3 to 20 carbon atoms, a substituted or unsubstituted non-fused aryl group having 6 to 40 carbon atoms, a substituted or unsubstituted fused aryl group having 6 to 12 carbon atoms, a substituted or unsubstituted aryl group of both fused and non-fused rings having 12 to 40 carbon atoms, a substituted or unsubstituted aralkyl group having 7 to 20 carbon atoms, a substituted or unsubstituted alkenyl group having 2 to 40 carbon atoms, a substituted or unsubstituted alkyl amino group having 1 to 40 carbon atoms, a substituted or unsubstituted aralkyl amino group having 7 to 60 carbon atoms, a substituted or unsubstituted alkylsilyl group having 3 to 20 carbon atoms, a substituted or unsubstituted arylsilyl group having 8 to 40 carbon atoms, a substituted or unsubstituted aralkylsilyl group having 8 to 40 carbon atoms, or a substituted or unsubstituted halogenated alkyl group having 1 to 40 carbon atoms; and in formulae (4), (6), and (7), $X_1$ to $X_6$ are each independently a sulfur atom, an oxygen atom, or a nitrogen atom substituted by a monoaryl group.

5. The device of claim 4, wherein the amine derivative comprises a compound of formula (1), and wherein $Ar_2$, $Ar_3$, or both are a naphthyl group.

6. The organic electroluminescence device of claim 1, wherein
the second host material comprises a carbazole skeleton.

7. The organic electroluminescence device of claim 6, wherein
the second host material comprises a compound of at least one formula selected from the group consisting of formulae (8), (9), (10), (11), and (12):

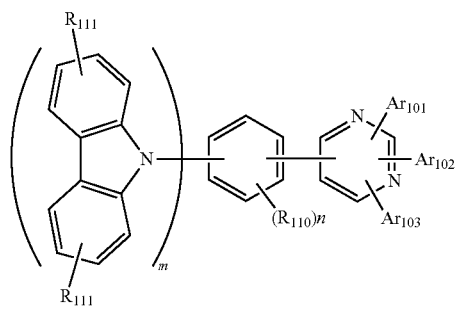

(8)

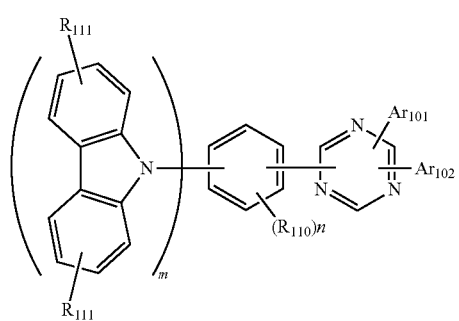

(9)

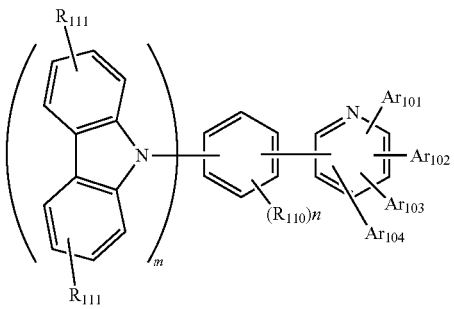

(10)

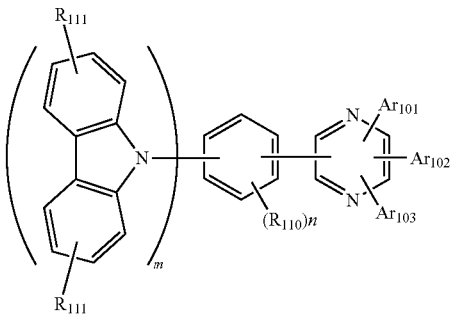

(11)

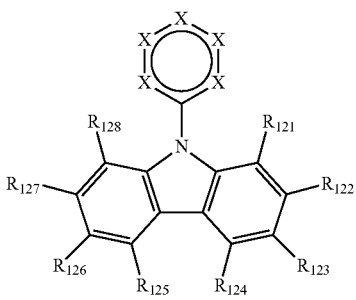

(12)

(12A)

wherein: in formulae (8) to (11), $Ar_{101}$ to $Ar_{104}$ are each indepedently a substituted or unsubstituted aryl group having 6 to 60 carbon atoms or a substituted or unsubstituted heterocyclic group having 3 to 60 carbon atoms;
in formulae (8) to (11), $R_{110}$ to $R_{111}$ are each independently a hydrogen atom, a halogen atom, a substituted or unsubstituted alkyl group having 1 to 40 carbon atoms, a substituted or unsubstituted heterocyclic group having 3 to 20 carbon atoms, a substituted or unsubstituted non-fused aryl group having 6 to 40 carbon atoms, a substituted or unsubstituted fused aryl group having 6 to 12 carbon atoms, a substituted or unsubstituted aryl group of both fused and non-fused rings having 12 to 40 carbon atoms, a substituted or unsubstituted aralkyl group having 7 to 20 carbon atoms, a substituted or unsubstituted alkenyl group having 2 to 40 carbon atoms, a substituted or unsubstituted alkyl amino group having 1 to 40 carbon atoms, a substituted or unsubstituted aralkyl amino group having 7 to 60 carbon atoms, a substituted or unsubstituted alkylsilyl group having 3 to 20 carbon atoms, a substituted or unsubstituted arylsilyl group having 8 to 40 carbon atoms, a substituted or unsubstituted aralkylsilyl group having 8 to 40 carbon atoms, or a substituted or unsubstituted halogenated alkyl group having 1 to 40 carbon atoms;

in formulae (8) to (11), n is an integer of from 1 to 4, m is an integer of from 1 to 4, and a sum (n+m) of n and m satisfies a relationship of $2 \leq (n+m) \leq 5$;

in formula (12), $R_{121}$ to $R_{128}$ each are independently a hydrogen atom, an aryl group, or an alkyl group, or are bonded with a skeleton of formula (12A);

in formulae (12) and (12A), each X is independently N or CH, with the proviso that from 1 to 4 of groups X are N;

when $R_{121}$ to $R_{128}$ are bonded with the skeleton of formula (12A), at least one combination selected from the group consisting of $R_{121}$ and $R_{122}$, $R_{122}$ and $R_{123}$, $R_{123}$ and $R_{124}$, $R_{125}$ and $R_{126}$, $R_{126}$ and $R_{127}$, and $R_{127}$ and $R_{128}$ is bonded with the skeleton of formula (12A); and in formula (12A), $R_{129}$ is a hydrogen atom, an aryl group, or an alkyl group.

8. The organic electroluminescence device of claim 6, wherein the second host material comprises a compound of at least one formula selected from the group consisting of formulae (8A), (9A), (10A), and (11A):

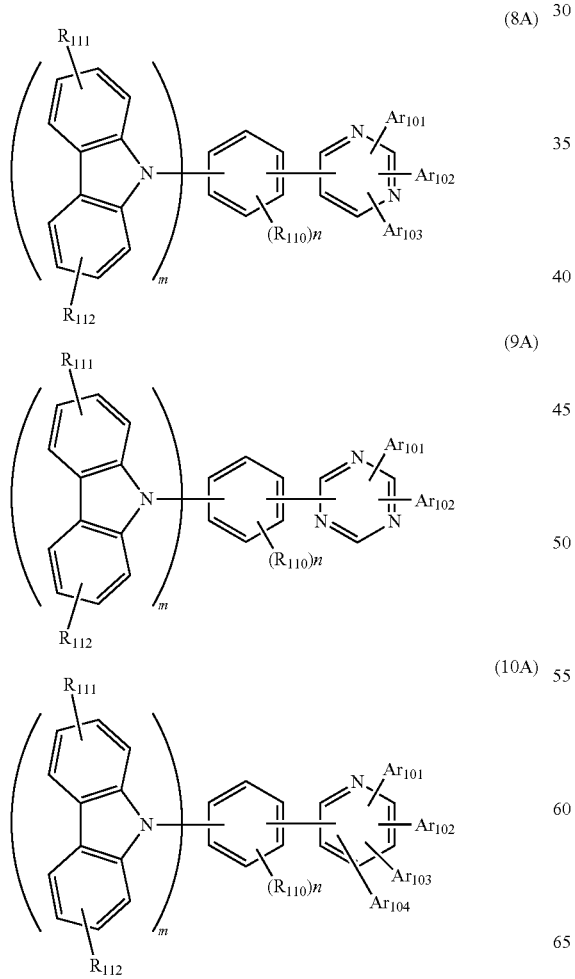

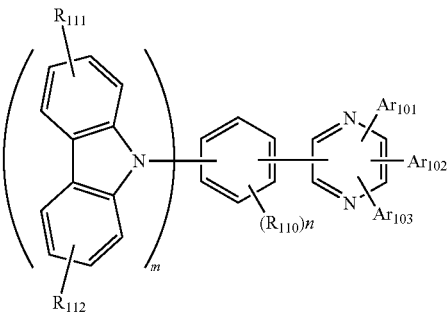

wherein $Ar_{101}$ to $Ar_{104}$ are each independently a hydrogen atom, a substituted or unsubstituted aryl group having 6 to 60 carbon atoms, or a substituted or unsubstituted heterocyclic group having 3 to 60 carbon atoms, with the proviso that $Ar_{101}$ to $Ar_{103}$ are not all hydrogen atoms in formulae (8A), (9A), and (11A), and $Ar_{101}$ to $Ar_{104}$ are not all hydrogen atoms in formula (10A);

$R_{110}$ to $R_{112}$ are each independently a hydrogen atom, a halogen atom, a substituted or unsubstituted alkyl group having 1 to 40 carbon atoms, a substituted or unsubstituted heterocyclic group having 3 to 20 carbon atoms, a substituted or unsubstituted non-fused aryl group having 6 to 40 carbon atoms, a substituted or unsubstituted fused aryl group having 6 to 12 carbon atoms, a substituted or unsubstituted aryl group of both fused and non-fused rings having 12 to 40 carbon atoms, a substituted or unsubstituted aralkyl group having 7 to 20 carbon atoms, a substituted or unsubstituted alkenyl group having 2 to 40 carbon atoms, a substituted or unsubstituted alkyl amino group having 1 to 40 carbon atoms, a substituted or unsubstituted aralkyl amino group having 7 to 60 carbon atoms, a substituted or unsubstituted alkylsilyl group having 3 to 20 carbon atoms, a substituted or unsubstituted arylsilyl group having 8 to 40 carbon atoms, a substituted or unsubstituted aralkylsilyl group having 8 to 40 carbon atoms, or a substituted or unsubstituted halogenated alkyl group having 1 to 40 carbon atoms; and n is an integer of from 1 to 4, m is an integer of from 1 to 4, and a sum (n+m) of n and m satisfies a relationship of $2 \leq (n+m) \leq 5$.

9. The organic electroluminescence device of claim 6, wherein the second host material comprises a compound of formula (13):

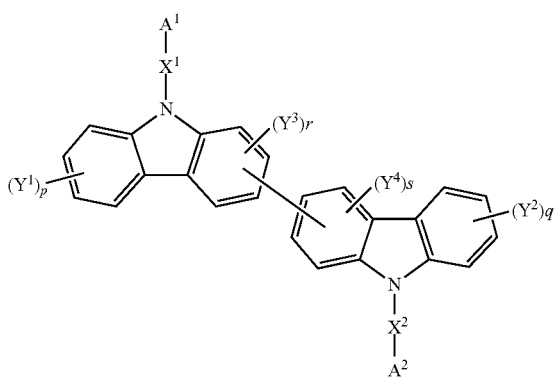

wherein in formula (13), $A^1$ is a substituted or unsubstituted nitrogen-containing heterocyclic group having 1 to 30 ring carbon atoms, with the proviso that $A^1$ does not comprise a carbazolyl group or an indolyl group;

$A^2$ is a substituted or unsubstituted aromatic hydrocarbon group having 6 to 30 ring carbon atoms, or a substituted or unsubstituted nitrogen-containing heterocyclic group having 1 to 30 ring carbon atoms;

$X^1$ and $X^2$ are each independently a single bond, a substituted or unsubstituted aromatic hydrocarbon group having 6 to 30 ring carbon atoms, a substituted or unsubstituted fused aromatic hydrocarbon group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms;

$Y^1$ to $Y^4$ are each independently a hydrogen atom, a fluorine atom, a cyano group, a substituted or unsubstituted alkyl group having 1 to 20 carbon atoms, a substituted or unsubstituted alkoxy group having 1 to 20 carbon atoms, a substituted or unsubstituted haloalkyl group having 1 to 20 carbon atoms, a substituted or unsubstituted haloalkoxy group having 1 to 20 carbon atoms, a substituted or unsubstituted alkylsilyl group having 1 to 10 carbon atoms, a substituted or unsubstituted arylsilyl group having 6 to 30 carbon atoms, a substituted or unsubstituted aromatic hydrocarbon group having 6 to 30 ring carbon atoms, a substituted or unsubstituted fused aromatic hydrocarbon group having 6 to 30 ring carbon atoms, a substituted or unsubstituted aromatic heterocyclic group having 2 to 30 ring carbon atoms, or a substituted or unsubstituted fused aromatic heterocyclic group having 2 to 30 ring carbon atoms, with the proviso that at least two adjacent groups selected from the group consisting of $Y^1$ to $Y^4$ are optionally bonded to each other to form a cyclic structure;

p and q each are independently an integer of from 1 to 4, and r and s each are independently an integer of from 1 to 3;

when p, q, r, and s each are greater than 1, $Y^1$ to $Y^4$ are optionally the same or different; and at least one group selected from the group consisting of $A^1$, $A^2$, $X^1$, $X^2$, $Y^1$, $Y^2$, $Y^3$, and $Y^4$ is a group derived from a monoazine derivative, a diazine derivative, or a triazine derivative.

10. The organic electroluminescence device of claim 6, wherein
the second host material comprises a compound of formula (14) or (15):

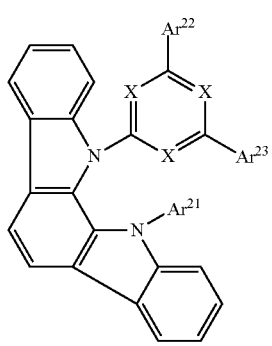

(14)

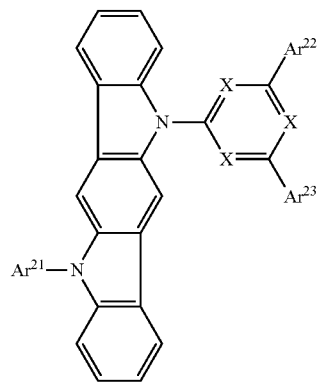

(15)

wherein each X is independently CH or N, with the proviso that at least one of X is N;
$Ar^{21}$ to $Ar^{23}$ each independently are a substituted or unsubstituted non-fused aromatic hydrocarbon group or aromatic heterocyclic group; and
$Ar^{22}$ and $Ar^{23}$ each optionally forms a fused ring with a ring including X.

11. The organic electroluminescence device of claim 6, wherein
the second host material comprises a compound of formula (16), (17), or both:

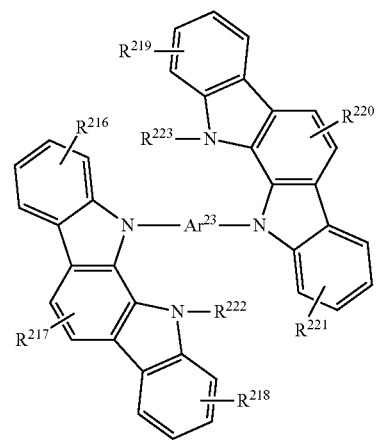

(16)

wherein in formula (16), $Ar^{23}$ is a divalent bonding group comprising a substituted or unsubstituted non-fused aromatic hydrocarbon group or aromatic heterocyclic group;
$R^{217}$ and $R^{220}$ are each independently a hydrogen atom, a substituted or unsubstituted non-fused aromatic hydrocarbon group, or an aromatic heterocyclic group;
$R^{222}$ and $R^{223}$ are each independently a substituted or unsubstituted non-fused aromatic hydrocarbon group or aromatic heterocyclic group; and
$R^{216}$, $R^{218}$, $R^{219}$ and $R^{221}$ are a hydrogen atom, alkyl group, aralkyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amido group, substituted or unsubstituted aromatic hydrocarbon group, or substituted or unsubstituted aromatic heterocyclic group;

at least one group selected from the group consisting of Ar$^{23}$, R$^{216}$, R$^{217}$, R$^{218}$, R$^{219}$, R$^{220}$, R$^{221}$, R$^{222}$, and R$^{223}$ is a group derived from a monoazine derivative, a diazine derivative or a triazine derivative,

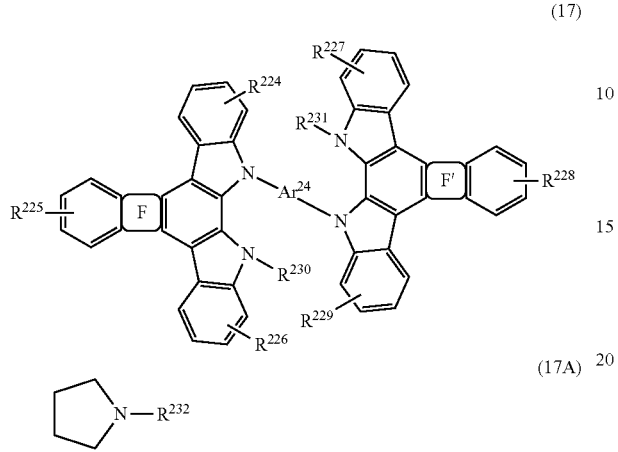

in formulae (17) and (17A), rings F and F' are each independently a heterocyclic ring fused to an adjacent ring;

F and F' are each independently of a formula (17A);

Ar$^{24}$ is a divalent bonding group including a substituted or unsubstituted non-fused aromatic hydrocarbon group or aromatic heterocyclic group;

R$^{230}$ to R$^{232}$ each independently are a substituted or unsubstituted non-fused aromatic hydrocarbon group or aromatic heterocyclic group;

R$^{224}$ to R$^{229}$ each independently are a hydrogen atom, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amido group, substituted or unsubstituted aromatic hydrocarbon group, or substituted or unsubstituted aromatic heterocyclic group;

at least one group selected from the group consisting of Ar$^{24}$, R$^{224}$, R$^{225}$, R$^{226}$, R$^{227}$, R$^{228}$, R$^{229}$, R$^{230}$, R$^{231}$, and R$^{232}$ is a group derived from a monoazine derivative, a diazine derivative, or a triazine derivative.

12. The organic electroluminescence device of claim 1, wherein
the second host material has a higher affinity level than the first host material.

13. The organic electroluminescence device of claim 1, wherein
the second host material has a higher ionization potential than the first host material.

14. The organic electroluminescence device of claim 1, wherein
the first and second luminescent materials each independently comprise iridium (Ir), palladium (Pd), platinum (Pt), or a combination thereof.

15. The organic electroluminescence device of claim 14, wherein
each of the first and second luminescent materials is independently an ortho-metalated complex of formula (20),

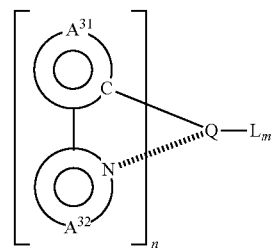

wherein A$^{31}$ is a ring bonded to A$^{32}$ and Q, and is a substituted or unsubstituted aromatic hydrocarbon ring group or a substituted or unsubstituted aromatic heterocyclic ring;

A$^{32}$ is an aromatic heterocyclic group bonded to A$^{31}$ and is a substituted or unsubstituted aromatic heterocyclic group comprising nitrogen in an aromatic hetero ring, a ring comprising A$^{31}$ and a ring comprising A$^{32}$ are optionally bonded to each other at portions other than A$^{31}$ and A$^{32}$ to form a fused ring or an unsaturated ring;

Q is palladium (Pd), iridium (Ir), or platinum (Pt);

L is a bidentate ligand; and m and n are each an integer, wherein, when Q is a divalent metal, n=2 and m=0, and when Q is a trivalent metal, n=3 and m=0, or n=2 and m=1.

16. The organic electroluminescence device of claim 1, wherein
the first luminescent material has a luminescence peak of a wavelength of 570 nm or more, and
the second luminescent material has a luminescence peak of a wavelength of 565 nm or less.

17. The device of claim 1, wherein a triplet energy gap (Eg(T)) of the first host material is 2.4 eV or more.

18. The device of claim 1, wherein an ionization potential difference between the first host material and a material of the hole transporting layer is 0.2 eV or less.

19. The device of claim 1, wherein a hole mobility of the first host material is larger than a hole mobility of the second host material.

20. The device of claim 1, wherein the second host material comprises a compound of at least one formula selected from the group consisting of formulae (21), (22), (23), (24), (25), and (26):

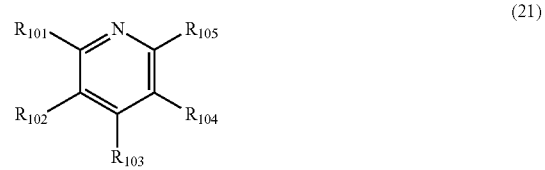

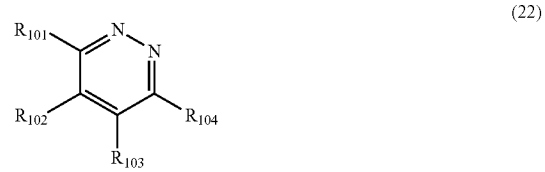

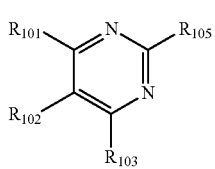
(23)
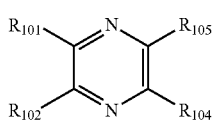
(24)
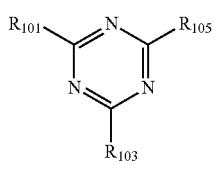
(25)
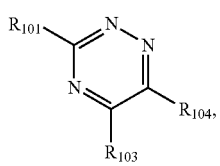
(26)
wherein $R_{101}$ to $R_{105}$ are each independently a substituted or unsubstituted aryl group, a substituted or unsubstituted heterocyclic group, or an alkyl group.
* * * * *